United States Patent
Ruf et al.

(10) Patent No.: US 8,664,257 B2
(45) Date of Patent: Mar. 4, 2014

(54) OXYGEN-SUBSTITUTED 3-HETEROAROYLAMINO-PROPIONIC ACID DERIVATIVES AND THEIR USE AS PHARMACEUTICALS

(75) Inventors: Sven Ruf, Frankfurt am Main (DE); Josef Pernerstorfer, Frankfurt am Main (DE); Thorsten Sadowski, Frankfurt am Main (DE); Georg Horstick, Frankfurt am Main (DE); Herman Schreuder, Frankfurt am Main (DE); Christian Buning, Frankfurt am Main (DE); Thomas Olpp, Frankfurt am Main (DE); Bodo Scheiper, Frankfurt am Main (DE); Klaus Wirth, Frankfurt am Main (DE)

(73) Assignee: Sanofi, Paris (FR)

( * ) Notice: Subject to any disclaimer, the term of this patent is extended or adjusted under 35 U.S.C. 154(b) by 0 days.

(21) Appl. No.: 13/575,008

(22) PCT Filed: Jan. 26, 2011

(86) PCT No.: PCT/EP2011/051038
§ 371 (c)(1),
(2), (4) Date: Oct. 22, 2012

(87) PCT Pub. No.: WO2011/092187
PCT Pub. Date: Aug. 4, 2011

(65) Prior Publication Data
US 2013/0046004 A1    Feb. 21, 2013

Related U.S. Application Data

(60) Provisional application No. 61/309,119, filed on Mar. 1, 2010.

(30) Foreign Application Priority Data

Jan. 26, 2010  (EP) ..................................... 10305080

(51) Int. Cl.
*C07D 231/20*   (2006.01)
*C07D 231/22*   (2006.01)
*C07D 401/04*   (2006.01)
*C07D 401/12*   (2006.01)

(52) U.S. Cl.
USPC ........ 514/404; 514/407; 514/538; 548/364.1; 548/365.7; 548/369.7

(58) Field of Classification Search
None
See application file for complete search history.

(56) References Cited

U.S. PATENT DOCUMENTS 5,258,397 A    11/1993  Lepage et al.
2004/0072802 A1  4/2004  Duan et al.

FOREIGN PATENT DOCUMENTS

| DE | 226883 A1 | 9/1985 |
|---|---|---|
| JP | 2000169453 | 6/2000 |
| JP | 2005145839 | 6/2005 |
| WO | WO94/27983 A1 | 12/1994 |
| WO | WO02/14311 A2 | 2/2002 |
| WO | WO2004/056815 A1 | 7/2004 |
| WO | WO2006/076202 A1 | 7/2006 |
| WO | WO2007/000582 A1 | 1/2007 |
| WO | WO2008/139941 A1 | 11/2008 |
| WO | WO2009/080226 A2 | 7/2009 |
| WO | WO2009/080227 A2 | 7/2009 |
| WO | WO2010/136493 A1 | 12/2010 |

OTHER PUBLICATIONS

Caballero, Esther et al., "N-Substituted Pyrrolines from Enamines and alpha-Dicarbonyls," Tetrahedron (1994), vol. 50, No. 26, pp. 7849-7856.

Chao, Julie et al., "The tissue kallikrein-kinin system protects against cardiovascular and renal diseases and ischemic stroke independently of blood pressure reduction," The Journal of Biological Chemistry (2006), vol. 387, pp. 665-675.

Davies, Stephen G. et al., "Asymmetric Synthesis of anti-alpha-Alkyl-beta-amino Acids," Journal of the Chemical Society, Perkin Transactions 1 (1994), pp. 1129-1139.

Davies, Stephen G. et al., "Asymmetric Synthesis of R-Beta-Amino Butanoic Acid and S-Beta-Tyrosine: Homochiral Lithium Amide Equivalents for Michael Additions to Alpha,Beta-Unsaturated Esters," Tetrahedron: Asymmetry (1991), vol. 2, No. 3, pp. 183-186.

Galjart, Niels J. et al., "Human Lysosomal Protective Protein Has Cathepsin A-like Activity Distinct from Its Protective Function," The Journal of Biological Chemistry (1991), vol. 266, No. 22, pp. 14754-14762.

(Continued)

*Primary Examiner* — Kamal Saeed
(74) *Attorney, Agent, or Firm* — Scully, Scott, Murphy & Presser, P.C.

(57) ABSTRACT

The present invention relates to compounds of the formula I, wherein A, D, E, G, $R^{10}$, $R^{30}$, $R^{40}$, $R^{50}$ and $R^{60}$ have the meanings indicated in the claims, which are valuable pharmaceutical active compounds. They are inhibitors of the protease cathepsin A, and are useful for the treatment of diseases such as atherosclerosis, heart failure, renal diseases, liver diseases or inflammatory diseases, for example. The invention furthermore relates to processes for the preparation of the compounds of the formula I, their use and pharmaceutical compositions comprising them.

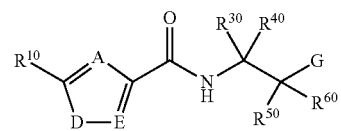

14 Claims, No Drawings

(56) References Cited

OTHER PUBLICATIONS

Hanna, William L. et al., "Dominant Chymotrypsin-Like Esterase Activity in Human Lymphocyte Granules Is Mediated by the Serine Carboxypeptidase Called Cathepsin A-Like Protective Protein," The Journal of Immunology (1994), vol. 153, pp. 4663-4672.

Hayashi, Izumi et al, "In vivo transfer of antisense oligonucleotide against urinary kininase blunts deoxycorticosterone acetate-salt hypertension in rats," British Journal of Pharmacology (2000), vol. 131, pp. 820-826.

Hodgetts, Kevin J. et al., "Ethyl 2-Chlorooxazole-4-carboxylate: A Versatile Intermediate for the Synthesis of Substituted Oxazoles," Organic Letters (2002), vol. 4, No. 17, pp. 2905-2907.

Ito, Hiroshi et al., "Effect of prolonged administration of a urinary kininase inhibitor, ebelactone B on the development of deoxycorticosterone acetate-salt hypertension in rats," British Journal of Pharmacology (1999), vol. 126, pp. 613-620.

Kelly, T. Ross et al., "Total Synthesis of Dimethyl Sulfomycinamate," Journal of Organic Chemistry (1996), vol. 61, pp. 4623-4633.

Lee, Sang-Hyeup et al., "Rhodium Carbenoid N—H Insertion Reactions of Primary Ureas: Solution and Solid-Phase Synthesis of Imidazolones," Organic Letters (2003), vol. 5, No. 4, pp. 511-514.

Linz, Wolfgang et al., "Vasopeptidase Inhibition Prevents Target Organ Damage and Improves Survival in Spontaneously Hypertensive Rats," Journal of the Renin-Angiotensin-Aldosterone System (2006), vol. 7, No. 3, pp. 155-161.

Liu, Wei-Min et al., "Synthesis and Herbicidal Activity of 2-(3-(Trifluoromethyl)-5-(alkoxy)-1H-pyrazol-1-yl)-4-aryloxypyrimidine Derivatives," Journal of Heterocyclic Chemistry (2007), vol. 44, pp. 967-971.

Mano, Junichi et al., "Microbial Production of Optically Active Beta-Phenylalanine through Stereoselective Degradation of Racemic Beta-Phenylalanine," Bioscience, Biotechnology, and Biochemistry (2006), vol. 70, No. 8, pp. 1941-1946.

Montalbetti, Christian A. G. N. et al., "Amide bond formation and peptide coupling," Tetrahedron (2005), vol. 61, pp. 10827-10852.

Ostrowska, Halina et al., "Ebelactone B, an Inhibitor of Extracellular Cathepsin A-Type Enzyme, Suppresses Platelet Aggregation Ex Vivo in Renovascular Hypertensive Rats," Journal of Cardiovascular Pharmacology (2005), vol. 45, pp. 348-353.

Reich, Michael et al., "Cathepsin A is expressed in primary human antigen-presenting cells," Immunology Letters (2010), vol. 128, pp. 143-147.

Rottier, Robbert J. et al., "Lack of PPCA expression only partially coincides with lysosomal storage in galactosialidosis mice: indirect evidence for spatial requirement of the catalytic rather than the protective function of PPCA," Human Molecular Genetics (1998), vol. 7, No. 11, pp. 1787-1794.

Rudenko, Gabby et al., "The atomic model of the human protective protein/cathepsin A suggests a structural basis for galactosialidosis," Proceedings of the National Academy of Sciences (1998), vol. 95, pp. 621-625.

Young, Gail L. et al., "4-Bromomethyl-2-chlorooxazole-a versatile oxazole cross-coupling unit for the synthesis of 2,4-disubstituted oxazoles," Tetrahedron Letters (2004), vol. 45, pp. 3797-3801.

Ostrowska, Halina, "Cathepsin A-Like Activity in Thrombin—Activated Human Platelets," Thrombosis Research (1997), vol. 86, No. 5, pp. 393-404.

Neitzel, Michael et al., "Reaktion von Cyansaureestern mit N- und N'-substituierten Carbonsaurehydraziden," Arch. Pharm. (Weinheim) (1980), vol. 313, pp. 867-878.

Mitsunobu, Oyo, "The Use of Diethyl Azodicarboxylate and Triphenylphosphine in Synthesis and Transformation of Natural Products," Synthesis (1981), p. 1-28.

Marceau, Francois et al., "Bradykinin Receptor Ligands: Therapeutic Perspectives," Nature Reviews (2004), vol. 3, pp. 845-852.

Scudi, John V., "The Preparation of Some Beta-Amino Acids," Journal of Medicinal Chemistry (1977), vol. 20, No. 1, pp. 79-85.

Tse, Man Kin et al., "Ruthenium-Catalyzed Asymmetric Epoxidation of Olefins Using H2O2, Part I: Synthesis of New Chiral N,N,N-Tridentate Pybox and Pyboxazine Ligands and Their Ruthenium Complexes," Chemistry—A European Journal (2006), vol. 12, pp. 1855-1874.

Gagnon, Paul E. et al., "Synthesis of Pyrazolones From alpha-Keto and alpha-Cyano Esters," Canadian Journal of Chemistry (1952), vol. 30, pp. 904-914.

Chemical Abstracts Summary (vol. 47 (1953), abstr. No. 61888) of New synthesis of alkyl esters of Beta-amino acids.

European Search Report dated Mar. 29, 2010 issued in EP10305080.

International Search Report dated Mar. 18, 2011 issued in PCT/EP2011/051038.

OXYGEN-SUBSTITUTED 3-HETEROAROYLAMINO-PROPIONIC ACID DERIVATIVES AND THEIR USE AS PHARMACEUTICALS

The present invention relates to compounds of the formula I,

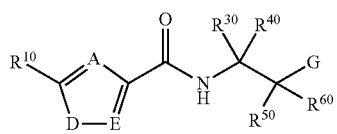

wherein A, D, E, G, $R^{10}$, $R^{30}$, $R^{40}$, $R^{50}$ and $R^{60}$ have the meanings indicated below, which are valuable pharmaceutical active compounds. They are inhibitors of the protease cathepsin A, and are useful for the treatment of diseases such as atherosclerosis, heart failure, renal diseases, liver diseases or inflammatory diseases, for example. The invention furthermore relates to processes for the preparation of the compounds of the formula I, their use and pharmaceutical compositions comprising them.

Cathepsin A (EC=3.4.16.5; gene symbol CTSA) is a protease also known as lysosomal carboxypeptidase A or protective protein. It belongs to a family of serine carboxypeptidases which contains only two other mammalian representatives, retinoid-inducible serine carboxypeptidase and vitellogenic carboxypeptidase-like protein. Within the cell cathepsin A resides in lysosomes where it forms a high molecular weight complex with beta-galactosidase and neuraminidase. The interaction of cathepsin A with these glycosidases is essential for their correct routing to the lysosome and protects them from intralysosomal proteolysis. A deficiency of cathepsin A resulting from various mutations in the ctsa gene leads to a secondary deficiency of beta-galactosidase and neuraminidase that is manifest as the autosomal recessive lysosomal storage disorder galactosialidosis (cf. A. d'Azzo et al., in "The Metabolic and Molecular Bases of Inherited Disease", vol. 2 (1995), 2835-2837). The majority of identified mutations in ctsa are missense mutations affecting the folding or the stability of the protein. None of them was shown to occur in the active site of the enzyme (G. Rudenko et al., Proc. Natl. Acad. Sci. USA 95 (1998), 621-625). Accordingly, the lysosomal storage disorder can be corrected with catalytically inactive cathepsin A mutants (N. J. Galjart et al., J. Biol. Chem. 266 (1991), 14754-14762). The structural function of cathepsin A is therefore separable from its catalytic activity. This is also underscored by the observation that in contrast to mice deficient in the ctsa gene, mice carrying a catalytically inactivating mutation in the ctsa gene do not develop signs of the human disease galactosialidosis (R. J. Rottier et al., Hum. Mol. Genet. 7 (1998), 1787-1794; V. Seyrantepe et al., Circulation 117 (2008), 1973-1981).

Cathepsin A displays carboxypeptidase activity at acidic pH and deamidase and esterase activities at neutral pH against various naturally occurring bioactive peptides. In vitro studies have indicated that cathepsin A converts angiotensin I to angiotensin 1-9 and bradykinin to bradykinin 1-8, which is the ligand for the bradykinin B1 receptor. It hydrolyzes endothelin-1, neurokinin and oxytocin, and deamidates substance P (cf. M. Hiraiwa, Cell. Mol. Life Sci. 56 (1999), 894-907). High cathepsin A activity has been detected in urine, suggesting that it is responsible for tubular bradykinin degradation (M. Saito et al., Int. J. Tiss. Reac. 17 (1995), 181-190). However, the enzyme can also be released from platelets and lymphocytes and is expressed in antigen-presenting cells where it might be involved in antigen processing (W. L. Hanna et al., J. Immunol. 153 (1994), 4663-4672; H. Ostrowska, Thromb. Res. 86 (1997), 393-404; M. Reich et al., Immunol. Lett. (online Nov. 30, 2009)). Immunohistochemistry of human organs revealed prominent expression in renal tubular cells, bronchial epithelial cells, Leydig's cells of the testis and large neurons of the brain (O. Sohma et al., Pediatr. Neurol. 20 (1999), 210-214). It is upregulated during differentiation of monocytes to macrophages (N. M. Stamatos et al., FEBS J. 272 (2005), 2545-2556). Apart from structural and enzymatic functions, cathepsin A has been shown to associate with neuraminidase and an alternatively spliced beta-galactosidase to form the cell-surface laminin and elastin receptor complex expressed on fibroblasts, smooth muscle cells, chondroblasts, leukocytes and certain cancer cell types (A. Hinek, Biol. Chem. 377 (1996), 471-480).

The importance of cathepsin A for the regulation of local bradykinin levels has been demonstrated in animal models of hypertension. Pharmacological inhibition of cathepsin A activity increased renal bradykinin levels and prevented the development of salt-induced hypertension (H. Ito et al., Br. J. Pharmacol. 126 (1999), 613-620). This could also be achieved by antisense oligonucleotides suppressing the expression of cathepsin A (I. Hajashi et al., Br. J. Pharmacol. 131 (2000), 820-826). Besides in hypertension, beneficial effects of bradykinin have been demonstrated in various further cardiovascular diseases and other diseases (cf. J. Chao et al., Biol. Chem. 387 (2006), 665-75; P. Madeddu et al., Nat. Clin. Pract. Nephrol. 3 (2007), 208-221). Key indications of cathepsin A inhibitors therefore include atherosclerosis, heart failure, cardiac infarction, cardiac hypertrophy, vascular hypertrophy, left ventricular dysfunction, in particular left ventricular dysfunction after myocardial infarction, renal diseases such as renal fibrosis, renal failure and kidney insufficiency; liver diseases such as liver fibrosis and liver cirrhosis, diabetes complications such as nephropathy, as well as organ protection of organs such as the heart and the kidney.

As indicated above, cathepsin A inhibitors can prevent the generation of the bradykinin B1 receptor ligand bradykinin 1-8 (M. Saito et al., Int. J. Tiss. Reac. 17 (1995), 181-190). This offers the opportunity to use cathepsin A inhibitors for the treatment of pain, in particular neuropathic pain, and inflammation, as has been shown for bradykinin B1 receptor antagonists (cf. F. Marceau et al., Nat. Rev. Drug Discov. 3 (2004), 845-852). Cathepsin A inhibitors can further be used as anti-platelet agents as has been demonstrated for the cathepsin A inhibitor ebelactone B, a propiolactone derivative, which suppresses platelet aggregation in hypertensive animals (H. Ostrowska et al., J. Cardiovasc. Pharmacol. 45 (2005), 348-353).

Further, like other serine proteases such as prostasin, elastase or matriptase, cathepsin A can stimulate the amiloride-sensitive epithelial sodium channel (ENaC) and is thereby involved in the regulation of fluid volumes across epithelial membranes (cf. C. Planes et al., Curr. Top. Dev. Biol. 78 (2007), 23-46). Thus, respiratory diseases can be ameliorated by the use of cathepsin A inhibitors, such as cystic fibrosis, chronic bronchitis, chronic obstructive pulmonary disease, asthma, respiratory tract infections and lung carcinoma. Cathepsin A modulation in the kidney could be used to promote diuresis and thereby induce a hypotensive effect.

Besides for the above-mentioned compound ebelactone B, an inhibitory effect on cathepsin A has been found for certain dipeptidic phenylalanine derivatives which are described in JP 2005/145839. There is a need for further compounds which inhibit cathepsin A and offer an opportunity for the treatment of the mentioned diseases and further diseases in which cathepsin A plays a role. The present invention satisfies this need by providing the oxygen-substituted 3-heteroaroylamino-propionic acid derivatives of the formula I defined below.

Certain compounds in which a 3-heteroaroylamino-propionic acid moiety can be present, have already been described. For example, in WO 2006/076202 amine derivatives, which modulate the activity of steroid nuclear receptors, are described which carry on the nitrogen atom of the amine function a heteroaroyl group and a further group which is defined very broadly. In US 2004/0072802 broadly-defined beta-amino acid derivatives are described which carry an acyl group on the beta-amino group and are inhibitors of matrix metalloproteases and/or tumor necrosis factor. In WO 2009/080226 and WO 2009/080227, which relate to antagonists of the platelet ADP receptor P2Y12 and inhibit platelet aggregation, pyrazoloylamino-substituted carboxylic acid derivatives are described which, however, additionally carry a carboxylic acid derivative group on the carbon atom carrying the pyrazoloylamino group. Other pyrazoloylamino-substituted compounds, in which the nitrogen atom of the amino group is connected to a ring system and which are inhibitors of the blood clotting enzymes factor Xa and/or factor VIIa, are described in WO 2004/056815.

A subject of the present invention is a compound of the formula I, in any of its stereoisomeric forms or a mixture of stereoisomeric forms in any ratio, or a physiologically acceptable salt thereof, or a physiologically acceptable solvate of any of them,

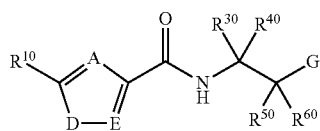

I wherein

A is chosen from the series consisting of $C(R^1)$ and N;
D is chosen from the series consisting of $N(R^2)$, O and S;
E is chosen from the series consisting of $C(R^3)$ and N;
G is chosen from the series consisting of $R^{71}$—O—C(O)—, $R^{72}$—N($R^{73}$)—C(O)—, NC— and tetrazol-5-yl;
$R^1$ is chosen from the series consisting of hydrogen, halogen, $(C_1-C_6)$-alkyl, Ar, HO—, $(C_1-C_6)$-alkyl-O—, $(C_1-C_6)$-alkyl-S(O)$_m$— and NC—;
$R^2$ is chosen from the series consisting of $(C_1-C_7)$-alkyl, $(C_3-C_7)$-cycloalkyl-$C_sH_{2s}$— and Ar—$C_sH_{2s}$—, wherein s is an integer chosen from the series consisting of 0, 1, 2 and 3;
$R^3$ is chosen from the series consisting of hydrogen, halogen, $(C_1-C_6)$-alkyl, $(C_1-C_6)$-alkyl-O—, $(C_1-C_6)$-alkyl-S(O)$_m$— and NC—;
$R^{10}$ is chosen from the series consisting of $R^{11}$—O—, $R^{12}$—N($R^{13}$)—C(O)—O— and Het$^2$—C(O)—O—;
$R^{11}$ is chosen from the series consisting of hydrogen, $R^{14}$, $(C_3-C_7)$-cycloalkyl, Ar and Het$^3$;
$R^{12}$ and $R^{13}$ are independently of each other chosen from the series consisting of hydrogen, $R^{15}$ and Ar;
$R^{14}$ is $(C_1-C_{10})$-alkyl which is optionally substituted by one or more identical or different substituents chosen from the series consisting of halogen, HO—, $R^{16}$—O—, oxo, $(C_3-C_7)$-cycloalkyl, Ar, Het$^1$, Het$^3$, NC—, $H_2N$—C(O)—, $(C_1-$ $C_4$)-alkyl-NH—C(O)—, di(($C_1$-$C_4$)-alkyl)N—C(O)—, Het$^1$—C(O)—, $(C_1$-$C_4$)-alkyl-C(O)—NH— and $(C_1$-$C_4$)-alkyl-S(O)$_m$—;
$R^{15}$ is $(C_1-C_6)$-alkyl which is optionally substituted by one or more identical or different substituents chosen from the series consisting halogen, HO— and $(C_1-C_6)$-alkyl-O—;
$R^{16}$ is $(C_1-C_6)$-alkyl which is optionally substituted by one or more identical or different substituents chosen from the series consisting of HO—, $(C_1-C_4)$-alkyl-O— and NC—;
$R^{30}$ is chosen from the series consisting of $R^{31}$, $(C_3-C_7)$-cycloalkyl, $R^{32}$—$C_uH_{2u}$— and Het$^3$—$C_uH_{2u}$—, wherein u is an integer chosen from the series consisting of 0, 1, 2 and 3;
$R^{31}$ is $(C_1-C_{10})$-alkyl which is optionally substituted by one or more identical or different substituents chosen from the series consisting of halogen, $(C_3-C_7)$-cycloalkyl, HO—, $(C_1-C_6)$-alkyl-O—, $(C_1-C_6)$-alkyl-S(O)$_m$— and NC—;
$R^{32}$ is chosen from the series consisting of phenyl and an aromatic 5-membered or 6-membered monocyclic heterocycle which comprises one, two or three identical or different ring heteroatoms chosen from the series consisting of nitrogen, oxygen and sulfur and is bonded via a ring carbon atom, wherein the phenyl and the heterocycle all are optionally substituted by one or more identical or different substituents chosen from the series consisting of halogen, $(C_1-C_6)$-alkyl, $(C_3-C_7)$-cycloalkyl, $R^{33}$, HO—, $(C_1-C_6)$-alkyl-O—, $R^{33}$—O—, $R^{33}$—$(C_1-C_4)$-alkyl-O—, —O—CH$_2$—O—, —O—CF$_2$—O—, $(C_1-C_6)$-alkyl-S(O)$_m$—, $H_2N$—S(O)$_2$—, $(C_1-C_4)$-alkyl-NH—S(O)$_2$—, di(($C_1$-$C_4$)-alkyl)N—S(O)$_2$—, $H_2N$—, $(C_1-C_6)$-alkyl-NH—, di(($C_1$-$C_6$)-alkyl)N—, Het$^1$, $(C_1-C_4)$-alkyl-C(O)—NH—, Ar—C(O)—NH—, $(C_1-C_4)$-alkyl-S(O)$_2$—NH— and NC—;
$R^{33}$ is chosen from the series consisting of phenyl and an aromatic 5-membered or 6-membered monocyclic heterocycle which comprises one, two or three identical or different ring heteroatoms chosen from the series consisting of nitrogen, oxygen and sulfur and is bonded via a ring carbon atom, wherein the phenyl and the heterocycle all are optionally substituted by one or more identical or different substituents chosen from the series consisting of halogen, $(C_1-C_6)$-alkyl, $(C_3-C_7)$-cycloalkyl, HO—, $(C_1-C_6)$-alkyl-O—, $(C_1-C_6)$-alkyl-S(O)$_m$—, $H_2N$—S(O)$_2$—, $(C_1-C_4)$-alkyl-NH—S(O)$_2$—, di(($C_1$-$C_4$)-alkyl)N—S(O)$_2$— and NC—;
$R^{40}$ is chosen from the series consisting of hydrogen and $(C_1-C_4)$-alkyl;
or $R^{30}$ and $R^{40}$ together are $(CH_2)_x$ which is optionally substituted by one or more identical or different $(C_1-C_4)$-alkyl substituents, wherein x is an integer chosen from the series consisting of 2, 3, 4 and 5;
$R^{50}$ is chosen from the series consisting of hydrogen, $(C_1-C_6)$-alkyl, HO— and $(C_1-C_6)$-alkyl-O—;
$R^{60}$ is chosen from the series consisting of hydrogen and $(C_1-C_6)$-alkyl;
or $R^{50}$ and $R^{60}$ together are $(CH_2)_y$ which is optionally substituted by one or more identical or different $(C_1-C_4)$-alkyl substituents, wherein y is an integer chosen from the series consisting of 2, 3, 4 and 5;
$R^{71}$ is chosen from the series consisting of hydrogen and $(C_1-C_8)$-alkyl which is optionally substituted by one or more identical or different substituents chosen from the series consisting $(C_1-C_6)$-alkyl-O— and $(C_1-C_6)$-alkyl-C(O)—O—;
$R^{72}$ is chosen from the series consisting of hydrogen, $(C_1-C_6)$-alkyl, $(C_3-C_6)$-cycloalkyl, —CH$_2$—(CH$_2$)$_b$—$(C_3$-$C_6)$-cycloalkyl, Het$^4$ and —(CH$_2$)$_b$—Het$^4$, where alkyl or cycloalkyl is optionally substituted by one or more identical or different substituents chosen from the series consisting of halogen, HO—, HOOC—, $(C_1-C_6)$-alkyl-O— and $(C_1-C_6)$-alkyl-C(O)—O—, NC—, N$((C_1-C_4)$-alkyl$)_2$ and b is 0, 1 or 2;

$R^{73}$ is chosen from the series consisting of hydrogen, $(C_1-C_6)$-alkyl;

or $R^{72}$ and $R^{73}$ together with the nitrogen atom to which they are bonded form a saturated 4-membered to 7-membered monocyclic heterocycle, which contain optionally one further ring heteroatom chosen from the series consisting of nitrogen, oxygen and sulfur, which is optionally substituted by one or more identical or different substituents chosen from the series consisting of halogen, $(C_1-C_4)$-alkyl, HO— and $(C_1-C_4)$-alkyl-O—;

Ar, independently of each other group Ar, is chosen from the series consisting of phenyl and an aromatic 5-membered or 6-membered monocyclic heterocycle which comprises one, two or three identical or different ring heteroatoms chosen from the series consisting of nitrogen, oxygen and sulfur and is bonded via a ring carbon atom, wherein the phenyl and the heterocycle all are optionally substituted by one or more identical or different substituents chosen from the series consisting of halogen, $(C_1-C_6)$-alkyl, $(C_1-C_6)$-alkyl-O—, —O—CH$_2$—O—, —O—CF$_2$—O—, $(C_1-C_6)$-alkyl-S(O)$_m$—, H$_2$N—S(O)$_2$— and NC—;

Het$^1$, independently of each other group Het$^1$, is a saturated or unsaturated 4-membered to 8-membered monocyclic heterocycle which comprises a ring nitrogen atom via which Het$^1$ is bonded and optionally one or two identical or different further ring heteroatoms chosen from the series consisting of nitrogen, oxygen and sulfur, which is optionally substituted by one or more identical or different substituents chosen from the series consisting of halogen, $(C_1-C_4)$-alkyl, HO—, $(C_1-C_4)$-alkyl-O—, oxo and NC—;

Het$^2$ is a saturated 4-membered to 7-membered monocyclic heterocycle which comprises a ring nitrogen atom via which Het$^2$ is bonded and optionally one further ring heteroatom chosen from the series consisting of nitrogen, oxygen and sulfur, which is optionally substituted by one or more identical or different substituents chosen from the series consisting of halogen, $(C_1-C_4)$-alkyl, HO— and $(C_1-C_4)$-alkyl-O—;

Het$^3$, independently of each other group Het$^3$, is a saturated 4-membered to 7-membered monocyclic heterocycle which comprises one or two identical or different ring heteroatoms chosen from the series consisting of nitrogen, oxygen and sulfur and is bonded via a ring carbon atom, which is optionally substituted by one or more identical or different substituents chosen from the series consisting of fluorine, $(C_1-C_4)$-alkyl and oxo;

Het$^4$, independently of each other group Het$^4$, is a saturated or unsaturated 4-membered to 8-membered monocyclic heterocycle which comprises one to four ring heteroatoms chosen from the series consisting of nitrogen, oxygen and sulfur which is optionally substituted by one or more identical or different substituents chosen from the series consisting of halogen, $(C_1-C_4)$-alkyl, HO—, $(C_1-C_4)$-alkyl-O—, oxo and NC—;

m, independently of each other number m, is an integer chosen from the series consisting of 0, 1 and 2;

wherein all cycloalkyl groups, independently of each other, are optionally substituted by one or more identical or different substituents chosen from the series consisting of fluorine and $(C_1-C_4)$-alkyl;

wherein all alkyl, $C_sH_{2s}$, $C_uH_{2u}$, $(CH_2)_x$ and $(CH_2)_y$ groups, independently of each other, and independently of any other substituents, are optionally substituted by one or more fluorine substituents.

If structural elements such as groups, substituents or numbers, for example, can occur several times in the compounds of the formula I, they are all independent of each other and can in each case have any of the indicated meanings, and they can in each case be identical to or different from any other such element. In a dialkylamino group, for example, the alkyl groups can be identical or different.

Alkyl groups, i.e. saturated hydrocarbon residues, can be linear (straight-chain) or branched. This also applies if these groups are substituted or are part of another group, for example an alkyl-O— group (alkyloxy group, alkoxy group) or an HO-substituted alkyl group (hydroxyalkyl group). Depending on the respective definition, the number of carbon atoms in an alkyl group can be 1, 2, 3, 4, 5, 6, 7, 8, 9 or 10, or 1, 2, 3, 4, 5, 6, 7 or 8, or 1, 2, 3, 4, 5 or 6, or 1, 2, 3 or 4, or 1, 2 or 3, or 1 or 2, or 1, for example. In one embodiment of the invention, a $(C_1-C_{10})$-alkyl group present in the compounds of the formula I is a $(C_1-C_8)$-alkyl group, in another embodiment a $(C_1-C_6)$-alkyl group, in another embodiment a $(C_1-C_4)$-alkyl group, in another embodiment a $(C_1-C_3)$-alkyl group, in another embodiment a $(C_1-C_2)$-alkyl group, in another embodiment a $(C_2-C_3)$-alkyl group, in another embodiment a methyl group. In one embodiment of the invention, a $(C_1-C_8)$-alkyl group present in any position of the compounds of the formula I is a $(C_1-C_6)$-alkyl group, in another embodiment a $(C_1-C_4)$-alkyl group, in another embodiment a $(C_1-C_3)$-alkyl group, in another embodiment a $(C_1-C_2)$-alkyl group, in another embodiment a $(C_2-C_3)$-alkyl group, in another embodiment a methyl group, where any $(C_1-C_8)$-alkyl group present in the compounds of the formula I can independently of each other $(C_1-C_8)$-alkyl group be a group of any of these embodiments. In one embodiment of the invention, a $(C_1-C_6)$-alkyl group present in any position of the compounds of the formula I is a $(C_1-C_4)$-alkyl group, in another embodiment a $(C_1-C_3)$-alkyl group, in another embodiment a $(C_1-C_2)$-alkyl group, in another embodiment a $(C_2-C_3)$-alkyl group, in another embodiment a methyl group, where any $(C_1-C_6)$-alkyl group present in the compounds of the formula I can independently of each other $(C_1-C_6)$-alkyl group be a group of any of these embodiments. In one embodiment of the invention, a $(C_1-C_4)$-alkyl group present in any position of the compounds of the formula I is a $(C_1-C_3)$-alkyl group, in another embodiment a $(C_1-C_2)$-alkyl group, in another embodiment a $(C_2-C_3)$-alkyl group, in another embodiment a methyl group, where any $(C_1-C_4)$-alkyl group present in the compounds of the formula I can independently of each other $(C_1-C_4)$-alkyl group be a group of any of these embodiments. Examples of alkyl groups are methyl, ethyl, propyl groups including propyl (i.e. n-propyl) and isopropyl, butyl groups including butyl (i.e. n-butyl), sec-butyl, isobutyl and tert-butyl, pentyl groups including pentyl (i.e. n-pentyl), 1-methylbutyl, isopentyl, neopentyl and tert-pentyl, hexyl groups including hexyl (i.e. n-hexyl), 3,3-dimethylbutyl and isohexyl, heptyl groups including heptyl (i.e. n-heptyl), octyl groups including octyl (i.e. n-octyl), nonyl groups including nonyl (i.e. n-nonyl), and decyl groups including decyl (i.e. n-decyl). Examples of alkyl-O— groups are methoxy, ethoxy, propoxy (i.e. n-propoxy), isopropoxy, butoxy (i.e. n-butoxy), isobutoxy, tert-butoxy, pentoxy (i.e. n-pentoxy). Examples of alkyl-S(O)$_m$— are methylsulfanyl-(CH$_3$—S—), methanesulfinyl-(CH$_3$—S(O)—), methanesulfonyl (CH$_3$—S(O)$_2$—), ethylsulfanyl-(CH$_3$—CH$_2$—S—), ethanesulfinyl-(CH$_3$—CH$_2$—S(O)—), ethanesulfonyl ($CH_3$—$CH_2$—$S(O)_2$—), 1-methylethylsulfanyl-(($CH_3$)$_2$CH—S—), 1-methylethanesulfinyl-(($CH_3$)$_2$CH—S(O)—), 1-methylethanesulfonyl (($CH_3$)$_2$CH—$S(O)_2$—). In one embodiment of the invention the number m is chosen from 0 and 2, wherein all numbers m are independent of each other and can be identical or different. In another embodiment the number m in any of its occurrences is, independently of its meaning in other occurrences, 0. In another embodiment the number m in any of its occurrences is, independently of its meaning in other occurrences, 2.

A substituted alkyl group can be substituted in any positions, provided that the respective compound is sufficiently stable and is suitable as a pharmaceutical active compound. The prerequisite that a specific group and a compound of the formula I are sufficiently stable and suitable as a pharmaceutical active compound, applies in general with respect to the definitions of all groups in the compounds of the formula I. In one embodiment of the invention, an individual carbon atom in any alkyl group in the compounds of the formula I, as well as in other groups such as cycloalkyl groups and heterocyclic groups, for example, independently of any other carbon atom does not carry more than one substituent which is bonded via an oxygen atom, nitrogen atom or sulfur atom, such as HO—, ($C_1$-$C_4$)-alkyl-O— or ($C_1$-$C_4$)-alkyl-$S(O)_m$-substituents, for example. An alkyl group which is optionally substituted by one or more fluorine substituents can be unsubstituted, i.e. not carry fluorine substituents, or substituted, for example by one, two, three, four, five, six, seven, eight, nine, ten or eleven fluorine substituents, or by one, two, three, four, five, six or seven fluorine substituents, or by one, two, three, four or five fluorine substituents, or by one, two or three fluorine substituents, which can be located in any positions. For example, in a fluoro-substituted alkyl group one or more methyl groups can carry three fluorine substituents each and be present as trifluoromethyl groups, and/or one or more methylene groups ($CH_2$) can carry two fluorine substituents each and be present as difluoromethylene groups. The explanations with respect to the substitution of a group by fluorine also apply if the group additionally carries other substituents and/or is part of another group, for example of an alkyl-O— group. Examples of fluoro-substituted alkyl groups are trifluoromethyl, 2-fluoroethyl, 1-fluoroethyl, 1,1-difluoroethyl, 2,2,2-trifluoroethyl, pentafluoroethyl, 3,3,3-trifluoropropyl, 2,2,3,3,3-pentafluoropropyl, 4,4,4-trifluorobutyl and heptafluoroisopropyl. Examples of fluoro-substituted alkyl-O— groups are trifluoromethoxy, 2,2,2-trifluoroethoxy, pentafluoroethoxy and 3,3,3-trifluoropropoxy. Examples of fluoro-substituted alkyl-S$(O)_m$— groups are trifluoromethylsulfanyl-($CF_3$—S—), trifluoromethanesulfinyl-($CF_3$—S(O)—) and trifluoromethanesulfonyl ($CF_3$—$S(O)_2$—).

The above explanations with respect to alkyl groups apply correspondingly to alkanediyl groups (divalent alkyl groups) including the divalent groups $C_sH_{2s}$, $C_uH_{2u}$, $(CH_2)_x$ and $(CH_2)_y$. Also the alkyl part of a substituted alkyl group may be regarded as an alkanediyl group. Thus, alkanediyl groups can also be linear or branched, the bonds to the adjacent groups can be located in any positions and can start from the same carbon atom or from different carbon atoms, and they can be substituted by fluorine substituents. Examples of alkanediyl groups including the groups $C_sH_{2s}$ and $C_uH_{2u}$ and, as far they constitute polymethylene chains, the groups $(CH_2)_x$ are —$CH_2$—, —$CH_2$—$CH_2$—, —$CH_2$—$CH_2$—$CH_2$—, —$CH_2$—$CH_2$—$CH_2$—$CH_2$—, —$CH_2$—$CH_2$—$CH_2$—$CH_2$—$CH_2$—, —CH($CH_3$)—, —C($CH_3$)$_2$—, —CH($CH_3$)—$CH_2$—, —$CH_2$—CH($CH_3$)—, —C($CH_3$)$_2$—$CH_2$—, —$CH_2$—C($CH_3$)$_2$—. Examples of fluoro-substituted alkanediyl groups, which can contain one, two, three, four, five or six fluorine substituents, or one, two, three or four fluorine substituents, or one or two fluorine substituents, for example, are —CHF—, —$CF_2$—, —$CF_2$—$CH_2$—, —$CH_2$—$CF_2$—, —$CF_2$—$CF_2$—, —CF($CH_3$)—, —C($CF_3$)$_2$—, —C($CH_3$)$_2$—$CF_2$—, —$CF_2$—C($CH_3$)$_2$—.

The number of ring carbon atoms in a ($C_3$-$C_7$)-cycloalkyl group can be 3, 4, 5, 6 or 7. Examples of cycloalkyl are cyclopropyl, cyclobutyl, cyclopentyl, cyclohexyl and cycloheptyl. As regards the optional substitution of cycloalkyl groups by one or more ($C_1$-$C_4$)-alkyl substituents, they be unsubstituted, i.e. not carry alkyl substituents, or substituted, for example by one, two, three or four, or by one or two, identical or different ($C_1$-$C_4$)-alkyl substituents, for example by methyl groups, which substituents can be located in any positions. Examples of such alkyl-substituted cycloalkyl groups are 1-methylcyclopropyl, 2,2-dimethylcyclopropyl, 1-methylcyclopentyl, 2,3-dimethylcyclopentyl, 1-methylcyclohexyl, 4-methylcyclohexyl, 4-isopropylcyclohexyl, 4-tert-butylcyclohexyl and 3,3,5,5-tetramethylcyclohexyl. As regards the optional substitution of cycloalkyl groups by one or more fluorine substituents, they can be unsubstituted, i.e. not carry fluorine substituents, or substituted, for example by one, two, three, four, five, six, seven, eight, nine, ten or eleven fluorine substituents, or by one, two, three, four, five or six fluorine substituents, or by one, two, three or four fluorine substituents, or by one or two fluorine substituents. The fluorine substituents can be located in any positions of the cycloalkyl group and can also be located in an alkyl substituent on the cycloalkyl group. Examples of fluoro-substituted cycloalkyl groups are 1-fluorocyclopropyl, 2,2-difluorocyclopropyl, 3,3-difluorocyclobutyl, 1-fluorocyclohexyl, 4,4-difluorocyclohexyl and 3,3,4,4,5,5-hexafluorocyclohexyl. Cycloalkyl groups can also be substituted simultaneously by fluorine and alkyl. Examples of ($C_3$-$C_7$)-cycloalkyl-substituted alkyl groups, which can represent $R^{11}$ or $R^{30}$, for example, are cyclopropylmethyl-, cyclobutylmethyl-, cyclopentylmethyl-, cyclohexylmethyl-, cycloheptylmethyl-, 1-cyclopropylethyl-, 2-cyclopropylethyl-, 1-cyclobutylethyl-, 2-cyclobutylethyl-, 1-cyclopentylethyl-, 2-cyclopentylethyl-, 1-cyclohexylethyl-, 2-cyclohexylethyl-, 1-cycloheptylethyl-, 2-cycloheptylethyl-. The explanations with respect cycloalkyl groups apply correspondingly to divalent cycloalkyl groups (cycloalkanediyl groups), which can occur in case the two groups $R^{30}$ and $R^{40}$ together are $(CH_2)_x$ or the two groups $R^{50}$ and $R^{60}$ together are $(CH_2)_y$. Also the cycloalkyl part of a substituted cycloalkyl group may be regarded as a cycloalkanediyl group. Thus, for example, the bonds through which a cycloalkanediyl group is connected to the adjacent groups, can be located in any positions and can start from the same ring carbon atom, as in the case of the cycloalkanediyl group which is present if $R^{30}$ and $R^{40}$ together are $(CH_2)_x$ or the two groups $R^{50}$ and $R^{60}$ together are $(CH_2)_y$, or from different ring carbon atoms.

In substituted phenyl groups the substituents can be located in any positions. In the case a the divalent substituents —O—$CH_2$—O— (methylenedioxy) and —O—$CF_2$-β-(difluoromethylenedioxy) which can be present on phenyl groups and aromatic heterocycles, the two oxygen atoms are bonded to adjacent ring carbon atoms of the phenyl group or the aromatic heterocycle and replace two hydrogen atoms of the parent system. In monosubstituted phenyl groups, the substituent can be located in the 2-position, the 3-position or the 4-position. In disubstituted phenyl groups, the substituents can be located in 2,3-position, 2,4-position, 2,5-position, 2,6-position, 3,4-position or 3,5-position. In trisubstituted phenyl groups, the substituents can be located in 2,3,4-position, 2,3,5-position, 2,3,6-position, 2,4,5-position, 2,4,6-position or 3,4,5-position. If a phenyl group carries four substituents, some of which can be fluorine atoms, for example, the substituents can be located in 2,3,4,5-position, 2,3,4,6-position or 2,3,5,6-position. If a polysubstituted phenyl group carries different substituents, each substituent can be located in any suitable position, and the present invention comprises all positional isomers. The number of substituents in an optionally substituted phenyl group can be one, two, three, four or five. In one embodiment of the invention, an optionally substituted phenyl group, independently of any other optionally substituted phenyl group in a compound of the formula I, carries one, two, three or four, in another embodiment one, two or three, in another embodiment one or two, in another embodiment one, identical or different substituents, and in another embodiment it is unsubstituted.

Likewise, in substituted heterocyclic groups, including aromatic 5-membered and 6-membered monocyclic heterocycles which can represent $R^{32}$, $R^{33}$ and Ar, saturated and unsaturated 4-membered to 8-membered monocyclic heterocycles which can represent $Het^1$, and saturated 4-membered to 7-membered monocyclic heterocycles which can represent $Het^2$ and $Het^3$, the substituents can be located in any positions and can be present on ring carbon atoms and/or on suitable ring nitrogen atoms. The present invention comprises all positional isomers. The number of substituents which can be present on substituted heterocycles in the compounds of the formula I, depends on the ring size, the number and type of the ring heteroatoms and the degree of unsaturation. In one embodiment of the invention, the number of identical or different substituents on any of the heterocyclic groups in the compounds of the formula I, independently of the number of substituents in any other occurrence of this group and the number of substituents in any other heterocyclic group in the compounds of the formula I, is one, two, three, four or five, in another embodiment one, two, three or four, in another embodiment one, two or three, in another embodiment one or two, in another embodiment one. Ring nitrogen atoms which optionally carry a substituent, include ring nitrogen atoms in saturated heterocyclic rings other than those via which such a ring is bonded, and the ring nitrogen atom in 5-membered aromatic heterocycles such as pyrrole, imidazole or triazole, which in the parent heterocycle carry a hydrogen atom. In one embodiment of the invention, the substituents on any such ring nitrogen atoms in heterocyclic groups are chosen from those of the substituents specified in the definition of the respective group which are bonded via a carbon atom, for example from the series consisting of $(C_1-C_6)$-alkyl, $(C_3-C_7)$-cycloalkyl and $R^{33}$, in another embodiment from the series consisting of $(C_1-C_6)$-alkyl and $(C_3-C_7)$-cycloalkyl, in the case of the aromatic heterocycle which can represent $R^{32}$, from the series consisting of $(C_1-C_6)$-alkyl and $(C_3-C_7)$-cycloalkyl in the case of the aromatic heterocycle which can represent $R^{33}$, and are $(C_1-C_6)$-alkyl in the case of the aromatic heterocycle which can represent Ar and $(C_1-C_4)$-alkyl in the case of $Het^1$, $Het^2$ and $Het^3$. Generally, besides optionally carrying the substituents indicated in the definition of the respective group, suitable ring nitrogen atoms in heterocyclic groups in the compounds of the formula I, in particular aromatic heterocyclic groups such as the heterocyclic groups which can represent $R^{32}$, $R^{33}$ and Ar, for example the ring nitrogen atom in a pyridinyl group, can also carry an oxido substituent —O⁻ and be present as an N-oxide.

The ring heteroatoms specified in the definitions of heterocyclic groups in the compounds of the formula I, including the aromatic 5-membered and 6-membered monocyclic heterocycles which can represent $R^{32}$, $R^{33}$ and Ar and the heterocycles which represent $Het^1$, $Het^2$, $Het^3$ and $Het^4$ can generally be present in any combination and located in any suitable ring positions, provided that the resulting group and the compound of the formula I are sufficiently stable and suitable as a pharmaceutical active compound, as mentioned above. In one embodiment of the invention, two oxygen atoms in any heterocyclic ring in the compounds of the formula I cannot be present in adjacent ring positions. In another embodiment, two ring heteroatoms in any non-aromatic heterocyclic ring in the compounds of the formula I cannot be present in adjacent ring positions. In another embodiment, two ring heteroatoms chosen from the series consisting of N atoms which carry a hydrogen atom or a substituent and are bonded to the adjacent ring atoms by single bonds, O atoms and S atoms in a non-aromatic heterocycle cannot be present in adjacent ring positions. In an aromatic heterocycle the choice of ring heteroatoms and their positions is limited by the prerequisite that the ring is aromatic, i.e., it comprises a cyclic system of six delocalized pi electrons. Thus, for example, in an aromatic monocyclic 6-membered heterocycle only nitrogen atoms can occur as ring heteroatoms, and in an aromatic monocyclic 5-membered heterocycle only one ring heteroatom chosen from the series consisting of O atoms, S atoms and N atoms carrying a hydrogen atom or a substituent, can be present. An unsaturated heterocycle which can represent $Het^1$, can be aromatic, for example in the case of a pyrrolyl, imidazolyl or triazolyl group which is bonded via a ring nitrogen atom and can represent $Het^1$, or non-aromatic and comprise one or two double bonds within the ring which can be present in any positions. In one embodiment, a 4-membered heterocycle representing $Het^1$ cannot be unsaturated. A heterocyclic group can be bonded via any ring carbon atom or via any suitable ring nitrogen atom, respectively, as indicated in the definition of the respective group. The group $Het^1$ can be 4-membered, 5-membered, 6-membered or 7-membered or 8-membered. The groups $Het^2$ and $Het^3$ can be 4-membered, 5-membered, 6-membered or 7-membered.

Examples of aromatic heterocycles, from any one or more of which the aromatic 5-membered and 6-membered monocyclic heterocycles which can represent $R^{32}$, $R^{33}$ and Ar and, as far as applicable, the group $Het^1$ are chosen in one embodiment of the invention, are pyrrole, furan, thiophene, imidazole, pyrazole, oxazole ([1,3]oxazole), isoxazole ([1,2]oxazole), thiazole ([1,3]thiazole), isothiazole ([1,2]thiazole), [1,2,3]triazole, [1,2,4]triazole, [1,3,4]oxadiazole, pyridine, pyridazine, pyrimidine and pyrazine, which can all be bonded via any ring carbon atom or via any suitable ring nitrogen atom, and which all are optionally substituted as indicated with respect to the compounds of formula I in general or in any embodiment specified above or below. Examples of specific residues of aromatic heterocycles, from any one or more of which the aromatic, 5-membered or 6-membered monocyclic heterocyclic residue which can represent $R^{32}$, $R^{33}$ or Ar and, as far as applicable, the group $Het^1$, are chosen in one embodiment of the invention, are pyrrol-1-yl, pyrrol-2-yl, pyrrol-3-yl, furan-2-yl, furan-3-yl, thiophen-2-yl (2-thienyl), thiophen-3-yl (3-thienyl), imidazol-1-yl, imidazol-2-yl, imidazol-4-yl, imidazol-5-yl, pyrazol-1-yl, pyrazol-3-yl, pyrazol-4-yl, pyrazol-5-yl, oxazol-2-yl, oxazol-4-yl, oxazol-5-yl, isoxazol-3-yl, isoxazol-4-yl, isoxazol-5-yl, thiazol-2-yl, thiazol-4-yl, thiazol-5-yl, isothiazol-3-yl, isothiazol-4-yl, isothiazol-5-yl, [1,2,3]triazol-1-yl, [1,2,3]triazol-4-yl, [1,2,3]triazol-5-yl, [1,2,4]triazol-1-yl, [1,2,4]triazol-3-yl, [1,2,4]triazol-4-yl, [1,3,4]oxadiazol-2-yl, pyridin-2-yl (2-pyridyl), pyridin-3-yl (3-pyridyl), pyridin-4-yl (4-pyridyl), pyridazin-3-yl, pyridazin-4-yl, pyrimidin-2-yl, pyrimidin-4-yl, and pyrazin-2-yl, which all are optionally substituted as indicated with respect to the compounds of formula I in general or in any embodiment specified above or below.

Examples of saturated heterocycles and non-aromatic unsaturated heterocycles, from any one or more of which the groups $Het^1$, $Het^2$, $Het^3$ and $Het^4$ are independently of each other chosen in one embodiment of the invention, as far as applicable with regard to the ring size and the degree of saturation, are azetidine, oxetane, thietane, pyrrolidine, 2,5-dihydro-1H-pyrrole, tetrahydrofuran, tetrahydrothiophene, pyrazolidine, imidazolidine, 4,5-dihydro-1H-imidazole, [1,3]dioxolane, oxazolidine, thiazolidine, piperidine, 1,2,3,6-tetrahydropyridine, tetrahydropyran, tetrahydrothiopyran, piperazine, [1,3]dioxane, [1,4]dioxane, morpholine, thiomorpholine, azepane, oxepane, thiepane, [1,3]diazepane, [1,4]diazepane, [1,4]oxazepane, [1,4]thiazepane and azocane, which all are optionally substituted as indicated with respect to the compounds of formula I in general or in any embodiment specified above or below. Examples of specific residues of saturated and non-aromatic unsaturated heterocycles, from any one or more of which the groups $Het^1$, $Het^2$, $Het^3$ and $Het^4$ are independently of each other chosen in one embodiment of the invention, as far as applicable with regard to the ring size, the degree of saturation and the kind of the atom via which the residue is bonded are azetidin-1-yl, oxetan-3-yl, thietan-3-yl, pyrrolidin-1-yl, pyrrolidin-2-yl, pyrrolidin-3-yl, 2,5-dihydro-1H-pyrrol-1-yl, tetrahydrofuran-2-yl, tetrahydrofuran-3-yl, tetrahydrothiophen-2-yl, tetrahydrothiophen-3-yl, pyrazolidin-1-yl, pyrazolidin-4-yl, imidazolidin-1-yl, imidazolidin-2-yl, imidazolidin-4-yl, 4,5-dihydro-1H-imidazol-2-yl, 1,3-dioxolan-2-yl, 1,3-dioxolan-4-yl, oxazolidin-2-yl, oxazolidin-3-yl, oxazolidin-4-yl, oxazolidin-5-yl, thiazolidin-2-yl, thiazolidin-3-yl, thiazolidin-4-yl, thiazolidin-5-yl, piperidin-1-yl, piperidin-2-yl, piperidin-3-yl, piperidin-4-yl, 1,2,3,6-tetrahydropyridin-1-yl, tetrahydropyran-2-yl, tetrahydropyran-3-yl, tetrahydropyran-4-yl, tetrahydrothiopyran-2-yl, tetrahydrothiopyran-3-yl, tetrahydrothiopyran-4-yl, piperazin-1-yl, piperazin-2-yl, [1,3]dioxan-2-yl, [1,3]dioxan-4-yl, [1,3]dioxan-5-yl, [1,4]dioxan-2-yl, morpholin-2-yl, morpholin-3-yl, morpholin-4-yl, thiomorpholin-2-yl, thiomorpholin-3-yl, thiomorpholin-4-yl, azepan-1-yl, azepan-2-yl, azepan-3-yl, azepan-4-yl, oxepan-2-yl, oxepan-3-yl, oxepan-4-yl, [1,3]diazepan-1-yl, [1,4]diazepan-1-yl, [1,4]oxazepan-1-yl and [1,4]thiazepan-1-yl, which all are optionally substituted as indicated with respect to the compounds of formula I in general or in any embodiment specified above or below.

Halogen is fluorine, chlorine, bromine or iodine. In one embodiment of the invention, halogen in any occurrence in the compounds of the formula I, independently of all other occurrences, is fluorine, chlorine or bromine, in another embodiment fluorine or chlorine, in another embodiment fluorine.

An oxo substituent, i.e. an oxygen atom which is bonded via a double bond, when bonded to a carbon atom, replaces two hydrogen atoms on the carbon atom of the parent system to which it is bonded. Thus, if a $CH_2$ group is substituted by oxo, it becomes a carbonyl group (C(O), C=O). An oxo substituent cannot be present on a carbon atom in an aromatic ring. Besides on carbon atoms, oxo substituents can also be present on a ring sulfur atom in the group $Het^1$, in particular if the group $Het^1$ is saturated, and in the group $Het^3$, to give the ring member S(O) (S=O, i.e. a sulfoxide group), if one oxo substituent is present on the sulfur atom, or the ring member $S(O)_2$ (S(=O)$_2$, i.e. a sulfone group), if two oxo substituents are present on the sulfur atom. As examples of heterocycles which can represent $Het^1$ and $Het^3$ and which carry oxo substituent a ring sulfur atom, 1,1-dioxo-tetrahydrothiophene, 1-oxo-thiomorpholine and 1,1-dioxo-thiomorpholine may be mentioned, which all are optionally substituted by further substituents such as ($C_1$-$C_4$)-alkyl substituents as indicated with respect to the compounds of formula I in general or in any embodiment specified above or below.

The present invention comprises all stereoisomeric forms of the compounds of the formula I, for example all enantiomers and diastereomers including cis/trans isomers. The invention likewise comprises mixtures of two or more stereoisomeric forms, for example mixtures of enantiomers and/or diastereomers including cis/trans isomers, in all ratios. Asymmetric centers contained in the compounds of the formula I, for example in unsubstituted or substituted alkyl groups, can all independently of each other have the S configuration or the R configuration. The invention relates to enantiomers, both the levorotatory and the dextrorotatory antipode, in enantiomerically pure form and essentially enantiomerically pure form, for example with a molar ratio of the two enantiomers of 99:1 or greater, and in the form of racemates and in the form of mixtures of the two enantiomers in all ratios. The invention likewise relates to diastereomers in the form of pure and essentially pure diastereomers and in the form of mixtures of two or more diastereomers in all ratios. The invention also comprises all cis/trans isomers of the compounds of the formula I in pure form and essentially pure form, for example with a molar ratio of the cis/trans isomers of 99:1 or greater, and in the form of mixtures of the cis isomer and the trans isomer in all ratios. Cis/trans isomerism can occur in substituted rings. The preparation of individual stereoisomers, if desired, can be carried out by resolution of a mixture according to customary methods, for example, by chromatography or crystallization, or by use of stereochemically uniform starting compounds in the synthesis or by stereoselective reactions. Optionally, before a separation of stereoisomers a derivatization can be carried out. The separation of a mixture of stereoisomers can be carried out at the stage of the compound of the formula I or at the stage of an intermediate in the course of the synthesis. The invention also comprises all tautomeric forms of the compounds of the formula I.

Physiologically acceptable salts, including pharmaceutically utilizable salts, of the compounds of the formula I generally comprise a nontoxic salt component. They can contain inorganic or organic salt components. Such salts can be formed, for example, from compounds of the formula I which contain an acidic group, for example a carboxylic acid group (hydroxycarbonyl group, HO—C(O)—), and nontoxic inorganic or organic bases. Suitable bases are, for example, alkali metal compounds or alkaline earth metal compounds, such as sodium hydroxide, potassium hydroxide, sodium carbonate or sodium hydrogencarbonate, or ammonia, organic amino compounds and quaternary ammonium hydroxides. Reactions of compounds of the formula I with bases for the preparation of the salts are in general carried out according to customary procedures in a solvent or diluent. Examples of salts of acidic groups thus are sodium, potassium, magnesium or calcium salts or ammonium salts which can also carry one or more organic groups on the nitrogen atom. Compounds of the formula I which contain a basic, i.e. protonatable, group, for example an amino group or a basic heterocycle, can be present in the form of their acid addition salts with physiologically acceptable acids, for example as salt with hydrogen chloride, hydrogen bromide, phosphoric acid, sulfuric acid, acetic acid, benzoic acid, methanesulfonic acid, p-toluenesulfonic acid, which in general can be prepared from the compounds of the formula I by reaction with an acid in a solvent or diluent according to customary procedures. If the compounds of the formula I simultaneously contain an acidic and a basic group in the molecule, the invention also includes internal salts (betaines, zwitterions) in addition to the salt forms mentioned. The present invention also comprises all salts of the compounds of the formula I which, because of low physiological tolerability, are not directly suitable for use as a pharmaceutical, but are suitable as intermediates for chemical reactions or for the preparation of physiologically acceptable salts, for example by means of anion exchange or cation exchange. The present invention also comprises all solvates of the compounds of the formula I and their salts, including physiologically acceptable solvates, such as hydrates, i.e. adducts with water, and adducts with alcohols like $(C_1-C_4)$-alkanols, as well as active metabolites of compounds of the formula I and prodrugs of the compounds of the formula I, i.e. compounds which in vitro may not necessarily exhibit pharmacological activity but which in vivo are converted into pharmacologically active compounds of the formula I, for example compounds which are converted by metabolic hydrolysis into a compound of the formula I, such as compounds in which a carboxylic acid group is present in esterified form or in the form of an amide.

In one embodiment of the invention, the group A is $C(R^1)$, in another embodiment A is N. In one embodiment of the invention, the group D is chosen from the series consisting of $N(R^2)$ and O, in another embodiment from the series consisting of $N(R^2)$ and S, in another embodiment from the series consisting of O and S, in another embodiment D is $N(R^2)$, in another embodiment D is O, in another embodiment D is S. In one embodiment of the invention, the group E is $C(R^3)$, in another embodiment E is N. In one embodiment of the invention, one or more of the groups A, D and E have any one or some of their meanings and any remaining groups A, D and E have all their meanings. For example, in one embodiment A is chosen from the series consisting of $C(R^1)$ and N, D is $N(R^2)$ and E is chosen from the series consisting of $C(R^3)$ and N, in another embodiment A is chosen from the series consisting of $C(R^1)$ and N, D is $N(R^2)$ and E is N, in another embodiment A is $C(R^1)$, D is $N(R^2)$ and E is chosen from the series consisting of $C(R^3)$ and N, in another embodiment A is $C(R^1)$, D is $N(R^2)$ and E is N, in another embodiment A is $C(R^1)$, D is chosen from the series consisting of $N(R^2)$ and O and D is N, in another embodiment A is N, D is chosen from the series consisting of from $N(R^2)$, O and S and E is $C(R^3)$, in another embodiment A is N, D is $N(R^2)$ and E is chosen from the series consisting of $C(R^3)$ and N. In one embodiment of the invention, one of the groups A and D is N and the other of the groups A and D is $C(R^1)$ or $C(R^3)$, respectively, in another embodiment one or both of the groups A and D are N and any remaining group A or D is $C(R^1)$ or $C(R^3)$, respectively, in another embodiment both of the groups A and D are N, and in another embodiment none of the groups A and D is N.

In terms of formulae resulting from formula I by incorporation of meanings of A, D or E, in one embodiment of the invention a compound of the formula I is a compound of any one or more of formulae I-1 to I-35, for example a compound of formula I-1, or a compound of formula I-2, or a compound of formula I-6, or a compound of formula I-9, or a compound of formula I-10, or a compound of formula I-14, or a compound of formula I-17, or a compound of formula I-19, or a compound of formula I-6 or formula I-14, or a compound of formula I-11 or formula I-12, or a compound of formula I-6 or formula I-10 or formula I-14, in any of its stereoisomeric forms or a mixture of stereoisomeric forms in any ratio, or a physiologically acceptable salt thereof, or a physiologically acceptable solvate of any of them, wherein in the compounds of formulae I-1 to I-35 the groups A, D, E, G, $R^1$, $R^2$, $R^3$, $R^{10}$, $R^{30}$, $R^{40}$, $R^{50}$ and $R^{60}$ are defined as in the compounds of formula I in general or in any embodiment specified above or below.

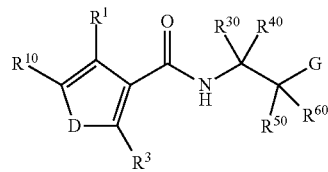

I-1

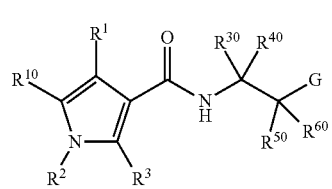

I-2

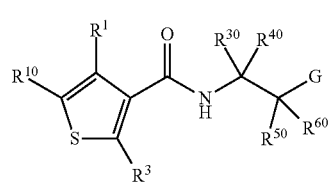

I-3

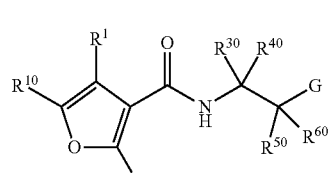

I-4

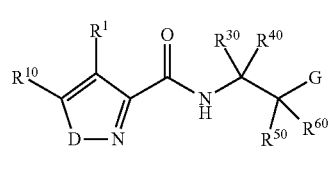

I-5

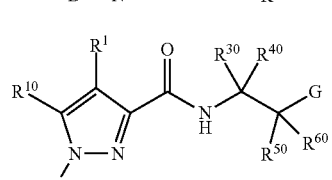

I-6

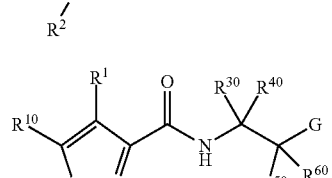

I-7

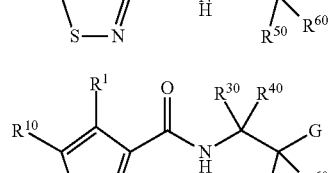

I-8

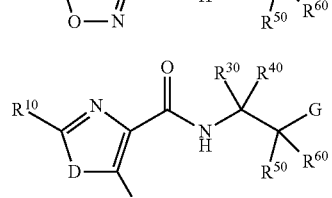

I-9

-continued
I-10
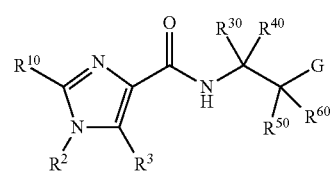
I-11
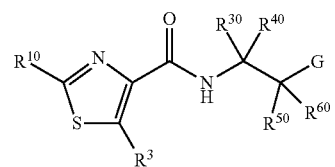
I-12
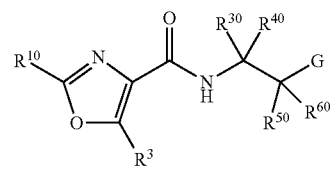
I-13
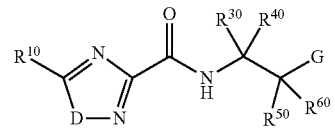
I-14
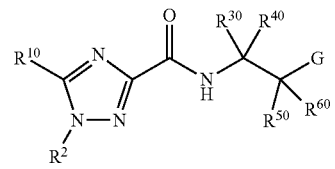
I-15
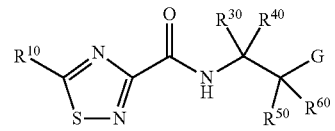
I-16
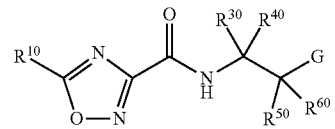
I-17
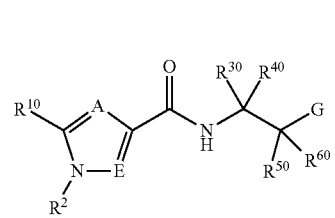
I-18
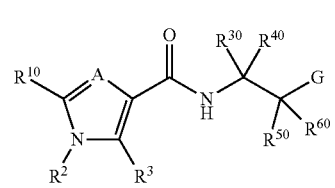
-continued
I-19
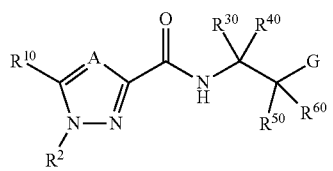
I-20
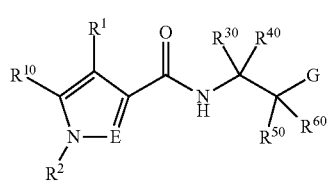
I-21
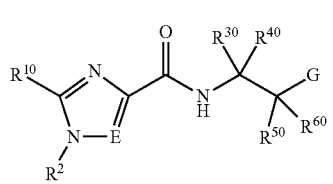
I-22
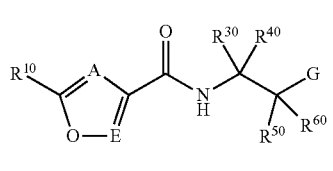
I-23
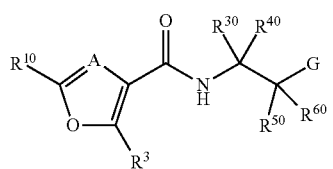
I-24
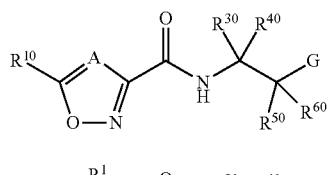
I-25
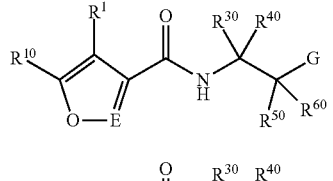
I-26
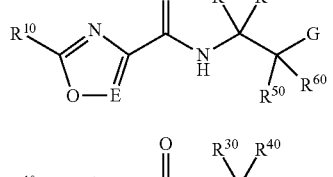
I-27
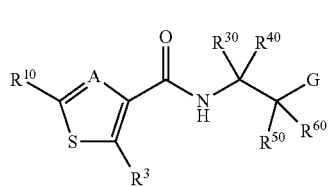
I-28

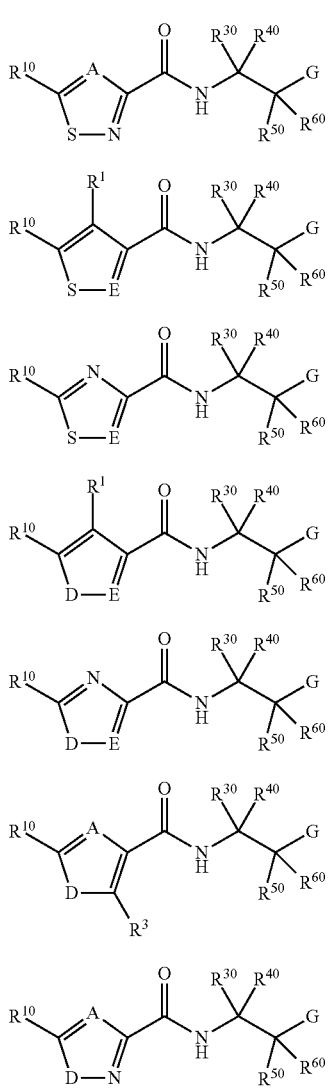

In one embodiment of the invention, the group G is chosen from the series consisting of $R^{71}$—O—C(O)—, $R^{72}$—N($R^{73}$)—C(O)— and tetrazol-5-yl, in another embodiment from the series consisting of $R^{71}$—O—C(O)— and $R^{72}$—N($R^{73}$)—C(O)—, in another embodiment G is $R^{71}$—O—C(O)—, and in another embodiment G is $R^{72}$—N($R^{73}$)—C(O)—.

In one embodiment of the invention, the group $R^1$ is chosen from the series consisting of hydrogen, halogen, ($C_1$-$C_6$)-alkyl, HO—, ($C_1$-$C_6$)-alkyl-O—, and NC—, in another embodiment from the series consisting of hydrogen, halogen, ($C_1$-$C_6$)-alkyl, ($C_1$-$C_6$)-alkyl-O— and NC—, in another embodiment from the series consisting of hydrogen, halogen, ($C_1$-$C_6$)-alkyl and NC—, in another embodiment from the series consisting of hydrogen, halogen, ($C_1$-$C_6$)-alkyl, HO— and ($C_1$-$C_6$)-alkyl-O—, in another embodiment from the series consisting of hydrogen, halogen, ($C_1$-$C_6$)-alkyl and ($C_1$-$C_6$)-alkyl-O—, in another embodiment from the series consisting of hydrogen, halogen and ($C_1$-$C_6$)-alkyl, in another embodiment from the series consisting of hydrogen and halogen, in another embodiment from the series consisting of hydrogen, fluorine and chlorine, and in another embodiment $R^1$ is hydrogen. In one embodiment of the invention, a ($C_1$-$C_6$)-alkyl group occurring in $R^1$ is a ($C_1$-$C_4$)-alkyl group, in another embodiment a ($C_1$-$C_2$)-alkyl group, in another embodiment it is methyl.

In one embodiment of the invention, the group $R^2$ is chosen from the series consisting of ($C_1$-$C_7$)-alkyl and ($C_3$-$C_7$)-cycloalkyl-$C_sH_{2s}$—, in another embodiment from the series consisting of ($C_3$-$C_7$)-cycloalkyl-$C_sH_{2s}$— and Ar—$C_sH_{2s}$—, in another embodiment $R^2$ is ($C_1$-$C_7$)-alkyl, in another embodiment $R^2$ is ($C_3$-$C_7$)-cycloalkyl-$C_sH_{2s}$—, and in another embodiment $R^2$ is Ar—$C_sH_{2s}$—. In one embodiment, s is an integer chosen from the series consisting of 0, 1 and 2, in another embodiment from the series consisting of 0 and 1, in another embodiment from the series consisting of 1 and 2, in another embodiments is 0, and in another embodiments is 1. In one embodiment of the invention, $R^2$ is Ar—$C_sH_{2s}$— and s is 0, i.e., $R^2$ is the group Ar and the group D thus is the group N(Ar). In one embodiment, the divalent alkanediyl group $C_sH_{2s}$ is a linear group. In one embodiment, a ($C_1$-$C_7$)-alkyl group representing $R^2$ is a ($C_3$-$C_7$)-alkyl group, in another embodiment a ($C_3$-$C_6$)-alkyl group. In one embodiment, a ($C_3$-$C_7$)-cycloalkyl group occurring in $R^2$ is a ($C_3$-$C_6$)-cycloalkyl group, in another embodiment a ($C_5$-$C_6$)-cycloalkyl group, in another embodiment a cyclopropyl group. In one embodiment, a group Ar occurring in $R^2$ is chosen from the series consisting of phenyl and an aromatic 5-membered or 6-membered heterocycle which comprises one or two identical or different ring heteroatoms chosen from the series consisting of nitrogen, oxygen and sulfur, which is bonded via a ring carbon atom, in another embodiment from the series consisting of phenyl and an aromatic 6-membered heterocycle which comprises one or two nitrogen atoms as ring heteroatoms, in another embodiment from the series consisting of phenyl, thiophenyl, pyridinyl and pyrimidinyl, in another embodiment from the series consisting of phenyl and thiophenyl, in another embodiment from the series consisting of phenyl, pyridinyl and pyrimidinyl, in another embodiment from the series consisting of phenyl and pyridinyl, and in another embodiment a group Ar occurring in $R^2$ is phenyl, which groups all are optionally substituted as indicated with respect to the compounds of formula I in general or in any embodiment specified above or below. In one embodiment, a group Ar occurring in $R^2$ is optionally substituted by one, two or three identical or different substituents, in another embodiment it is optionally substituted by one or two identical or different substituents, in another embodiment it is optionally substituted by one substituent, in another embodiment it is substituted by one, two or three identical or different substituents, in another embodiment it is substituted by one or two identical or different substituents, and in another embodiment it is substituted by one substituent. In one embodiment, the substituents which are optionally present on a group Ar occurring in $R^2$, are chosen from the series consisting of halogen, ($C_1$-$C_6$)-alkyl, ($C_1$-$C_6$)-alkyl-O—, ($C_1$-$C_6$)-alkyl-S(O)$_m$— and NC—, in another embodiment from the series consisting of halogen, ($C_1$-$C_6$)-alkyl, ($C_1$-$C_6$)-alkyl-O— and ($C_1$-$C_6$)-alkyl-S(O)$_m$—, in another embodiment from the series consisting of halogen, ($C_1$-$C_6$)-alkyl and ($C_1$-$C_6$)-alkyl-S(O)$_m$—, in another embodiment from the series consisting of halogen and ($C_1$-$C_6$)-alkyl, in another embodiment from the series consisting of halogen, in another embodiment from the series consisting of fluorine and chlorine, in another embodiment from the series consisting of fluorine, chlorine and methyl. In one embodiment of the invention, a ($C_1$-$C_6$)-alkyl group occurring in $R^2$ is a ($C_1$-$C_4$)-alkyl group, in another embodiment a ($C_1$-$C_2$)-alkyl group, in another embodiment it is methyl.

Examples of groups Ar which can occur in $R^2$, and from any one or more of which a group Ar occurring in $R^2$ is chosen in one embodiment of the invention, are phenyl, 2-fluoro-phenyl, 3-fluoro-phenyl, 4-fluoro-phenyl, 2-chloro-phenyl, 3-chloro-phenyl, 4-chloro-phenyl, 3-bromo-phenyl, 4-bromo-phenyl, 2,3-dichloro-phenyl, 2,4-dichloro-phenyl, 2,5-dichloro-phenyl, 2,6-dichloro-phenyl, 3,4-dichloro-phenyl, 2,3-difluoro-phenyl, 2,4-difluoro-phenyl, 2,5-difluoro-phenyl, 2,6-difluoro-phenyl, 3,4-difluoro-phenyl, 2-chloro-6-fluoro-phenyl, 3,4,5-trifluoro-phenyl, 2-methyl-phenyl (o-tolyl), 3-methyl-phenyl (m-tolyl), 4-methyl-phenyl (p-tolyl), 2,3-dimethyl-phenyl, 2,4-dimethyl-phenyl, 2,5-dimethyl-phenyl, 2,6-dimethyl-phenyl, 3,4-dimethyl-phenyl, 2-ethyl-phenyl, 3-ethyl-phenyl, 4-ethyl-phenyl, 3-isopropyl-phenyl, 3-tert-butyl-phenyl, 4-tert-butyl-phenyl, 3-trifluoromethyl-phenyl, 4-trifluoromethyl-phenyl, 2-fluoro-5-methyl-phenyl, 3-chloro-2-methyl-phenyl, 5-chloro-2-methyl-phenyl, 5-chloro-2-fluoro-3-methyl-phenyl, 2-fluoro-3-trifluoromethyl-phenyl, 2-fluoro-5-trifluoromethyl-phenyl, 4-fluoro-3-trifluoromethyl-phenyl, 5-fluoro-3-trifluoromethyl-phenyl, 3-chloro-4-trifluoromethyl-phenyl, 5-chloro-2-trifluoromethyl-phenyl, 5-chloro-3-trifluoromethyl-phenyl, 2-methoxy-phenyl, 3-methoxy-phenyl, 4-methoxy-phenyl, 3-ethoxy-phenyl, 3-propoxy-phenyl, 3-isopropoxy-phenyl, 4-tert-butoxy-phenyl, 3-trifluoromethoxy-phenyl, 4-trifluoromethoxy-phenyl, 3-(2,2,2-trifluoroethoxy)-phenyl, 5-chloro-2-methoxy-phenyl, 3-chloro-4-methoxy-phenyl, 5-fluoro-3-isopropoxy-phenyl, 2-fluoro-3-trifluoromethoxy-phenyl, 4-methoxy-3,5-dimethyl-phenyl, 3-methoxy-5-trifluoromethyl-phenyl, 2,3-methylenedioxy-phenyl, 2,3-difluoromethylenedioxy-phenyl, 3,4-methylenedioxy-phenyl, 3,4-difluoromethylenedioxy-phenyl, 3-methylsulfanyl-phenyl, 3-ethylsulfanyl-phenyl, 3-trifluoromethylsulfanyl-phenyl, 3-methanesulfonyl-phenyl, 3-ethanesulfonyl-phenyl, 3-sulfamoyl-phenyl, 2-cyano-phenyl, 3-cyano-phenyl, 4-cyano-phenyl, thiophen-2-yl, thiophen-3-yl, 3-chloro-thiophen-2-yl, 4-chloro-thiophen-2-yl, 5-chloro-thiophen-2-yl, 4,5-dichloro-thiophen-2-yl, 5-chloro-thiophen-3-yl, 2,5-dichloro-thiophen-3-yl, 4-methyl-thiophen-2-yl, 5-methyl-thiophen-3-yl, 4,5-dimethyl-thiophen-2-yl, pyridin-2-yl, pyridin-3-yl, pyridin-4-yl, 2-chloro-pyridin-3-yl, 5-chloro-pyridin-2-yl, 6-chloro-pyridin-3-yl, 2-chloro-pyridin-4-yl, 2,6-dichloro-pyridin-3-yl, 6-methoxy-pyridin-3-yl, 2-chloro-6-methoxy-pyridin-3-yl.

In one embodiment of the invention, the group $R^3$ is chosen from the series consisting of hydrogen, halogen, $(C_1-C_6)$-alkyl, $(C_1-C_6)$-alkyl-O—, and NC—, in another embodiment from the series consisting of hydrogen, halogen, $(C_1-C_6)$-alkyl and NC—, in another embodiment from the series consisting of hydrogen, halogen, $(C_1-C_6)$-alkyl and $(C_1-C_6)$-alkyl-O—, in another embodiment from the series consisting of hydrogen, halogen and $(C_1-C_6)$-alkyl, in another embodiment from the series consisting of hydrogen and halogen, in another embodiment from the series consisting of hydrogen and $(C_1-C_6)$-alkyl, in another embodiment from the series consisting of hydrogen, fluorine and chlorine, in another embodiment $R^3$ is hydrogen, and in another embodiment $R^3$ is $(C_1-C_6)$-alkyl. In one embodiment of the invention, a $(C_1-C_6)$-alkyl group occurring in $R^3$ is a $(C_1-C_4)$-alkyl group, in another embodiment a $(C_1-C_2)$-alkyl group, in another embodiment it is methyl.

In one embodiment of the invention, the group $R^{10}$ is chosen from the series consisting of $R^{11}$—O— and $R^{12}$—N($R^{13}$)—C(O)—O—, in another embodiment from the series consisting of $R^{12}$—N($R^{13}$)—C(O)—O— and $Het^2$—C(O)—O—, and in another embodiment $R^{10}$ is $R^{11}$—O—. In one embodiment, the group $Het^2$ which can occur in the group $R^{10}$, is a saturated 4-membered to 6-membered, in another embodiment a 5-membered or 6-membered, in another embodiment a 5-membered, monocyclic heterocycle which, besides the ring nitrogen via which $Het^2$ is bonded, optionally comprises one further ring heteroatom chosen from the series nitrogen, oxygen and sulfur. In one embodiment, the group $Het^2$ which can occur in the group $R^{10}$, does not comprise a further ring heteroatom besides the ring nitrogen atom via which $Het^2$ is bonded. In one embodiment, the number of substituents which are optionally present on a group $Het^2$ which can occur in $R^{10}$, is one, two, three or four, in another embodiment one, two or three, in another embodiment one or two, in another embodiment one, and in another embodiment such a group $Het^2$ is unsubstituted. In one embodiment, the substituents which are optionally present on a group $Het^2$ which can occur in the group $R^{10}$, are chosen from the series consisting of fluorine, $(C_1-C_4)$-alkyl, HO— and $(C_1-C_4)$-alkyl-O—, in another embodiment from the series consisting of $(C_1-C_4)$-alkyl, HO— and $(C_1-C_4)$-alkyl-O—, in another embodiment from the series consisting of $(C_1-C_4)$-alkyl and HO— and $(C_1-C_4)$-alkyl-O—, in another embodiment they are $(C_1-C_4)$-alkyl substituents, and in another embodiment they are HO— substituents.

In one embodiment of the invention, the group $R^{11}$ is chosen from the series consisting of hydrogen, $R^{14}$, $(C_3-C_7)$-cycloalkyl and $Het^3$, in another embodiment from the series consisting of hydrogen and $R^{14}$, in another embodiment from the series consisting of hydrogen, $R^{14}$ and $(C_3-C_7)$-cycloalkyl, in another embodiment from the series consisting of $(C_3-C_7)$-cycloalkyl, Ar and $Het^3$, in another embodiment from the series consisting of $(C_3-C_7)$-cycloalkyl and $Het^3$, in another embodiment $R^{11}$ is hydrogen, in another embodiment $R^{11}$ is $R^{14}$, and in another embodiment $R^{11}$ is Ar. In one embodiment, a group Ar representing $R^{11}$ is phenyl which is optionally substituted as indicated with respect to the compounds of formula I in general or in any embodiment specified above or below. In one embodiment, a group Ar representing $R^{11}$ is optionally substituted by one, two or three identical or different substituents, in another embodiment it is optionally substituted by one or two identical or different substituents, in another embodiment it is optionally substituted by one substituent. In one embodiment, the substituents which are optionally present on a group Ar representing $R^{11}$, are chosen from the series consisting of halogen, $(C_1-C_4)$-alkyl, $(C_1-C_4)$-alkyl-O— and NC—, in another embodiment from the series consisting of halogen, $(C_1-C_4)$-alkyl and $(C_1-C_4)$-alkyl-O—, in another embodiment from the series consisting of halogen and $(C_1-C_4)$-alkyl. In one embodiment, a $(C_3-C_7)$-cycloalkyl group representing $R^{11}$ is a $(C_3-C_6)$-cycloalkyl group. In one embodiment, a group $Het^3$ representing $R^{11}$ is a saturated 4-membered to 6-membered monocyclic heterocycle which comprises one or two identical or different ring heteroatoms, in another embodiment one ring heteroatom, which are chosen from the series consisting of nitrogen, oxygen and sulfur, in another embodiment it comprises one ring heteroatom chosen from the series consisting of nitrogen and oxygen, in another embodiment one ring heteroatom chosen from the series consisting of oxygen and sulfur, and in another embodiment it comprises one oxygen atom as ring heteroatom, wherein the heterocycle is bonded via a ring carbon atom and is optionally substituted by one, two, three or four, in another embodiment by one or two, identical or different substituents chosen from the series consisting of fluorine, $(C_1-C_4)$-alkyl and oxo, in another embodiment from the series consisting of fluorine and $(C_1-C_4)$-alkyl.

In one embodiment of the invention, the groups $R^{12}$ and $R^{13}$ are independently of each other chosen from the series consisting of hydrogen and $R^{15}$, in another embodiment from the series consisting of $R^{15}$ and Ar, and in another embodiment they are identical or different groups $R^{15}$. In one embodiment, one of the groups $R^{12}$ and $R^{13}$ is chosen from the series consisting of $R^{15}$ and Ar, and the other is a group $R^{15}$. In one embodiment, a group Ar representing $R^{12}$ or $R^{13}$ is phenyl which is optionally substituted by one or two, in another embodiment by one, identical or different substituents chosen from the series consisting of halogen and $(C_1-C_4)$-alkyl, and in another embodiment it is unsubstituted phenyl.

In one embodiment of the invention, the $(C_1-C_{10})$-alkyl group representing the group $R^{14}$ is a $(C_1-C_8)$-alkyl group, in another embodiment a $(C_1-C_7)$-alkyl group, in another embodiment a $(C_1-C_4)$-alkyl group, in another embodiment a $(C_1-C_3)$-alkyl group, in another embodiment a $(C_1-C_2)$-alkyl group, in another embodiment a methyl group, in another embodiment a $(C_4-C_8)$-alkyl group, in another embodiment a $(C_4-C_7)$-alkyl group, in another embodiment a $(C_5-C_7)$-alkyl group, in another embodiment a $C_6$-alkyl group, wherein all these alkyl groups are linear or branched as applies to alkyl groups in the compounds of the formula I in general, and are optionally substituted by one or more identical or different substituents as indicated with respect to the compounds of formula I in general or in any embodiment specified above or below. In one embodiment of the invention, the number of optional substituents in an alkyl group representing $R^{14}$ is one, two, three or four, in another embodiment one, two or three, in another embodiment one or two, in another embodiment one. In one embodiment, an alkyl group representing $R^{14}$ is unsubstituted, and in another embodiment it is substituted by one, two, three or four, in another embodiment by one, two or three, in another embodiment by one or two, in another embodiment by one substituent as indicated.

In one embodiment, a $(C_3-C_7)$-cycloalkyl group occurring as a substituent on an alkyl group representing $R^{14}$ is a $(C_3-C_6)$-cycloalkyl group, in another embodiment it is a cyclopropyl group. In one embodiment, a group Ar occurring as a substituent on an alkyl group representing $R^{14}$ is phenyl or an aromatic 5-membered or 6-membered monocyclic heterocycle which comprises one or two identical or different ring heteroatoms chosen from the series consisting of nitrogen, oxygen and sulfur, and in another embodiment comprises one nitrogen atom as ring heteroatom and in the case of a 5-membered heterocycle one additional ring heteroatom chosen from the series consisting of nitrogen, oxygen and sulfur, and in another embodiment a group Ar occurring as a substituent in an alkyl group representing $R^{14}$ is chosen from phenyl, pyrazolyl, isoxazolyl and thiazolyl, wherein all these groups Ar are optionally substituted by one or more identical or different substituents as indicated with respect to the compounds of formula I in general or in any embodiment specified above or below. In one embodiment, the number of optional substituents on a group Ar occurring as a substituent in an alkyl group representing $R^{14}$ is one, two or three, in another embodiment one or two, in another embodiment one. In one embodiment, the substituents which are optionally present on a group Ar occurring as a substituent in an alkyl group representing $R^{14}$, are chosen from the series consisting of halogen, $(C_1-C_4)$-alkyl, $(C_1-C_4)$-alkyl-O— and NC—, in another embodiment from the series consisting of halogen, $(C_1-C_4)$-alkyl and $(C_1-C_4)$-alkyl-O—, in another embodiment from the series consisting of halogen and $(C_1-C_4)$-alkyl, and in another embodiment they are $(C_1-C_4)$-alkyl groups.

In one embodiment, a group $Het^1$ occurring as a substituent on an alkyl group representing $R^{14}$ is a saturated or unsaturated 4-membered to 6-membered heterocycle, in another embodiment a 5-membered or 6-membered heterocycle, which comprises a ring nitrogen atom via which $Het^1$ is bonded and optionally one further ring heteroatom chosen from the series consisting of nitrogen, oxygen and sulfur, which is optionally substituted as indicated with respect to the compounds of formula I in general or in any embodiment specified above or below. In one embodiment, a group $Het^1$ occurring as a substituent on an alkyl group representing $R^{14}$ does not comprise any further ring heteroatom besides the ring nitrogen atom via which $Het^1$ is bonded. In one embodiment, a group $Het^1$ occurring as a substituent on an alkyl group representing $R^{14}$ is saturated, in another embodiment it is unsaturated. In one embodiment, the number of substituents which are optionally present on a group $Het^1$ occurring as a substituent on an alkyl group representing $R^{14}$ is one, two, three or four, in another embodiment one, two or three, in another embodiment one or two, in another embodiment one. In one embodiment, the substituents which are optionally present on a group $Het^1$ occurring as a substituent on an alkyl group representing $R^{14}$ are chosen from the series consisting of halogen, $(C_1-C_4)$-alkyl, HO—, $(C_1-C_4)$-alkyl-O— and oxo, in another embodiment from the series consisting of fluorine, $(C_1-C_4)$-alkyl, HO— and oxo, in another embodiment from the series consisting of fluorine, $(C_1-C_4)$-alkyl and oxo, in another embodiment from the series consisting of $(C_1-C_4)$-alkyl and oxo, and in another embodiment they are oxo substituents. In one embodiment, the number of oxo substituents which are optionally present on a group $Het^1$ occurring as a substituent on an alkyl group representing $R^{14}$, is not greater than two, and in another embodiment it is not greater than one.

In one embodiment, a group $Het^1$ occurring in the substituent $Het^1$—C(O)— on an alkyl group representing $R^{14}$ is a 4-membered to 6-membered heterocycle, in another embodiment a 5-membered or 6-membered heterocycle, which is saturated or unsaturated and comprises a ring nitrogen atom via which $Het^1$ is bonded and optionally one further ring heteroatom chosen from the series consisting of nitrogen, oxygen and sulfur, and which is optionally substituted as indicated with respect to the compounds of formula I in general or in any embodiment specified above or below. In one embodiment, a group $Het^1$ occurring in the substituent $Het^1$—C(O)— on an alkyl group representing $R^{14}$ does not comprise any further ring heteroatom besides the ring nitrogen atom via which $Het^1$ is bonded. In one embodiment, a group $Het^1$ occurring in the substituent $Het^1$—C(O)— on an alkyl group representing $R^{14}$ is saturated or comprises one double bond within the ring, and in another embodiment it is saturated. In one embodiment, the number of substituents which are optionally present on a group $Het^1$ occurring in the substituent $Het^1$—C(O)— on an alkyl group representing $R^{14}$ is one, two, three or four, in another embodiment one, two or three, in another embodiment one or two, in another embodiment one. In one embodiment, the substituents which are optionally present on a group $Het^1$ occurring in the substituent $Het^1$—C(O)— on an alkyl group representing $R^{14}$ are chosen from the series consisting of halogen, $(C_1-C_4)$-alkyl, HO—, $(C_1-C_4)$-alkyl-O— and oxo, in another embodiment from the series consisting of fluorine, $(C_1-C_4)$-alkyl, HO— and oxo, in another embodiment from the series consisting of fluorine, $(C_1-C_4)$-alkyl and oxo, in another embodiment from $(C_1-C_4)$-alkyl and oxo, in another embodiment they are oxo substituents, and in another embodiment they are $(C_1-C_4)$-alkyl substituents. In one embodiment, the number of oxo substituents which are optionally present on a group $Het^1$ occurring in the substituent $Het^1$—C(O)— on an alkyl group representing $R^{14}$, is not greater than two, and in another embodiment it is not greater than one, and in another embodiment no oxo substituents are present on such a group $Het^1$.

In one embodiment, a group $Het^3$ occurring as a substituent on an alkyl group representing $R^{14}$ is a saturated 4-membered to 6-membered monocyclic heterocycle which comprises one or two identical or different ring heteroatoms, and in another embodiment comprises one ring heteroatom, which are chosen from the series consisting of nitrogen, oxygen and sulfur, and is bonded via a ring carbon atom and is optionally substituted as indicated with respect to the compounds of formula I in general or in any embodiment specified above or below. In one embodiment, the ring heteroatoms in a group $Het^3$ occurring as a substituent on an alkyl group representing $R^{14}$ are chosen from the series consisting of nitrogen and oxygen, in another embodiment from the series consisting of oxygen and sulfur, in another embodiment they are nitrogen atoms, and in another embodiment they are oxygen atoms. In one embodiment, the number of substituents which are optionally present on a group $Het^3$ occurring as a substituent on an alkyl group representing $R^{14}$ is one, two, three or four, in another embodiment one, two or three, in another embodiment one or two, in another embodiment one. In one embodiment, the substituents which are optionally present on a group $Het^3$ occurring as a substituent on an alkyl group representing $R^{14}$ are chosen from the series consisting of fluorine and $(C_1-C_4)$-alkyl, in another embodiment from the series consisting of $(C_1-C_4)$-alkyl and oxo, in another embodiment they are $(C_1-C_4)$-alkyl substituents, and in another embodiment they are oxo substituents. In one embodiment, the number of oxo substituents which are optionally present on a group $Het^3$ occurring as a substituent on an alkyl group representing $R^{14}$, is not greater than two, and in another embodiment it is not greater than one.

In one embodiment, the substituents which are optionally present on an alkyl group representing $R^{14}$ are chosen from the series consisting of halogen, HO—, $R^{16}$—O—, oxo, $(C_3-C_7)$-cycloalkyl, Ar, $Het^1$, $Het^3$, $H_2N$—C(O)—, $(C_1-C_4)$-alkyl-NH—C(O)—, di$((C_1-C_4)$-alkyl)N—C(O)— and $Het^1$—C(O)—, in another embodiment from the series consisting of halogen, HO—, $R^{16}$—O—, oxo, $(C_3-C_7)$-cycloalkyl, $Het^1$, $Het^3$, $H_2N$—C(O)—, $(C_1-C_4)$-alkyl-NH—C(O)—, di$((C_1-C_4)$-alkyl)N—C(O)— and $Het^1$—C(O)—, in another embodiment from the series consisting of halogen, HO—, $R^{16}$—O—, oxo, $(C_3-C_7)$-cycloalkyl, $Het^1$, $Het^3$, di$((C_1-C_4)$-alkyl)N—C(O)— and $Het^1$—C(O)—, in another embodiment from the series consisting of halogen, HO—, $R^{16}$—O—, oxo, $(C_3-C_7)$-cycloalkyl, $Het^1$ and $Het^3$, in another embodiment from the series consisting of halogen, HO—, $R^{16}$—O—, oxo, $(C_3-C_7)$-cycloalkyl, Ar, $Het^1$ and $Het^3$, in another embodiment from the series consisting of HO—, $R^{16}$—O—, oxo, $(C_3-C_7)$-cycloalkyl, Ar, $Het^1$, di$((C_1-C_4)$-alkyl)N—C(O)— and $Het^1$—C(O)—, in another embodiment from the series consisting of HO—, $R^{16}$—O—, oxo, $(C_3-C_7)$-cycloalkyl, Ar, di$((C_1-C_4)$-alkyl)N—C(O)— and $Het^1$—C(O)—, in another embodiment from the series consisting of HO—, $R^{16}$—O—, oxo, $(C_3-C_7)$-cycloalkyl and Ar, in another embodiment from the series consisting of HO—, $R^{16}$—O—, oxo, $(C_3-C_7)$-cycloalkyl, di$((C_1-C_4)$-alkyl)N—C(O)— and $Het^1$—C(O)—, in another embodiment from the series consisting of HO—, $R^{16}$—O—, oxo, $(C_3-C_7)$-cycloalkyl, $Het^1$ and $Het^3$, in another embodiment from the series consisting of HO—, $R^{16}$—O—, oxo, $(C_3-C_7)$-cycloalkyl and $Het^3$, in another embodiment from the series consisting of HO—, oxo, $(C_3-C_7)$-cycloalkyl and $Het^3$, in another embodiment from the series consisting of HO—, oxo and $(C_3-C_7)$-cycloalkyl, in another embodiment from the series consisting of HO—, oxo and $Het^3$, in another embodiment from the series consisting of HO— and oxo, in another embodiment from the series consisting of HO—, $R^{16}$—O—, $(C_3-C_7)$-cycloalkyl and $Het^3$, in another embodiment from the series consisting of HO—, $(C_3-C_7)$-cycloalkyl and $Het^3$, in another embodiment from the series consisting of HO— and $(C_3-C_7)$-cycloalkyl, in another embodiment from the series consisting of HO— and $Het^3$, in another embodiment they are HO— substituents, and in another embodiment they are oxo substituents. In one embodiment, the number of oxo substituents which are optionally present on an alkyl group representing $R^{14}$, is not greater than two, and in another embodiment it is not greater than one. In one embodiment, halogen atoms occurring as substituents on an alkyl group representing $R^{14}$, are chosen from the series consisting of fluorine and chlorine atoms, and in another embodiment they are fluorine atoms and, besides being substituted by an other substituents, in this latter embodiment an alkyl group representing $R^{14}$ is thus optionally substituted by fluorine substituents as applies to alkyl groups in the compounds of the formula I in general.

Examples of groups which can represent $R^{14}$, and from any one or more of which $R^{14}$ is chosen in one embodiment of the invention, are methyl, ethyl, propyl, isopropyl, butyl, isobutyl, cyclopropylmethyl, benzyl, 2-hydroxy-ethyl, 2-hydroxy-propyl, 2-hydroxy-butyl, 2-hydroxy-2-methyl-propyl, 2-hydroxy-2-methyl-butyl, 2-hydroxy-3-methyl-butyl, 2-hydroxy-2,3-dimethyl-butyl, 2-hydroxy-3,3-dimethyl-butyl, 2-ethyl-2-hydroxy-butyl, 2-hydroxy-2,3,3-trimethyl-butyl, 2-ethyl-2-hydroxy-3-methyl-butyl, 2-ethyl-2-hydroxy-3,3-dimethyl-butyl, 2-cyclopropyl-2-hydroxy-ethyl, 2-cyclopropyl-2-hydroxy-propyl, 2-cyclopropyl-2-hydroxy-butyl, 2-oxo-propyl, 2-oxo-butyl, 3-methyl-2-oxo-butyl, 3,3-dimethyl-2-oxo-butyl, 2-cyclopropyl-2-oxo-ethyl.

In case the optionally substituted alkyl group representing $R^{14}$, including the examples of groups listed afore which can represent $R^{14}$, contains a chiral carbon atom, the compound of the formula I can be present with respect to this carbon atom in any of it stereoisomeric forms, i.e. in R configuration or in S configuration, or in the form of a mixture of the stereoisomeric forms in any ratio, for example as a mixture of the two stereoisomeric forms in a molar ratio of 1:1, as applies to all chiral carbon atoms in the compounds of the formula I. In one embodiment of the invention, the compound of the formula I has at a chiral carbon atom in $R^{14}$ pure stereochemical configuration, either R configuration or S configuration, or essentially pure stereochemical configuration, for example with a molar ratio of the two configurations of 99:1 or greater.

In one embodiment of the invention, the $(C_1-C_6)$-alkyl group representing the group $R^{15}$ is a $(C_1-C_4)$-alkyl group, in another embodiment a $(C_1-C_2)$-alkyl group, in another embodiment a methyl group, wherein all these alkyl groups are optionally substituted by one or more identical or different substituents as indicated with respect to the compounds of formula I in general or in any embodiment specified above or below. In one embodiment of the invention, the number of optional substituents in an alkyl group representing $R^{15}$ is one or two, in another embodiment one. In one embodiment, the alkyl group representing $R^{15}$ is unsubstituted. In one embodiment, the substituents which are optionally present on an alkyl group representing $R^{15}$ are chosen from the series consisting of HO— and $(C_1-C_4)$-alkyl-O—.

In one embodiment of the invention, the $(C_1-C_6)$-alkyl group representing the group $R^{16}$ is a $(C_1-C_4)$-alkyl group, in another embodiment a $(C_1-C_3)$-alkyl group, in another embodiment a $(C_2-C_3)$-alkyl group, in another embodiment an ethyl group, in another embodiment a methyl group, wherein all these alkyl groups are optionally substituted by one or more identical or different substituents as indicated with respect to the compounds of formula I in general or in any embodiment specified above or below. In one embodiment of the invention, the number of optional substituents in an alkyl group representing $R^{16}$ is one or two, in another embodiment one. In one embodiment, an alkyl group representing $R^{14}$ is unsubstituted, in another embodiment it is substituted by one or two identical or different substituents, in another embodiment it is substituted by one substituent. In one embodiment, the substituents which are optionally present on an alkyl group representing $R^{15}$ are chosen from the series consisting of HO— and $(C_1$-$C_4)$-alkyl-O—, in another embodiment they are HO— substituents, in another embodiment they are $(C_1$-$C_4)$-alkyl-O— substituents, and in another embodiment they are $(C_1$-$C_2)$-alkyl-O— substituents.

In one embodiment of the invention, the group $R^{30}$ is chosen from the series consisting of $R^{31}$, $(C_3$-$C_7)$-cycloalkyl and Het$^3$—$C_uH_{2u}$—, in another embodiment from the series consisting of $(C_3$-$C_7)$-cycloalkyl, $R^{32}$—$C_uH_{2u}$— and Het$^3$—$C_uH_{2u}$—, in another embodiment from the series consisting of $R^{32}$—$C_uH_{2u}$— and Het$^3$—$C_uH_{2u}$—, in another embodiment $R^{30}$ is $R^{32}$—$C_uH_{2u}$—, and in another embodiment $R^{30}$ is $R^{31}$. In one embodiment, u is an integer chosen from the series consisting of 0, 1 and 2, in another embodiment from the series consisting of 0 and 1, in another embodiment from the series consisting of 1 and 2, in another embodiment u is 0, and in another embodiment u is 1. In one embodiment, $R^{30}$ is $R^{32}$—$C_uH_{2u}$— and u is 0, i.e., in this embodiment $R^{30}$ is chosen from the series consisting of phenyl and an aromatic 5-membered or 6-membered monocyclic heterocycle which comprises one, two or three identical or different ring heteroatoms chosen from the series consisting of nitrogen, oxygen and sulfur and is bonded via a ring carbon atom, wherein the phenyl and the heterocycle all are optionally substituted as indicated with respect to the compounds of formula I in general or in any embodiment specified above or below. In one embodiment, the divalent alkanediyl group $C_uH_{2u}$ is a linear group.

In one embodiment, the $(C_3$-$C_7)$-cycloalkyl group representing $R^{30}$ is a $(C_3$-$C_6)$-cycloalkyl group, in another embodiment a $(C_5$-$C_6)$-cycloalkyl group, in another embodiment a cyclopropyl group. In one embodiment, a group Het$^3$ occurring in $R^{30}$ is a saturated 4-membered to 6-membered monocyclic heterocycle, in another embodiment a saturated 5-membered or 6-membered heterocycle, in another embodiment a saturated 6-membered heterocycle, which comprises one or two identical or different ring heteroatoms, and in another embodiment comprises one ring heteroatom, which are chosen from the series consisting of nitrogen, oxygen and sulfur, and is bonded via a ring carbon atom and is optionally substituted as indicated with respect to the compounds of formula I in general or in any embodiment specified above or below. In one embodiment, the ring heteroatoms in a group Het$^3$ occurring in $R^{30}$ are chosen from the series consisting of nitrogen and oxygen, in another embodiment from the series consisting of oxygen and sulfur, in another embodiment they are nitrogen atoms, and in another embodiment they are oxygen atoms. In one embodiment, the number of substituents which are optionally present on a group Het$^3$ occurring in $R^{30}$ is one, two, three or four, in another embodiment one, two or three, in another embodiment one or two, in another embodiment one, and in another embodiment a group Het$^3$ occurring in $R^{30}$ is unsubstituted. In one embodiment, the substituents which are optionally present on a group Het$^3$ occurring in $R^{30}$ are chosen from the series consisting of fluorine and $(C_1$-$C_4)$-alkyl, in another embodiment they are $(C_1$-$C_4)$-alkyl substituents.

In one embodiment of the invention, the $(C_1$-$C_{10}$-alkyl group representing $R^{31}$ is a $(C_1$-$C_8)$-alkyl group, in another embodiment a $(C_1$-$C_4)$-alkyl group, in another embodiment a $(C_1$-$C_3)$-alkyl group, in another embodiment a $(C_1$-$C_2)$-alkyl group, in another embodiment a methyl group, in another embodiment a $(C_4$-$C_8)$-alkyl group, in another embodiment a $(C_5$-$C_8)$-alkyl group, wherein all these alkyl groups are optionally substituted by one or more identical or different substituents as indicated with respect to the compounds of formula I in general or in any embodiment specified above or below. In one embodiment of the invention, the number of optional substituents in an alkyl group representing $R^{31}$ is one, two or three, in another embodiment one or two, in another embodiment one. In one embodiment, an alkyl group representing $R^{31}$ is unsubstituted, and in another embodiment it is substituted by one, two or three, in another embodiment by one or two, in another embodiment by one substituent as indicated. In one embodiment, the optional substituents on an alkyl group representing $R^{31}$ are chosen from the series consisting of halogen, $(C_3$-$C_7)$-cycloalkyl, $(C_1$-$C_8)$-alkyl-O— and NC—, in another embodiment from the series consisting of halogen, $(C_3$-$C_7)$-cycloalkyl and $(C_1$-$C_8)$-alkyl-O—, in another embodiment from the series consisting of halogen and $(C_3$-$C_7)$-cycloalkyl, and in another embodiment they are $(C_3$-$C_7)$-cycloalkyl substituents. In one embodiment, halogen atoms occurring as substituents on an alkyl group representing $R^{31}$, are chosen from the series consisting of fluorine and chlorine atoms, and in another embodiment they are fluorine atoms and, besides being substituted by an other substituents, in this latter embodiment an alkyl group representing $R^{31}$ is thus optionally substituted by fluorine substituents as applies to alkyl groups in the compounds of the formula I in general. In one embodiment, a $(C_3$-$C_7)$-cycloalkyl group occurring as a substituent on an alkyl group representing $R^{30}$ is a $(C_3$-$C_6)$-cycloalkyl group, in another embodiment a $(C_5$-$C_6)$-cycloalkyl group, in another embodiment a cyclopropyl group.

In one embodiment of the invention, the group $R^{32}$ is chosen from the series consisting of phenyl and an aromatic 5-membered or 6-membered monocyclic heterocycle which comprises one or two identical or different ring heteroatoms, in another embodiment one ring heteroatom, which are chosen from the series consisting of nitrogen, oxygen and sulfur, and is bonded via a ring carbon atom, in another embodiment from the series consisting of phenyl and an aromatic 6-membered monocyclic heterocycle which comprises one or two nitrogen atoms as ring heteroatoms, wherein the phenyl and the heterocycle all are optionally substituted by one or more identical or different substituents as indicated with respect to the compounds of formula I in general or in any embodiment specified above or below. In one embodiment, the ring heteroatoms in an aromatic heterocycle representing $R^{32}$ are chosen from the series consisting of nitrogen and sulfur, in another embodiment they are nitrogen atoms. In one embodiment, $R^{32}$ is chosen from the series consisting of phenyl and an aromatic 6-membered heterocycle as defined, in another embodiment $R^{32}$ is a 6-membered monocyclic heterocycle as defined, in another embodiment $R^{32}$ is chosen from the series consisting of phenyl, thiophenyl and pyridinyl, in another embodiment from the series consisting of phenyl and pyridinyl, in another embodiment $R^{32}$ is phenyl, and in another embodiment $R^{32}$ is pyridinyl, all of which are optionally substituted by one or more identical or different substituents as indicated with respect to the compounds of formula I in general or in any embodiment specified above or below. In one embodiment, the number of substituents which are optionally present on a phenyl group and an aromatic heterocycle representing $R^{32}$ is one, two, three or four, in another embodiment one, two or three, in another embodiment one or two, in another embodiment one.

In one embodiment, the substituents which are optionally present on a phenyl group and an aromatic heterocycle representing $R^{32}$, in particular on a phenyl group, are chosen from the series the series consisting of from halogen, $(C_1-C_6)$-alkyl, $(C_3-C_7)$-cycloalkyl, $R^{33}$, $(C_1-C_6)$-alkyl-O—, $R^{33}$—O—, $R^{33}$—$(C_1-C_4)$-alkyl-O—, —O—$CH_2$—O—, —O—$CF_2$—O—, $(C_1-C_6)$-alkyl-S(O)$_m$—, $H_2N$—S(O)$_2$—, $(C_1-C_4)$-alkyl-NH—S(O)$_2$—, di(($C_1-C_4$)-alkyl)N—S(O)$_2$—, $(C_1-C_6)$-alkyl-NH—, di(($C_1-C_6$)-alkyl)N—, Het$^1$, $(C_1-C_4)$-alkyl-C(O)—NH—, Ar—C(O)—NH—, $(C_1-C_4)$-alkyl-S(O)$_2$—NH— and NC—, in another embodiment from the series consisting of halogen, $(C_1-C_6)$-alkyl, $(C_3-C_7)$-cycloalkyl, $R^{33}$, $(C_1-C_6)$-alkyl-O—, $R^{33}$—O—, $R^{33}$—$(C_1-C_4)$-alkyl-O—, —O—$CH_2$—O—, —O—$CF_2$—O—, $(C_1-C_6)$-alkyl-S(O)$_m$—, $H_2N$—S(O)$_2$—, $(C_1-C_4)$-alkyl-NH—S(O)$_2$—, di(($C_1-C_4$)-alkyl)N—S(O)$_2$—, $(C_1-C_6)$-alkyl-NH—, di(($C_1-C_6$)-alkyl)N—, Het$^1$ and NC—, in another embodiment from the series consisting of halogen, $(C_1-C_6)$-alkyl, $(C_3-C_7)$-cycloalkyl, $R^{33}$, $(C_1-C_6)$-alkyl-O—, $R^{33}$—O—, $R^{33}$—$(C_1-C_4)$-alkyl-O—, —O—$CH_2$—O—, —O—$CF_2$—O—, $(C_1-C_6)$-alkyl-S(O)$_m$—, $(C_1-C_6)$-alkyl-NH—, di(($C_1-C_6$)-alkyl)N—, Het$^1$ and NC—, in another embodiment from the series consisting of halogen, $(C_1-C_6)$-alkyl, $R^{33}$, $(C_1-C_6)$-alkyl-O—, $R^{33}$—O—, —O—$CH_2$—O—, —O—$CF_2$—O—, $(C_1-C_6)$-alkyl-S(O)$_m$—, Het$^1$ and NC—, in another embodiment from the series consisting of halogen, $(C_1-C_6)$-alkyl, $R^{33}$, $(C_1-C_6)$-alkyl-O—, $R^{33}$—O—, —O—$CH_2$—O—, —O—$CF_2$—O— and NC—, in another embodiment from the series consisting of halogen, $(C_1-C_6)$-alkyl, $R^{33}$, $(C_1-C_6)$-alkyl-O—, $R^{33}$—O— and NC—, in another embodiment from the series consisting of halogen, $(C_1-C_6)$-alkyl, $(C_3-C_7)$-cycloalkyl, $R^{33}$, $(C_1-C_6)$-alkyl-O—, $R^{33}$—O—, $R^{33}$—$(C_1-C_4)$-alkyl-O—, —O—$CH_2$—O—, —O—$CF_2$—O—, $(C_1-C_6)$-alkyl-S(O)$_m$—, di(($C_1-C_4$)-alkyl)N—S(O)$_2$—, $H_2N$—, di(($C_1-C_6$)-alkyl)N—, Het$^1$, $(C_1-C_4)$-alkyl-C(O)—NH—, Ar—C(O)—NH— and NC—, in another embodiment from the series consisting of halogen, $(C_1-C_6)$-alkyl, $(C_3-C_7)$-cycloalkyl, $R^{33}$, $(C_1-C_6)$-alkyl-O—, $R^{33}$—O—, $R^{33}$—$(C_1-C_4)$-alkyl-O—, —O—$CH_2$—O—, —O—$CF_2$—O—, $(C_1-C_6)$-alkyl-S(O)$_m$—, di(($C_1-C_4$)-alkyl)N—S(O)$_2$—, $H_2N$—, di(($C_1-C_6$)-alkyl)N—, Het$^1$ and NC—, in another embodiment from the series consisting of halogen, $(C_1-C_6)$-alkyl, $(C_3-C_7)$-cycloalkyl, $R^{33}$, $(C_1-C_6)$-alkyl-O—, $R^{33}$—O—, $R^{33}$—$(C_1-C_4)$-alkyl-O—, $(C_1-C_6)$-alkyl-S(O)$_m$—, di(($C_1-C_4$)-alkyl)N—S(O)$_2$—, di(($C_1-C_6$)-alkyl)N—, Het$^1$ and NC—, in another embodiment from the series consisting of halogen, $(C_1-C_6)$-alkyl, $R^{33}$, $(C_1-C_6)$-alkyl-O— and $R^{33}$—O—, in another embodiment from the series consisting of halogen, $(C_1-C_6)$-alkyl, $R^{33}$ and $(C_1-C_6)$-alkyl-O—, in another embodiment from the series consisting of halogen, $(C_1-C_6)$-alkyl and $R^{33}$, in another embodiment from the series consisting of halogen and $(C_1-C_6)$-alkyl. In one embodiment, in case that substituents from the series consisting of $(C_3-C_7)$-cycloalkyl, $R^{33}$, $R^{33}$—O—, $R^{33}$—$(C_1-C_4)$-alkyl-O—, —O—$CH_2$—O—, —O—$CF_2$—O—, Het$^1$ and Ar—C(O)—NH— are present on a phenyl group and an aromatic heterocycle representing $R^{32}$, not more than two such substituents, in another embodiment not more than one such substituent, are present, either without any other substituents or together with any other substituents.

In one embodiment, a $(C_1-C_6)$-alkyl group occurring in a substituent on a phenyl group and an aromatic heterocycle representing $R^{32}$ is a $(C_1-C_4)$-alkyl group, in another embodiment a $(C_1-C_3)$-alkyl group, in another embodiment a $(C_1-C_2)$-alkyl group, in another embodiment a methyl group. In one embodiment, a $(C_3-C_7)$-cycloalkyl group occurring as a substituent on a phenyl group and an aromatic heterocycle representing $R^{32}$ is a $(C_3-C_6)$-cycloalkyl group, in another embodiment a $(C_3-C_5)$-cycloalkyl group, in another embodiment a $(C_3-C_4)$-cycloalkyl group, in another embodiment it is a cyclopropyl group. In one embodiment, a group Ar occurring in a substituent on a phenyl group and an aromatic heterocycle representing $R^{32}$ is chosen from the series consisting of phenyl and an aromatic 5-membered or 6-membered heterocycle which comprises one or two identical or different ring heteroatoms, in another embodiment one ring heteroatom, chosen from the series consisting of nitrogen, oxygen and sulfur, which is bonded via a ring carbon atom, and in another embodiment it is a phenyl group, which groups all are optionally substituted as indicated with respect to the compounds of formula I in general or in any embodiment specified above or below. In one embodiment, the number of optional substituents on a group Ar occurring in a substituent on a phenyl group and an aromatic heterocycle representing $R^{32}$ is one or two, in another embodiment one, and the optional substituents are chosen from the series consisting of halogen, $(C_1-C_4)$-alkyl, $(C_1-C_4)$-alkyl-O—, $(C_1-C_4)$-alkyl-S(O)$_m$— and NC—, in another embodiment from the series consisting of halogen, $(C_1-C_4)$-alkyl and $(C_1-C_4)$-alkyl-O—, in another embodiment from the series consisting of halogen and $(C_1-C_4)$-alkyl, and in another embodiment such a group Ar is unsubstituted.

In one embodiment, a group Het$^1$ occurring as a substituent on a phenyl group or an aromatic heterocycle representing $R^{32}$ is a saturated or unsaturated 4-membered to 6-membered monocyclic heterocycle, in another embodiment a 5-membered or 6-membered heterocycle, which comprises a ring nitrogen atom via which Het$^1$ is bonded and optionally one or two further ring heteroatoms, in another embodiment one further ring heteroatom, which are chosen from the series consisting of nitrogen, oxygen and sulfur, which is optionally substituted as indicated with respect to the compounds of formula I in general or in any embodiment specified above or below. In one embodiment, a group Het$^1$ occurring as a substituent on a phenyl group or an aromatic heterocycle representing $R^{32}$ does not comprise any further ring heteroatom besides the ring nitrogen atom via which Het$^1$ is bonded. In one embodiment, a group Het$^1$ occurring as a substituent on a phenyl group or an aromatic heterocycle representing $R^{32}$ is saturated, in another embodiment it is unsaturated. In one embodiment, the number of substituents which are optionally present on a group Het$^1$ occurring as a substituent on a phenyl group or an aromatic heterocycle representing $R^{32}$ is one, two, three or four, in another embodiment one, two or three, in another embodiment one or two, in another embodiment one, and in another embodiment such a group Het$^1$ is unsubstituted. In one embodiment, the substituents which are optionally present on a group Het$^1$ occurring as a substituent on a phenyl group or an aromatic heterocycle representing $R^{32}$ are chosen from the series consisting of halogen, $(C_1-C_4)$-alkyl, HO—, $(C_1-C_4)$-alkyl-O— and oxo, in another embodiment from the series consisting of fluorine, $(C_1-C_4)$-alkyl, HO— and oxo, in another embodiment from the series consisting of fluorine, $(C_1-C_4)$-alkyl and oxo, and in another embodiment they are $(C_1-C_4)$-alkyl substituents.

Examples of groups $R^{32}$ from any one or more of which $R^{32}$ is chosen in one embodiment of the invention, are phenyl, 2-fluoro-phenyl, 3-fluoro-phenyl, 4-fluoro-phenyl, 2-chloro-phenyl, 3-chloro-phenyl, 4-chloro-phenyl, 3-bromo-phenyl, 4-bromo-phenyl, 2,3-dichloro-phenyl, 2,4-dichloro-phenyl, 2,5-dichloro-phenyl, 2,6-dichloro-phenyl, 3,4-dichloro-phenyl, 2,3-difluoro-phenyl, 2,4-difluoro-phenyl, 2,5-difluoro-phenyl, 2,6-difluoro-phenyl, 3,4-difluoro-phenyl, 2-chloro-6-fluoro-phenyl, 3,4,5-trifluoro-phenyl, 2-methyl-phenyl (o-tolyl), 3-methyl-phenyl (m-tolyl), 4-methyl-phenyl (p-tolyl), 2,3-dimethyl-phenyl, 2,4-dimethyl-phenyl, 2,5-dimethyl-phenyl, 2,6-dimethyl-phenyl, 3,4-dimethyl-phenyl, 2-ethyl-phenyl, 3-ethyl-phenyl, 4-ethyl-phenyl, 3-isopropyl-phenyl, 3-tert-butyl-phenyl, 4-tert-butyl-phenyl, 3-trifluoromethyl-phenyl, 4-trifluoromethyl-phenyl, 2-fluoro-5-methyl-phenyl, 3-chloro-2-methyl-phenyl, 5-chloro-2-methyl-phenyl, 5-chloro-2-fluoro-3-methyl-phenyl, 2-fluoro-3-trifluoromethyl-phenyl, 2-fluoro-5-trifluoromethyl-phenyl, 4-fluoro-3-trifluoromethyl-phenyl, 5-fluoro-3-trifluoromethyl-phenyl, 3-chloro-4-trifluoromethyl-phenyl, 5-chloro-2-trifluoromethyl-phenyl, 5-chloro-3-trifluoromethyl-phenyl, 2-methoxy-phenyl, 3-methoxy-phenyl, 4-methoxy-phenyl, 3-ethoxy-phenyl, 3-propoxy-phenyl, 3-isopropoxy-phenyl, 4-tert-butoxy-phenyl, 3-trifluoromethoxy-phenyl, 4-trifluoromethoxy-phenyl, 3-(2,2,2-trifluoroethoxy)-phenyl, 5-chloro-2-methoxy-phenyl, 3-chloro-4-methoxy-phenyl, 5-fluoro-3-isopropoxy-phenyl, 2-fluoro-3-trifluoromethoxy-phenyl, 4-methoxy-3,5-dimethyl-phenyl, 3-methoxy-5-trifluoromethyl-phenyl, 2,3-methylenedioxy-phenyl, 2,3-difluoromethylenedioxy-phenyl, 3,4-methylenedioxy-phenyl, 3,4-difluoromethylenedioxy-phenyl, 3-methylsulfanyl-phenyl, 3-ethylsulfanyl-phenyl, 3-trifluoromethylsulfanyl-phenyl, 3-methanesulfonyl-phenyl, 3-ethanesulfonyl-phenyl, 3-sulfamoyl-phenyl, 2-cyano-phenyl, 3-cyano-phenyl, 4-cyano-phenyl, thiophen-2-yl, thiophen-3-yl, 3-chloro-thiophen-2-yl, 4-chloro-thiophen-2-yl, 5-chloro-thiophen-2-yl, 4,5-dichloro-thiophen-2-yl, 5-chloro-thiophen-3-yl, 2,5-dichloro-thiophen-3-yl, 4-methyl-thiophen-2-yl, 5-methyl-thiophen-3-yl, 4,5-dimethyl-thiophen-2-yl, pyridin-2-yl, pyridin-3-yl, pyridin-4-yl, 2-chloro-pyridin-3-yl, 5-chloro-pyridin-2-yl, 6-chloro-pyridin-3-yl, 2-chloro-pyridin-4-yl, 2,6-dichloro-pyridin-3-yl, 6-methoxy-pyridin-3-yl, 2-chloro-6-methoxy-pyridin-3-yl.

In one embodiment of the invention, the group $R^{33}$ is chosen from the series consisting of phenyl and an aromatic 5-membered or 6-membered monocyclic heterocycle which comprises one or two identical or different ring heteroatoms, in another embodiment one ring heteroatom, which is chosen from the series consisting of nitrogen, oxygen and sulfur, and is bonded via a ring carbon atom, wherein the phenyl and the heterocycle all are optionally substituted by one or more identical or different substituents as indicated with respect to the compounds of formula I in general or in any embodiment specified above or below. In one embodiment, the ring heteroatoms in an aromatic heterocycle representing $R^{33}$ are chosen from the series consisting of nitrogen and sulfur, in another embodiment they are nitrogen atoms. In one embodiment, $R^{33}$ is chosen from the series consisting of phenyl and an aromatic 6-membered heterocycle as defined, in another embodiment from the series consisting of phenyl and an aromatic 6-membered heterocycle which comprises one or two nitrogen atoms as ring heteroatoms, in another embodiment $R^{33}$ is a 6-membered monocyclic heterocycle as defined, in another embodiment it is an aromatic 6-membered heterocycle which comprises one or two nitrogen atoms as ring heteroatoms, in another embodiment $R^{33}$ is chosen from the series consisting of phenyl, thiophenyl and pyridinyl, in another embodiment from the series consisting of phenyl and pyridinyl, in another embodiment $R^{33}$ is phenyl, and in another embodiment $R^{33}$ is pyridinyl, all of which are optionally substituted by one or more identical or different substituents as indicated with respect to the compounds of formula I in general or in any embodiment specified above or below. In one embodiment, the number of substituents which are optionally present on a phenyl group and an aromatic heterocycle representing $R^{33}$ is one, two or three, in another embodiment one or two, in another embodiment one.

In one embodiment, the substituents which are optionally present on a phenyl group and an aromatic heterocycle representing $R^{33}$, are chosen from the series consisting of halogen, $(C_1-C_6)$-alkyl, $(C_3-C_7)$-cycloalkyl, HO—, $(C_1-C_6)$-alkyl-O—, $(C_1-C_6)$-alkyl-S(O)$_m$—, $H_2N$—S(O)$_2$—, di(($C_1$-$C_4$)-alkyl)N—S(O)$_2$— and NC—, in another embodiment from the series consisting of halogen, $(C_1-C_6)$-alkyl, $(C_3-C_7)$-cycloalkyl, HO—, $(C_1-C_6)$-alkyl-O—, $H_2N$—S(O)$_2$—, di(($C_1-C_4$)-alkyl)N—S(O)$_2$— and NC—, in another embodiment from the series consisting of halogen, $(C_1-C_6)$-alkyl, $(C_3-C_7)$-cycloalkyl, HO—, $(C_1-C_6)$-alkyl-O— and NC—, are chosen from the series the series consisting of halogen, $(C_1-C_4)$-alkyl, $(C_1-C_4)$-alkyl-O—, $(C_1-C_4)$-alkyl-S(O)$_m$— and NC—, in another embodiment from the series consisting of halogen, $(C_1-C_4)$-alkyl, $(C_1-C_4)$-alkyl-O— and NC—, in another embodiment from the series consisting of halogen, $(C_1-C_4)$-alkyl and $(C_1-C_4)$-alkyl-O—, in another embodiment from the series consisting of halogen and $(C_1-C_4)$-alkyl. In one embodiment, a $(C_1-C_6)$-alkyl group occurring in a substituent on a phenyl group and an aromatic heterocycle representing $R^{33}$ is a $(C_1-C_4)$-alkyl group, in another embodiment a $(C_1-C_3)$-alkyl group, in another embodiment a $(C_1-C_2)$-alkyl group, in another embodiment a methyl group. In one embodiment, a $(C_3-C_7)$-cycloalkyl group occurring as a substituent on a phenyl group and an aromatic heterocycle representing $R^{32}$ is a $(C_3-C_6)$-cycloalkyl group, in another embodiment a $(C_3-C_5)$-cycloalkyl group, in another embodiment a $(C_3-C_4)$-cycloalkyl group, in another embodiment it is a cyclopropyl group.

In one embodiment of the invention, the group $R^{40}$ is chosen from the series consisting of hydrogen and $(C_1-C_2)$-alkyl, in another embodiment from the series consisting of hydrogen and methyl, and in another embodiment $R^{40}$ is hydrogen. In case $R^{30}$ and $R^{40}$ are different and the carbon atom carrying $R^{30}$ and $R^{40}$ thus is chiral, in one embodiment of the invention the compound of the formula I has at this carbon atom pure stereochemical configuration, either R configuration or S configuration, or essentially pure stereochemical configuration, for example with a molar ratio of the two configurations of 99:1 or greater. In case $R^{30}$ is $R^{32}$—$C_uH_{2u}$— and u is 0, i.e. $R^{30}$ is phenyl or an aromatic heterocycle as defined, $R^{40}$ is hydrogen and $R^{50}$ is hydrogen, in one embodiment of the invention the compound of the formula I has at the carbon atom carrying $R^{30}$ and $R^{40}$ pure S configuration, or essentially pure S configuration, for example with a molar ratio of S configuration to R configuration of 99:1 or greater.

In case $R^{30}$ and $R^{40}$ together are a divalent group $(CH_2)_x$, the two groups $R^{30}$ and $R^{40}$ together with the carbon atom carrying them form a cycloalkane ring chosen from cyclopropane, cyclobutane, cyclopentane and cyclohexane, which carries the moieties —C(O)—NH and —C($R^{50}$)($R^{60}$)-G depicted in formula I on the same ring carbon atom. In one embodiment of the invention, the number of $(C_1-C_4)$-alkyl substituents which are optionally present on the group $(CH_2)_x$, is one, two, three or four, in another embodiment one or two, and in another embodiment no alkyl substituents are present on the group $(CH_2)_x$. In one embodiment, a $(C_1-C_4)$-alkyl group occurring as a substituent on the group $(CH_2)_x$ is a methyl group. In one embodiment, the integer x is chosen from the series consisting of 2, 4 and 5, in another embodiment from 4 and 5, in another embodiment x is 2, and in another embodiment x is 4. In one embodiment of the invention, $R^{30}$ and $R^{40}$ together cannot be $(CH_2)_x$, and in this embodiment $R^{30}$ and $R^{40}$ thus only have their other meanings as defined.

In one embodiment of the invention, the group $R^{50}$ is chosen from the series consisting of hydrogen, $(C_1-C_4)$-alkyl and HO—, in another embodiment from the series consisting of hydrogen and $(C_1-C_4)$-alkyl, in another embodiment from the series consisting of hydrogen and $(C_1-C_2)$-alkyl, in another embodiment from the series consisting of hydrogen and methyl, in another embodiment from the series consisting of hydrogen and HO—, and in another embodiment $R^{50}$ is hydrogen.

In one embodiment of the invention, the group $R^{60}$ is chosen from the series consisting of hydrogen and $(C_1-C_4)$-alkyl, in another embodiment from the series consisting of hydrogen and $(C_1-C_3)$-alkyl, in another embodiment from the series consisting of hydrogen and $(C_1-C_2)$-alkyl, in another embodiment from the series consisting of hydrogen and methyl, and in another embodiment $R^{60}$ is hydrogen. In one embodiment of the invention, $R^{50}$ and $R^{60}$ both are hydrogen. In case $R^{50}$ and $R^{60}$ are different and the carbon atom carrying $R^{50}$ and $R^{60}$ thus is chiral, in one embodiment of the invention the compound of the formula I has at this carbon atom pure stereochemical configuration, either R configuration or S configuration, or essentially pure stereochemical configuration, for example with a molar ratio of the two configurations of 99:1 or greater.

In case $R^{50}$ and $R^{60}$ together are a divalent group $(CH_2)_y$, the two groups $R^{50}$ and $R^{60}$ together with the carbon atom carrying them form a cycloalkane ring chosen from cyclopropane, cyclobutane, cyclopentane and cyclohexane, which carries the moieties —$C(R^{30})(R^{40})$— and G depicted in formula I on the same ring carbon atom. In one embodiment of the invention, the number of $(C_1-C_4)$-alkyl substituents which are optionally present on the group $(CH_2)_y$, is one, two, three or four, in another embodiment one or two, and in another embodiment no alkyl substituents are present on the group $(CH_2)_y$. In one embodiment, a $(C_1-C_4)$-alkyl group occurring as a substituent on the group $(CH_2)_y$ is a methyl group. In one embodiment, the integer y is chosen from the series consisting of 2, 4 and 5, in another embodiment from 4 and 5, in another embodiment y is 2, and in another embodiment y is 4. In one embodiment of the invention, $R^{50}$ and $R^{60}$ together cannot be $(CH_2)_y$, and in this embodiment $R^{50}$ and $R^{60}$ thus only have their other meanings as defined. In one embodiment of the invention, $R^{50}$ and $R^{60}$ together cannot be $(CH_2)_y$ if simultaneously $R^{30}$ and $R^{40}$ together are $(CH_2)_x$.

In one embodiment of the invention, the group $R^{71}$ is chosen from the series consisting of hydrogen and $(C_1-C_6)$-alkyl, in another embodiment from the series consisting of hydrogen and $(C_1-C_4)$-alkyl, in another embodiment from the series consisting of hydrogen and $(C_1-C_3)$-alkyl, in another embodiment from the series consisting of hydrogen and $(C_1-C_2)$-alkyl, in another embodiment $R^{71}$ is hydrogen, in another embodiment $R^{71}$ is $(C_1-C_6)$-alkyl, in another embodiment $R^{71}$ is $(C_1-C_4)$-alkyl, in another embodiment $R^{71}$ is $(C_1-C_3)$-alkyl, and in another embodiment $R^{71}$ is $(C_1-C_2)$-alkyl, wherein all these alkyl groups are optionally substituted as indicated with respect to the compounds of formula I in general or in any embodiment specified above or below. In one embodiment, the number of substituents which are optionally present on an alkyl group representing $R^{71}$ is one or two, in another embodiment it is one, in another embodiment an alkyl group representing $R^{71}$ is unsubstituted. In one embodiment, substituents which are optionally present on an alkyl group representing $R^{71}$ are $(C_1-C_6)$-alkyl-O— substituents, in another embodiment $(C_1-C_4)$-alkyl-O— substituents, in another embodiment $(C_1-C_3)$-alkyl-O— substituents, in another embodiment $(C_1-C_6)$-alkyl-C(O)—O— substituents, in another embodiment $(C_1-C_4)$-alkyl-C(O)—O— substituents, in another embodiment $(C_1-C_3)$-alkyl-C(O)—O— substituents.

In one embodiment the group $R^{72}$ is chosen from the series consisting of hydrogen, $(C_1-C_6)$-alkyl, $(C_3-C_6)$-cycloalkyl —$CH_2$—$(CH_2)_b$—$(C_3-C_6)$-cycloalkyl and —$(CH_2)_b$—$Het^4$, where alkyl or cycloalkyl is optionally substituted by one or more identical or different substituents chosen from the series consisting of halogen, HO—, HOOC—, $(C_1-C_6)$-alkyl-O— and $(C_1-C_6)$-alkyl-C(O)—O—, NC—, $N((C_1-C_4)$-alkyl$)_2$ and b is 0, 1 or 2 and the group $R^{73}$ is chosen from the series consisting hydrogen, $(C_1-C_6)$-alkyl.

In another embodiment the groups $R^{72}$ and $R^{73}$ together with the nitrogen atom to which they are bonded form a saturated 4-membered to 7-membered monocyclic heterocycle, which contain optionally one further ring heteroatom chosen from the series consisting of nitrogen, oxygen and sulfur, which is optionally substituted by one or more identical or different substituents chosen from the series consisting of halogen, $(C_1-C_4)$-alkyl, HO— and $(C_1-C_4)$-alkyl-O—.

In another embodiment the group $R^{72}$ is chosen from the series consisting of hydrogen, $(C_1-C_6)$-alkyl, $(C_3-C_6)$-cycloalkyl, $Het^4$ and —$CH_2$—$Het^4$, where alkyl or cycloalkyl is optionally substituted by one or more identical or different substituents chosen from the series consisting of halogen, HO—, HOOC—, $(C_1-C_6)$-alkyl-O— and $(C_1-C_6)$-alkyl-C(O)—O—, NC—, $N((C_1-C_4)$-alkyl$)_2$ and the group $R^{73}$ is chosen from the series consisting hydrogen, $(C_1-C_6)$-alkyl.

In another embodiment the groups $R^{72}$ and $R^{73}$ together with the nitrogen atom to which they are bonded form a saturated 5-membered to 6-membered monocyclic heterocycle, which contain optionally one further ring heteroatom chosen from the series consisting of nitrogen, oxygen and sulfur, which is optionally substituted by one or more identical or different substituents chosen from the series consisting of halogen, $(C_1-C_4)$-alkyl, HO— and $(C_1-C_4)$-alkyl-O—.

In one embodiment the group $R^{72}$ is chosen from the series consisting of hydrogen, $(C_1-C_6)$-alkyl, $(C_3-C_6)$-cycloalkyl and —$CH_2$—$Het^4$, where alkyl or cycloalkyl is optionally substituted by one or more identical or different substituents chosen from the series consisting of halogen, HO—, HOOC—, $(C_1-C_6)$-alkyl-O— and $(C_1-C_6)$-alkyl-C(O)—O—, NC—, $N((C_1-C_4)$-alkyl$)_2$ and the group $R^{73}$ is chosen from the series consisting hydrogen and $(C_1-C_6)$-alkyl.

In another embodiment the groups $R^{72}$ and $R^{73}$ together with the nitrogen atom to which they are bonded form a saturated 5-membered to 6-membered monocyclic heterocycle, which contain no further ring heteroatoms, which is optionally substituted by one or more identical or different substituents chosen from the series consisting of halogen, $(C_1-C_4)$-alkyl, HO— and $(C_1-C_4)$-alkyl-O—.

In one embodiment the group $R^{72}$ is chosen from the series consisting of hydrogen, 2,2-dimethyl-butane-3yl, 2,2-dimethyl-propane-3yl, pentan-3yl, propane-2yl, 2-methyl-propane-2yl, butane-1yl, butane-2yl, 2-methyl-butane-3yl, 2-methyl-butane-2-yl, —$CH_2CHF_2$, —$CHCF_3$, $CH_2CN$, —$CH_2CH_2OCH_3$, —$CH(CH_2OH)CH(CH_3)_2$, —$CH_2C(CH_3)_2$—$CH_2OH$, $CH(C_2H_5)CH_2OCH_3$, $CH_2CH_2CH_2N$ $(CH_3)_2$, cyclopropane, cyclobutane, cyclopentane, cyclohexane and —$CH_2$—$Het^4$ and the group $R^{73}$ is hydrogen. In another embodiment the groups $R^{72}$ and $R^{73}$ together with the nitrogen atom to which they are bonded form pyrrolidine, which is optionally substituted by HO—. In another embodiment the group $R^{72}$ is chosen from the series consisting of hydrogen, $(C_1-C_6)$-alkyl, where alkyl is substituted by one or more times by HO— and the group $R^{73}$ is hydrogen.

In one embodiment of the invention, the groups $R^{72}$ and $R^{73}$ are independently of each other chosen from the series consisting of hydrogen and $(C_1-C_2)$-alkyl, in another embodiment from the series consisting of hydrogen and methyl. In one embodiment, one of the groups $R^{72}$ and $R^{73}$ is hydrogen and the other is chosen from the series consisting of hydrogen and $(C_1-C_4)$-alkyl, in another embodiment from the series consisting of hydrogen and $(C_1-C_2)$-alkyl, in another embodiment from the series consisting of hydrogen an methyl, and in another embodiment both groups $R^{72}$ and $R^{73}$ are hydrogen.

In one embodiment of the invention the group $Het^4$, independently of each other group $Het^4$, is a saturated or unsaturated 4-membered to 8-membered monocyclic heterocycle which comprises one to four ring heteroatoms chosen from the series consisting of nitrogen, oxygen and sulfur which is optionally substituted by one or more identical or different substituents chosen from the series consisting of halogen, $(C_1-C_4)$-alkyl, HO—, $(C_1-C_4)$-alkyl-O—, oxo and NC—;

In another embodiment the group $Het^4$, independently of each other group $Het^4$, is a saturated or unsaturated 5-membered to 6-membered monocyclic heterocycle which comprises one to four ring heteroatoms chosen from the series consisting of nitrogen, oxygen and sulfur which is optionally substituted by one or more identical or different substituents chosen from the series consisting of halogen, $(C_1-C_4)$-alkyl, HO—, $(C_1-C_4)$-alkyl-O—, oxo and NC—;

In another embodiment the group $Het^4$, independently of each other group $Het^4$, is a unsaturated 5-membered to 6-membered monocyclic heterocycle which comprises one to four ring heteroatoms chosen from the series consisting of nitrogen, oxygen and sulfur which is optionally substituted by one or more identical or different substituents chosen from the series consisting of halogen, $(C_1-C_4)$-alkyl, HO—, $(C_1-C_4)$-alkyl-O— and NC—;

In another embodiment the group $Het^4$, independently of each other group $Het^4$, is selected from 1,2-oxadiazolyl, tetrazlolyl, pyrazolyl, furanyl, pyridinyl, pyrizinyl, which is optionally substituted by methyl.

In one embodiment of the invention, a group Ar in any occurrence in the compounds of the formula I, independently of each other group Ar, is chosen from the series consisting of phenyl and an aromatic 5-membered or 6-membered monocyclic heterocycle which comprises one or two identical or different ring heteroatoms, in another embodiment one ring heteroatom, which is chosen from the series consisting of nitrogen, oxygen and sulfur, and which is bonded via a ring carbon atom, in another embodiment Ar is chosen from the series consisting of phenyl and an aromatic 6-membered heterocycle which comprises one or two nitrogen atoms as ring heteroatoms, in another embodiment Ar is chosen from the series consisting of phenyl, thiophenyl and pyridinyl, in another embodiment from the series consisting of phenyl and thiophenyl, in another embodiment from the series consisting of phenyl and pyridinyl, in another embodiment a group Ar is phenyl, and in another embodiment a group Ar is pyridinyl, wherein the phenyl and all heterocycles are optionally substituted as indicated with respect to the compounds of formula I in general or in any embodiment specified above or below. In one embodiment, the number of substituents which are optionally present on a group Ar, independently of each other group Ar, is one, two, three or four, in another embodiment one, two or three, in another embodiment one or two, in another embodiment one, and in another embodiment a group Ar is unsubstituted. In one embodiment, in case that substituents from the series consisting of —O—$CH_2$—O— and —O—$CF_2$—O— are present on a group Ar, not more than two such substituents, in another embodiment not more than one such substituent, are present, either without any other substituents or together with any other substituents.

In one embodiment, the substituents which are optionally present on a group Ar, independently of each other group Ar, are chosen from the series consisting of halogen, $(C_1-C_6)$-alkyl, $(C_1-C_6)$-alkyl-O—, —O—$CH_2$—O—, —O—$CF_2$—O—, $(C_1-C_6)$-alkyl-S(O)$_m$— and NC—, in another embodiment from the series consisting of halogen, $(C_1-C_6)$-alkyl, $(C_1-C_6)$-alkyl-O—, $(C_1-C_6)$-alkyl-S(O)$_m$— and NC—, in another embodiment from the series consisting of halogen, $(C_1-C_6)$-alkyl, $(C_1-C_6)$-alkyl-O— and NC—, in another embodiment from the series consisting of halogen, $(C_1-C_6)$-alkyl and $(C_1-C_6)$-alkyl-O—, in another embodiment from the series consisting of halogen, $(C_1-C_4)$-alkyl and $(C_1-C_4)$-alkyl-O—, in another embodiment from the series consisting of halogen and $(C_1-C_4)$-alkyl.

A subject of the invention are all compounds of the formula I wherein any one or more structural elements such as groups, substituents and numbers are defined as in any of the specified embodiments or definitions of the elements or have one or more of the specific meanings which are mentioned herein as examples of elements, wherein all combinations of one or more specified embodiments and/or definitions and/or specific meanings of the elements are a subject of the present invention. Also with respect to all such compounds of the formula I, all their stereoisomeric forms and mixtures of stereoisomeric forms in any ratios, and their physiologically acceptable salts, and the physiologically acceptable solvates of any of them, are a subject of the present invention.

As an example of compounds of the invention which with respect to any structural elements are defined as in specified embodiments of the invention or definitions of such elements, compounds of the formula I may be mentioned wherein A is chosen from the series consisting of $C(R^1)$ and N;
D is chosen from the series consisting of $N(R^2)$, O and S;
E is N;
$R^1$ is chosen from the series consisting of hydrogen, halogen and $(C_1-C_4)$-alkyl;
$R^2$ is chosen from the series consisting of $(C_3-C_7)$-cycloalkyl-$C_sH_{2s}$— and Ar—$C_sH_{2s}$—, wherein s is an integer chosen from the series consisting of 0, 1 and 2;
and all other groups and numbers are defined as in the general definition of the compounds of the formula I or in any specified embodiments of the invention or definitions of structural elements, in any of their stereoisomeric forms or a mixture of stereoisomeric forms in any ratio, and their physiologically acceptable salts, and the physiologically acceptable solvates of any of them.

As another such example, compounds of the formula I may be mentioned, wherein

A is chosen from the series consisting of $C(R^1)$ and N;
D is $N(R^2)$;
E is N;
$R^1$ is chosen from the series consisting of hydrogen, halogen and $(C_1-C_4)$-alkyl;
$R^2$ is Ar—$C_sH_{2s}$—, wherein s is an integer chosen from the series consisting of 0, 1 and 2;
and all other groups and numbers are defined as in the general definition of the compounds of the formula I or in any specified embodiments of the invention or definitions of structural elements, in any of their stereoisomeric forms or a mixture of stereoisomeric forms in any ratio, and their physiologically acceptable salts, and the physiologically acceptable solvates of any of them.

As another such example, compounds of the formula I may be mentioned, wherein

A is $C(R^1)$;
D is $N(R^2)$;
E is N;
$R^1$ is chosen from the series consisting of hydrogen, halogen and $(C_1-C_4)$-alkyl;
$R^2$ is Ar—$C_sH_{2s}$—, wherein s is 0;
the group Ar in the group $R^2$, irrespective of the meaning of Ar in other positions in the compounds of the formula I, is chosen from the series consisting of phenyl and an aromatic 6-membered heterocycle which comprises one or two nitrogen atoms as ring heteroatoms, wherein the phenyl and the heterocycle are all optionally substituted by one, two or three identical or different substituents chosen from the series consisting of halogen, $(C_1-C_6)$-alkyl, $(C_1-C_6)$-alkyl-O—, $(C_1-C_6)$-alkyl-S(O)$_m$— and NC—;
and all other groups and numbers are defined as in the general definition of the compounds of the formula I or in any specified embodiments of the invention or definitions of structural elements, in any of their stereoisomeric forms or a mixture of stereoisomeric forms in any ratio, and their physiologically acceptable salts, and the physiologically acceptable solvates of any of them.

As another such example, compounds of the formula I may be mentioned, wherein $R^{10}$ is $R^{11}$—O—;
$R^{11}$ is chosen from the series consisting of hydrogen and $R^{14}$;
$R^{14}$ is $(C_1-C_8)$-alkyl which is optionally substituted by one, two or three identical or different substituents chosen from the series consisting of HO—, $R^{16}$—O—, oxo, $(C_3-C_7)$-cycloalkyl, Ar, Het$^1$ and Het$^3$;
$R^{16}$ is $(C_1-C_6)$-alkyl which is optionally substituted by one or two identical or different substituents chosen from the series consisting of HO— and $(C_1-C_4)$-alkyl-O—;
and all other groups and numbers are defined as in the general definition of the compounds of the formula I or in any specified embodiments of the invention or definitions of structural elements, in any of their stereoisomeric forms or a mixture of stereoisomeric forms in any ratio, and their physiologically acceptable salts, and the physiologically acceptable solvates of any of them.

As another such example, compounds of the formula I may be mentioned, wherein

G is chosen from the series consisting of $R^{71}$—O—C(O)— and $R^{72}$—N($R^{73}$)—C(O)—;
$R^{30}$ is $R^{32}$—$C_uH_{2u}$—, wherein u is an integer chosen from the series consisting of 0 and 1;
$R^{32}$ is chosen from the series consisting of phenyl and an aromatic 6-membered monocyclic heterocycle which comprises one or two nitrogen atoms as ring heteroatoms, wherein the phenyl and the heterocycle all are optionally substituted by one, two or three identical or different substituents chosen from the series consisting of halogen, $(C_1-C_6)$-alkyl, $(C_3-C_7)$-cycloalkyl, $R^{33}$, $(C_1-C_6)$-alkyl-O—, $R^{33}$—O—, $R^{33}$—$(C_1-C_4)$-alkyl-O—, —O—$CH_2$—O—, —O—$CF_2$—O—, $(C_1-C_6)$-alkyl-S(O)$_m$—, $(C_1-C_6)$-alkyl-NH—, di(($C_1-C_6$)-alkyl)N—, Het$^1$ and NC—;
$R^{33}$ is chosen from the series consisting of phenyl and pyridinyl which all are optionally substituted by one, two or three identical or different substituents chosen from the series consisting of halogen, $(C_1-C_4)$-alkyl, $(C_1-C_4)$-alkyl-O—, $(C_1-C_4)$-alkyl-S(O)$_m$— and NC—;
$R^{40}$ is hydrogen;
$R^{50}$ is hydrogen;
$R^{60}$ is hydrogen;
and all other groups and numbers are defined as in the general definition of the compounds of the formula I or in any specified embodiments of the invention or definitions of structural elements, in any of their stereoisomeric forms or a mixture of stereoisomeric forms in any ratio, and their physiologically acceptable salts, and the physiologically acceptable solvates of any of them.

As another such example, compounds of the formula I may be mentioned, wherein

A is chosen from the series consisting of $C(R^1)$ and N;
D is $N(R^2)$;
E is chosen from the series consisting of $C(R^3)$ and N;
G is chosen from the series consisting of $R^{71}$—O—C(O)— and $R^{72}$—N($R^{73}$)—C(O)—;
$R^1$ is chosen from the series consisting of hydrogen, halogen, $(C_1-C_6)$-alkyl, HO— and $(C_1-C_6)$-alkyl-O—;
$R^2$ is chosen from the series consisting of $(C_1-C_7)$-alkyl, $(C_3-C_7)$-cycloalkyl-$C_sH_{2s}$— and Ar—$C_sH_{2s}$—, wherein s is an integer chosen from the series consisting of 0, 1, 2 and 3;
$R^3$ is chosen from the series consisting of hydrogen, halogen, $(C_1-C_6)$-alkyl and $(C_1-C_6)$-alkyl-O—;
$R^{10}$ is chosen from the series consisting of $R^{11}$—O—, $R^{12}$—N($R^{13}$)—C(O)—O— and Het$^2$—C(O)—O—;
$R^{11}$ is chosen from the series consisting of hydrogen, $R^{14}$, $(C_3-C_7)$-cycloalkyl and Het$^3$;
$R^{12}$ and $R^{13}$ are independently of each other chosen from the series consisting of hydrogen, $R^{15}$ and Ar;
$R^{14}$ is $(C_{10}-C_{10})$-alkyl which is optionally substituted by one or more identical or different substituents chosen from the series consisting of halogen, HO—, $R^{16}$—O—, oxo, $(C_3-C_7)$-cycloalkyl, Ar, Het$^1$, Het$^3$, NC—, $H_2N$—C(O)—, $(C_1-C_4)$-alkyl-NH—C(O)—, di(($C_1-C_4$)-alkyl)N—C(O)— and Het$^1$—C(O)—;
$R^{15}$ is $(C_1-C_6)$-alkyl;
$R^{16}$ is $(C_1-C_6)$-alkyl which is optionally substituted by one or more identical or different substituents chosen from the series consisting of HO— and $(C_1-C_4)$-alkyl-O—;
$R^{30}$ is chosen from the series consisting of $(C_3-C_7)$-cycloalkyl, $R^{32}$—$C_uH_{2u}$— and Het$^3$—$C_uH_{2u}$—, wherein u is an integer chosen from the series consisting of 0, 1, 2 and 3;
$R^{32}$ is chosen from the series consisting of phenyl and an aromatic 6-membered monocyclic heterocycle which comprises one or two nitrogen atoms as ring heteroatoms, wherein the phenyl and the heterocycle all are optionally substituted by one or more identical or different substituents chosen from the series consisting of halogen, $(C_1-C_6)$-alkyl, $(C_3-C_7)$-cycloalkyl, $R^{33}$, HO—, $(C_1-C_6)$-alkyl-O—, $R^{33}$—O—, $R^{33}$—$(C_1-C_4)$-alkyl-O—, —O—$CH_2$—O—, —O—$CF_2$—O—, $(C_1-C_6)$-alkyl-S(O)$_m$—, di(($C_1-C_4$)-alkyl)N—S(O)$_2$—, $H_2N$—, di(($C_1-C_6$)-alkyl)N—, Het$^1$, $(C_1-C_4)$-alkyl-C(O)—NH—, Ar—C(O)—NH— and NC—;
$R^{33}$ is chosen from the series consisting of phenyl and an aromatic 6-membered monocyclic heterocycle which comprises one or two nitrogen atoms as ring heteroatoms, wherein the phenyl and the heterocycle all are optionally substituted by one or more identical or different substituents chosen from the series consisting of halogen, $(C_1-C_6)$- alkyl, $(C_3\text{-}C_7)$-cycloalkyl, HO—, $(C_1\text{-}C_6)$-alkyl-O—, $(C_1\text{-}C_6)$-alkyl-S(O)$_m$—, H$_2$N—S(O)$_2$—, di(($C_1\text{-}C_4$)-alkyl)N—S(O)$_2$— and NC—;

$R^{40}$ is hydrogen;

$R^{50}$ is chosen from the series consisting of hydrogen and HO—;

$R^{60}$ is hydrogen;

$R^{71}$ is chosen from the series consisting of hydrogen and $(C_1\text{-}C_8)$-alkyl which is optionally substituted by one or more identical or different substituents chosen from the series consisting $(C_1\text{-}C_6)$-alkyl-O— and $(C_1\text{-}C_6)$-alkyl-C(O)—O—;

$R^{72}$ and $R^{73}$ are independently of each other chosen from the series consisting of hydrogen and $(C_1\text{-}C_4)$-alkyl;

Ar, independently of each other group Ar, is chosen from the series consisting of phenyl and an aromatic 5-membered or 6-membered monocyclic heterocycle which comprises one, two or three identical or different ring heteroatoms chosen from the series consisting of nitrogen, oxygen and sulfur and is bonded via a ring carbon atom, wherein the phenyl and the heterocycle all are optionally substituted by one or more identical or different substituents chosen from the series consisting of halogen, $(C_1\text{-}C_6)$-alkyl, $(C_1\text{-}C_6)$-alkyl-O—, —O—CH$_2$—O—, —O—CF$_2$—O—, $(C_1\text{-}C_6)$-alkyl-S(O)$_m$— and NC—;

Het$^1$, independently of each other group Het$^1$, is a saturated or unsaturated 4-membered to 8-membered monocyclic heterocycle which comprises a ring nitrogen atom via which Het$^1$ is bonded and optionally one or two identical or different further ring heteroatoms chosen from the series consisting of nitrogen, oxygen and sulfur, which is optionally substituted by one or more identical or different substituents chosen from the series consisting of halogen, $(C_1\text{-}C_4)$-alkyl, HO—, $(C_1\text{-}C_4)$-alkyl-O—, oxo and NC—;

Het$^2$ is a saturated 4-membered to 7-membered monocyclic heterocycle which comprises a ring nitrogen atom via which Het$^2$ is bonded and optionally one further ring heteroatom chosen from the series consisting of nitrogen, oxygen and sulfur, which is optionally substituted by one or more identical or different substituents chosen from the series consisting of halogen, $(C_1\text{-}C_4)$-alkyl, HO— and $(C_1\text{-}C_4)$-alkyl-O—;

Het$^3$, independently of each other group Het$^3$, is a saturated 4-membered to 7-membered monocyclic heterocycle which comprises one or two identical or different ring heteroatoms chosen from the series consisting of nitrogen, oxygen and sulfur and is bonded via a ring carbon atom, which is optionally substituted by one or more identical or different substituents chosen from the series consisting of fluorine, $(C_1\text{-}C_4)$-alkyl and oxo;

m, independently of each other number m, is an integer chosen from the series consisting of 0, 1 and 2;

wherein all cycloalkyl groups, independently of each other, are optionally substituted by one or more identical or different substituents chosen from the series consisting of fluorine and $(C_1\text{-}C_4)$-alkyl;

wherein all alkyl, $C_sH_{2s}$, $C_uH_{2u}$, $(CH_2)_x$ and $(CH_2)_y$ groups, independently of each other, and independently of any other substituents, are optionally substituted by one or more fluorine substituents;

in any of their stereoisomeric forms or a mixture of stereoisomeric forms in any ratio, and their physiologically acceptable salts, and the physiologically acceptable solvates of any of them.

As another such example, compounds of the formula I may be mentioned, wherein

A is C(R$^1$);

D is N(R$^2$);

E is N;

G is chosen from the series consisting of R$^{71}$—O—C(O)— and R$^{72}$—N(R$^{73}$)—C(O)—;

R$^1$ is chosen from the series consisting of hydrogen, halogen and $(C_1\text{-}C_4)$-alkyl;

R$^2$ is Ar—$C_sH_{2s}$—, wherein s is 0;

R$^{10}$ is R$^{11}$—O—;

R$^{11}$ is chosen from the series consisting of hydrogen and R$^{14}$;

R$^{14}$ is $(C_1\text{-}C_{10})$-alkyl which is optionally substituted by one, two or three identical or different substituents chosen from the series consisting of HO—, R$^{16}$—O—, oxo, $(C_3\text{-}C_7)$-cycloalkyl, Ar, Het$^1$, di(($C_1\text{-}C_4$)-alkyl)N— and Het$^1$—C(O)—;

R$^{16}$ is $(C_1\text{-}C_6)$-alkyl which is optionally substituted by one or two identical or different substituents chosen from the series consisting of HO— and $(C_1\text{-}C_4)$-alkyl-O—;

R$^{30}$ is R$^{32}$—$C_uH_{2u}$—, wherein u is an integer chosen from the series consisting of 0 and 1;

R$^{32}$ is chosen from the series consisting of phenyl and an aromatic 6-membered monocyclic heterocycle which comprises one or two nitrogen atoms as ring heteroatoms, wherein the phenyl and the heterocycle all are optionally substituted by one, two or three identical or different substituents chosen from the series consisting of halogen, $(C_1\text{-}C_6)$-alkyl, $(C_3\text{-}C_7)$-cycloalkyl, R$^{33}$, $(C_1\text{-}C_6)$-alkyl-O—, R$^{33}$—O—, R$^{33}$—$(C_1\text{-}C_4)$-alkyl-O—, —O—CH$_2$—O—, —O—CF$_2$—O—, $(C_1\text{-}C_6)$-alkyl-S(O)$_m$—, di(($C_1\text{-}C_6$)-alkyl)N—, Het$^1$ and NC—;

R$^{33}$ is chosen from the series consisting of phenyl and pyridinyl which all are optionally substituted by one, two or three identical or different substituents chosen from the series consisting of halogen, $(C_1\text{-}C_4)$-alkyl, $(C_1\text{-}C_4)$-alkyl-O—, $(C_1\text{-}C_4)$-alkyl-S(O)$_m$— and NC—;

R$^{40}$ is hydrogen;

R$^{50}$ is hydrogen;

R$^{60}$ is hydrogen;

R$^{71}$ is chosen from the series consisting of hydrogen and $(C_1\text{-}C_8)$-alkyl which is optionally substituted by one substituent chosen from the series consisting $(C_1\text{-}C_6)$-alkyl-O— and $(C_1\text{-}C_6)$-alkyl-C(O)—O—;

R$^{72}$ and R$^{73}$ are independently of each other chosen from the series consisting of hydrogen and $(C_1\text{-}C_2)$-alkyl;

Ar is chosen from the series consisting of phenyl and an aromatic 6-membered heterocycle which comprises one or two nitrogen atoms as ring heteroatoms, wherein the phenyl and the heterocycle are all optionally substituted by one, two or three identical or different substituents chosen from the series consisting of halogen, $(C_1\text{-}C_6)$-alkyl, $(C_1\text{-}C_6)$-alkyl-O—, $(C_1\text{-}C_6)$-alkyl-S(O)$_m$— and NC—;

Het$^1$, independently of each other group Het$^1$, is a saturated or unsaturated 4-membered to 6-membered monocyclic heterocycle which comprises a ring nitrogen atom via which Het$^1$ is bonded and optionally one further ring heteroatom chosen from the series consisting of nitrogen, oxygen and sulfur, which is optionally substituted by one, two or three identical or different substituents chosen from the series consisting of fluorine, $(C_1\text{-}C_4)$-alkyl, HO— and oxo;

m, independently of each other number m, is an integer chosen from the series consisting of 0, 1 and 2;

wherein all cycloalkyl groups, independently of each other, are optionally substituted by one or more identical or different substituents chosen from the series consisting of fluorine and $(C_1\text{-}C_4)$-alkyl;

wherein all alkyl, $C_sH_{2s}$ and $C_uH_{2u}$ groups, independently of each other, and independently of any other substituents, are optionally substituted by one or more fluorine substituents; in any of their stereoisomeric forms or a mixture of stereoisomeric forms in any ratio, and their physiologically acceptable salts, and the physiologically acceptable solvates of any of them.

A subject of the invention also is a compound of the formula I which is chosen from any of the specific compounds of the formula I which are disclosed herein, or is any one of the specific compounds of the formula I which are disclosed herein, irrespective thereof whether they are disclosed as a free compound and/or as a specific salt, or a physiologically acceptable salt thereof, or a physiologically acceptable solvate of any of them, wherein the compound of the formula I is a subject of the invention in any of its stereoisomeric forms or a mixture of stereoisomeric forms in any ratio. For example, a subject of the invention is a compound of the formula I which is chosen from 3-[(5-Hydroxy-1-phenyl-1H-pyrazole-3-carbonyl)-amino]-3-(4-methoxy-phenyl)-propionic acid,
3-(3-tert-Butoxy-phenyl)-3-{[1-(2,5-dimethyl-phenyl)-5-hydroxy-1H-pyrazole-3-carbonyl]-amino}-propionic acid,
(S)-3-{[1-(2-Fluoro-phenyl)-5-methoxy-1H-pyrazole-3-carbonyl]-amino}-3-o-tolyl-propionic acid,
3-(3-Fluoro-2-methyl-phenyl)-3-{[1-(4-fluoro-phenyl)-5-hydroxy-1H-pyrazole-3-carbonyl]-amino}-propionic acid,
3-(2-Chloro-5-fluoro-phenyl)-3-{[1-(4-fluoro-phenyl)-5-hydroxy-1H-pyrazole-3-carbonyl]-amino}-propionic acid,
(S)-3-[(5-Methoxy-1-phenyl-1H-pyrazole-3-carbonyl)-amino]-3-o-tolyl-propionic acid,
3-[(5-Hydroxy-1-phenyl-1H-pyrazole-3-carbonyl)-amino]-3-(2-methoxy-5-trifluoromethyl-phenyl)-propionic acid,
3-(2-Fluoro-4-methyl-phenyl)-3-[(5-hydroxy-1-phenyl-1H-pyrazole-3-carbonyl)-amino]-propionic acid,
3-{[1-(2-Chloro-phenyl)-5-hydroxy-1H-pyrazole-3-carbonyl]-amino}-3-(2'-fluoro-biphenyl-4-yl)-propionic acid,
3-[(5-Methoxy-1-phenyl-1H-pyrazole-3-carbonyl)-amino]-3-(4-pyridin-2-yl-phenyl)-propionic acid,
3-{[1-(2-Fluoro-phenyl)-5-hydroxy-1H-pyrazole-3-carbonyl]-amino}-3-(4-methanesulfonyl-phenyl)-propionic acid,
(S)-3-{[5-Hydroxy-1-(2-methanesulfonyl-phenyl)-1H)-pyrazole-3-carbonyl]-amino}-3-O— tolyl-propionic acid,
3-{[1-(2-Fluoro-phenyl)-5-methoxy-1H-pyrazole-3-carbonyl]-amino}-3-(4-methoxy-2-methyl-phenyl)-propionic acid,
(S)-3-{[1-(2-Fluoro-phenyl)-5-methoxy-1H-pyrazole-3-carbonyl]-amino}-3-(2-trifluoromethyl-phenyl)-propionic acid,
3-(2,3-Dimethyl-phenyl)-3-{[1-(2-fluoro-phenyl)-5-methoxy-1H-pyrazole-3-carbonyl]-amino}-propionic acid,
3-{[5-Cyclopropyl methoxy-1-(2-fluoro-phenyl)-1H-pyrazole-3-carbonyl]-amino}-3-(3-fluoro-2-methyl-phenyl)-propionic acid,
(S)-3-{[5-Cyclopropyl methoxy-1-(2-fluoro-phenyl)-1H-pyrazole-3-carbonyl]-amino}-3-m-tolyl-propionic acid,
(S)-3-{[1-(2-Fluoro-phenyl)-5-((R)-2-hydroxy-3,3-dimethyl-butoxy)-1H-pyrazole-3-carbonyl]-amino}-3-o-tolyl-propionic acid,
(S)-3-{[1-(2-Fluoro-phenyl)-5-((S)-2-hydroxy-3,3-dimethyl-butoxy)-1H-pyrazole-3-carbonyl]-amino}-3-o-tolyl-propionic acid,
(S)-3-{[5-(3,3-Dimethyl-2-oxo-butoxy)-1-(2-fluoro-phenyl)-1H-pyrazole-3-carbonyl]-amino}-3-o-tolyl-propionic acid,
(S)-3-(2,4-Dichloro-phenyl)-3-{[1-(2-fluoro-phenyl)-5-(2-hydroxy-2-methyl-propoxy)-1H-pyrazole-3-carbonyl]-amino}-propionic acid,
(S)-3-{[5-(2-Cyclopropyl-2-hydroxy-propoxy)-1-(2-fluoro-phenyl)-1H-pyrazole-3-carbonyl]-amino}-3-o-tolyl-propionic acid,
(S)-3-{[1-(2-Fluoro-phenyl)-5-((R)-2-hydroxy-2,3,3-trimethyl-butoxy)-1H-pyrazole-3-carbonyl]-amino}-3-o-tolyl-propionic acid,
(S)-3-{[1-(2-Fluoro-phenyl)-5-((S)-2-hydroxy-2,3,3-trimethyl-butoxy)-1H-pyrazole-3-carbonyl]-amino}-3-o-tolyl-propionic acid,
(S)-3-(2-Chloro-phenyl)-3-{[1-(2-fluoro-phenyl)-5-((R)-2-hydroxy-2,3,3-trimethyl-butoxy)-1H-pyrazole-3-carbonyl]-amino}-propionic acid,
(S)-3-(2-Chloro-phenyl)-3-{[1-(2-fluoro-phenyl)-5-((S)-2-hydroxy-2,3,3-trimethyl-butoxy)-1H-pyrazole-3-carbonyl]-amino}-propionic acid,
(S)-3-(2,4-Dichloro-phenyl)-3-{[5-(2-ethyl-2-hydroxy-butoxy)-1-(2-fluoro-phenyl)-1H-pyrazole-3-carbonyl]-amino}-propionic acid,
(S)-3-(2,3-Dimethyl-phenyl)-3-{[1-(2-fluoro-phenyl)-5-((R)-2-hydroxy-3,3-dimethyl-butoxy)-1H-pyrazole-3-carbonyl]-amino}-propionic acid,
(S)-3-(2,4-Dimethyl-phenyl)-3-{[1-(2-fluoro-phenyl)-5-((R)-2-hydroxy-3,3-dimethyl-butoxy)-1H-pyrazole-3-carbonyl]-amino}-propionic acid,
(S)-3-(2,5-Dimethyl-phenyl)-3-{[1-(2-fluoro-phenyl)-5-((R)-2-hydroxy-3,3-dimethyl-butoxy)-1H-pyrazole-3-carbonyl]-amino}-propionic acid,
(S)-3-(2-Chloro-phenyl)-3-{[1-(2-fluoro-phenyl)-5-((R)-2-hydroxy-3,3-dimethyl-butoxy)-1H-pyrazole-3-carbonyl]-amino}-propionic acid,
(S)-3-(2,3-Dichloro-phenyl)-3-{[1-(2-fluoro-phenyl)-5-((R)-2-hydroxy-3,3-dimethyl-butoxy)-1H-pyrazole-3-carbonyl]-amino}-propionic acid,
(S)-3-(2,4-Dichloro-phenyl)-3-{[1-(2-fluoro-phenyl)-5-((R)-2-hydroxy-3,3-dimethyl-butoxy)-1H-pyrazole-3-carbonyl]-amino}-propionic acid,
(S)-3-(2,5-Dichloro-phenyl)-3-{[1-(2-fluoro-phenyl)-5-((R)-2-hydroxy-3,3-dimethyl-butoxy)-1H-pyrazole-3-carbonyl]-amino}-propionic acid,
(S)-3-{[1-(2-Fluoro-phenyl)-5-((R)-2-hydroxy-3,3-dimethyl-butoxy)-1H-pyrazole-3-carbonyl]-amino}-3-(4-methoxy-2-methyl-phenyl)-propionic acid,
(S)-3-{[1-(2-Fluoro-phenyl)-5-((R)-2-hydroxy-3,3-dimethyl-butoxy)-1H-pyrazole-3-carbonyl]-amino}-3-(4-methoxy-phenyl)-propionic acid,
(S)-3-{[1-(2-Fluoro-phenyl)-5-((R)-2-hydroxy-3,3-dimethyl-butoxy)-1H-pyrazole-3-carbonyl]-amino}-3-(4-methanesulfonyl-phenyl)-propionic acid,
(S)-3-(2-Fluoro-phenyl)-3-{[1-(2-fluoro-phenyl)-5-((R)-2-hydroxy-3,3-dimethyl-butoxy)-1H-pyrazole-3-carbonyl]-amino}-propionic acid,
(S)-3-{[1-(2-Fluoro-phenyl)-5-((R)-2-hydroxy-3,3-dimethyl-butoxy)-1H-pyrazole-3-carbonyl]-amino}-3-phenyl-propionic acid,
(S)-3-{[1-(2-Fluoro-phenyl)-5-((R)-2-hydroxy-3,3-dimethyl-butoxy)-1H-pyrazole-3-carbonyl]-amino}-3-(2-trifluoromethyl-phenyl)-propionic acid,
(S)-3-{[1-(2-Fluoro-phenyl)-5-((R)-2-hydroxy-3,3-dimethyl-butoxy)-1H-pyrazole-3-carbonyl]-amino}-3-(4-trifluoromethyl-phenyl)-propionic acid, (S)-3-{[5-((R)-2-Hydroxy-3,3-dimethyl-butoxy)-1-phenyl-1H-pyrazole-3-carbonyl]-amino}-3-o-tolyl-propionic acid,
(S)-3-{[5-((R)-2-Hydroxy-3,3-dimethyl-butoxy)-1-phenyl-1H-pyrazole-3-carbonyl]-amino}-3-p-tolyl-propionic acid,
(S)-3-(2,3-Dimethyl-phenyl)-3-{[5-((R)-2-hydroxy-3,3-dimethyl-butoxy)-1-phenyl-1H-pyrazole-3-carbonyl]-amino}-propionic acid,
(S)-3-{[5-((R)-2-Hydroxy-3,3-dimethyl-butoxy)-1-phenyl-1H-pyrazole-3-carbonyl]-amino}-3-phenyl-propionic acid,
(S)-3-(2-Chloro-phenyl)-3-{[5-((R)-2-hydroxy-3,3-dimethyl-butoxy)-1-phenyl-1H-pyrazole-3-carbonyl]-amino}-propionic acid,
(S)-3-(2,3-Dichloro-phenyl)-3-{[5-((R)-2-hydroxy-3,3-dimethyl-butoxy)-1-phenyl-1H-pyrazole-3-carbonyl]-amino}-propionic acid,
(S)-3-(2,4-Dichloro-phenyl)-3-{[5-((R)-2-hydroxy-3,3-dimethyl-butoxy)-1-phenyl-1H-pyrazole-3-carbonyl]-amino}-propionic acid,
(S)-3-(2,4-Dichloro-phenyl)-3-{[1-(3-fluoro-phenyl)-5-((R)-2-hydroxy-3,3-dimethyl-butoxy)-1H-pyrazole-3-carbonyl]-amino}-propionic acid,
(S)-3-{[1-(3-Fluoro-phenyl)-5-((R)-2-hydroxy-3,3-dimethyl-butoxy)-1H-pyrazole-3-carbonyl]-amino}-3-o-tolyl-propionic acid,
(S)-3-(2,4-Dimethyl-phenyl)-3-{[1-(3-fluoro-phenyl)-5-((R)-2-hydroxy-3,3-dimethyl-butoxy)-1H-pyrazole-3-carbonyl]-amino}-propionic acid,
(S)-3-{[1-(2-Chloro-phenyl)-5-((R)-2-hydroxy-3,3-dimethyl-butoxy)-1H-pyrazole-3-carbonyl]-amino}-3-o-tolyl-propionic acid,
(S)-3-{[1-(2-Chloro-phenyl)-5-((R)-2-hydroxy-3,3-dimethyl-butoxy)-1H-pyrazole-3-carbonyl]-amino}-3-m-tolyl-propionic acid,
(S)-3-{[1-(2-Chloro-phenyl)-5-((R)-2-hydroxy-3,3-dimethyl-butoxy)-1H-pyrazole-3-carbonyl]-amino}-3-m-tolyl-propionic acid,
(S)-3-(2-Chloro-phenyl)-3-{[1-(2-chloro-phenyl)-5-((R)-2-hydroxy-3,3-dimethyl-butoxy)-1H-pyrazole-3-carbonyl]-amino}-propionic acid,
(S)-3-{[1-(2-Chloro-phenyl)-5-((R)-2-hydroxy-3,3-dimethyl-butoxy)-1H-pyrazole-3-carbonyl]-amino}-3-(2,3-dichloro-phenyl)-propionic acid,
(S)-3-{[1-(2-Chloro-phenyl)-5-((R)-2-hydroxy-3,3-dimethyl-butoxy)-1H-pyrazole-3-carbonyl]-amino}-3-(2,4-dichloro-phenyl)-propionic acid,
(S)-3-{[1-(2-Chloro-phenyl)-5-((R)-2-hydroxy-3,3-dimethyl-butoxy)-1H-pyrazole-3-carbonyl]-amino}-3-phenyl-propionic acid,
(S)-3-{[1-(4-Fluoro-phenyl)-5-((R)-2-hydroxy-3,3-dimethyl-butoxy)-1H-pyrazole-3-carbonyl]-amino}-3-phenyl-propionic acid,
(S)-3-{[1-(4-Fluoro-phenyl)-5-((R)-2-hydroxy-3,3-dimethyl-butoxy)-1H-pyrazole-3-carbonyl]-amino}-3-o-tolyl-propionic acid,
(S)-3-(2,3-Dimethyl-phenyl)-3-{[1-(2-fluoro-phenyl)-5-((S)-2-hydroxy-3,3-dimethyl-butoxy)-1H-pyrazole-3-carbonyl]-amino}-propionic acid,
(S)-3-(2,4-Dimethyl-phenyl)-3-{[1-(2-fluoro-phenyl)-5-((S)-2-hydroxy-3,3-dimethyl-butoxy)-1H-pyrazole-3-carbonyl]-amino}-propionic acid,
(S)-3-(2,5-Dimethyl-phenyl)-3-{[1-(2-fluoro-phenyl)-5-((S)-2-hydroxy-3,3-dimethyl-butoxy)-1H-pyrazole-3-carbonyl]-amino}-propionic acid,
(S)-3-(2-Chloro-phenyl)-3-{[1-(2-fluoro-phenyl)-5-((S)-2-hydroxy-3,3-dimethyl-butoxy)-1H-pyrazole-3-carbonyl]-amino}-propionic acid,
(S)-3-(2,3-Dichloro-phenyl)-3-{[1-(2-fluoro-phenyl)-5-((S)-2-hydroxy-3,3-dimethyl-butoxy)-1H-pyrazole-3-carbonyl]-amino}-propionic acid,
(S)-3-(2,4-Dichloro-phenyl)-3-{[1-(2-fluoro-phenyl)-5-((S)-2-hydroxy-3,3-dimethyl-butoxy)-1H-pyrazole-3-carbonyl]-amino}-propionic acid,
(S)-3-(2,5-Dichloro-phenyl)-3-{[1-(2-fluoro-phenyl)-5-((S)-2-hydroxy-3,3-dimethyl-butoxy)-1H-pyrazole-3-carbonyl]-amino}-propionic acid,
(S)-3-{[1-(2-Fluoro-phenyl)-5-((S)-2-hydroxy-3,3-dimethyl-butoxy)-1H-pyrazole-3-carbonyl]-amino}-3-(4-methoxy-2-methyl-phenyl)-propionic acid,
(S)-3-{[1-(2-Fluoro-phenyl)-5-((S)-2-hydroxy-3,3-dimethyl-butoxy)-1H-pyrazole-3-carbonyl]-amino}-3-(4-methoxy-phenyl)-propionic acid,
(S)-3-{[1-(2-Fluoro-phenyl)-5-((S)-2-hydroxy-3,3-dimethyl-butoxy)-1H-pyrazole-3-carbonyl]-amino}-3-(4-methanesulfonyl-phenyl)-propionic acid,
(S)-3-(2-Fluoro-phenyl)-3-{[1-(2-fluoro-phenyl)-5-((S)-2-hydroxy-3,3-dimethyl-butoxy)-1H-pyrazole-3-carbonyl]-amino}-propionic acid,
(S)-3-{[1-(2-Fluoro-phenyl)-5-((S)-2-hydroxy-3,3-dimethyl-butoxy)-1H-pyrazole-3-carbonyl]-amino}-3-phenyl-propionic acid,
(S)-3-{[1-(2-Fluoro-phenyl)-5-((S)-2-hydroxy-3,3-dimethyl-butoxy)-1H-pyrazole-3-carbonyl]-amino}-3-(2-trifluoromethyl-phenyl)-propionic acid,
(S)-3-{[1-(2-Fluoro-phenyl)-5-((S)-2-hydroxy-3,3-dimethyl-butoxy)-1H-pyrazole-3-carbonyl]-amino}-3-(4-trifluoromethyl-phenyl)-propionic acid,
(S)-3-{[5-((S)-2-Hydroxy-3,3-dimethyl-butoxy)-1-phenyl-1H-pyrazole-3-carbonyl]-amino}-3-o-tolyl-propionic acid,
(S)-3-{[5-((S)-2-Hydroxy-3,3-dimethyl-butoxy)-1-phenyl-1H-pyrazole-3-carbonyl]-amino}-3-p-tolyl-propionic acid,
(S)-3-(2,3-Dimethyl-phenyl)-3-{[5-((S)-2-hydroxy-3,3-dimethyl-butoxy)-1-phenyl-1H-pyrazole-3-carbonyl]-amino}-propionic acid,
(S)-3-{[5-((S)-2-Hydroxy-3,3-dimethyl-butoxy)-1-phenyl-1H-pyrazole-3-carbonyl]-amino}-3-phenyl-propionic acid,
(S)-3-(2-Chloro-phenyl)-3-{[5-((S)-2-hydroxy-3,3-dimethyl-butoxy)-1-phenyl-1H-pyrazole-3-carbonyl]-amino}-propionic acid,
(S)-3-(2,3-Dichloro-phenyl)-3-{[5-((S)-2-hydroxy-3,3-dimethyl-butoxy)-1-phenyl-1H-pyrazole-3-carbonyl]-amino}-propionic acid,
(S)-3-(2,4-Dichloro-phenyl)-3-{[5-((S)-2-hydroxy-3,3-dimethyl-butoxy)-1-phenyl-1H-pyrazole-3-carbonyl]-amino}-propionic acid,
(S)-3-(2,4-Dichloro-phenyl)-3-{[1-(3-fluoro-phenyl)-5-((S)-2-hydroxy-3,3-dimethyl-butoxy)-1H-pyrazole-3-carbonyl]-amino}-propionic acid,
(S)-3-{[1-(3-Fluoro-phenyl)-5-((S)-2-hydroxy-3,3-dimethyl-butoxy)-1H-pyrazole-3-carbonyl]-amino}-3-o-tolyl-propionic acid,
(S)-3-(2,4-Dimethyl-phenyl)-3-{[1-(3-fluoro-phenyl)-5-((S)-2-hydroxy-3,3-dimethyl-butoxy)-1H-pyrazole-3-carbonyl]-amino}-propionic acid,
(S)-3-{[1-(2-Chloro-phenyl)-5-((S)-2-hydroxy-3,3-dimethyl-butoxy)-1H-pyrazole-3-carbonyl]-amino}-3-o-tolyl-propionic acid, (S)-3-{[1-(2-Chloro-phenyl)-5-((S)-2-hydroxy-3,3-dimethyl-butoxy)-1H-pyrazole-3-carbonyl]-amino}-3-m-tolyl-propionic acid,
(S)-3-{[1-(2-Chloro-phenyl)-5-((S)-2-hydroxy-3,3-dimethyl-butoxy)-1H-pyrazole-3-carbonyl]-amino}-3-m-tolyl-propionic acid,
(S)-3-(2-Chloro-phenyl)-3-{[1-(2-chloro-phenyl)-5-((S)-2-hydroxy-3,3-dimethyl-butoxy)-1H-pyrazole-3-carbonyl]-amino}-propionic acid,
(S)-3-{[1-(2-Chloro-phenyl)-5-((S)-2-hydroxy-3,3-dimethyl-butoxy)-1H-pyrazole-3-carbonyl]-amino}-3-(2,3-dichloro-phenyl)-propionic acid,
(S)-3-{[1-(2-Chloro-phenyl)-5-((S)-2-hydroxy-3,3-dimethyl-butoxy)-1H-pyrazole-3-carbonyl]-amino}-3-(2,4-dichloro-phenyl)-propionic acid,
(S)-3-{[1-(2-Chloro-phenyl)-5-((S)-2-hydroxy-3,3-dimethyl-butoxy)-1H-pyrazole-3-carbonyl]-amino}-3-phenyl-propionic acid,
(S)-3-{[1-(4-Fluoro-phenyl)-5-((S)-2-hydroxy-3,3-dimethyl-butoxy)-1H-pyrazole-3-carbonyl]-amino}-3-phenyl-propionic acid,
(S)-3-{[1-(4-Fluoro-phenyl)-5-((S)-2-hydroxy-3,3-dimethyl-butoxy)-1H-pyrazole-3-carbonyl]-amino}-3-o-tolyl-propionic acid,
(S)-3-{[1-(2-Fluoro-phenyl)-5-((R)-2-hydroxy-2,3,3-trimethyl-butoxy)-1H-pyrazole-3-carbonyl]-amino}-3-m-tolyl-propionic acid,
(S)-3-{[1-(3-Fluoro-phenyl)-5-((R)-2-hydroxy-2,3,3-trimethyl-butoxy)-1H-pyrazole-3-carbonyl]-amino}-3-o-tolyl-propionic acid,
(S)-3-{[1-(4-Fluoro-phenyl)-5-((R)-2-hydroxy-2,3,3-trimethyl-butoxy)-1H-pyrazole-3-carbonyl]-amino}-3-o-tolyl-propionic acid,
(S)-3-{[1-(2-Chloro-phenyl)-5-((R)-2-hydroxy-2,3,3-trimethyl-butoxy)-1H-pyrazole-3-carbonyl]-amino}-3-o-tolyl-propionic acid,
(S)-3-{[5-((R)-2-Hydroxy-2,3,3-trimethyl-butoxy)-1-phenyl-1H-pyrazole-3-carbonyl]-amino}-3-o-tolyl-propionic acid,
(S)-3-{[1-(2-Chloro-phenyl)-5-((R)-2-hydroxy-2,3,3-trimethyl-butoxy)-1H-pyrazole-3-carbonyl]-amino}-3-m-tolyl-propionic acid,
(S)-3-{[1-(3-Fluoro-phenyl)-5-((R)-2-hydroxy-2,3,3-trimethyl-butoxy)-1H-pyrazole-3-carbonyl]-amino}-3-m-tolyl-propionic acid,
(S)-3-{[5-((R)-2-Hydroxy-2,3,3-trimethyl-butoxy)-1-phenyl-1H-pyrazole-3-carbonyl]-amino}-3-m-tolyl-propionic acid,
(S)-3-{[1-(2-Fluoro-phenyl)-5-((R)-2-hydroxy-2,3,3-trimethyl-butoxy)-1H-pyrazole-3-carbonyl]-amino}-3-p-tolyl-propionic acid,
(S)-3-{[1-(3-Fluoro-phenyl)-5-((R)-2-hydroxy-2,3,3-trimethyl-butoxy)-1H-pyrazole-3-carbonyl]-amino}-3-p-tolyl-propionic acid,
(S)-3-{[1-(4-Fluoro-phenyl)-5-((R)-2-hydroxy-2,3,3-trimethyl-butoxy)-1H-pyrazole-3-carbonyl]-amino}-3-p-tolyl-propionic acid,
(S)-3-{[1-(2-Chloro-phenyl)-5-((R)-2-hydroxy-2,3,3-trimethyl-butoxy)-1H-pyrazole-3-carbonyl]-amino}-3-p-tolyl-propionic acid,
(S)-3-(2,3-Dimethyl-phenyl)-3-{[5-((R)-2-hydroxy-2,3,3-trimethyl-butoxy)-1-phenyl-1H-pyrazole-3-carbonyl]-amino}-propionic acid,
(S)-3-(2,3-Dimethyl-phenyl)-3-{[1-(2-fluoro-phenyl)-5-((R)-2-hydroxy-2,3,3-trimethyl-butoxy)-1H-pyrazole-3-carbonyl]-amino}-propionic acid,
(S)-3-(2,3-Dimethyl-phenyl)-3-{[1-(3-fluoro-phenyl)-5-((R)-2-hydroxy-2,3,3-trimethyl-butoxy)-1H-pyrazole-3-carbonyl]-amino}-propionic acid,
(S)-3-(2,3-Dimethyl-phenyl)-3-{[1-(4-fluoro-phenyl)-5-((R)-2-hydroxy-2,3,3-trimethyl-butoxy)-1H-pyrazole-3-carbonyl]-amino}-propionic acid,
(S)-3-(2,4-Dimethyl-phenyl)-3-{[5-((R)-2-hydroxy-2,3,3-trimethyl-butoxy)-1-phenyl-1H-pyrazole-3-carbonyl]-amino}-propionic acid,
(S)-3-(2,4-Dimethyl-phenyl)-3-{[1-(2-fluoro-phenyl)-5-((R)-2-hydroxy-2,3,3-trimethyl-butoxy)-1H-pyrazole-3-carbonyl]-amino}-propionic acid,
(S)-3-(2,4-Dimethyl-phenyl)-3-{[1-(3-fluoro-phenyl)-5-((R)-2-hydroxy-2,3,3-trimethyl-butoxy)-1H-pyrazole-3-carbonyl]-amino}-propionic acid,
(S)-3-(2,4-Dimethyl-phenyl)-3-{[1-(4-fluoro-phenyl)-5-((R)-2-hydroxy-2,3,3-trimethyl-butoxy)-1H-pyrazole-3-carbonyl]-amino}-propionic acid,
(S)-3-{[1-(2-Chloro-phenyl)-5-((R)-2-hydroxy-2,3,3-trimethyl-butoxy)-1H-pyrazole-3-carbonyl]-amino}-3-(2,4-dimethyl-phenyl)-propionic acid,
(S)-3-(2-Chloro-phenyl)-3-{[5-((R)-2-hydroxy-2,3,3-trimethyl-butoxy)-1-phenyl-1H-pyrazole-3-carbonyl]-amino}-propionic acid,
(S)-3-(2-Chloro-phenyl)-3-{[1-(2-chloro-phenyl)-5-((R)-2-hydroxy-2,3,3-trimethyl-butoxy)-1H-pyrazole-3-carbonyl]-amino}-propionic acid,
(S)-3-(2-Chloro-phenyl)-3-{[1-(3-fluoro-phenyl)-5-((R)-2-hydroxy-2,3,3-trimethyl-butoxy)-1H-pyrazole-3-carbonyl]-amino}-propionic acid,
(S)-3-(2-Chloro-phenyl)-3-{[1-(4-fluoro-phenyl)-5-((R)-2-hydroxy-2,3,3-trimethyl-butoxy)-1H-pyrazole-3-carbonyl]-amino}-propionic acid,
(S)-3-(2,3-Dichloro-phenyl)-3-{[5-((R)-2-hydroxy-2,3,3-trimethyl-butoxy)-1-phenyl-1H-pyrazole-3-carbonyl]-amino}-propionic acid,
(S)-3-(2,3-Dichloro-phenyl)-3-{[1-(2-fluoro-phenyl)-5-((R)-2-hydroxy-2,3,3-trimethyl-butoxy)-1H-pyrazole-3-carbonyl]-amino}-propionic acid,
(S)-3-(2,3-Dichloro-phenyl)-3-{[1-(3-fluoro-phenyl)-5-((R)-2-hydroxy-2,3,3-trimethyl-butoxy)-1H-pyrazole-3-carbonyl]-amino}-propionic acid,
(S)-3-(2,3-Dichloro-phenyl)-3-{[1-(4-fluoro-phenyl)-5-((R)-2-hydroxy-2,3,3-trimethyl-butoxy)-1H-pyrazole-3-carbonyl]-amino}-propionic acid,
(S)-3-(2,4-Dichloro-phenyl)-3-{[5-((R)-2-hydroxy-2,3,3-trimethyl-butoxy)-1-phenyl-1H-pyrazole-3-carbonyl]-amino}-propionic acid,
(S)-3-(2,4-Dichloro-phenyl)-3-{[1-(2-fluoro-phenyl)-5-((R)-2-hydroxy-2,3,3-trimethyl-butoxy)-1H-pyrazole-3-carbonyl]-amino}-propionic acid,
(S)-3-(2,4-Dichloro-phenyl)-3-{[1-(3-fluoro-phenyl)-5-((R)-2-hydroxy-2,3,3-trimethyl-butoxy)-1H-pyrazole-3-carbonyl]-amino}-propionic acid,
(S)-3-(2,4-Dichloro-phenyl)-3-{[1-(4-fluoro-phenyl)-5-((R)-2-hydroxy-2,3,3-trimethyl-butoxy)-1H-pyrazole-3-carbonyl]-amino}-propionic acid,
(S)-3-(2,5-Dichloro-phenyl)-3-{[5-((R)-2-hydroxy-2,3,3-trimethyl-butoxy)-1-phenyl-1H-pyrazole-3-carbonyl]-amino}-propionic acid,
(S)-3-(2,5-Dichloro-phenyl)-3-{[1-(2-fluoro-phenyl)-5-((R)-2-hydroxy-2,3,3-trimethyl-butoxy)-1H-pyrazole-3-carbonyl]-amino}-propionic acid,
(S)-3-{[1-(2-Fluoro-phenyl)-5-((S)-2-hydroxy-2,3,3-trimethyl-butoxy)-1H-pyrazole-3-carbonyl]-amino}-3-m-tolyl-propionic acid, (S)-3-{[1-(3-Fluoro-phenyl)-5-((S)-2-hydroxy-2,3,3-trimethyl-butoxy)-1H-pyrazole-3-carbonyl]-amino}-3-o-tolyl-propionic acid,
(S)-3-{[1-(4-Fluoro-phenyl)-5-((S)-2-hydroxy-2,3,3-trimethyl-butoxy)-1H-pyrazole-3-carbonyl]-amino}-3-o-tolyl-propionic acid,
(S)-3-{[1-(2-Chloro-phenyl)-5-((S)-2-hydroxy-2,3,3-trimethyl-butoxy)-1H-pyrazole-3-carbonyl]-amino}-3-o-tolyl-propionic acid,
(S)-3-{[5-((S)-2-Hydroxy-2,3,3-trimethyl-butoxy)-1-phenyl-1H-pyrazole-3-carbonyl]-amino}-3-o-tolyl-propionic acid,
(S)-3-{[1-(2-Chloro-phenyl)-5-((S)-2-hydroxy-2,3,3-trimethyl-butoxy)-1H-pyrazole-3-carbonyl]-amino}-3-m-tolyl-propionic acid,
(S)-3-{[1-(3-Fluoro-phenyl)-5-((S)-2-hydroxy-2,3,3-trimethyl-butoxy)-1H-pyrazole-3-carbonyl]-amino}-3-m-tolyl-propionic acid,
(S)-3-{[5-((S)-2-Hydroxy-2,3,3-trimethyl-butoxy)-1-phenyl-1H-pyrazole-3-carbonyl]-amino}-3-m-tolyl-propionic acid,
(S)-3-{[1-(2-Fluoro-phenyl)-5-((S)-2-hydroxy-2,3,3-trimethyl-butoxy)-1H-pyrazole-3-carbonyl]-amino}-3-p-tolyl-propionic acid,
(S)-3-{[1-(3-Fluoro-phenyl)-5-((S)-2-hydroxy-2,3,3-trimethyl-butoxy)-1H-pyrazole-3-carbonyl]-amino}-3-p-tolyl-propionic acid,
(S)-3-{[1-(4-Fluoro-phenyl)-5-((S)-2-hydroxy-2,3,3-trimethyl-butoxy)-1H-pyrazole-3-carbonyl]-amino}-3-p-tolyl-propionic acid,
(S)-3-{[1-(2-Chloro-phenyl)-5-((S)-2-hydroxy-2,3,3-trimethyl-butoxy)-1H-pyrazole-3-carbonyl]-amino}-3-p-tolyl-propionic acid,
(S)-3-(2,3-Dimethyl-phenyl)-3-{[5-((S)-2-hydroxy-2,3,3-trimethyl-butoxy)-1-phenyl-1H-pyrazole-3-carbonyl]-amino}-propionic acid,
(S)-3-(2,3-Dimethyl-phenyl)-3-{[1-(2-fluoro-phenyl)-5-((S)-2-hydroxy-2,3,3-trimethyl-butoxy)-1H-pyrazole-3-carbonyl]-amino}-propionic acid,
(S)-3-(2,3-Dimethyl-phenyl)-3-{[1-(3-fluoro-phenyl)-5-((S)-2-hydroxy-2,3,3-trimethyl-butoxy)-1H-pyrazole-3-carbonyl]-amino}-propionic acid,
(S)-3-(2,3-Dimethyl-phenyl)-3-{[1-(4-fluoro-phenyl)-5-((S)-2-hydroxy-2,3,3-trimethyl-butoxy)-1H-pyrazole-3-carbonyl]-amino}-propionic acid,
(S)-3-(2,4-Dimethyl-phenyl)-3-{[5-((S)-2-hydroxy-2,3,3-trimethyl-butoxy)-1-phenyl-1H-pyrazole-3-carbonyl]-amino}-propionic acid,
(S)-3-(2,4-Dimethyl-phenyl)-3-{[1-(2-fluoro-phenyl)-5-((S)-2-hydroxy-2,3,3-trimethyl-butoxy)-1H-pyrazole-3-carbonyl]-amino}-propionic acid,
(S)-3-(2,4-Dimethyl-phenyl)-3-{[1-(3-fluoro-phenyl)-5-((S)-2-hydroxy-2,3,3-trimethyl-butoxy)-1H-pyrazole-3-carbonyl]-amino}-propionic acid,
(S)-3-(2,4-Dimethyl-phenyl)-3-{[1-(4-fluoro-phenyl)-5-((S)-2-hydroxy-2,3,3-trimethyl-butoxy)-1H-pyrazole-3-carbonyl]-amino}-propionic acid,
(S)-3-{[1-(2-Chloro-phenyl)-5-((S)-2-hydroxy-2,3,3-trimethyl-butoxy)-1H-pyrazole-3-carbonyl]-amino}-3-(2,4-dimethyl-phenyl)-propionic acid,
(S)-3-(2-Chloro-phenyl)-3-{[5-((S)-2-hydroxy-2,3,3-trimethyl-butoxy)-1-phenyl-1H-pyrazole-3-carbonyl]-amino}-propionic acid,
(S)-3-(2-Chloro-phenyl)-3-{[1-(2-chloro-phenyl)-5-((S)-2-hydroxy-2,3,3-trimethyl-butoxy)-1H-pyrazole-3-carbonyl]-amino}-propionic acid,
(S)-3-(2-Chloro-phenyl)-3-{[1-(3-fluoro-phenyl)-5-((S)-2-hydroxy-2,3,3-trimethyl-butoxy)-1H-pyrazole-3-carbonyl]-amino}-propionic acid,
(S)-3-(2-Chloro-phenyl)-3-{[1-(4-fluoro-phenyl)-5-((S)-2-hydroxy-2,3,3-trimethyl-butoxy)-1H-pyrazole-3-carbonyl]-amino}-propionic acid,
(S)-3-(2,3-Dichloro-phenyl)-3-{[5-((S)-2-hydroxy-2,3,3-trimethyl-butoxy)-1-phenyl-1H-pyrazole-3-carbonyl]-amino}-propionic acid,
(S)-3-(2,3-Dichloro-phenyl)-3-{[1-(2-fluoro-phenyl)-5-((S)-2-hydroxy-2,3,3-trimethyl-butoxy)-1H-pyrazole-3-carbonyl]-amino}-propionic acid,
(S)-3-(2,3-Dichloro-phenyl)-3-{[1-(3-fluoro-phenyl)-5-((S)-2-hydroxy-2,3,3-trimethyl-butoxy)-1H-pyrazole-3-carbonyl]-amino}-propionic acid,
(S)-3-(2,3-Dichloro-phenyl)-3-{[1-(4-fluoro-phenyl)-5-((S)-2-hydroxy-2,3,3-trimethyl-butoxy)-1H-pyrazole-3-carbonyl]-amino}-propionic acid,
(S)-3-(2,4-Dichloro-phenyl)-3-{[5-((S)-2-hydroxy-2,3,3-trimethyl-butoxy)-1-phenyl-1H-pyrazole-3-carbonyl]-amino}-propionic acid,
(S)-3-(2,4-Dichloro-phenyl)-3-{[1-(2-fluoro-phenyl)-5-((S)-2-hydroxy-2,3,3-trimethyl-butoxy)-1H-pyrazole-3-carbonyl]-amino}-propionic acid,
(S)-3-(2,4-Dichloro-phenyl)-3-{[1-(3-fluoro-phenyl)-5-((S)-2-hydroxy-2,3,3-trimethyl-butoxy)-1H-pyrazole-3-carbonyl]-amino}-propionic acid,
(S)-3-(2,4-Dichloro-phenyl)-3-{[1-(4-fluoro-phenyl)-5-((S)-2-hydroxy-2,3,3-trimethyl-butoxy)-1H-pyrazole-3-carbonyl]-amino}-propionic acid,
(S)-3-(2,5-Dichloro-phenyl)-3-{[5-((S)-2-hydroxy-2,3,3-trimethyl-butoxy)-1-phenyl-1H-pyrazole-3-carbonyl]-amino}-propionic acid,
(S)-3-(2,5-Dichloro-phenyl)-3-{[1-(2-fluoro-phenyl)-5-((S)-2-hydroxy-2,3,3-trimethyl-butoxy)-1H-pyrazole-3-carbonyl]-amino}-propionic acid,
(S)-3-{[1-(2-Fluoro-phenyl)-5-((R)-2-hydroxy-2,3-dimethyl-butoxy)-1H-pyrazole-3-carbonyl]-amino}-3-o-tolyl-propionic acid,
(S)-3-{[5-((R)-2-Hydroxy-2,3-dimethyl-butoxy)-1-phenyl-1H-pyrazole-3-carbonyl]-amino}-3-o-tolyl-propionic acid,
(S)-3-{[1-(3-Fluoro-phenyl)-5-((R)-2-hydroxy-2,3-dimethyl-butoxy)-1H-pyrazole-3-carbonyl]-amino}-3-o-tolyl-propionic acid,
(S)-3-{[1-(4-Fluoro-phenyl)-5-((R)-2-hydroxy-2,3-dimethyl-butoxy)-1H-pyrazole-3-carbonyl]-amino}-3-o-tolyl-propionic acid,
(S)-3-{[1-(2-Chloro-phenyl)-5-((R)-2-hydroxy-2,3-dimethyl-butoxy)-1H-pyrazole-3-carbonyl]-amino}-3-o-tolyl-propionic acid,
(S)-3-{[5-((R)-2-Hydroxy-2,3-dimethyl-butoxy)-1-phenyl-1H-pyrazole-3-carbonyl]-amino}-3-phenyl-propionic acid,
(S)-3-(2-Chloro-phenyl)-3-{[1-(2-fluoro-phenyl)-5-((R)-2-hydroxy-2,3-dimethyl-butoxy)-1H-pyrazole-3-carbonyl]-amino}-propionic acid,
(S)-3-(2-Chloro-phenyl)-3-{[1-(3-fluoro-phenyl)-5-((R)-2-hydroxy-2,3-dimethyl-butoxy)-1H-pyrazole-3-carbonyl]-amino}-propionic acid,
(S)-3-(2,3-Dichloro-phenyl)-3-{[5-((R)-2-hydroxy-2,3-dimethyl-butoxy)-1-phenyl-1H-pyrazole-3-carbonyl]-amino}-propionic acid,
(S)-3-(2,3-Dichloro-phenyl)-3-{[1-(2-fluoro-phenyl)-5-((R)-2-hydroxy-2,3-dimethyl-butoxy)-1H-pyrazole-3-carbonyl]-amino}-propionic acid, S)-3-(2,3-Dichloro-phenyl)-3-{[1-(3-fluoro-phenyl)-5-((R)-2-hydroxy-2,3-dimethyl-butoxy)-1H-pyrazole-3-carbonyl]-amino}-propionic acid, (S)-3-(2,4-Dichloro-phenyl)-3-{[5-((R)-2-hydroxy-2,3-dimethyl-butoxy)-1-phenyl-1H-pyrazole-3-carbonyl]-amino}-propionic acid, (S)-3-(2,4-Dichloro-phenyl)-3-{[1-(2-fluoro-phenyl)-5-((R)-2-hydroxy-2,3-dimethyl-butoxy)-1H-pyrazole-3-carbonyl]-amino}-propionic acid, (S)-3-{[1-(2-Fluoro-phenyl)-5-((R)-2-hydroxy-2,3-dimethyl-butoxy)-1H-pyrazole-3-carbonyl]-amino}-3-p-tolyl-propionic acid, (S)-3-{[5-((R)-2-Hydroxy-2,3-dimethyl-butoxy)-1-phenyl-1H-pyrazole-3-carbonyl]-amino}-3-p-tolyl-propionic acid, S)-3-(2,4-Dimethyl-phenyl)-3-{[5-((R)-2-hydroxy-2,3-dimethyl-butoxy)-1-phenyl-1H-pyrazole-3-carbonyl]-amino}-propionic acid, (S)-3-(2,4-Dimethyl-phenyl)-3-{[1-(2-fluoro-phenyl)-5-((R)-2-hydroxy-2,3-dimethyl-butoxy)-1H-pyrazole-3-carbonyl]-amino}-propionic acid, (S)-3-{[1-(2-Fluoro-phenyl)-5-((S)-2-hydroxy-2,3-dimethyl-butoxy)-1H-pyrazole-3-carbonyl]-amino}-3-o-tolyl-propionic acid, (S)-3-{[5-((S)-2-Hydroxy-2,3-dimethyl-butoxy)-1-phenyl-1H-pyrazole-3-carbonyl]-amino}-3-o-tolyl-propionic acid, (S)-3-{[1-(3-Fluoro-phenyl)-5-((S)-2-hydroxy-2,3-dimethyl-butoxy)-1H-pyrazole-3-carbonyl]-amino}-3-o-tolyl-propionic acid, (S)-3-{[1-(4-Fluoro-phenyl)-5-((S)-2-hydroxy-2,3-dimethyl-butoxy)-1H-pyrazole-3-carbonyl]-amino}-3-o-tolyl-propionic acid, (S)-3-{[1-(2-Chloro-phenyl)-5-((S)-2-hydroxy-2,3-dimethyl-butoxy)-1H-pyrazole-3-carbonyl]-amino}-3-o-tolyl-propionic acid, (S)-3-{[5-((S)-2-Hydroxy-2,3-dimethyl-butoxy)-1-phenyl-1H-pyrazole-3-carbonyl]-amino}-3-phenyl-propionic acid, (S)-3-(2-Chloro-phenyl)-3-{[1-(2-fluoro-phenyl)-5-((S)-2-hydroxy-2,3-dimethyl-butoxy)-1H-pyrazole-3-carbonyl]-amino}-propionic acid, (S)-3-(2-Chloro-phenyl)-3-{[1-(3-fluoro-phenyl)-5-((S)-2-hydroxy-2,3-dimethyl-butoxy)-1H-pyrazole-3-carbonyl]-amino}-propionic acid, (S)-3-(2,3-Dichloro-phenyl)-3-{[5-((S)-2-hydroxy-2,3-dimethyl-butoxy)-1-phenyl-1H-pyrazole-3-carbonyl]-amino}-propionic acid, (S)-3-(2,3-Dichloro-phenyl)-3-{[1-(2-fluoro-phenyl)-5-((S)-2-hydroxy-2,3-dimethyl-butoxy)-1H-pyrazole-3-carbonyl]-amino}-propionic acid, S)-3-(2,3-Dichloro-phenyl)-3-{[1-(3-fluoro-phenyl)-5-((S)-2-hydroxy-2,3-dimethyl-butoxy)-1H-pyrazole-3-carbonyl]-amino}-propionic acid, (S)-3-(2,4-Dichloro-phenyl)-3-{[5-((S)-2-hydroxy-2,3-dimethyl-butoxy)-1-phenyl-1H-pyrazole-3-carbonyl]-amino}-propionic acid, (S)-3-(2,4-Dichloro-phenyl)-3-{[1-(2-fluoro-phenyl)-5-((S)-2-hydroxy-2,3-dimethyl-butoxy)-1H-pyrazole-3-carbonyl]-amino}-propionic acid, (S)-3-{[1-(2-Fluoro-phenyl)-5-((S)-2-hydroxy-2,3-dimethyl-butoxy)-1H-pyrazole-3-carbonyl]-amino}-3-p-tolyl-propionic acid, (S)-3-{[5-((S)-2-Hydroxy-2,3-dimethyl-butoxy)-1-phenyl-1H-pyrazole-3-carbonyl]-amino}-3-p-tolyl-propionic acid, S)-3-(2,4-Dimethyl-phenyl)-3-{[5-((S)-2-hydroxy-2,3-dimethyl-butoxy)-1-phenyl-1H-pyrazole-3-carbonyl]-amino}-propionic acid, (S)-3-(2,4-Dimethyl-phenyl)-3-{[1-(2-fluoro-phenyl)-5-((S)-2-hydroxy-2,3-dimethyl-butoxy)-1H-pyrazole-3-carbonyl]-amino}-propionic acid, (S)-3-{[1-(2-Fluoro-phenyl)-5-(2-hydroxy-2,3-dimethyl-butoxy)-1H-pyrazole-3-carbonyl]-amino}-3-o-tolyl-propionic acid, (S)-3-(4-Fluoro-phenyl)-3-{[1-(2-fluoro-phenyl)-5-((R)-2-hydroxy-2,3,3-trimethyl-butoxy)-1H-pyrazole-3-carbonyl]-amino}-propionic acid, (S)-3-(2,4-Dimethyl-phenyl)-3-{[1-(2-fluoro-phenyl)-5-((S)-2-hydroxy-2,3-dimethyl-butoxy)-1H-pyrazole-3-carbonyl]-amino}-propionic acid, 3-Cyclohexyl-3-{[1-(2-fluoro-phenyl)-5-((S)-2-hydroxy-2,3,3-trimethyl-butoxy)-1H-pyrazole-3-carbonyl]-amino}-propionic acid, (S)-3-(3-Chloro-phenyl)-3-{[1-(2-fluoro-phenyl)-5-((R)-2-hydroxy-2,3,3-trimethyl-butoxy)-1H-pyrazole-3-carbonyl]-amino}-propionic acid, (S)-3-(2-Chloro-phenyl)-3-{[1-(2-fluoro-phenyl)-5-(2-hydroxy-2,3-dimethyl-butoxy)-1H-pyrazole-3-carbonyl]-amino}-propionic acid, (S)-3-(2,3-Dichloro-phenyl)-3-{[1-(2-fluoro-phenyl)-5-((R)-2-hydroxy-3,3-dimethyl-butoxy)-1H-pyrazole-3-carbonyl]-amino}-propionic acid, (S)-3-(2-Chloro-phenyl)-3-{[5-(3,3-dimethyl-2-oxo-butoxy)-1-(2-fluoro-phenyl)-1H-pyrazole-3-carbonyl]-amino}-propionic acid, (S)-3-(3-Cyano-phenyl)-3-{[1-(2-fluoro-phenyl)-5-((R)-2-hydroxy-2,3,3-trimethyl-butoxy)-1H-pyrazole-3-carbonyl]-amino}-propionic acid, (S)-3-(3-Fluoro-phenyl)-3-{[1-(2-fluoro-phenyl)-5-((R)-2-hydroxy-2,3,3-trimethyl-butoxy)-1H-pyrazole-3-carbonyl]-amino}-propionic acid, (S)-3-{[1-(2-Fluoro-phenyl)-5-((R)-2-hydroxy-2,3,3-trimethyl-butoxy)-1H-pyrazole-3-carbonyl]-amino}-3-p-tolyl-propionic acid, (S)-3-{[1-(2-Fluoro-phenyl)-5-((S)-2-hydroxy-2,3,3-trimethyl-butoxy)-1H-pyrazole-3-carbonyl]-amino}-3-p-tolyl-propionic acid, (S)-3-(3-Fluoro-phenyl)-3-{[1-(2-fluoro-phenyl)-5-(2-hydroxy-2,3-dimethyl-butoxy)-1H-pyrazole-3-carbonyl]-amino}-propionic acid, (S)-3-{[1-(2-Fluoro-phenyl)-5-((S)-2-hydroxy-2,3-dimethyl-butoxy)-1H-pyrazole-3-carbonyl]-amino}-3-(2-methoxy-phenyl)-propionic acid, (S)-3-{[1-(2-Fluoro-phenyl)-5-((S)-2-hydroxy-2,3-dimethyl-butoxy)-1H-pyrazole-3-carbonyl]-amino}-3-(2-trifluoromethyl-phenyl)-propionic acid, (S)-3-(3-Chloro-phenyl)-3-{[1-(2-fluoro-phenyl)-5-(2-hydroxy-2,3-dimethyl-butoxy)-1H-pyrazole-3-carbonyl]-amino}-propionic acid, 3-Cyclohexyl-3-{[1-(2-fluoro-phenyl)-5-((R)-2-hydroxy-2,3-dimethyl-butoxy)-1H-pyrazole-3-carbonyl]-amino}-propionic acid, (S)-3-{[1-(2-Fluoro-phenyl)-5-(2-hydroxy-2,3-dimethyl-butoxy)-1H-pyrazole-3-carbonyl]-amino}-3-p-tolyl-propionic acid (S)-3-{[1-(2-Fluoro-phenyl)-5-((R)-2-hydroxy-3,3-dimethyl-butoxy)-1H-pyrazole-3-carbonyl]-amino}-3-p-tolyl-propionic acid, (S)-3-(2-Chloro-phenyl)-3-{[1-(2-fluoro-phenyl)-5-((S)-2-hydroxy-2,3,3-trimethyl-butoxy)-1H-pyrazole-3-carbonyl]-amino}-propionic acid, (S)-3-(2-Chloro-phenyl)-3-{[1-(2-fluoro-phenyl)-5-((R)-2-hydroxy-2,3,3-trimethyl-butoxy)-1H-pyrazole-3-carbonyl]-amino}-propionic acid, (S)-3-{[5-(3,3-Dimethyl-2-oxo-butoxy)-1-(2-fluoro-phenyl)-1H-pyrazole-3-carbonyl]-amino}-3-p-tolyl-propionic acid, (S)-3-{[1-(2-Fluoro-phenyl)-5-((S)-2-hydroxy-3,3-dimethyl-butoxy)-1H-pyrazole-3-carbonyl]-amino}-3-m-tolyl-propionic acid, (S)-3-(2-Chloro-phenyl)-3-{[1-(2-fluoro-phenyl)-5-((R)-2-hydroxy-3,3-dimethyl-butoxy)-1H-pyrazole-3-carbonyl]-amino}-propionic acid, (S)-3-(4-Chloro-phenyl)-3-{[1-(2-fluoro-phenyl)-5-((S)-2-hydroxy-3,3-dimethyl-butoxy)-1H-pyrazole-3-carbonyl]-amino}-propionic acid, (S)-3-(3-Chloro-phenyl)-3-{[1-(2-fluoro-phenyl)-5-((R)-2-hydroxy-3,3-dimethyl-butoxy)-1H-pyrazole-3-carbonyl]-amino}-propionic acid, (S)-3-(3-Chloro-phenyl)-3-{[5-(3,3-dimethyl-2-oxo-butoxy)-1-(2-fluoro-phenyl)-1H-pyrazole-3-carbonyl]-amino}-propionic acid, (S)-3-(2-Chloro-phenyl)-3-{[1-(2-fluoro-phenyl)-5-((S)-2-hydroxy-3,3-dimethyl-butoxy)-1H-pyrazole-3-carbonyl]-amino}-propionic acid, (S)-3-(3-Chloro-phenyl)-3-{[1-(2-fluoro-phenyl)-5-((S)-2-hydroxy-2,3,3-trimethyl-butoxy)-1H-pyrazole-3-carbonyl]-amino}-propionic acid, (S)-3-{[1-(2-Fluoro-phenyl)-5-((S)-2-hydroxy-2,3,3-trimethyl-butoxy)-1H-pyrazole-3-carbonyl]-amino}-3-(2-trifluoromethyl-phenyl)-propionic acid, (S)-3-(2,3-Dichloro-phenyl)-3-{[1-(2-fluoro-phenyl)-5-((S)-2-hydroxy-3,3-dimethyl-butoxy)-1H-pyrazole-3-carbonyl]-amino}-propionic acid, (S)-3-{[1-(2-Fluoro-phenyl)-5-((S)-2-hydroxy-3,3-dimethyl-butoxy)-1H-pyrazole-3-carbonyl]-amino}-3-p-tolyl-propionic acid, (S)-3-{[1-(2-Fluoro-phenyl)-5-(2-hydroxy-2,3-dimethyl-butoxy)-1H-pyrazole-3-carbonyl]-amino}-3-(3-methoxy-phenyl)-propionic acid, 3-Cyclohexyl-3-{[1-(2-fluoro-phenyl)-5-((S)-2-hydroxy-2,3-dimethyl-butoxy)-1H-pyrazole-3-carbonyl]-amino}-propionic acid, (S)-3-{[1-(2-Fluoro-phenyl)-5-((R)-2-hydroxy-3,3-dimethyl-butoxy)-1H-pyrazole-3-carbonyl]-amino}-3-m-tolyl-propionic acid, (S)-3-{[5-(3,3-Dimethyl-2-oxo-butoxy)-1-(2-fluoro-phenyl)-1H-pyrazole-3-carbonyl]-amino}-3-m-tolyl-propionic acid, (S)-3-{[1-(2-Fluoro-phenyl)-5-((R)-2-hydroxy-2,3-dimethyl-butoxy)-1H-pyrazole-3-carbonyl]-amino}-3-(3-methoxy-phenyl)-propionic acid, (S)-3-(3-Cyano-phenyl)-3-{[1-(2-fluoro-phenyl)-5-(2-hydroxy-2,3-dimethyl-butoxy)-1H-pyrazole-3-carbonyl]-amino}-propionic acid, (S)-3-(2,6-Difluoro-phenyl)-3-{[1-(2-fluoro-phenyl)-5-(2-hydroxy-2,3-dimethyl-butoxy)-1H-pyrazole-3-carbonyl]-amino}-propionic acid, (S)-3-(3-Chloro-phenyl)-3-{[1-(2-fluoro-phenyl)-5-((S)-2-hydroxy-3,3-dimethyl-butoxy)-1H-pyrazole-3-carbonyl]-amino}-propionic acid, (S)-3-{[1-(2-Fluoro-phenyl)-5-((S)-2-hydroxy-2,3,3-trimethyl-butoxy)-1H-pyrazole-3-carbonyl]-amino}-3-(2-methoxy-phenyl)-propionic acid, (S)-3-{[1-(2-Fluoro-phenyl)-5-(2-hydroxy-2,3-dimethyl-butoxy)-1H-pyrazole-3-carbonyl]-amino}-3-(2-methoxy-phenyl)-propionic acid, (S)-3-{[1-(2-Fluoro-phenyl)-5-(2-hydroxy-2,3-dimethyl-butoxy)-1H-pyrazole-3-carbonyl]-amino}-3-(2-trifluoromethyl-phenyl)-propionic acid, 3-Cyclohexyl-3-{[1-(2-fluoro-phenyl)-5-(2-hydroxy-2,3-dimethyl-butoxy)-1H-pyrazole-3-carbonyl]-amino}-propionic acid, 3-{[1-(2-Fluoro-phenyl)-5-(2-hydroxy-2,3-dimethyl-butoxy)-1H-pyrazole-3-carbonyl]-amino}-5-methyl-hexanoic acid, (R)-3-(4-Chloro-phenyl)-3-{[1-(2-fluoro-phenyl)-5-(2-hydroxy-3,3-dimethyl-butoxy)-1H-pyrazole-3-carbonyl]-amino}-propionic acid, (S)-3-(2,4-Dichloro-phenyl)-3-{[1-(2-fluoro-phenyl)-5-((R)-2-hydroxy-2,3-dimethyl-butoxy)-1H-pyrazole-3-carbonyl]-amino}-propionic acid, (S)-3-(2,6-Difluoro-phenyl)-3-{[1-(2-fluoro-phenyl)-5-((S)-2-hydroxy-2,3-dimethyl-butoxy)-1H-pyrazole-3-carbonyl]-amino}-propionic acid, 3-{[1-(2-Fluoro-phenyl)-5-((S)-2-hydroxy-2,3,3-trimethyl-butoxy)-1H-pyrazole-3-carbonyl]-amino}-4-phenyl-butyric acid, (S)-3-(3-Fluoro-phenyl)-3-{[1-(2-fluoro-phenyl)-5-((S)-2-hydroxy-2,3,3-trimethyl-butoxy)-1H-pyrazole-3-carbonyl]-amino}-propionic acid, 3-Cyclohexyl-3-{[1-(2-fluoro-phenyl)-5-((R)-2-hydroxy-2,3,3-trimethyl-butoxy)-1H-pyrazole-3-carbonyl]-amino}-propionic acid, 3-{[1-(2-Fluoro-phenyl)-5-((R)-2-hydroxy-2,3-dimethyl-butoxy)-1H-pyrazole-3-carbonyl]-amino}-4-phenyl-butyric acid, (S)-3-{[1-(2-Fluoro-phenyl)-5-((R)-2-hydroxy-2,3-dimethyl-butoxy)-1H-pyrazole-3-carbonyl]-amino}-3-(2-methoxy-phenyl)-propionic acid, 3-{[1-(2-Fluoro-phenyl)-5-((R)-2-hydroxy-2,3-dimethyl-butoxy)-1H-pyrazole-3-carbonyl]-amino}-5-methyl-hexanoic acid, (1-{[1-(2-Fluoro-phenyl)-5-((R)-2-hydroxy-2,3-dimethyl-butoxy)-1H-pyrazole-3-carbonyl]-amino}-cyclopentyl)-acetic acid, (1-{[1-(2-Fluoro-phenyl)-5-((S)-2-hydroxy-2,3-dimethyl-butoxy)-1H-pyrazole-3-carbonyl]-amino}-cyclopentyl)-acetic acid, 3-{[1-(2-Fluoro-phenyl)-5-((S)-2-hydroxy-2,3-dimethyl-butoxy)-1H-pyrazole-3-carbonyl]-amino}-4-phenyl-butyric acid, 3-{[1-(2-Fluoro-phenyl)-5-((R)-2-hydroxy-2,3-dimethyl-butoxy)-1H-pyrazole-3-carbonyl]-amino}-2-phenyl-propionic acid, (S)-3-(4-Chloro-phenyl)-3-{[1-(2-fluoro-phenyl)-5-((R)-2-hydroxy-3,3-dimethyl-butoxy)-1H-pyrazole-3-carbonyl]-amino}-propionic acid, 3-{[1-(2-Fluoro-phenyl)-5-(2-hydroxy-2,3-dimethyl-butoxy)-1H-pyrazole-3-carbonyl]-amino}-4-phenyl-butyric acid, 3-{[1-(2-Fluoro-phenyl)-5-((S)-2-hydroxy-2,3-dimethyl-butoxy)-1H-pyrazole-3-carbonyl]-amino}-2-phenyl-propionic acid, (S)-4-(4-Cyano-phenyl)-3-{[1-(2-fluoro-phenyl)-5-((S)-2-hydroxy-2,3,3-trimethyl-butoxy)-1H-pyrazole-3-carbonyl]-amino}-butyric acid, (S)-3-{[1-(2-Fluoro-phenyl)-5-((S)-2-hydroxy-2,3-dimethyl-butoxy)-1H-pyrazole-3-carbonyl]-amino}-3-o-tolyl-propionic acid, (S)-4-(4-Cyano-phenyl)-3-{[1-(2-fluoro-phenyl)-5-((S)-2-hydroxy-2,3-dimethyl-butoxy)-1H-pyrazole-3-carbonyl]-amino}-butyric acid, (S)-3-(2-Fluoro-phenyl)-3-{[1-(2-fluoro-phenyl)-5-((S)-2-hydroxy-2,3-dimethyl-butoxy)-1H-pyrazole-3-carbonyl]-amino}-propionic acid,
(S)-4-(4-Cyano-phenyl)-3-{[1-(2-fluoro-phenyl)-5-(2-hydroxy-2,3-dimethyl-butoxy)-1H-pyrazole-3-carbonyl]-amino}-butyric acid,
(S)-3-{[1-(2-Fluoro-phenyl)-5-((S)-2-hydroxy-2,3-dimethyl-butoxy)-1H-pyrazole-3-carbonyl]-amino}-4-phenyl-butyric acid,
(S)-3-{[1-(2-Fluoro-phenyl)-5-(2-hydroxy-2,3-dimethyl-butoxy)-1H-pyrazole-3-carbonyl]-amino}-4-phenyl-butyric acid,
(S)-3-(2,3-Dichloro-phenyl)-3-{[5-(3,3-dimethyl-2-oxo-butoxy)-1-(2-fluoro-phenyl)-1H-pyrazole-3-carbonyl]-amino}-propionic acid,
(S)-3-{[1-(2-Fluoro-phenyl)-5-((S)-2-hydroxy-2,3-dimethyl-butoxy)-1H-pyrazole-3-carbonyl]-amino}-3-(4-methoxy-phenyl)-propionic acid,
(S)-3-{[1-(2-Fluoro-phenyl)-5-((S)-2-hydroxy-2,3-dimethyl-butoxy)-1H-pyrazole-3-carbonyl]-amino}-5-methyl-hexanoic acid,
(S)-3-{[1-(2-Fluoro-phenyl)-5-(2-hydroxy-2,3-dimethyl-butoxy)-1H-pyrazole-3-carbonyl]-amino}-5-methyl-hexanoic acid,
(1-{[1-(2-Fluoro-phenyl)-5-(2-hydroxy-2,3-dimethyl-butoxy)-1H-pyrazole-3-carbonyl]-amino}-cyclopentyl)-acetic acid,
(S)-3-(4-Fluoro-phenyl)-3-{[1-(2-fluoro-phenyl)-5-(2-hydroxy-2,3-dimethyl-butoxy)-1H-pyrazole-3-carbonyl]-amino}-propionic acid,
(S)-3-(2,4-Dimethyl-phenyl)-3-{[1-(2-fluoro-phenyl)-5-(2-hydroxy-2,3-dimethyl-butoxy)-1H-pyrazole-3-carbonyl]-amino}-propionic acid,
(S)-3-(2-Fluoro-phenyl)-3-{[1-(2-fluoro-phenyl)-5-(2-hydroxy-2,3-dimethyl-butoxy)-1H-pyrazole-3-carbonyl]-amino}-propionic acid,
(S)-3-(2,3-Dimethoxy-phenyl)-3-{[1-(2-fluoro-phenyl)-5-(2-hydroxy-2,3-dimethyl-butoxy)-1H-pyrazole-3-carbonyl]-amino}-propionic acid,
(S)-3-{[1-(2-Fluoro-phenyl)-5-(2-hydroxy-2,3-dimethyl-butoxy)-1H-pyrazole-3-carbonyl]-amino}-3-(4-methoxy-phenyl)-propionic acid,
(S)-3-(2,4-Dichloro-phenyl)-3-{[1-(2-fluoro-phenyl)-5-((S)-2-hydroxy-2,3-dimethyl-butoxy)-1H-pyrazole-3-carbonyl]-amino}-propionic acid,
(S)-3-{[1-(2-Fluoro-phenyl)-5-((R)-2-hydroxy-2,3-dimethyl-butoxy)-1H-pyrazole-3-carbonyl]-amino}-3-(4-methoxy-phenyl)-propionic acid,
3-{[1-(2-Fluoro-phenyl)-5-((S)-2-hydroxy-2,3,3-trimethyl-butoxy)-1H-pyrazole-3-carbonyl]-amino}-5-methyl-hexanoic acid,
(S)-3-{[1-(2-Fluoro-phenyl)-5-((S)-2-hydroxy-2,3,3-trimethyl-butoxy)-1H-pyrazole-3-carbonyl]-amino}-4-phenyl-butyric acid,
(1-{[1-(2-Fluoro-phenyl)-5-((R)-2-hydroxy-2,3,3-trimethyl-butoxy)-1H-pyrazole-3-carbonyl]-amino}-cyclopentyl)-acetic acid,
(S)-3-(2-Fluoro-phenyl)-3-{[1-(2-fluoro-phenyl)-5-((R)-2-hydroxy-2,3,3-trimethyl-butoxy)-1H-pyrazole-3-carbonyl]-amino}-propionic acid,
(S)-3-(2,3-Dimethoxy-phenyl)-3-{[1-(2-fluoro-phenyl)-5-((R)-2-hydroxy-2,3,3-trimethyl-butoxy)-1H-pyrazole-3-carbonyl]-amino}-propionic acid,
(S)-3-{[1-(2-Fluoro-phenyl)-5-((R)-2-hydroxy-2,3,3-trimethyl-butoxy)-1H-pyrazole-3-carbonyl]-amino}-3-(3-methoxy-phenyl)-propionic acid,
(S)-3-{[1-(2-Fluoro-phenyl)-5-((R)-2-hydroxy-2,3-dimethyl-butoxy)-1H-pyrazole-3-carbonyl]-amino}-3-o-tolyl-propionic acid,
(S)-3-{[1-(2-Fluoro-phenyl)-5-((R)-2-hydroxy-2,3-dimethyl-butoxy)-1H-pyrazole-3-carbonyl]-amino}-5-methyl-hexanoic acid,
(S)-3-(2,4-Dimethyl-phenyl)-3-{[1-(2-fluoro-phenyl)-5-((R)-2-hydroxy-2,3-dimethyl-butoxy)-1H-pyrazole-3-carbonyl]-amino}-propionic acid,
(S)-3-{[1-(2-Fluoro-phenyl)-5-((R)-2-hydroxy-2,3-dimethyl-butoxy)-1H-pyrazole-3-carbonyl]-amino}-3-p-tolyl-propionic acid,
(S)-3-(2-Chloro-phenyl)-3-{[1-(2-fluoro-phenyl)-5-((R)-2-hydroxy-2,3-dimethyl-butoxy)-1H-pyrazole-3-carbonyl]-amino}-propionic acid,
(S)-3-(2-Fluoro-phenyl)-3-{[1-(2-fluoro-phenyl)-5-((R)-2-hydroxy-2,3-dimethyl-butoxy)-1H-pyrazole-3-carbonyl]-amino}-propionic acid,
(S)-3-{[1-(2-Fluoro-phenyl)-5-((R)-2-hydroxy-2,3-dimethyl-butoxy)-1H-pyrazole-3-carbonyl]-amino}-3-(2-trifluoromethyl-phenyl)-propionic acid,
(S)-3-{[1-(2-Fluoro-phenyl)-5-((R)-2-hydroxy-2,3-dimethyl-butoxy)-1H-pyrazole-3-carbonyl]-amino}-4-phenyl-butyric acid,
(S)-3-(3-Cyano-phenyl)-3-{[1-(2-fluoro-phenyl)-5-((R)-2-hydroxy-2,3-dimethyl-butoxy)-1H-pyrazole-3-carbonyl]-amino}-propionic acid,
(S)-3-(2,3-Dimethoxy-phenyl)-3-{[1-(2-fluoro-phenyl)-5-((R)-2-hydroxy-2,3-dimethyl-butoxy)-1H-pyrazole-3-carbonyl]-amino}-propionic acid,
(S)-4-(4-Cyano-phenyl)-3-{[1-(2-fluoro-phenyl)-5-((R)-2-hydroxy-2,3-dimethyl-butoxy)-1H-pyrazole-3-carbonyl]-amino}-butyric acid,
(S)-3-(2,6-Difluoro-phenyl)-3-{[1-(2-fluoro-phenyl)-5-((R)-2-hydroxy-2,3-dimethyl-butoxy)-1H-pyrazole-3-carbonyl]-amino}-propionic acid,
(S)-3-(3-Fluoro-phenyl)-3-{[1-(2-fluoro-phenyl)-5-((R)-2-hydroxy-2,3-dimethyl-butoxy)-1H-pyrazole-3-carbonyl]-amino}-propionic acid,
(S)-3-{[1-(2-Fluoro-phenyl)-5-((S)-2-hydroxy-2,3-dimethyl-butoxy)-1H-pyrazole-3-carbonyl]-amino}-3-o-tolyl-propionic acid,
3-{[1-(2-Fluoro-phenyl)-5-((S)-2-hydroxy-2,3-dimethyl-butoxy)-1H-pyrazole-3-carbonyl]-amino}-5-methyl-hexanoic acid,
(S)-3-(4-Fluoro-phenyl)-3-{[1-(2-fluoro-phenyl)-5-((S)-2-hydroxy-2,3-dimethyl-butoxy)-1H-pyrazole-3-carbonyl]-amino}-propionic acid,
(S)-3-(2-Chloro-phenyl)-3-{[1-(2-fluoro-phenyl)-5-((S)-2-hydroxy-2,3-dimethyl-butoxy)-1H-pyrazole-3-carbonyl]-amino}-propionic acid,
(S)-3-(3-Cyano-phenyl)-3-{[1-(2-fluoro-phenyl)-5-((S)-2-hydroxy-2,3-dimethyl-butoxy)-1H-pyrazole-3-carbonyl]-amino}-propionic acid,
(S)-3-{[1-(2-Fluoro-phenyl)-5-((S)-2-hydroxy-2,3-dimethyl-butoxy)-1H-pyrazole-3-carbonyl]-amino}-3-(3-methoxy-phenyl)-propionic acid,
(S)-3-(3-Fluoro-phenyl)-3-{[1-(2-fluoro-phenyl)-5-((S)-2-hydroxy-2,3-dimethyl-butoxy)-1H-pyrazole-3-carbonyl]-amino}-propionic acid,
(S)-3-(3-Chloro-phenyl)-3-{[1-(2-fluoro-phenyl)-5-((S)-2-hydroxy-2,3-dimethyl-butoxy)-1H-pyrazole-3-carbonyl]-amino}-propionic acid,
(S)-3-{[1-(2-Fluoro-phenyl)-5-((S)-2-hydroxy-2,3,3-trimethyl-butoxy)-1H-pyrazole-3-carbonyl]-amino}-5-methyl-hexanoic acid, (1-{[1-(2-Fluoro-phenyl)-5-((S)-2-hydroxy-2,3,3-trimethyl-butoxy)-1H-pyrazole-3-carbonyl]-amino}cyclopentyl)-acetic acid, (S)-3-(4-Fluoro-phenyl)-3-{[1-(2-fluoro-phenyl)-5-((S)-2-hydroxy-2,3,3-trimethyl-butoxy)-1H-pyrazole-3-carbonyl]-amino}-propionic acid, (S)-3-(2,4-Dimethyl-phenyl)-3-{[1-(2-fluoro-phenyl)-5-((S)-2-hydroxy-2,3,3-trimethyl-butoxy)-1H-pyrazole-3-carbonyl]-amino}-propionic acid, (S)-3-(2-Fluoro-phenyl)-3-{[1-(2-fluoro-phenyl)-5-((S)-2-hydroxy-2,3,3-trimethyl-butoxy)-1H-pyrazole-3-carbonyl]-amino}-propionic acid, (S)-3-(2,3-Dimethoxy-phenyl)-3-{[1-(2-fluoro-phenyl)-5-((S)-2-hydroxy-2,3,3-trimethyl-butoxy)-1H-pyrazole-3-carbonyl]-amino}-propionic acid, (S)-3-{[1-(2-Fluoro-phenyl)-5-((S)-2-hydroxy-2,3,3-trimethyl-butoxy)-1H-pyrazole-3-carbonyl]-amino}-3-(3-methoxy-phenyl)-propionic acid, (S)-3-{[1-(2-Fluoro-phenyl)-5-((R)-2-hydroxy-2,3,3-trimethyl-butoxy)-1H-pyrazole-3-carbonyl]-amino}-5-methyl-hexanoic acid, (S)-3-{[1-(2-Fluoro-phenyl)-5-((R)-2-hydroxy-2,3,3-trimethyl-butoxy)-1H-pyrazole-3-carbonyl]-amino}-3-(2-trifluoromethyl-phenyl)-propionic acid, (S)-4-(4-Cyano-phenyl)-3-{[1-(2-fluoro-phenyl)-5-((R)-2-hydroxy-2,3,3-trimethyl-butoxy)-1H-pyrazole-3-carbonyl]-amino}-butyric acid, (S)-3-{[1-(2-Fluoro-phenyl)-5-((R)-2-hydroxy-2,3,3-trimethyl-butoxy)-1H-pyrazole-3-carbonyl]-amino}-3-(4-methoxy-phenyl)-propionic acid, (S)-3-{[1-(2-Fluoro-phenyl)-5-(2-hydroxy-2-phenyl-propoxy)-1H-pyrazole-3-carbonyl]-amino}-3-o-tolyl-propionic acid, 1-(2-Fluoro-phenyl)-5-methoxy-1H-pyrazole-3-carboxylic acid {(S)-2-[(pyridin-2-ylmethyl)-carbamoyl]-1-o-tolyl-ethyl}-amide; compound with trifluoro-acetic acid, 1-(2-Fluoro-phenyl)-5-methoxy-1H-pyrazole-3-carboxylic acid [(S)-2-(cyclopropylmethyl-carbamoyl)-1-o-tolyl-ethyl]-amide, 1-(2-Fluoro-phenyl)-5-methoxy-1H-pyrazole-3-carboxylic acid [(S)-2-[(furan-2-yl ethyl)-carbamoyl]-1-o-tolyl-ethyl]-amide, 1-(2-Fluoro-phenyl)-5-methoxy-1H-pyrazole-3-carboxylic acid [(S)-2-(3-dimethylamino-propylcarbamoyl)-1-o-tolyl-ethyl]-amide;

1-(2-Fluoro-phenyl)-5-methoxy-1H-pyrazole-3-carboxylic acid [(S)-2-(1-ethyl-propylcarbamoyl)-1-o-tolyl-ethyl]-amide, 1-(2-Fluoro-phenyl)-5-methoxy-1H-pyrazole-3-carboxylic acid ((S)-2-cyclohexylcarbamoyl-1-o-tolyl-ethyl)amide, 1-(2-Fluoro-phenyl)-5-methoxy-1H-pyrazole-3-carboxylic acid [(S)-3-((S)-3-hydroxy-pyrrolidin-1-yl)-3-oxo-1-o-tolyl-propyl]-amide, 1-(2-Fluoro-phenyl)-5-methoxy-1H-pyrazole-3-carboxylic acid [(S)-1-o-tolyl-2-((R)-1,2,2-trimethyl-propylcarbamoyl)-ethyl]-amide, 1-(2-Fluoro-phenyl)-5-methoxy-1H-pyrazole-3-carboxylic acid [(S)-3-((R)-3-hydroxy-pyrrolidin-1-yl)-3-oxo-1-o-tolyl-propyl]-amide, 1-(2-Fluoro-phenyl)-5-methoxy-1H-pyrazole-3-carboxylic acid [(S)-2-((S)-sec-butylcarbamoyl)-1-o-tolyl-ethyl]-amide, 1-(2-Fluoro-phenyl)-5-methoxy-1H-pyrazole-3-carboxylic acid [(S)-3-((S)-3-hydroxy-piperidin-1-yl)-3-oxo-1-o-tolyl-propyl]-amide, 1-(2-Fluoro-phenyl)-5-methoxy-1H-pyrazole-3-carboxylic acid [(S)-2-(carbamoylmethyl-methyl-carbamoyl)-1-o-tolyl-ethyl]-amide, 1-(2-Fluoro-phenyl)-5-methoxy-1H-pyrazole-3-carboxylic acid [(S)-2-((R)-1-cyclopropyl-ethylcarbamoyl)-1-o-tolyl-ethyl]-amide, 1-(2-Fluoro-phenyl)-5-methoxy-1H-pyrazole-3-carboxylic acid [(S)-2-((S)-1-cyclopropyl-ethylcarbamoyl)-1-o-tolyl-ethyl]-amide, 1-(2-Fluoro-phenyl)-5-methoxy-1H-pyrazole-3-carboxylic acid ((S)-2-cyclobutylcarbamoyl-1-o-tolyl-ethyl)-amide, 1-(2-Fluoro-phenyl)-5-methoxy-1H-pyrazole-3-carboxylic acid [(S)-2-[(pyridin-3-ylmethyl)-carbamoyl]-1-o-tolyl-ethyl]-amide; compound with trifluoro-acetic acid, 1-(2-Fluoro-phenyl)-5-methoxy-1H-pyrazole-3-carboxylic acid ((S)-2-cyclopentylcarbamoyl-1-o-tolylethyl)-amide, 1-(2-Fluoro-phenyl)-5-methoxy-1H-pyrazole-3-carboxylic acid [(S)-2-(2-methoxy-1-methyl-ethylcarbamoyl)-1-o-tolyl-ethyl]-amide, 1-(2-Fluoro-phenyl)-5-methoxy-1H-pyrazole-3-carboxylic acid [(S)-2-(2,2-difluoro-ethylcarbamoyl)-1-o-tolyl-ethyl]-amide, 1-(2-Fluoro-phenyl)-5-methoxy-1H-pyrazole-3-carboxylic acid [(S)-1-o-tolyl-2-(2,2,2-trifluoro-ethylcarbamoyl)-ethyl]-amide, 1-(2-Fluoro-phenyl)-5-methoxy-1H-pyrazole-3-carboxylic acid [(S)-2-(2-cyclopropyl-ethylcarbamoyl)-1-o-tolyl-ethyl]-amide, 1-(2-Fluoro-phenyl)-5-methoxy-1H-pyrazole-3-carboxylic acid {(S)-2-[(pyrimidin-5-ylmethyl)-carbamoyl]-1-o-tolyl-ethyl}-amide, 1-(2-Fluoro-phenyl)-5-methoxy-1H-pyrazole-3-carboxylic acid ((S)-2-butylcarbamoyl-1-o-tolyl-ethyl)-amide, 1-(2-Fluoro-phenyl)-5-methoxy-1H-pyrazole-3-carboxylic acid {(S)-2-[(furan-3-ylmethyl)-carbamoyl]-1-o-tolyl-ethyl}-amide, 1-(2-Fluoro-phenyl)-5-methoxy-1H-pyrazole-3-carboxylic acid {(S)-2-[(pyridin-4-ylmethyl)-carbamoyl]-1-o-tolyl-ethyl}-amide; compound with trifluoro-acetic acid, 1-(2-Fluoro-phenyl)-5-methoxy-1H-pyrazole-3-carboxylic acid [(S)-2-(1,1-dimethyl-propylcarbamoyl)-1-o-tolyl-ethyl]-amide, 1-(2-Fluoro-phenyl)-5-methoxy-1H-pyrazole-3-carboxylic acid [(S)-2-((R)-sec-butylcarbamoyl)-1-o-tolyl-ethyl]-amide, 1-(2-Fluoro-phenyl)-5-methoxy-1H-pyrazole-3-carboxylic acid ((S)-2-isobutylcarbamoyl-1-o-tolyl-ethyl)-amide, 1-(2-Fluoro-phenyl)-5-methoxy-1H-pyrazole-3-carboxylic acid [(S)-1-o-tolyl-2-((S)-1,2,2-trimethyl-propylcarbamoyl)-ethyl]-amide, 1-(2-Fluoro-phenyl)-5-methoxy-1H-pyrazole-3-carboxylic acid [(S)-2-(1-methoxymethyl-propylcarbamoyl)-1-o-tolyl-ethyl]-amide, 1-(2-Fluoro-phenyl)-5-methoxy-1H-pyrazole-3-carboxylic acid ((S)-2-tert-butylcarbamoyl-1-o-tolyl-ethyl)-amide, 1-(2-Fluoro-phenyl)-5-methoxy-1H-pyrazole-3-carboxylic acid [(S)-2-(5-methyl-1H-pyrazol-3-ylcarbamoyl)-1-o-tolyl-ethyl]-amide, 1-(2-Fluoro-phenyl)-5-methoxy-1H-pyrazole-3-carboxylic acid [(S)-2-(2,2-dimethyl-propylcarbamoyl)-1-o-tolyl-ethyl]-amide, 1-(2-Fluoro-phenyl)-5-methoxy-1H-pyrazole-3-carboxylic acid [(S)-2-(3-hydroxy-2,2-dimethyl-propylcarbamoyl)-1-o-tolyl-ethyl]-amide, 1-(2-Fluoro-phenyl)-5-methoxy-1H-pyrazole-3-carboxylic acid [(S)-2-(cyanomethyl-carbamoyl)-1-o-tolyl-ethyl]-amide, 1-(2-Fluoro-phenyl)-5-methoxy-1H-pyrazole-3-carboxylic acid [(S)-2-((R)-1-hydroxymethyl-2-methyl-propylcarbamoyl)-1-o-tolyl-ethyl]-amide, 1-(2-Fluoro-phenyl)-5-methoxy-1H-pyrazole-3-carboxylic acid ((S)-2-[(1H-tetrazol-5-ylmethyl)-carbamoyl]-1-o-tolyl-ethyl]-amide, 1-(2-Fluoro-phenyl)-5-methoxy-1H-pyrazole-3-carboxylic acid ((S)-2-isopropylcarbamoyl-1-o-tolylethyl)-amide, 1-(2-Fluoro-phenyl)-5-methoxy-1H-pyrazole-3-carboxylic acid [(S)-2-(1-methyl-1H-pyrazol-3-ylcarbamoyl)-1-o-tolyl-ethyl]-amide, 1-(2-Fluoro-phenyl)-5-methoxy-1H-pyrazole-3-carboxylic acid [(S)-2-(2-oxo-pyrrolidin-3-ylcarbamoyl)-1-o-tolyl-ethyl]-amide, 1-(2-Fluoro-phenyl)-5-methoxy-1H-pyrazole-3-carboxylic acid [(S)-2-(5-methyl-isoxazol-3-ylcarbamoyl)-1-o-tolyl-ethyl]-amide, 1-(2-Fluoro-phenyl)-5-methoxy-1H-pyrazole-3-carboxylic acid ((S)-2-cyclopropylcarbamoyl-1-o-tolyl-ethyl)-amide, 1-(2-Fluoro-phenyl)-5-methoxy-1H-pyrazole-3-carboxylic acid {(S)-2-[(isoxazol-5-ylmethyl)-carbamoyl]-1-o-tolyl-ethyl}-amide, 1-(2-Fluoro-phenyl)-5-methoxy-1H-pyrazole-3-carboxylic acid [(S)-2-(2-methoxy-ethylcarbamoyl)-1-o-tolyl-ethyl]-amide, 1-(2-Fluoro-phenyl)-5-methoxy-1H-pyrazole-3-carboxylic acid [(S)-2-((S)-1-hydroxymethyl-2-methyl-propylcarbamoyl)-1-o-tolyl-ethyl]-amide, 1-(2-Fluoro-phenyl)-5-methoxy-1H-pyrazole-3-carboxylic acid [(S)-2-((S)-2-methoxy-1-methyl-ethylcarbamoyl)-1-o-tolyl-ethyl]-amide, 1-(2-Fluoro-phenyl)-5-methoxy-1H-pyrazole-3-carboxylic acid ((S)-2-{[(S)-1-(tetrahydro-furan-2-yl)methyl]-carbamoyl}-1-o-tolyl-ethyl)-amide and 1-(2-Fluoro-phenyl)-5-methoxy-1H-pyrazole-3-carboxylic acid [(S)-2-((R)-1,2-dimethyl-propylcarbamoyl)-1-o-tolyl-ethyl]-amide, or which is any one of these compounds, or a physiologically acceptable salt thereof, or a physiologically acceptable solvate of any of them, wherein the compound of the formula I is a subject of the invention in any of its stereoisomeric forms or a mixture of stereoisomeric forms in any ratio, unless a specific stereoisomeric form is specified with respect to any carbon atoms in the respective compound.

Another subject of the present invention are processes for the preparation of the compounds of the formula I which are outlined below and by which the compounds are obtainable. For example, the preparation of the compounds of the formula I can be carried out by reacting a compound of the formula II with a compound of the formula III with formation of an amide bond. Various synthetic methods for the formation of the amide bond are described in C. A. G. N. Montalbetti et al., Tetrahedron 61 (2005), 10827-10852, for example.

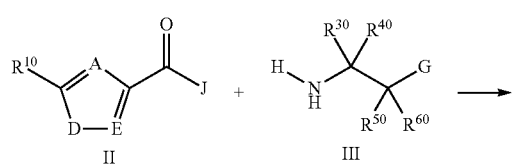

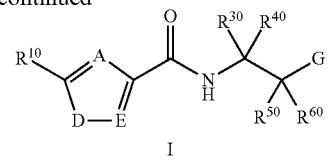

The groups A, D, E, G, $R^{10}$, $R^{30}$, $R^{40}$, $R^{50}$ and $R^{60}$ in the compounds of the formulae II and III are defined as in the compounds of the formula I and additionally functional groups can be present in protected form or in the form of a precursor group which is later converted into the final group. The group J in the compounds of the formula II can be HO— (hydroxy), i.e. the compound of the formula II can thus be a carboxylic acid, or another group which can be replaced by the group NH in the compound of the formula III in a substitution reaction, for example an aryloxy group such as optionally substituted phenoxy or an alkyloxy group such as a $(C_1-C_4)$-alkyl-O— group, for example a $(C_1-C_3)$-alkyl-O— group like methoxy or ethoxy, or halogen, for example chlorine or bromine, and the compound of the formula II can thus be a reactive ester like an aryl ester or alkyl ester, for example a methyl ester or ethyl ester, or an acid halide, for example an acid chloride or acid bromide, of the respective carboxylic acid. The compounds of the formulae II and III can also be employed, and the compounds of the formula I obtained, in the form of a salt, for example an acid addition salt such as an hydrohalide, for example a hydrochloride, of the compound of the formula III and/or an alkaline metal salt, for example a sodium salt, of a compound of the formula II in which J is HO—. Likewise, in all other reactions in the preparation of the compounds of the formula I, including the preparation of starting compounds, compounds can also be employed and/or products obtained in the form a salt.

In case a compound of the formula II is employed in which J is HO—, the carboxylic acid group HO—C(O)— is generally activated in situ by means of a customary amide coupling reagent or converted into a reactive carboxylic acid derivative which can be prepared in situ or isolated. For example, the compound of the formula II in which J is HO— can be converted into an acid halide, such as the compound of the formula II in which J is chlorine or bromine, by treatment with thionyl chloride, phosphorus pentachloride, phosphorus tribromide or oxalyl chloride, or treated with an alkyl chloroformate like ethyl chloroformate or isobutyl chloroformate to give a mixed anhydride. In a favorable method for the conversion into the acid chloride, the acid is treated with oxalyl chloride in the presence of a catalytic amount of an amide such as N,N-dimethylformamide in an inert solvent such as a hydrocarbon or chlorinated hydrocarbon or an ether, at temperatures from about 0° C. to about 60° C., for example at room temperature. Customary amide coupling reagents which can be employed, are propanephosphonic anhydride, N,N'-carbonyldiazoles like N,N'-carbonyldiimidazole (CU), carbodiimides like 1,3-diisopropylcarbodiimide (DIC), 1,3-dicyclohexylcarbodiimide (DCC) or 1-(3-dimethylaminopropyl)-3-ethylcarbodiimide hydrochloride (EDC), carbodiimides together with additives like 1-hydroxy-benzotriazole (HOBT) or 1-hydroxy-7-azabenzotriazole (HOAT), uronium-based coupling reagents like O—(7-azabenzotriazol-1-yl)-N,N,N',N'-tetramethyluronium hexafluorophosphate (HATU), O-(benzotriazol-1-yl)-N,N,N',N'-tetramethyluronium hexafluorophosphate (HBTU) or O-(cyano(ethoxycarbonyl)methyleneamino)-N,N,N',N'-tetramethyluronium tetrafluoroborate (TOTU), and phosphonium-based coupling reagents like (benzotriazol-1-yloxy)tris(dimethylamino)phosphonium hexafluorophosphate (BOP), (benzotriazol-1-yloxy)tripyrrolidinophosphonium hexafluorophosphate (PyBOP) or bromotripyrrolidinophosphonium hexafluorophosphate (PyBroP).

The reaction conditions for the preparation of the compounds of the formula I from compounds of the formulae II and III depend on the particulars of the specific case, for example the meaning of the group J or the employed coupling reagent, and are familiar to a skilled person in view of the general knowledge in the art. For example, in case a compound of the formula II in which J is alkyl-O—, like methoxy or ethoxy, is reacted with a compound of the formula III, generally the reaction is carried out in an inert solvent, for example a hydrocarbon or chlorinated hydrocarbon like benzene, toluene, xylene, chlorobenzene, dichloromethane, chloroform or dichloroethane, an ether like tetrahydrofuran (THF), 2-methyltetrahydrofuran, dioxane, dibutyl ether, diisopropyl ether or dimethoxyethane (DME), or a mixture of solvents, at elevated temperatures, for example at temperatures from about 40° C. to about 140° C., in particular at temperatures from about 50° C. to about 120° C., for example at about the boiling temperature of the solvent. In case a compound of the formula II in which J is halogen, like chlorine or bromine, is reacted with a compound of the formula III, generally the reaction is likewise carried out in an inert solvent, for example a hydrocarbon or chlorinated hydrocarbon or ether like the aforementioned ones, an ester like ethyl acetate or butyl acetate, a nitrile like acetonitrile, or water, or a mixture of solvents including a mixture of water and an organic solvent which is miscible or immiscible with water, at temperatures from about −10° C. to about 100° C., in particular at temperatures from about 0° C. to about 80° C., for example at about room temperature. Favorably, the reaction of a compound of the formula II in which J is halogen with a compound of the formula III is carried out in the presence of a base such as a tertiary amine, like triethylamine, N-ethyldiisopropylamine (EDIA), N-methylmorpholine, N-ethylmorpholine or pyridine, or an inorganic base such as an alkaline metal hydroxide, carbonate or hydrogencarbonate, like sodium hydroxide, potassium hydroxide, sodium carbonate or sodium hydrogencarbonate.

In case a compound of the formula II in which J is HO— is reacted with a compound of the formula III and the carboxylic acid group is activated by means of an amide coupling reagent such as, for example, a carbodiimide or TOTU, the reaction is generally carried out under anhydrous conditions in an inert aprotic solvent, for example an ether like THF, dioxane or DME, an amide like N,N-dimethylformamide (DMF) or N-methylpyrrolidone (NMP), at temperatures from about −10° C. to about 40° C., in particular at temperatures from about 0° C. to about 30° C., for example at room temperature, in the presence of a base such as a tertiary amine, like triethylamine, EDIA, N-methylmorpholine or N-ethylmorpholine. In case the compound of the formula III is employed in the form of an acid addition salt in the reaction with the compound of the formula II, usually a sufficient amount of a base is added in order to liberate the free compound of the formula III.

As indicated above, during the formation of the amide bond between the compounds of the formulae II and III functional groups in the compounds of the formulae II and III can be present in protected form or in the form of a precursor group. Depending on the particulars of the specific case, it may be necessary or advisable for avoiding an undesired course of the reaction or side reactions to temporarily block any functional groups by protective groups and remove them later, or to let functional groups be present in the form of a precursor group which is later converted into the desired final group. This applies correspondingly to all reactions in the course of the synthesis of the compounds of the formula I including the synthesis of intermediates, starting compounds and building blocks. Respective synthetic strategies are commonly used in the art. Details about protective groups and their introduction and removal are described in P. G. M. Wuts and T. W. Greene, Greene's Protective Groups in Organic Synthesis, 4. ed. (2007), John Wiley & Sons, for example. Examples of protective groups which may be mentioned, are benzyl protective groups which may occur in the form of benzyl ethers of hydroxy groups and benzyl esters of carboxylic acid groups from which the benzyl group can be removed by catalytic hydrogenation in the presence of a palladium catalyst, tert-butyl protective groups which may occur in the form of tert-butyl esters of carboxylic acid groups from which the tert-butyl group can be removed by treatment with trifluoroacetic acid, acyl protective groups which may be used to protect hydroxy groups and amino groups in the form of esters and amides and which can be cleaved by acidic or basic hydrolysis, and alkyloxycarbonyl protective groups which may occur in the form of tert-butoxycarbonyl derivatives of amino groups which can be cleaved by treatment with trifluoroacetic acid. Undesired reactions of carboxylic acid groups, for example the carboxylic acid group present in the compound of the formula III in case G is a carboxylic acid group in the desired compound of the formula I, can also be avoided by employing them in the reaction with the compounds of the formula II in the form of other esters, for example in the form of alkyl esters like the methyl or ethyl ester which can be cleaved by hydrolysis, for example by means of an alkaline metal hydroxide like sodium hydroxide or lithium hydroxide. As examples of a precursor group, the cyano group (NC—, N≡C—) may be mentioned which can be converted into a carboxylic acid group, a carboxylic acid ester group and a carboxamide group under hydrolytic conditions or into a aminomethyl group by reduction, and the nitro group which can be converted into an amino group by reduction, for example by catalytic hydrogenation or by reduction with sodium dithionite, for example. A further example of a precursor group is an oxo group, which may initially be present in the course of the synthesis of compounds of the formula I containing a hydroxy group, and which can be reduced, for example with a complex hydride such as sodium borohydride, or reacted with an organometallic compound, for example a Grignard compound. If any protective groups or precursor groups are present in the compounds of the formulae II and III and the direct product of the reaction is not yet the desired final compound, the removal of the protective group or conversion into the desired compound can in general also be carried out in situ.

The starting compounds for the synthesis of the compounds of the formula I can generally be prepared according to procedures described in the literature or analogously to such procedures, or are commercially available. As an example of the synthesis of compounds of the formula II, synthetic procedures for the synthesis of compounds of the formula II in which A is $C(R^1)$, D is $N(R^2)$ and E is N, i.e. of 5-oxygen-substituted pyrazole-3-carboxylic acids and acid derivatives, are outlined in the following. In one such procedure, oxalacetic acid of the formula IV is reacted with a substituted hydrazine of the formula V in a solvent such as water in the presence of an acid, such as sulfuric acid, hydrochloric acid or acetic acid, to give a 5-hydroxy-pyrazole-3- carboxylic acid of the formula IIa in which R and $R^1$ are hydrogen and which can then be reacted with a compound of the formula III.

a compound of the formula IIa in which R is hydrogen, i.e. a carboxylic acid, can easily be converted into a compound of the formula IIa in which is R is $(C_1-C_4)$-alkyl, or into another

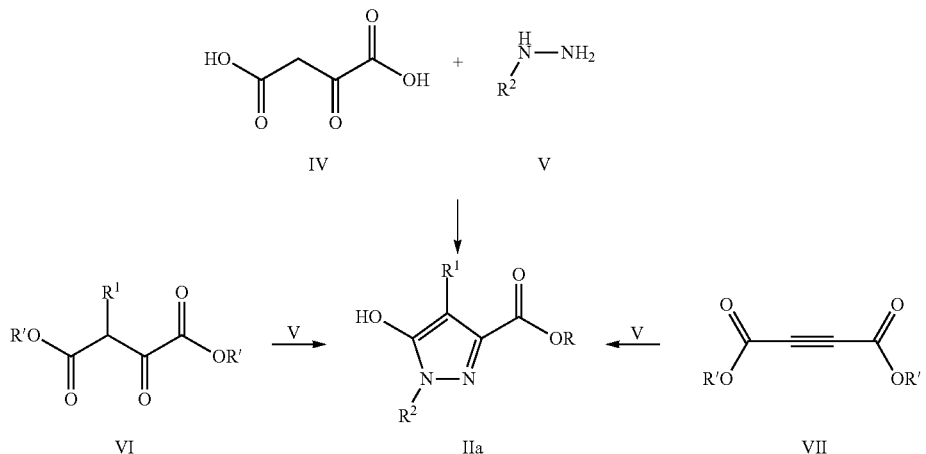

In a similar manner can diethyl oxalacetate, i.e. the compound of the formula VI in which $R^1$ is hydrogen and R' is ethyl, be reacted with a substituted hydrazine to give a compound of the formula IIa in which $R^1$ is hydrogen and R is ethyl, and can substituted oxalylacetates, for example compounds of the formula VI in which $R^1$ is an alkyl group such as methyl or ethyl and R' is ethyl, be reacted with a substituted hydrazine, for example by heating the components and/or treating them with a base such as an alkaline metal hydroxide like sodium hydroxide or potassium hydroxide, to give a compound of the formula IIa in which $R^1$ is hydrogen or has another meaning than hydrogen, respectively, and R is an alkyl group, as described in S. Sugiura et al., J. Med. Chem. 20 (1997), 80-85; P. E. Gagnon et al., Can. J. Chem. 30 (1952), 904-914; or JP 2000/169453, for example. Compounds of the formula IIa, in which $R^1$ is hydrogen and R is an alkyl group such as methyl, can also be prepared by reaction of an acetylenedicarboxylate of the formula VII, for example dimethyl acetylenedicarboxylate, with a hydrazine derivative in a solvent such as an alcohol like methanol in the presence of a base such as a tertiary amine, for example triethylamine or EDIA (cf. E. Buchner, Chem. Ber. 22 (1889), 2929-2932). The groups $R^1$ and $R^2$ in the compounds of the formulae IIa, V and VI are defined as in the compounds of the formula I and additionally functional groups can be present in protected form or in the form of a precursor group which is later converted into the final group. Depending on the individual case, in these procedures $R^1$ is in particular hydrogen or a group such as $(C_1-C_6)$-alkyl, for example methyl or ethyl, and $R^2$ is in particular an aromatic group such as an optionally substituted phenyl group or aromatic heterocyclic group. The group R' in the compounds of the formulae VI and VII is $(C_1-C_4)$-alkyl, for example methyl or ethyl. As indicated, the group R in the compounds of the formula IIa can be hydrogen or $(C_1-C_4)$-alkyl, for example methyl or ethyl. The compounds of the formula IIa, as well as other suitable compounds occurring in the synthesis of the compounds of the formula I and the compounds of the formula I themselves, can also be present in other tautomeric forms, in particular the form in which the hydroxy group in 5-position is present as an oxo group and the ring nitrogen atom in 2-position carries a hydrogen atom.

If desired for the intended use of the compound of the formula IIa in the synthesis of the compound of the formula I, carboxylic acid ester, as well as a compound of the formula IIa is $(C_1-C_4)$-alkyl can be converted into a compound of the formula IIa in which R is hydrogen. Such conversions can be performed under standard conditions which are well known to a person skilled in the art. For example, an esterification of a carboxylic acid to give an ester such as a methyl or ethyl ester can be performed by treating the carboxylic acid in the respective alcohol as solvent with an acid like hydrogen chloride or with thionyl chloride, and a saponification of a carboxylic acid ester such as a methyl or ethyl ester to give the carboxylic acid can be performed by treating the ester in a solvent such as an alcohol like methanol or ethanol, an ether like THF or dioxane, or a ketone like methyl isobutyl ketone, or a mixture thereof in the presence of water with a base such as an alkaline metal hydroxide like sodium hydroxide or lithium hydroxide. This applies just so to carboxylic acid groups and carboxylic acid ester groups in other compounds occurring in the synthesis of the compounds of the formula I.

Compounds of the formula IIa can readily be converted into compounds of the formula IIb, which are substituted on the hydroxy group in 5-position and which can likewise be reacted with a compound of the formula III, by reaction with an electrophilic reagent of the formula VIII.

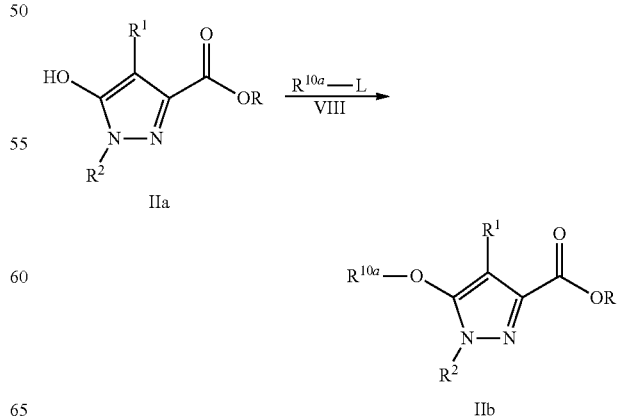

The groups $R^1$, $R^2$ and R in the compounds of the formula IIb are defined as in the compounds of the formula IIb. The group $R^{10a}$ in the compounds of the formulae IIb and VIII is chosen from the series consisting $R^{11}$, $R^{12}$—N($R^{13}$)—C(O)— and Het$^2$—C(O)— wherein $R^{11}$, $R^{12}$. $R^{13}$ and Het$^2$ are defined as in the compounds of the formula I, except that $R^{11}$ is not hydrogen, and additionally functional groups can be present in protected form or in the form of a precursor group which is later converted into the final group, i.e. the group $R^{10a}$—O— is substantially defined as the group $R^{10}$ in the compounds of the formula I, except that it is not a hydroxy group. The group L in the compounds of the formula VIII is a nucleophilically substitutable leaving group which can be replaced by the oxygen atom of the hydroxy group in the compound of the formula IIa in the respective reaction type, for example halogen such as fluorine, chlorine, bromine or iodine, or a sulfonyloxy group such as methanesulfonyloxy, trifluoromethanesulfonyloxy, toluenesulfonyloxy, methoxysulfonyloxy or ethoxysulfonyloxy, or L can also be a hydroxy group and in the latter case the compounds of the formulae IIa and VIII reacted under the conditions of the Mitsunobu reaction, for example.

In case the group $R^{10a}$ is $R^{12}$—N($R^{13}$)—C(O)— or Het$^2$—C(O)—, the group L in the respective compounds of the formula VIII advantageously is chlorine and the compound of the formula VIII thus is an acyclic or cyclic carbamyl chloride. The reaction of such a compound of the formula VIII with a compound of the formula IIa is generally carried out in an inert solvent, for example a hydrocarbon or a chlorinated hydrocarbon like toluene, dichloromethane or dichloroethane, an ether like THF or dioxane, in the presence of a base such as an amine like triethylamine or EDIA, or an inorganic base like a basic alkaline metal salt, for example a carbonate like sodium carbonate or cesium carbonate, at temperatures from about 0° C. to about 80° C., in particular from about 20° C. to about 60° C.

In case the group $R^{10a}$ in the compound of the formula VIII is $R^{11}$, the group $R^{11}$ is a group such as alkyl, for example, the group L is halogen or a sulfonyloxy group and the compound of the formula VIII thus is an alkyl halide, an alkyl sulfonate or a dialkyl sulfate, or a respective compound of another type, the reaction of the compounds of the formulae IIa and VIII is an O-alkylation and constitutes a nucleophilic substitution reaction. Suitable conditions for such a reaction are well known to a person skilled in the art and have extensively been described in the literature, for example in S. Sugiura et al., J. Med. Chem. 80 (1977), 80-85; W.-M. Liu et al., J. Heterocycl. Chem. 44 (2007), 967-971; or U.S. Pat. No. 5,258,397. Generally the reaction is carried out in an inert solvent, for example a hydrocarbon or chlorinated hydrocarbon such as benzene, toluene, chlorobenzene, dichloromethane, chloroform or dichloroethane, an ether such as THF, dioxane, dibutyl ether, diisopropyl ether or DME, an alcohol such as methanol, ethanol or isopropanol, a ketone such as acetone, butan-2-one or methyl isobutyl ketone, an ester such as ethyl acetate or butyl acetate, a nitrile such acetonitrile, an amide such as DMF or NMP, or a mixture of solvents, including two-phasic mixtures with aqueous solutions, at temperatures from about −20° C. to about 100° C., for example at temperatures from about 0° C. to about 80° C., depending on the particulars of the specific case. The reaction can also be carried out in the presence of an ionic liquid. Generally it is favorable for enhancing the nucleophilicity of the compound of the formula IIa and/or binding an acid which is liberated during the reaction, to add a base, for example a tertiary amine, such as triethylamine, EDIA or N-methylmorpholine, or an inorganic base such as an alkaline metal hydride, hydroxide, carbonate or hydrogencarbonate like sodium hydride, sodium hydroxide, potassium hydroxide, sodium carbonate, potassium carbonate, cesium carbonate or sodium hydrogencarbonate, or an alkoxide or amide such as sodium methoxide, sodium ethoxide, potassium methoxide, potassium tert-butoxide, sodium amide or lithium diisopropylamide, wherein a compound of the formula IIa can also be treated with a base separately before the reaction with the compound of the formula VIII. By the choice of the reaction conditions, such as the solvent and the base, as well as the choice of the group L in the compound of the formula VIII, which compound can in the case that $R^{10a}$ is methyl be a halide such as iodomethane or bromomethane, a sulfonate such as methyl tosylate, or a sulfate such as dimethyl sulfate, for example, it is also possible to control the regioselectivity of the reaction with the compound of the formula IIa which reaction can, besides on the oxygen atom of the hydroxy group in 5-position, also occur on the ring nitrogen atom in 2-position, as is known to a person skilled in the art. If a compound of the formula IIa in which R is hydrogen, is reacted with a compound of the formula VIII in which $R^{10a}$ is $R^{11}$, besides on the hydroxy group in 5-position can a reaction with the compound of the formula VIII also occur on the carboxylic acid group, and the latter can be converted into an ester. For the subsequent reaction step, such an ester group can be converted in the carboxylic acid, as outlined above.

In case the group $R^{10a}$ in the compound of the formula VIII is $R^{11}$, the group $R^{11}$ is a group such as alkyl, for example, the group L is hydroxy and the compound of the formula VIII thus is an alkanol, or a respective compound of another type, the reaction of the compounds of the formulae IIa and VIII can be performed under the conditions of the Mitsunobu reaction, as mentioned above. The Mitsunobu reaction is generally performed in an inert solvent, such as a hydrocarbon or chlorinated hydrocarbon like toluene or dichloromethane, or an ether like THF or dioxane, in the presence of an azodicarboxylate such as diethyl azodicarboxylate, diisopropyl azodicarboxylate or di(4-chlorobenzyl) azodicarboxylate, and a phosphine such as triphenylphosphine or tributylphosphine, at temperatures from about 0° C. to about 40° C., for example at about room temperature (cf. O. Mitsunobu, Synthesis (1981), 1-28).

Compounds of the formula II for use in the synthesis of compounds of the formula I in which the groups A, D and E have other meanings than in the compounds of the formulae IIa and IIb which are exemplarily discussed above, can likewise be prepared according to procedures, or analogously to procedures, which are described in the literature and are generally known to a person skilled in the art, the synthetic strategy in a specific case being dependent on the kind of the heterocycle. For example, a procedure for the synthesis of compounds of the formula II in which A is N, D is N($R^2$) and E is N, i.e. of 5-oxygen-substituted [1,2,4]triazole-3-carboxylic acid derivatives, which comprises the alcoholysis of 2-imino-1,3,4-oxadiazole derivatives, is described in DD 226883. The oxadiazole derivatives may be obtained from acylhydrazines by reaction with a cyanate as described in M. Neitzel et al., Arch. Pharm. 313 (1980), 867-878. A procedure for the synthesis of compounds of the formula II in which A is N, D is N($R^2$) and E is C($R^3$), i.e. of 2-oxygen-substituted imidazole-4-carboxylic acid derivatives, which comprises the reaction of an alpha-diazo-beta-ketoester with a substituted urea in the presence of a rhodium catalyst, is described in S.-H. Lee et al., Org. Lett. 5 (2003), 511-514 and WO 2008/139941. The hydroxy group in the 2-position of the obtained imidazole derivative can then by alkylated with triethyloxonium tetrafluoroborate, for example. A procedure for the synthesis of compounds of the formula II in which A is $C(R^1)$, D is $N(R^2)$ and E is $C(R^3)$, i.e. of 5-oxygen-substituted pyrrole-3-carboxylic acid derivatives, which comprises the reaction of an alpha-dicarbonyl compound with an N-substituted beta-amino-acrylic acid ester, is described in E. Caballero et al., Tetrahedron 50 (1994), 7849-7865. A procedure for the synthesis of compounds of the formula II in which A is N, D is O and E is $C(R^3)$, i.e. of 2-oxygen-substituted [1,3]oxazole-4-carboxylic acid derivatives, which comprises the exchange of the chlorine atom in ethyl 2-chloro-oxazole-3-carboxylate with an oxygen substituent, is described in G. L. Young et al., Tetrahedron Lett. 45 (2004), 3797-3801; and WO 2007/000582. The 2-chloro-oxazole-3-carboxylate may be obtained by condensation of ethyl bromopyruvate and urea, diazotation of the obtained 2-amino-oxazole derivative and treatment with copper chloride as described in K. J. Hodgetts et al., Org. Lett. 4 (2002), 2905-2907. A similar procedure for the synthesis of compounds of the formula II in which A is N, D is S and E is $C(R^3)$, i.e. of 2-oxygen-substituted [1,3]thiazole-4-carboxylic acid derivatives, which comprises the exchange of the bromine atom in ethyl 2-bromo-thiazole-3-carboxylates, which may be obtained from halo-pyruvates by condensation with thiourea and diazotation of the obtained 2-amino-thiazole derivative and treatment with a copper bromide as is also described in T. R. Kelly et al., J. Org. Chem. 61 (1996), 4623-4633, with an oxygen substituent, is described in WO 94/27983; WO 02/14311 and WO 2009/104155. Likewise further compounds of the formula II can be prepared.

The β-amino acids and derivatives of the formula III are commercially available or can be synthesized by well-known standard methods, or analogously to such methods, from readily available starting compounds. For example, for the preparation of β-amino acids and their alkyl esters of the formula III in which $R^{50}$ and $R^{60}$ are hydrogen, can carbonyl compounds of the formula $R^{30}$—C(O)—$R^{40}$, in particular aldehydes of the formula $R^{32}$—C(O)—H, be reacted with malonic acid mono-ethyl ester and ammonia in the presence of a base such as an alkaline metal hydroxide like potassium hydroxide in a solvent such as an alcohol like ethanol, as described in V. M. Rodionov et al., Izv. Akad. Nauk SSSR, Ser. Khim. (1952), 696-702 (Chem. Abstr. 47 (1953), abstr. no. 61888), or ammonia added to the double bond in the condensation product of the carbonyl compound with malonic acid or diethyl malonate and in the case of the condensation product with diethyl malonate the reaction product treated with an acid such as hydrochloric acid, as described in V. Scudi, J. Am. Chem. Soc. 57 (1935), 1279; or M. K. Tse et al., Chem. Eur. J. 12 (2006), 1855-1874, and in the obtained product an ester group hydrolyzed to the carboxylic acid, or a carboxylic acid group esterified, respectively, as desired and outlined above. Enantiomerically pure such compounds of the formula III, for example, can be obtained from the racemic compounds by crystallization of a salt with an optically active acid, such as tartaric acid, by stereoselective enzymatic or microbial degradation, for example as described in the mentioned article by M. K. Tse et al., or in J. Mano et al., Bioscience, Biotechnology and Biochemistry 70 (2006), 1941-1946. In another strategy for the synthesis of such compounds, in particular compounds in which $R^{40}$, $R^{50}$ and $R^{60}$ are hydrogen and $R^{30}$ is $R^{32}$, the respective 3-substituted acrylic acid, which can be obtained from the corresponding aldehyde, is converted into the acid chloride, for example with oxalyl chloride, and the acid chloride converted with an alcohol into an ester, for example into the tert-butyl ester using tert-butanol, and the amino group is then introduced by reaction with the lithium salt of an optically active amine, for example the lithium salt of (R)-(+)-N-benzyl-N-(1-phenylethyl)amine, and in the obtained 3-substituted tert-butyl 3-(N-benzyl-N-(1-phenylethyl)amino)propionate the benzyl group and the phenylethyl group is cleaved off by means of catalytic hydrogenation (cf. S. G. Davies et al., Tetrahedron: Asymmetry 2 (1991), 183-186); S. G. Davies et al., J. Chem. Soc. Perkin Trans. 1 (1994), 1129-1139).

The introduction of the structural moieties of the compounds of the formula in the course of the synthesis can also occur in another order than outlined above. For example, in the case of compounds of the formula I in which $R^{10}$ is another group than hydroxy, instead of preparing a compound of the formula II which contains the group $R^{10}$ and reacting it with a compound of the formula III, also a compound of the formula IIc, which specifically comprises a hydroxy group in place of the group $R^{10}$, can be reacted with a compound of the formula III, and the obtained compound of the formula Ia then modified on the hydroxy group by reaction with a compound of the formula VIII to give a compound of the formula I in which $R^{10}$ is different from hydroxy, i.e. a compound of the formula Ib. At the end, like in the compounds of the formula I when prepared as outlined above, any protective groups in the compounds of the formula Ib may still be deprotected and/or precursor group converted into the final groups.

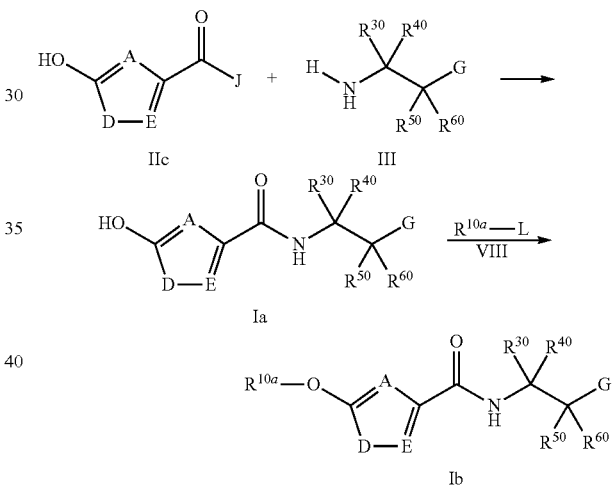

The groups A, D, E, G, $R^{30}$, $R^{40}$, $R^{50}$ and $R^{60}$ in the compounds of the formulae Ia, Ib and IIc are defined as in the compounds of the formula I and additionally functional groups can be present in protected form or in the form of a precursor group which is later converted into the final group. The group J in the compounds of the formula IIc is defined as in the compounds of the formula II. The group $R^{10a}$ in the compounds of the formula Ib is defined as in the compounds of the formulae IIb and VIII. The explanations given above on the reaction of the compounds of the formulae II and III and the reaction of the compounds of the formulae IIa and VIII apply correspondingly to the reaction of the compounds of the formulae IIc and III and the reaction of the compounds Ia and VIII, respectively.

For obtaining further compounds of the formula I, various transformations of functional groups can be carried out under standard conditions in compounds of the formula I or intermediates or starting compounds of the synthesis of the compounds of the formula I. For example, a hydroxy group, including a hydroxy group representing $R^{10}$ in a compound of the formula I, can be etherified, as outlined above, for example by alkylation with a halogen compound, for example a bromide or iodide, in the presence of a base such an alkali metal carbonate like potassium carbonate or cesium carbonate in an inert solvent such as an amide like DMF or NMP or a ketone like acetone or butan-2-one, or with the respective alcohol under the conditions of the Mitsunobu reaction referred to above. A hydroxy group can be esterified to give a carboxylic acid ester or a sulfonic acid ester, or converted into a halide by treatment with a halogenating agent. Halogen atoms can also be introduced by means of suitable halogenating agents which replace a hydrogen atom in the starting compound, for example by means of elemental bromine, sulfuryl chloride or 1-chloromethyl-4-fluoro-1,4-diazoniabicyclo[2.2.2]octane bis(tetrafluoroborate), which introduce a bromine, chlorine and fluorine substituent, respectively, for example in the 4-position of a compound of the formula IIb. A halogen atom can generally be replaced with a variety of groups in substitution reactions which may also be transition-metal catalyzed reactions. A nitro group can be reduced to an amino group, for example by catalytic hydrogenation. An amino group can be modified under standard conditions for alkylation, for example by reaction with a halogen compound or by reductive amination of a carbonyl compound, or for acylation or sulfonylation, for example by reaction with an activated carboxylic acid or a carboxylic acid derivate like an acid chloride or anhydride or a sulfonic acid chloride. A carboxylic ester group can be hydrolyzed under acidic or basic conditions to give a carboxylic acid. An acid group can be activated or converted into a reactive derivative as outlined above and reacted with an alcohol or an amine or ammonia to give an ester or amide. A primary amide can be dehydrated to give a nitrile. A sulfur atom in an alkyl-S— group or in a heterocyclic ring can be oxidized with a peroxide like hydrogen peroxide or a peracid to give a sulfoxide moiety $S(O)$ or a sulfone moiety $S(O)_2$. A carboxylic acid group, carboxylic acid ester group and a ketone group can be reduced to an alcohol, for example with a complex hydride such al lithium aluminium hydride, lithium borohydride or sodium borohydride, or reacted with an organometallic compound or a Grignard compound to give an alcohol. Primary and secondary hydroxy groups can also be oxidized to the oxo groups. All reactions in the preparation of the compounds of the formula I are known per se and can be carried out in a manner familiar to a person skilled in the art according to, or analogously to, procedures which are described in the standard literature, for example in Houben-Weyl, Methods of Organic Chemistry, Thieme; or Organic Reactions, John Wiley & Sons; or R. C. Larock, Comprehensive Organic Transformations: A Guide to Functional Group Preparations, 2. ed. (1999), John Wiley & Sons, and the references quoted therein.

Another subject of the present invention are the novel starting compounds and intermediates occurring in the synthesis of the compounds of the formula I, including the compounds of the formulae Ia, Ib, II, IIa, IIb, IIc, III, V, VI and VIII, wherein the groups A, D, E, G, J, L, $R^2$, $R^{10}$, $R^{10a}$, $R^{30}$, $R^{40}$, $R^{50}$ and $R^{60}$ are defined as above, in any of their stereoisomeric forms or a mixture of stereoisomeric forms in any ratio, and their salts, and solvates of any of them, and their use as synthetic intermediates or starting compounds. All general explanations, specifications of embodiments and definitions of numbers and groups given above with respect to the compounds of the formula I apply correspondingly to the said intermediates and starting compounds. A subject of the invention is in particular the novel specific starting compounds and intermediates described herein. Independently thereof whether they are described as a free compound and/or as a specific salt, they are a subject of the invention both in the form of the free compounds and in the form of their salts, and if a specific salt is described, additionally in the form of this specific salt.

The compounds of the formula I inhibit the protease cathepsin A as can be demonstrated in the pharmacological test described below and in other tests which are known to a person skilled in the art. The compounds of the formula I and their physiologically acceptable salts and solvates therefore are valuable pharmaceutical active compounds. The compounds of the formula I and their physiologically acceptable salts and solvates can be used for the treatment of cardiovascular diseases such as heart failure including systolic heart failure, diastolic heart failure, diabetic heart failure and heart failure with preserved ejection fraction, cardiomyopathy, myocardial infarction, left ventricular dysfunction including left ventricular dysfunction after myocardial infarction, cardiac hypertrophy, myocardial remodeling including myocardial remodeling after infarction or after cardiac surgery, valvular heart diseases, vascular hypertrophy, vascular remodeling including vascular stiffness, hypertension including pulmonary hypertension, portal hypertension and systolic hypertension, atherosclerosis, peripheral arterial occlusive disease (PAOD), restenosis, thrombosis and vascular permeability disorders, ischemia and/or reperfusion damage including ischemia and/or reperfusion damage of the heart and ischemia and/or reperfusion damage of the retina, inflammation and inflammatory diseases such as rheumatoid arthritis and osteoarthritis, renal diseases such as renal papillary necrosis and renal failure including renal failure after ischemia/reperfusion, pulmonary diseases such as cystic fibrosis, chronic bronchitis, chronic obstructive pulmonary disease (COPD), asthma, acute respiratory distress syndrome (ARDS), respiratory tract infections and lung carcinoma, immunological diseases, diabetic complications including diabetic nephropathy and diabetic cardiomyopathy, fibrotic diseases such as pulmonary fibrosis including idiopathic lung fibrosis, cardiac fibrosis, vascular fibrosis, perivascular fibrosis, renal fibrosis including renal tubulointerstitial fibrosis, fibrosing skin conditions including keloid formation, collagenosis and scleroderma, and liver fibrosis, liver diseases such as liver cirrhosis, pain such as neuropathic pain, diabetic pain and inflammatory pain, macular degeneration, neurodegenerative diseases or psychiatric disorders, or for cardioprotection including cardioprotection after myocardial infarction and after cardiac surgery, or for renoprotection, for example. The compounds of the formula I and their physiologically acceptable salts and solvates can be used as diuretic (stand-alone treatment or in combination with established diuretics). The treatment of diseases is to be understood as meaning both the therapy of existing pathological changes or malfunctions of the organism or of existing symptoms with the aim of relief, alleviation or cure, and the prophylaxis or prevention of pathological changes or malfunctions of the organism or of symptoms in humans or animals which are susceptible thereto and are in need of such a prophylaxis or prevention, with the aim of a prevention or suppression of their occurrence or of an attenuation in the case of their occurrence. For example, in patients who on account of their disease history are susceptible to myocardial infarction, by means of the prophylactic or preventive medicinal treatment the occurrence or re-occurrence of a myocardial infarction can be prevented or its extent and sequalae decreased, or in patients who are susceptible to attacks of asthma, by means of the prophylactic or preventive medicinal treatment such attacks can be prevented or their severity decreased. The treatment of diseases can occur both in acute cases and in chronic cases. The efficacy of the compounds of the formula I can be demonstrated in the pharmacological test described below and in other tests which are known to a person skilled in the art. The compounds of the formula I with G selected from $R^{72}$—$N(R^{73})$—$C(O)$— and their physiologically acceptable salts and solvates can also be used as prodrugs.

The compounds of the formula I and their physiologically acceptable salts and solvates can therefore be used in animals, in particular in mammals and specifically in humans, as a pharmaceutical or medicament on their own, in mixtures with one another or in the form of pharmaceutical compositions. A subject of the present invention also are the compounds of the formula I and their physiologically acceptable salts and solvates for use as a pharmaceutical, as well as pharmaceutical compositions and medicaments which comprise an efficacious dose of at least one compound of the formula I and/or a physiologically acceptable salt thereof and/or solvate thereof as an active ingredient and a pharmaceutically acceptable carrier, i.e. one or more pharmaceutically innocuous, or non-hazardous, vehicles and/or excipients, and optionally one or more other pharmaceutical active compounds. A subject of the present invention furthermore are the compounds of the formula I and their physiologically acceptable salts and solvates for use in the treatment of the diseases mentioned above or below, including the treatment of any one of the mentioned diseases, for example the treatment of heart failure, myocardial infarction, cardiac hypertrophy, diabetic nephropathy, diabetic cardiomyopathy, cardiac fibrosis, or ischemia and/or reperfusion damage, or for cardioprotection, the use of the compounds of the formula I and their physiologically acceptable salts and solvates for the manufacture of a medicament for the treatment of the diseases mentioned above or below, including the treatment of any one of the mentioned diseases, for example the treatment of heart failure, myocardial infarction, cardiac hypertrophy, diabetic nephropathy, diabetic cardiomyopathy, cardiac fibrosis, or ischemia and/or reperfusion damage, or for cardioprotection, wherein the treatment of diseases comprises their therapy and prophylaxis as mentioned above, as well as their use for the manufacture of a medicament for the inhibition of cathepsin A. A subject of the invention also are methods for the treatment of the diseases mentioned above or below, including the treatment of any one of the mentioned diseases, for example the treatment of heart failure, myocardial infarction, cardiac hypertrophy, diabetic nephropathy, diabetic cardiomyopathy, cardiac fibrosis, or ischemia and/or reperfusion damage, or for cardioprotection, which comprise administering an efficacious amount of at least one compound of the formula I and/or a physiologically acceptable salt thereof and/or solvate thereof to a human or an animal which is in need thereof. The compounds of the formula I and pharmaceutical compositions and medicaments comprising them can be administered enterally, for example by oral, sublingual or rectal administration, parenterally, for example by intravenous, intramuscular, subcutaneous or intraperitoneal injection or infusion, or by another type of administration such as topical, percutaneous, transdermal, intra-articular or intraocular administration.

The compounds of the formula I and their physiologically acceptable salts and solvates can also be used in combination with other pharmaceutical active compounds, wherein in such a combination use the compounds of the formula I and/or their physiologically acceptable salts and/or solvates and one or more other pharmaceutical active compounds can be present in one and the same pharmaceutical composition or in two or more pharmaceutical compositions for separate, simultaneous or sequential administration. Examples of such other pharmaceutical active compounds are diuretics, aquatics, angiotensin converting enzyme (ACE) inhibitors, angiotensin receptor blockers, renin inhibitors, beta blockers, digoxin, aldosterone antagonists, NO donors, nitrates, hydralazines, ionotropes, vasopressin receptor antagonists, soluble guanylate cyclase activators, statins, peroxisome proliferator-activated receptor-alpha (PPAR-α) activators, peroxisome proliferator-activated receptor-gamma (PPAR-γ) activators, rosiglitazone, pioglitazone, metformin, sulfonylureas, glucagon-like peptide 1 (GLP-1) agonists, dipeptidyl peptidase IV (DPPIV) inhibitors, insulins, anti-Arrhythmics, endothelin receptor antagonists, calcium antagonists, phosphodiesterase inhibitors, phosphodiesterase type 5 (PDE5) inhibitors, factor II/factor IIa inhibitors, factor IX/factor IXa inhibitors, factor X/factor Xa inhibitors, factor XIII/factor XIIIa inhibitors, heparins, glycoprotein IIb/IIIa antagonists, P2Y12 receptor antagonists, clopidogrel, coumarins, cyclooxygenase inhibitors, acetylsalicylic acid, RAF kinase inhibitors and p38 mitogen-activated protein kinase inhibitors. A subject of the present invention also is the said combination use of any one or more of the compounds of the formula I disclosed herein and their physiologically acceptable salts and solvates, with any one or more, for example one or two, of the mentioned other pharmaceutical active compounds.

The pharmaceutical compositions and medicaments according to the invention normally contain from about 0.5 to about 90 percent by weight of compounds of the formula I and/or physiologically acceptable salts and/or solvates thereof, and an amount of active ingredient of the formula I and/or its physiologically acceptable salt and/or solvate which in general is from about 0.2 mg to about 1.5 g, particularly from about 0.2 mg to about 1 g, more particularly from about 0.5 mg to about 0.5 g, for example from about 1 mg to about 0.3 g, per unit dose. Depending on the kind of the pharmaceutical composition and other particulars of the specific case, the amount may deviate from the indicated ones. The production of the pharmaceutical compositions and medicaments can be carried out in a manner known per se. For this, the compounds of the formula I and/or their physiologically acceptable salts and/or solvates are mixed together with one or more solid or liquid vehicles and/or excipients, if desired also in combination with one or more other pharmaceutical active compounds such as those mentioned above, and brought into a suitable form for dosage and administration, which can then be used in human medicine or veterinary medicine.

As vehicles, which may also be looked upon as diluents or bulking agents, and excipients suitable organic and inorganic substances can be used which do not react in an undesired manner with the compounds of the formula I. As examples of types of excipients, or additives, which can be contained in the pharmaceutical compositions and medicaments, lubricants, preservatives, thickeners, stabilizers, disintegrants, wetting agents, agents for achieving a depot effect, emulsifiers, salts, for example for influencing the osmotic pressure, buffer substances, colorants, flavorings and aromatic substances may be mentioned. Examples of vehicles and excipients are water, vegetable oils, waxes, alcohols such as ethanol, isopropanol, 1,2-propanediol, benzyl alcohols, glycerol, polyols, polyethylene glycols or polypropylene glycols, glycerol triacetate, polyvinylpyrrolidone, gelatin, cellulose, carbohydrates such as lactose or starch like corn starch, sodium chloride, stearic acid and its salts such as magnesium stearate, talc, lanolin, petroleum jelly, or mixtures thereof, for example saline or mixtures of water with one or more organic solvents such as mixtures of water with alcohols. For oral and rectal use, pharmaceutical forms such as, for example, tablets, film-coated tablets, sugar-coated tablets, granules, hard and soft gelatin capsules, suppositories, solutions, including oily, alcoholic or aqueous solutions, syrups, juices or drops, furthermore suspensions or emulsions, can be used. For parenteral use, for example by injection or infusion, pharmaceutical forms such as solutions, for example aqueous solutions, can be used. For topical use, pharmaceutical forms such as ointments, creams, pastes, lotions, gels, sprays, foams, aerosols, solutions or powders can be used. Further suitable pharmaceutical forms are, for example, implants and patches and forms adapted to inhalation. The compounds of the formula I and their physiologically acceptable salts can also be lyophilized and the obtained lyophilizates used, for example, for the production of injectable compositions. In particular for topical application, also liposomal compositions are suitable. The pharmaceutical compositions and medicaments can also contain one or more other active ingredients and/or, for example, one or more vitamins.

As usual, the dosage of the compounds of the formula I depends on the circumstances of the specific case and is adjusted by the physician according to the customary rules and procedures. It depends, for example, on the compound of the formula I administered and its potency and duration of action, on the nature and severity of the individual syndrome, on the sex, age, weight and the individual responsiveness of the human or animal to be treated, on whether the treatment is acute or chronic or prophylactic, or on whether further pharmaceutical active compounds are administered in addition to a compound of the formula I. Normally, in the case of administration to an adult weighing about 75 kg, a dose from about 0.1 mg to about 100 mg per kg per day, in particular from about 1 mg to about 20 mg per kg per day, for example from about 1 mg to about 10 mg per kg per day (in each case in mg per kg of body weight), is administered. The daily dose can be administered in the form of a single dose or divided into a number of individual doses, for example two, three or four individual doses. The administration can also be carried out continuously, for example by continuous injection or infusion. Depending on the individual behavior in a specific case, it may be necessary to deviate upward or downward from the indicated dosages.

Besides as a pharmaceutical active compound in human medicine and veterinary medicine, the compounds of the formula I can also be employed as an aid in biochemical investigations or as a scientific tool or for diagnostic purposes, for example in in-vitro diagnoses of biological samples, if an inhibition of cathepsin A is intended. The compounds of the formula I and their salts can also be used as intermediates, for example for the preparation of further pharmaceutical active substances.

The following examples illustrate the invention.
Abbreviations
ACN acetonitrile
DCM dichloromethane
DMF N,N-dimethylformamide
DMSO dimethyl sulfoxide
EA ethyl acetate
EDIA N-ethyl-diisopropylamine
FA formic acid
MOH methanol
NEM N-ethyl-morpholine
TFA trifluoroacetic acid
THF tetrahydrofuran
TOTU O-(cyano(ethoxycarbonyl)methyleneamino)-N,N,N',N'-tetramethyluronium tetrafluoroborate When example compounds containing a basic group were purified by preparative high pressure liquid chromatography (HPLC) on reversed phase (RP) column material and, as customary, the eluent was a gradient mixture of water and acetonitrile containing trifluoroacetic acid, they were in part obtained in the form of their acid addition salts with trifluoroacetic acid, depending on the details of the work-up such as evaporation or lyophilization conditions. In the names of the example compounds and the structural formulae such contained trifluoroacetic acid is not specified. Likewise are other acid components of example compounds obtained in the form of an acid addition salt in general not specified in the name and the formula.

The prepared compounds were in general characterized by spectroscopic data and chromatographic data, in particular mass spectra (MS) and HPLC retention times (Rt; in min) which were obtained by combined analytical HPLC/MS characterization (LC/MS), and/or nuclear magnetic resonance (NMR) spectra. Unless specified otherwise, $^1$H-NMR spectra were recorded at 500 MHz in $D_6$-DMSO as solvent at 298 K. In the NMR characterization, the chemical shift δ (in ppm), the number of hydrogen atoms (H), and the multiplicity (s: singlet, d: doublet, dd: doublet of doublets, t: triplet, q: quartet, m: multiplet) of the peaks as determined from the graphically depicted spectra are given. In the MS characterization, in general the mass number (m/z) of the peak of the molecular ion [M], for example [M$^+$], or of a related ion such as the ion [M+1], for example [(M+1)$^+$], i.e. the protonated molecular ion [(M+H)$^+$], or the ion [M−1], for example [(M−1)$^−$], i.e. the deprotonated molecular ion [(M−H)$^−$], which was formed depending on the ionization method used, is given. Generally, the ionization method was electrospray ionization (ES). The particulars of the LC/MS methods used are as follows.

Method LC1
Column: YMC-Pack Jsphere H80, 33×2.1 mm, 4 μm; flow: 1.3 ml/min; room temperature; eluent A: water+0.05% FA; eluent B: ACN+0.05% FA; gradient: from 95% A+5% B to 5% A+95% B within 2.5 min; MS ionization method: ES$^+$ Method LC2
Column: Waters XBridge C18, 50×4.6 mm, 2.5 μm; flow: 1.3 ml/min; room temperature; eluent A: water+0.1% FA; eluent B: ACN+0.08% FA; gradient: from 97% A+3% B to 40% A+60% B within 3.5 min, then to 2% A+98% B within 0.5 min, then 2% A+98% B for 1.0 min, then to 97% A+3% B within 0.2 min, then 97% A+3% B for 1.3 min; MS ionization method: ES$^−$ Method LC3
Column: YMC-Pack Jsphere H80, 33×2.1 mm, 4 μm; flow: 1.0 ml/min; room temperature; eluent A: water+0.05% TFA; eluent B: ACN+0.05% TFA; gradient: 98% A+2% B for 1.0 min, then to 5% A+95% B within 4.0 min, then 5% A+95% B for 1.25 min; MS ionization method: ES$^+$ Method LC4
Column: Waters XBridge C18, 50×4.6 mm, 2.5 μm; flow: 1.3 ml/min; 40° C.; eluent A: water+0.1% FA; eluent B: ACN+0.1% FA; gradient: from 97% A+3% B to 40% A+60% B within 3.5 min, then to 2% A+98% B within 0.5 min, then 2% A+98% B for 1.0 min, then to 97% A+3% B within 0.2 min, then 97% A+3% B for 1.3 min; MS ionization method: ES$^−$ Method LC5
Column: Waters XBridge C18, 50×4.6 mm, 2.5 μm; flow: 1.7 ml/min; 40° C.; eluent A: water+0.05% FA; eluent B: ACN+0.05% TFA; gradient: from 95% A+5% B to 5% A+95% B within 3.3 min, then 5% A+95% B for 0.55 min, then to 95% A+5% B within 0.15 min; MS ionization method: ES$^+$ Method LC6

Column: Waters XBridge C18, 50×4.6 mm, 2.5 µm; flow: 1.7 ml/min; 50° C.; eluent A: water+0.05% TFA; eluent B: ACN+0.05% TFA; gradient: 95% A+5% B for 0.2 min, then to 5% A+95% B within 2.2 min, then 5% A+95% B for 1.1 min, then to 95% A+5% B within 0.1 min, then 95% A+5% B for 0.9 min; MS ionization method: ES+

Method LC7

Column: Waters XBridge C18, 50×4.6 mm, 2.5 µm; flow: 1.7 ml/min; 40° C.; eluent A: water+0.05% TFA; eluent B: ACN+0.05% TFA; gradient: 95% A+5% B for 0.2 min, then to 5% A+95% B within 2.2 min, then 5% A+95% B for 0.8 min, then to 95% A+5% B within 0.1 min, then 95% A+5% B for 0.7 min; MS ionization method: ES+

Method LC8

Column: Waters XBridge C18, 50×4.6 mm, 2.5 µm; flow: 1.7 ml/min; 40° C.; eluent A: water+0.05% TFA; eluent B: ACN+0.05% TFA; gradient: 95% A+5% B for 0.3 min, then to 5% A+95% B within 3.2 min, then 5% A+95% B for 0.5 min; MS ionization method: ES+

Method LC9

Column: Merck Chromolith FastGrad RP-18e, 50×2 mm; flow: 2.0 ml/min; room temperature; eluent A: water+0.05% TFA; eluent B: ACN+0.05% TFA; gradient: 98% A+2% B for 0.2 min, then to 2% A+98% B within 2.2 min, then 2% A+98% B for 0.8 min, then to 98% A+2% B within 0.1 min, then 98% A+2% B for 0.7 min; MS ionization method: ES+

Method LC10

Column: Waters XBridge C18, 50×4.6 mm, 2.5 µm; flow: 1.3 ml/min; 45° C.; eluent A: water+0.1% FA; eluent B: ACN+0.1% FA; gradient: from 97% A+3% B to 40% A+60% B within 3.5 min, then to 2% A+98% B within 0.5 min, then 2% A+98% B for 1.0 min, then to 97% A+3% B within 0.2 min, then 97% A+3% B for 1.3 min; MS ionization method: ES+

Method LC11

Column: Waters HPLC BEH C18, 50×2.1 mm, 1.7 µm; flow: 0.9 ml/min; 55° C.; eluent A: water+0.1% FA; eluent B: ACN+0.08% FA; gradient: from 95% A+5% B to 5% A+95% B within 1.1 min, then 5% A+95% B for 0.6 min, then to 95% A+5% B within 0.1 min, then 95% A+5% B for 0.2 min; MS ionization method: ES+

Method LC12

Column: YMC-Pack Jsphere H80, 33×2.1 mm, 4 µm; flow: 1.0 ml/min; room temperature; eluent A: water+0.05% TFA; eluent B: MOH+0.05% TFA; gradient: 98% A+2% B for 1.0 min, then to 5% A+95% B within 4.0 min, then 5% A+95% B for 1.25 min; MS ionization method: ES+

Method LC13.

Column: Waters XBridge C18, 50×4.6, 2.5 µm; flow: 1.3 ml/min; room temperature; eluent A: water+0.1% FA; eluent B: ACN+0.08% FA; gradient: from 97% A+3% B to 2% A+98% B within 18.0 min, then 2% A+98% B for 1.0 min, then to 97% A+3% B within 0.5 min, then 97% A+3% B for 0.5 min; MS ionization method: ES+

Method LC14

Column: Waters XBridge C18 4.6*50 mm; 2.5 um, flow: 1.3 ml/min; eluent A H₂O+0.1% FA; eluent B: ACN+0.08% FA; gradient: from 97% A+3% B to 2% A+98% B within 18 min, then 2% A+98% B for 1 min, then to 97% A+3% B within 0.5 min then to 97:3 for 0.5 min.

SYNTHESIS EXAMPLE 1

1-(2-Fluoro-phenyl)-5-hydroxy-1H-pyrazole-3-carboxylic acid

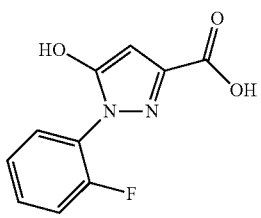 [SMILES: O=C(O)c1cc(O)n(-c2ccccc2F)n1]

Sulfuric acid (400 ml) was added slowly to water (400 ml). After cooling to 5° C., 2-fluoro-phenylhydrazine hydrochloride (123 g, 757 mmol) was added resulting in a brown suspension. Then a solution of oxalacetic acid (100 g, 757 mmol) in water (400 ml) was added slowly during a period of 25 min. After 2 h the conversion was complete and the solid was filtered. After washing with water the solid was dried. The product was obtained as light brown solid (151 g, 90%).

Analogously as described in synthesis example 1, the following compounds were prepared:
5-hydroxy-1-phenyl-1H-pyrazole-3-carboxylic acid
1-(2-fluoro-phenyl)-5-hydroxy-1H-pyrazole-3-carboxylic acid
1-(2,5-dimethyl-phenyl)-5-hydroxy-1H-pyrazole-3-carboxylic acid
1-(3,5-dimethyl-phenyl)-5-hydroxy-1H-pyrazole-3-carboxylic acid
1-(2-chloro-phenyl)-5-hydroxy-1H-pyrazole-3-carboxylic acid
1-(3-chloro-phenyl)-5-hydroxy-1H-pyrazole-3-carboxylic acid
1-(4-chloro-phenyl)-5-hydroxy-1H-pyrazole-3-carboxylic acid
1-(3-chloro-4-fluoro-phenyl)-5-hydroxy-1H-pyrazole-3-carboxylic acid
5-hydroxy-1-(3-methoxy-phenyl)-1H-pyrazole-3-carboxylic acid
1-(2-chloro-pyridin-4-yl)-5-hydroxy-1H-pyrazole-3-carboxylic acid
1-(5-chloro-pyridin-2-yl)-5-hydroxy-1H-pyrazole-3-carboxylic acid
5-hydroxy-1-(4-trifluoromethyl-pyrimidin-2-yl)-1H-pyrazole-3-carboxylic acid
5-hydroxy-1-(pyridin-4-yl)-1H-pyrazole-3-carboxylic acid
5-hydroxy-1-(pyridin-3-yl)-1H-pyrazole-3-carboxylic acid
5-hydroxy-1-(2-trifluoromethyl-phenyl)-1H-pyrazole-3-carboxylic acid
5-hydroxy-1-(3,5-difluoro-phenyl)-1H-pyrazole-3-carboxylic acid
5-hydroxy-1-(2,5-difluoro-phenyl)-1H-pyrazole-3-carboxylic acid
5-hydroxy-1-(2,6-difluoro-phenyl)-1H-pyrazole-3-carboxylic acid
1-(3-chloro-2-fluoro-phenyl)-5-hydroxy-1H-pyrazole-3-carboxylic acid
1-cyclopentyl-5-hydroxy-1H-pyrazole-3-carboxylic acid
1-cyclohexyl-5-hydroxy-1H-pyrazole-3-carboxylic acid 5-hydroxy-1-(3-sulfamoyl-phenyl)-1H-pyrazole-3-carboxylic acid
5-hydroxy-1-(2-methanesulfonyl-phenyl)-1H-pyrazole-3-carboxylic acid
1-tert-butyl-5-hydroxy-1H-pyrazole-3-carboxylic acid

SYNTHESIS EXAMPLE 2

(S)-3-{[1-(2-Fluoro-phenyl)-5-hydroxy-1H-pyrazole-3-carbonyl]-amino}-3-o-tolyl-propionic acid

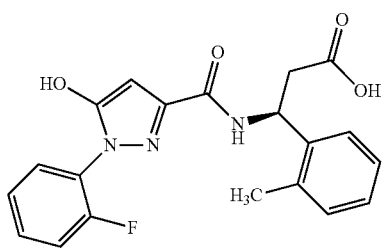 [SMILES: Cc1ccccc1[C@H](CC(=O)O)NC(=O)c1cc(O)n(-c2ccccc2F)n1]

0.45 mmol of 1-(2-fluoro-phenyl)-5-hydroxy-1H-pyrazole-3-carboxylic acid were dissolved in 5 ml of DMF, 0.54 mmol of TOTU and 1.125 mmol of NEM were added, and the mixture was stirred for 5 min at room temperature. Then 0.495 mmol of (S)-3-amino-3-o-tolyl-propionic acid were added and the mixture stirred overnight at room temperature. The solvent was evaporated in vacuo and the residue subjected to preparative HPLC to give the title compound in a yield of 28%.

SYNTHESIS EXAMPLE 3

5-Methoxy-1-phenyl-1H-pyrazole-3-carboxylic acid

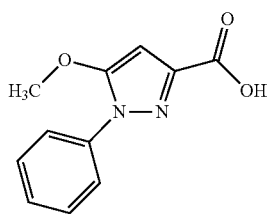 [SMILES: COc1cc(C(=O)O)nn1-c1ccccc1]

600 mg (2.94 mmol) of 5-hydroxy-1-phenyl-1H-pyrazole-3-carboxylic acid were dissolved in 30 ml of DMF, 1.92 (5.9 mmol) of cesium carbonate and 1.04 g (7.35 mmol) of iodomethane were added, and the resulting mixture was heated for 4 h to 80° C. The mixture was filtrated and the solvent removed in vacuo. The residue was dissolved in 20 ml of MOH and 5.9 ml of an aqueous 1 M solution of sodium hydroxide. After stirring overnight the reaction was complete. The solvent was removed and the residue subjected to preparative HPLC to give the title compound in a yield of 38%.

Analogously as described in synthesis example 3, the following compounds were prepared:
1-(2-fluoro-phenyl)-5-methoxy-1H-pyrazole-3-carboxylic acid
1-(2-chloro-phenyl)-5-methoxy-1H-pyrazole-3-carboxylic acid
1-(3-fluoro-phenyl)-5-methoxy-1H-pyrazole-3-carboxylic acid
1-(2,5-difluoro-phenyl)-5-methoxy-1H-pyrazole-3-carboxylic acid
1-tert-butyl-5-methoxy-1H-pyrazole-3-carboxylic acid

SYNTHESIS EXAMPLE 4

Methyl 1-(2-fluoro-phenyl)-5-hydroxy-1H-pyrazole-3-carboxylate

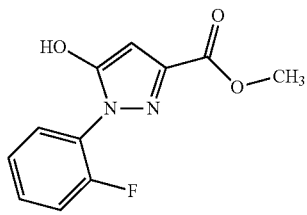 [SMILES: COC(=O)c1cc(O)n(-c2ccccc2F)n1]

1 g (4.5 mmol) of 1-(2-fluoro-phenyl)-5-hydroxy-1H-pyrazole-3-carboxylic acid was dissolved in 20 ml of MOH. 535 mg (4.5 mmol) of thionyl chloride was added with caution and the mixture is stirred for 4 h at room temperature. Then the solvent was removed in vacuo to give 900 mg (85%) of the crude title compound which was used in the following step without further purification.

SYNTHESIS EXAMPLE 5

Methyl 1-(2-fluoro-phenyl)-5-hydroxy-1H-pyrazole-3-carboxylate

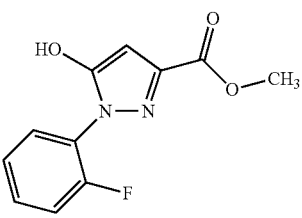 [SMILES: COC(=O)c1cc(O)n(-c2ccccc2F)n1]

Dimethyl acetylenedicarboxylate (87.4 g, 757 mmol) was added to a solution of 2-fluoro-phenylhydrazine hydrochloride (100 g, 615 mmol) in methanol (1 l) at 0° C. Then triethylamine (125 g, 1.23 mol) was added slowly during 60 min. The solution was stirred for 16 h at room temperature, the solvent then removed under reduced pressure and the residue dissolved in EA (500 ml). After washing with aqueous hydrochloric acid (500 ml), the solvent was removed under reduced pressure. The title compound was obtained as an almost white solid in quantitative yield.

SYNTHESIS EXAMPLE 6

5-Cyclopropylmethoxy-1-(2-fluoro-phenyl)-1H-pyrazole-3-carboxylic acid

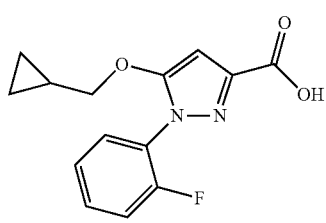 [SMILES: O=C(O)c1cc(OCC2CC2)n(-c2ccccc2F)n1]

Step 1: 5-Cyclopropylmethoxy-1-(2-fluoro-phenyl)-1H-pyrazole-3-carboxylic acid methyl ester 150 mg (0.635 mmol) of methyl 1-(2-fluoro-phenyl)-5-hydroxy-1H-pyrazole-3-carboxylate were dissolved in 8 ml of THF. 207 mg (0.635 mmol) of cesium carbonate and 400 mg (2.96 mmol) of bromomethyl-cyclopropane were added and the mixture was heated to 50° C. for 6 h. Then the mixture was filtrated and the solvent removed in vacuo. The crude title compound was used in the next step without further purification.

Step 2: 5-Cyclopropylmethoxy-1-(2-fluoro-phenyl)-1H-pyrazole-3-carboxylic acid The crude compound obtained in step 1 was dissolved in 10 ml of methanol. 1.4 ml of an aqueous 1 M solution of sodium hydroxide were added and the mixture was stirred overnight at room temperature. The solvent was removed in vacuo and the residue purified by preparative HPLC to give 102 mg (58%) of the title compound Analogously as described in synthesis example 6, the following compounds were prepared:
5-cyclopropylmethoxy-1-phenyl-1H-pyrazole-3-carboxylic acid
5-cyclopropylmethoxy-1-(2,6-difluoro-phenyl)-1H-pyrazole-3-carboxylic acid
5-dimethylcarbamoyl-methoxy-1-(2-fluoro-phenyl)-1H-pyrazole-3-carboxylic acid
(using 2 equivalents of 2-chloro-N,N-dimethyl-acetamide instead of bromomethyl-cyclopropane in step 1)
1-(2-fluoro-phenyl)-5-(2-oxo-2-pyrrolidin-1-yl-ethoxy)-1H-pyrazole-3-carboxylic acid
(using 2 equivalents of 2-chloro-1-pyrrolidin-1-yl-ethanone instead of bromomethyl-cyclopropane in step 1)

SYNTHESIS EXAMPLE 7

1-(2-Fluoro-phenyl)-5-methoxy-1H-pyrazole-3-carboxylic acid

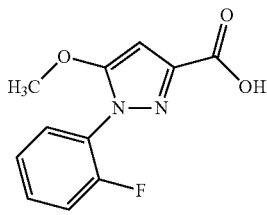 [SMILES: COc1cc(C(=O)O)nn1-c1ccccc1F]

Step 1: Methyl 1-(2-fluoro-phenyl)-5-methoxy-1H-pyrazole-3-carboxylate

Potassium carbonate (27.8 g, 201 mmol) and water (3.62 g, 201 mmol) were added to a suspension of methyl 1-(2-fluoro-phenyl)-5-hydroxy-1H-pyrazole-3-carboxylate (31.6 g, 134 mmol) in methyl isobutyl ketone (323 ml) at room temperature. Then dimethyl sulfate (16.9 g, 134 mmol) was added slowly and the mixture was stirred for 2.5 h. Water was added and the phases were separated. The organic phase was evaporated to give 27.4 g of the title compound as a white solid.

Step 2: 1-(2-Fluoro-phenyl)-5-methoxy-1H-pyrazole-3-carboxylic acid 109 ml of an aqueous 2 M solution of sodium hydroxide (218 mmol) were added to a solution of the crude methyl ester obtained in step 1 in methyl isobutyl ketone. After 16 h at room temperature the conversion was complete and the phases were separated.

The aqueous phase was acidified to pH 3 with hydrochloric acid and extracted with EA. The organic phases were evaporated to give 18.9 g (59% over two steps) of the title compound.

Analogously as described in synthesis example 7, the following compounds were prepared, using diethyl sulfate instead of dimethyl sulfate in step 1:
5-ethoxy-1-(2-fluoro-phenyl)-1H-pyrazole-3-carboxylic acid
5-ethoxy-1-(2-chloro-phenyl)-1H-pyrazole-3-carboxylic acid
5-ethoxy-1-phenyl-1H-pyrazole-3-carboxylic acid

SYNTHESIS EXAMPLE 8

Ethyl (S)-3-amino-3-(2-methyl-phenyl)-propionate

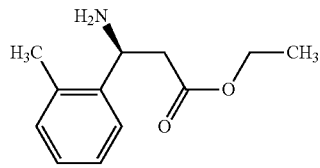

(S)-3-Amino-3-(2-methyl-phenyl)propionic acid (10.0 g, 55.8 mmol) was suspended in 2-methyltetrahydrofuran (100 ml) and ethanol (25.7 g, 558 mmol) was added. The mixture was heated to 80° C. and thionyl chloride (6.64 g, 55.8 mmol) was added slowly. After 2 h at 80° C. the solvents were almost completely removed by distillation. After cooling the mixture was stirred at room temperature for 16 h. Then more solvent was removed under reduced pressure to give the title compound in the form of ethyl (S)-3-amino-3-(2-methyl-phenyl)-propionate hydrochloride together with some 2-methyltetrahydrofuran in quantitative yield.

SYNTHESIS EXAMPLE 9

Ethyl (S)-3-{[1-(2-fluoro-phenyl)-5-methoxy-1H-pyrazole-3-carbonyl]-amino}-3-(2-methyl-phenyl)-propionate

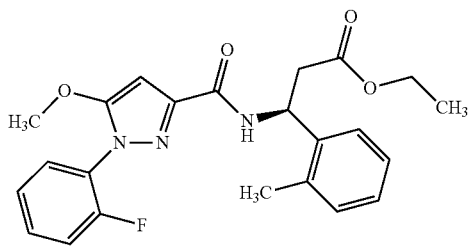 [SMILES: CCOC(=O)C[C@H](NC(=O)c1cc(OC)n(-c2ccccc2F)n1)c1ccccc1C]

Step 1: 1-(2-Fluoro-phenyl)-5-methoxy-1H-pyrazole-3-carbonyl chloride

A suspension of 1-(2-fluoro-phenyl)-5-methoxy-1H-pyrazole-3-carboxylic acid (39.1 g, 167 mmol) in 2-methyltetrahydrofuran (300 ml) was cooled to 0° C. and DMF (293 µl, 3.81 mmol) was added. Oxalyl chloride (23.1 g, 182 mmol) was added dropwise. After 16 h at room temperature ca. 100 ml of the solvent were removed by distillation. The resulting suspension of the title compound was used directly in the next step.

Step 2: Ethyl (S)-3-{[1-(2-fluoro-phenyl)-5-methoxy-1H-pyrazole-3-carbonyl]-amino}-3-(2-methyl-phenyl)-propionate A solution of ethyl (S)-3-amino-3-(2-methyl-phenyl)-propionate hydrochloride (42.4 g, 174 mmol) in 2-methyltetrahydrofuran (200 ml) was added to the suspension of 1-(2-fluoro-phenyl)-5-methoxy-1H-pyrazole-3-carbonyl chloride in ca. 200 ml of 2-methyltetrahydrofuran obtained in step 1. Triethylamine (33.5 g, 331 mmol) was added dropwise under ice cooling. After the complete addition of the triethylamine the conversion was complete and water was added. The phases were separated and the organic phase was washed with water and evaporated. The residue was dissolved in 2-methyltetrahydrofuran (500 ml) and washed with 1 M hydrochloric acid. The organic phase was dried and the solvent was removed under reduced pressure to give 70.4 g (99% over two step) of the title compound as a light brown oil.

SYNTHESIS EXAMPLE 10

(S)-3-{[1-(2-Fluoro-phenyl)-5-methoxy-1H-pyrazole-3-carbonyl]-amino}-3-(2-methyl-phenyl)-propionic acid

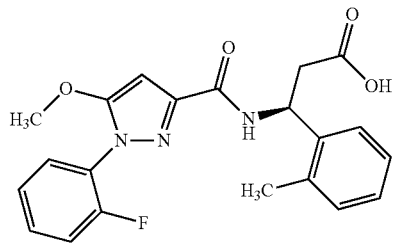 [SMILES: COc1cc(C(=O)N[C@@H](CC(=O)O)c2ccccc2C)nn1-c1ccccc1F]

82.8 ml of an aqueous 4 M solution of sodium hydroxide (331 mmol) were added to a solution of ethyl (S)-3-{[1-(2-fluoro-phenyl)-5-methoxy-1H-pyrazole-3-carbonyl]-amino}-3-(2-methyl-phenyl)-propionate (70.4 g, 165 mmol) in 2-methyltetrahydrofuran (500 ml) at room temperature. The mixture was stirred at room temperature for 2 h, then at 40° C. for 2 h and then at room temperature for 16 h. The phases were separated and the aqueous phase acidified to pH 3 with hydrochloric acid. The product partially precipitated upon acidification. The aqueous filtrate was extracted with EA. The extracts were evaporated and the residue was washed with isopropyl acetate. The two batches were combined to give 53.6 g (82%) of the title compound as a white crystalline powder.

SYNTHESIS EXAMPLE 11

5-(2-Cyano-benzyloxy)-1-(2-fluoro-phenyl)-1H-pyrazole-3-carboxylic acid

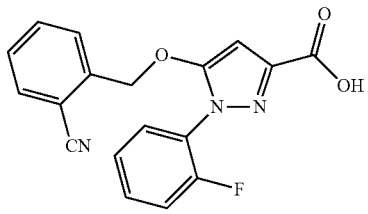 [SMILES: N#Cc1ccccc1COc1cc(C(=O)O)nn1-c1ccccc1F]

1-(2-Fluoro-phenyl)-5-hydroxy-1H-pyrazole-3-carboxylic acid methyl ester (200 mg, 0.847 mmol) were dissolved in 5 ml of DMF and cesium carbonate (552 mg, 1.7 mmol) and 2-bromomethyl-benzonitrile (166 mg, 0.85 mmol) were added. The mixture was stirred for 5 h at 60° C., filtrated and the solvent was removed in vacuo. The obtained residue of crude 5-(2-cyano-benzyloxy)-1-(2-fluoro-phenyl)-1H-pyrazole-3-carboxylic acid methyl ester (235 mg, 79%) was dissolved in a mixture of THF, MOH and water (3 ml each), lithium hydroxide (64.1 mg, 2.7 mmol) was added, and the mixture was stirred overnight at room temperature. After evaporation of the solvent the residue was subjected to column chromatography (silica gel, DCM/MOH 9:1) to give 195 mg (86%) of the title compound.

SYNTHESIS EXAMPLE 12

(S)-3-{[5-(2-Cyano-benzyloxy)-1-(2-fluoro-phenyl)-1H-pyrazole-3-carbonyl]-amino}-3-O— tolyl-propionic acid ethyl ester

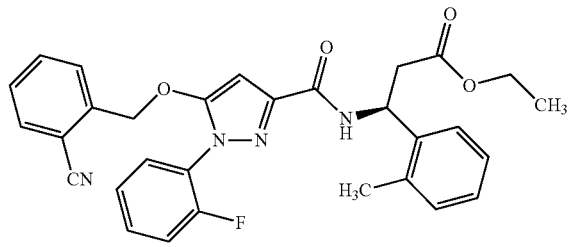 [SMILES: CCOC(=O)C[C@H](NC(=O)c1cc(OCc2ccccc2C#N)n(-c2ccccc2F)n1)c1ccccc1C]

190 mg (0.56 mmol) of (2-cyano-benzyloxy)-1-(2-fluoro-phenyl)-1H-pyrazole-3-carboxylic acid were dissolved in 6 ml of DMF, and 213.5 mg (0.56 mmol) of O-(7-azabenzotriazol-1-yl)-N,N,N',N'-tetramethyluronium hexafluorophosphate and 145.5 mg (1.12 mmol) of NEM were added. Then 116.7 mg (0.56 mmol) of ethyl (S)-3-amino-3-(2-methyl-phenyl)-propionate were added and the mixture was stirred for 3 h at room temperature. The solvent was removed in vacuo and the residue subjected to column chromatography (silica gel, DCM/MOH 100:1) to give 210 mg (71%) of the title compound.

SYNTHESIS EXAMPLE 13

(S)-3-{[5-(2-Cyano-benzyloxy)-1-(2-fluoro-phenyl)-1H-pyrazole-3-carbonyl]-amino}-3-o-tolyl-propionic acid

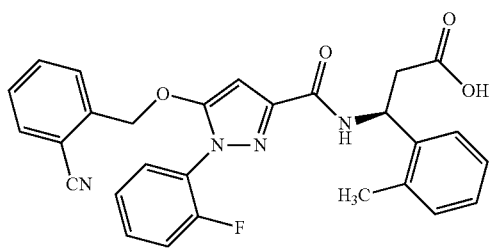 [SMILES: Cc1ccccc1[C@H](CC(=O)O)NC(=O)c1cc(OCc2ccccc2C#N)n(-c2ccccc2F)n1]

210 mg (0.4 mmol) of (S)-3-{[5-(2-cyano-benzyloxy)-1-(2-fluoro-phenyl)-1H-pyrazole-3-carbonyl]-amino}-3-o-tolyl-propionic acid ethyl ester were dissolved in a mixture of THF, MOH and water (2 ml each), lithium hydroxide (28.7 mg, 1.2 mmol) was added, and the mixture was stirred for 3 h at room temperature. After evaporation of the solvent the residue was subjected to aqueous work-up using EA and a 10% aqueous solution of citric acid. After evaporation of the organic phase the residue was subjected to column chromatography (silica gel, DCM/MOH 10:1) to give 45 mg (23%) of the title compound.

SYNTHESIS EXAMPLE 14

(S)-3-{[1-(2-Fluoro-phenyl)-5-(3-methyl-oxetan-3-ylmethoxy)-1H-pyrazole-3-carbonyl]-amino}-3-(2-methyl-phenyl)-propionic acid ethyl ester

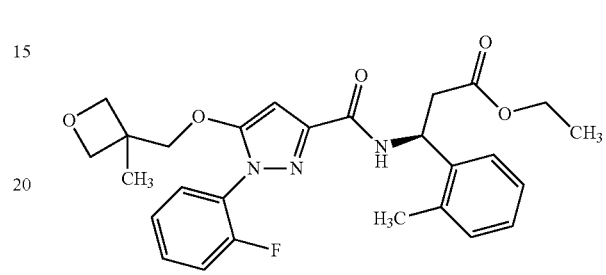

101 mg (0.245 mmol) of (S)-3-{[1-(2-fluoro-phenyl)-5-hydroxy-1H-pyrazole-3-carbonyl]-amino}-3-(2-methyl-phenyl)-propionic acid ethyl ester (prepared from 1-(2-fluoro-phenyl)-5-hydroxy-1H-pyrazole-3-carboxylic acid and ethyl (S)-3-amino-3-(2-methyl-phenyl)-propionate analogously as described in synthesis example 2) were dissolved in 3 ml of DMF, and 160 mg (0.5 mmol) of cesium carbonate and 41.3 mg (0.245 mmol) of 3-bromomethyl-3-methyl-oxetane were added. The mixture was stirred for 4 h at 65° C. After evaporation of the solvent the residue was subjected to an aqueous work-up with EA and 10% aqueous solution of citric acid. After removal of the solvent from the organic phase 100 mg (82%) of the product are obtained.

SYNTHESIS EXAMPLE 15

(S)-3-{[1-(2-Fluoro-phenyl)-5-(3-methyl-oxetan-3-ylmethoxy)-1H-pyrazole-3-carbonyl]-amino}-3-(2-methyl-phenyl)-propionic acid

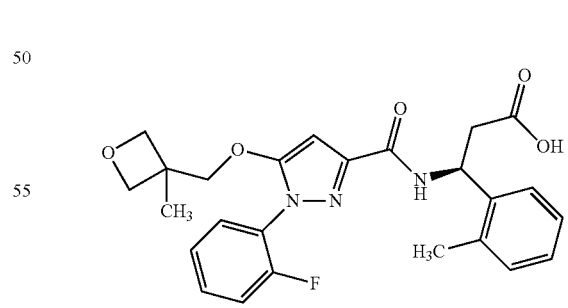

100 mg (0.2 mmol) of (S)-3-{[1-(2-fluoro-phenyl)-5-(3-methyl-oxetan-3-ylmethoxy)-1H-pyrazole-3-carbonyl]-amino}-3-(2-methyl-phenyl)-propionic acid ethyl ester were dissolved in a mixture of THF, MOH and water (2 ml each), and 14.5 mg (0.61 mmol) of lithium hydroxide were added. The mixture was stirred overnight at room temperature and the solvent removed. The residue was subjected to column chromatography (silica gel, DCM/MOH 9:1) to give 75 mg (75%) of the title compound.

SYNTHESIS EXAMPLE 16

Pyrrolidine-1-carboxylic acid 5-((S)-2-carboxy-1-o-tolyl-ethylcarbamoyl)-2-(2-fluoro-phenyl)-2H-pyrazol-3-yl ester

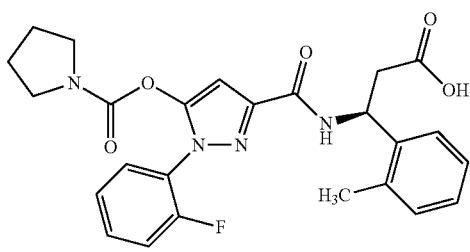 [SMILES: Cc1ccccc1[C@H](CC(=O)O)NC(=O)c1cc(OC(=O)N2CCCC2)n(-c2ccccc2F)n1]

Step 1: 1-(2-Fluoro-phenyl)-5-(pyrrolidine-1-carbonyloxy)-1H-pyrazole-3-carboxylic acid 150 mg (0.675 mmol) of 1-(2-fluoro-phenyl)-5-hydroxy-1H-pyrazole-3-carboxylic acid were dissolved in 5 ml of THF. 440 mg (1.35 mmol) of cesium carbonate and 90.2 mg (0.675 mmol) of pyrrolidine-1-carbonyl chloride were added and the mixture was heated to 50° C. for 4 h. Then the mixture was filtrated and the filtrate containing the title compound directly used in the next step.

Step 2: Pyrrolidine-1-carboxylic acid 5-((S)-2-carboxy-1-o-tolyl-ethylcarbamoyl)-2-(2-fluoro-phenyl)-2H-pyrazol-3-yl ester 0.675 mmol of TOTU and 1.35 mmol of EDIA were added to the filtrate containing 1-(2-fluoro-phenyl)-5-(pyrrolidine-1-carbonyloxy)-1H-pyrazole-3-carboxylic acid obtained in step 1. The mixture was stirred for 5 min at room temperature, and then 0.675 mmol of (S)-3-amino-3-(2-methyl-phenyl)-propionic acid were added and the mixture was stirred overnight at RT. Then the solvent was evaporated and the residue subjected to preparative HPLC to give the title compound in a yield of 67%.

Analogously as described in synthesis example 16, step 1, the following compounds were prepared:

5-dimethylcarbamoyloxy-1-(2-fluoro-phenyl)-1H-pyrazole-3-carboxylic acid 1-(2-fluoro-phenyl)-5-(piperidine-1-carbonyloxy)-1H-pyrazole-3-carboxylic acid 1-(2-fluoro-phenyl)-5-(methyl-phenyl-carbamoyloxy)-1H-pyrazole-3-carboxylic acid

SYNTHESIS EXAMPLE 17

4-Bromo-1-(2-fluoro-phenyl)-5-methoxy-1H-pyrazole-3-carboxylic acid

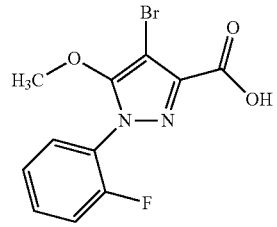 [SMILES: COc1c(Br)c(C(=O)O)nn1-c1ccccc1F]

50 mg (0.21 mmol) of 1-(2-fluoro-phenyl)-5-methoxy-1H-pyrazole-3-carboxylic acid were dissolved in 1.5 ml of acetic acid, sodium acetate (35 mg, 0.42 mmol) and bromine (50 mg, 0.21 mmol) were added and the mixture was stirred for 60 min. The solvent was removed in vacuo and the residue subjected to an aqueous work-up. The obtained crude title compound (60 mg) was used in the next step without further purification.

SYNTHESIS EXAMPLE 18

4-Chloro-1-(2-fluoro-phenyl)-5-methoxy-1H-pyrazole-3-carboxylic acid

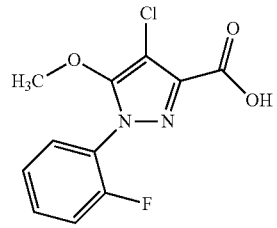 [SMILES: COc1c(Cl)c(C(=O)O)nn1-c1ccccc1F]

Step 1: 4-Chloro-1-(2-fluoro-phenyl)-5-methoxy-1H-pyrazole-3-carboxylic acid methyl ester 300 mg (1.2 mmol) of 1-(2-fluoro-phenyl)-5-methoxy-1H-pyrazole-3-carboxylic acid methyl ester was dissolved in 3 ml of acetic acid. 162 mg (1.2 mmol) of sulfuryl chloride were added and the mixture stirred for 4 h at room temperature. The solvent was removed in vacuo and the residue subjected to acidic aqueous work-up. The obtained crude title compound (330 mg) was used in the hydrolysis step without further purification.

Step 2: 4-Chloro-1-(2-fluoro-phenyl)-5-methoxy-1H-pyrazole-3-carboxylic acid

The crude 4-chloro-1-(2-fluoro-phenyl)-5-methoxy-1H-pyrazole-3-carboxylic acid methyl ester obtained (330 mg, 1.16 mmol) obtained in step 1 was dissolved in 6 ml of dioxane and 5.8 ml of an aqueous 1 M solution of lithium hydroxide were added. The mixture was stirred for 30 min at 56° C. Acidic aqueous work-up gave 320 mg (100%) of the title compound.

SYNTHESIS EXAMPLE 19

4-Fluoro-1-(2-fluoro-phenyl)-5-methoxy-1H-pyrazole-3-carboxylic acid

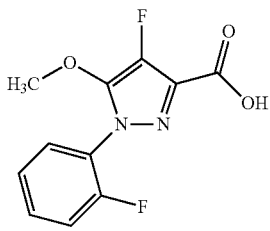

Step 1: 4-Fluoro-1-(2-fluoro-phenyl)-5-methoxy-1H-pyrazole-3-carboxylic acid methyl ester 200 mg (0.8 mmol) of 1-(2-fluoro-phenyl)-5-methoxy-1H-pyrazole-3-carboxylic acid methyl ester were dissolved in 2 ml of acetonitrile and 745 mg (1.99 mmol) of 1-chloro-methyl-4-fluoro-1,4-diazoniabicyclo[2.2.2]octane bis(tetrafluoroborate) (Selectfluor®) were added. The mixture was stirred overnight. Then, irrespective of the incomplete reaction, diethyl ether, water and 2 N hydrochloric acid were added, the organic phase was separated, the solvent evaporated and the residue subjected to preparative HPLC. 70 mg (33%) of the title compound were obtained.

Step 2: 4-Fluoro-1-(2-fluoro-phenyl)-5-methoxy-1H-pyrazole-3-carboxylic acid 70 mg (0.26 mmol) of 4-fluoro-1-(2-fluoro-phenyl)-5-methoxy-1H-pyrazole-3-carboxylic acid methyl ester were dissolved in 1.3 ml of dioxane and 1.305 ml of a 1 M aqueous solution of lithium hydroxide were added. The mixture was stirred at 56° C. for 30 min, then water and 2 N hydrochloric acid were added and the mixture extracted with diethyl ether. The organic phase was evaporated to give 67 mg (33%) of the title compound.

SYNTHESIS EXAMPLE 20

1-(2-Fluoro-phenyl)-5-isopropoxy-1H-pyrazole-3-carboxylic acid

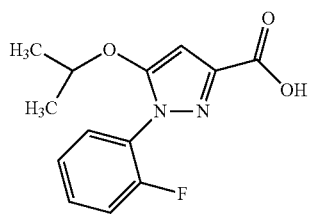 [SMILES: CC(C)Oc1cc(C(=O)O)nn1-c1ccccc1F]

Step 1: Methyl 1-(2-fluoro-phenyl)-5-isopropoxy-1H-pyrazole-3-carboxylate 150 mg (0.635 mmol) of 1-(2-fluoro-phenyl)-5-hydroxy-1H-pyrazole-3-carboxylic acid methyl ester, 166.6 mg (0.635 mmol) of triphenylphosphine and 38.16 mg (0.635 mmol) of 2-propanol were dissolved in 1.5 ml of DCM, and then a solution of 0.635 mmol of di(4-chlorobenzyl) azodicarboxylate in 1.5 ml of DCM was added. After stirring at room temperature for 4 h, the mixture was filtered and the solvent removed in vacuo. The obtained crude title compound was used in the hydrolysis step without further purification.

Step 2: 1-(2-Fluoro-phenyl)-5-isopropoxy-1H-pyrazole-3-carboxylic acid

The crude methyl 1-(2-fluoro-phenyl)-5-isopropoxy-1H-pyrazole-3-carboxylate obtained in step 1 was dissolved in 6 ml of MOH, 2 ml of an aqueous 1 M solution of sodium hydroxide were added, and the mixture was stirred for 5 h at 40° C. The solvent was removed and the residue subjected to acidic aqueous work-up to give 70% of the title compound.

SYNTHESIS EXAMPLE 21

(S)-3-{[1-(2-Fluoro-phenyl)-5-methoxy-1H-pyrazole-3-carbonyl]-amino}-3-(2-methyl-phenyl)-propionic acid amide

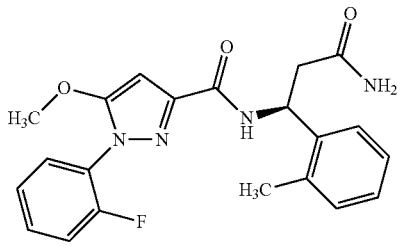 [SMILES: COc1cc(C(=O)N[C@@H](CC(N)=O)c2ccccc2C)nn1-c1ccccc1F]

DMF (1.8 mg, 25 µmol) and oxalyl chloride (160 mg, 1.26 mmol) were added to a solution of (S)-3-{[1-(2-fluoro-phenyl)-5-methoxy-1H-pyrazole-3-carbonyl]-amino}-3-(2-methyl-phenyl)-propionic acid (500 mg, 1.26 mmol) in DCM (5 ml) at room temperature. After 16 h at room temperature a 33% aqueous solution of ammonia (649 mg, 12.6 mmol) was added and the mixture was stirred for further 16 h. The solvent was removed under reduced pressure and the residue was purified by preparative HPLC to give 170 mg (34%) of the title compound as a colorless oil.

SYNTHESIS EXAMPLE 22

(S)-3-{[5-(3,3-Dimethyl-2-oxo-butoxy)-1-(2-fluoro-phenyl)-1H-pyrazole-3-carbonyl]-amino}-3-o-tolyl-propionic acid

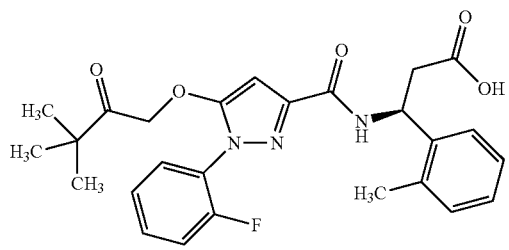 [SMILES: Cc1ccccc1[C@H](CC(=O)O)NC(=O)c1cc(OCC(=O)C(C)(C)C)n(-c2ccccc2F)n1]

Step 1: 5-(3,3-Dimethyl-2-oxo-butoxy)-1-(2-fluoro-phenyl)-1H-pyrazole-3-carboxylic acid methyl ester 200 mg (0.85 mmol) of 1-(2-fluoro-phenyl)-5-hydroxy-1H-pyrazole-3-carboxylic acid methyl ester were dissolved in 5 ml of DMF. 552 mg (1.7 mmol) of cesium carbonate and 152 mg (0.85 mmol) of 1-bromo-3,3-dimethyl-butan-2-one were added and the mixture was heated to 50° C. for 6 h. Then the mixture was filtered and the solvent removed in vacuo. The obtained crude title compound was subjected to hydrolysis without further purification.

Step 2: 5-(3,3-Dimethyl-2-oxo-butoxy)-1-(2-fluoro-phenyl)-1H-pyrazole-3-carboxylic acid 100 mg (0.3 mmol) of 5-(3,3-dimethyl-2-oxo-butoxy)-1-(2-fluoro-phenyl)-1H-pyrazole-3-carboxylic acid methyl ester were dissolved in 5 ml of MOH. 0.7 mmol of lithium hydroxide and 2 ml of water were added and the mixture stirred overnight at room temperature. The solvent was removed in vacuo and the residue subjected to aqueous workup with a 10% solution of citric acid and DCM. The organic phase was dried and the solvent removed in vacuo to give the title compound.

Step 3: (S)-3-{[5-(3,3-Dimethyl-2-oxo-butoxy)-1-(2-fluoro-phenyl)-1H-pyrazole-3-carbonyl]-amino}-3-o-tolyl-propionic acid 324 mg (0.675 mmol) of 5-(3,3-dimethyl-2-oxo-butoxy)-1-(2-fluoro-phenyl)-1H-pyrazole-3-carboxylic acid were dissolved in 5 ml of DMF and 0.675 mmol of TOTU and 1.35 mmol of EDIA were added. The mixture was stirred for 5 min at room temperature, then 0.675 mmol of (S)-3-amino-3-(2-methyl-phenyl)-propionic acid were added and the mixture was stirred overnight at room temperature. After evaporation of the solvent, the residue was subjected to preparative HPLC to give the title compound in a yield of 67%.

Analogously as described in synthesis example 22, steps 1 and 2, the following compounds were prepared, using chloro-acetone, 1-bromo-butan-2-one and 2-bromo-1-cyclopropyl-ethanone, respectively, instead of 1-bromo-3,3-dimethyl-butan-2-one in step 1:

1-(2-fluoro-phenyl)-5-(2-oxo-propoxy)-1H-pyrazole-3-carboxylic acid 1-(2-fluoro-phenyl)-5-(2-oxo-butoxy)-1H-pyrazole-3-carboxylic acid 5-(2-cyclopropyl-2-oxo-ethoxy)-1-(2-fluoro-phenyl)-1H-pyrazole-3-carboxylic acid

SYNTHESIS EXAMPLE 23

(S)-3-{[1-(2-Fluoro-phenyl)-5-(2-hydroxy-3,3-dimethyl-butoxy)-1H-pyrazole-3-carbonyl]-amino}-3-o-tolyl-propionic acid

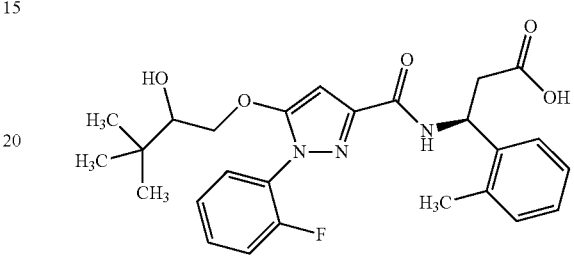

50 mg (0.1 mmol) of (S)-3-{[5-(3,3-dimethyl-2-oxo-butoxy)-1-(2-fluoro-phenyl)-1H-pyrazole-3-carbonyl]-amino}-3-o-tolyl-propionic acid were dissolved in 5 ml of DCM and 0.05 mmol of sodium borohydride were added. The mixture was stirred at room temperature overnight. The solvent was removed in vacuo and the residue subjected to preparative HPLC to given 52% of the title compound.

SYNTHESIS EXAMPLE 24

(S)-3-{[1-(2-Fluoro-phenyl)-5-((R)-2-hydroxy-3,3-dimethyl-butoxy)-1H-pyrazole-3-carbonyl]-amino}-3-o-tolyl-propionic acid and (S)-3-{[1-(2-fluoro-phenyl)-5-((S)-2-hydroxy-3,3-dimethyl-butoxy)-1H-pyrazole-3-carbonyl]-amino}-3-o-tolyl-propionic acid

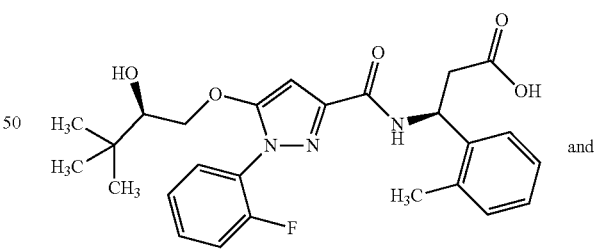

and

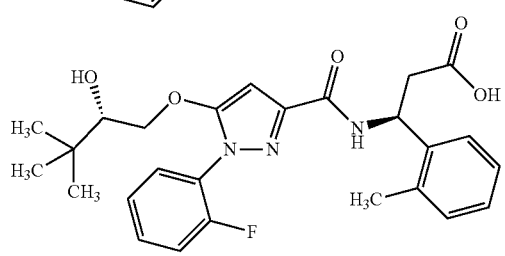

100 mg of (S)-3-{[1-(2-fluoro-phenyl)-5-(2-hydroxy-3,3-dimethyl-butoxy)-1H-pyrazole-3-carbonyl]-amino}-3-o- tolyl-propionic acid were separated into the two diastereomeric title compounds by HPLC on a chiral column (Chiralpak AD-H/55, 250×4.6 mm) at 30° C. (eluent: heptane/ethanol/MOH (15:1:1)+0.1% TFA; flow: 1.0 ml/min). 45 mg of the first diastereomer (retention time 16.35 min) eluted from the column and 40 mg of the second diastereomer (retention time 21.15 min) eluted from the column were obtained, one of them being the diastereomer with R configuration in the alcohol moiety and the other of them being the diastereomer with S configuration in the alcohol moiety (the stereochemistry in the alcohol moiety was not determined; it was arbitrarily assigned R configuration in the first diastereomer eluted from the column and S configuration in the second diastereomer eluted from the column).

SYNTHESIS EXAMPLE 25

1-(2-Fluoro-phenyl)-5-(2-hydroxy-2,3,3-trimethyl-butoxy)-1H-pyrazole-3-carboxylic acid

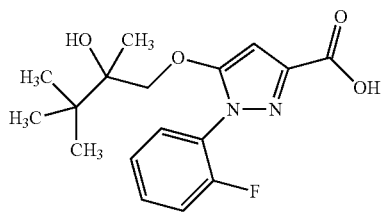 [SMILES: CC(C)(C)C(C)(O)COc1cc(C(=O)O)nn1-c1ccccc1F]

610 mg (1.9 mmol) of 5-(3,3-dimethyl-2-oxo-butoxy)-1-(2-fluoro-phenyl)-1H-pyrazole-3-carboxylic acid were dissolved in 20 ml of dry THF under argon and cooled to 0° C. 1.4 ml of a 3 M solution of methylmagnesium bromide in diethyl ether (4.2 mmol) were added over 10 min. The mixture was allowed to reach room temperature overnight and then diluted with 50 ml of water and 30 ml of EA. After phase separation, the aqueous phase was adjusted to pH=3 by addition of 1 M hydrochloric acid. The precipitate which formed was dissolved by addition of 40 ml of DCM, the organic phase was separated, dried over sodium sulfate and evaporated. 390 mg (61%) of the title compound were obtained.

Analogously as described in synthesis example 25, the following compounds were prepared, using ethylmagnesium bromide instead of methylmagnesium bromide in the case of 5-(2-ethyl-2-hydroxy-butoxy)-1-(2-fluoro-phenyl)-1H-pyrazole-3-carboxylic acid:

1-(2-fluoro-phenyl)-5-(2-hydroxy-2-methyl-butoxy)-1H-pyrazole-3-carboxylic acid 1-(2-fluoro-phenyl)-5-(2-hydroxy-2-methyl-propoxy)-1H-pyrazole-3-carboxylic acid 5-(2-ethyl-2-hydroxy-butoxy)-1-(2-fluoro-phenyl)-1H-pyrazole-3-carboxylic acid 5-(2-cyclopropyl-2-hydroxy-propoxy)-1-(2-fluoro-phenyl)-1H-pyrazole-3-carboxylic acid

SYNTHESIS EXAMPLE 26

(S)-3-{[1-(2-Fluoro-phenyl)-5-((R)-2-hydroxy-2,3,3-trimethyl-butoxy)-1H-pyrazole-3-carbonyl]-amino}-3-o-tolyl-propionic acid and (S)-3-{[1-(2-fluoro-phenyl)-5-((S)-2-hydroxy-2,3,3-trimethyl-butoxy)-1H-pyrazole-3-carbonyl]-amino}-3-o-tolyl-propionic acid

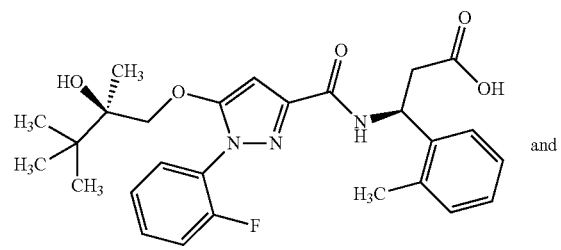

and

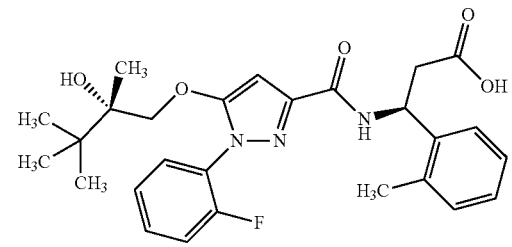

390 mg (1.16 mmol) of 1-(2-fluoro-phenyl)-5-(2-hydroxy-2,3,3-trimethyl-butoxy)-1H-pyrazole-3-carboxylic-acid were dissolved in 6 ml of DMF, 380 mg of TOTU (1.16 mmol) and 420 mg of NEM (3.6 mmol) were added and the mixture was stirred for 5 min at room temperature. Then 208 mg (1.16 mmol) of (S)-3-amino-3-(2-methyl-phenyl)-propionic acid were added and the mixture was stirred overnight at room temperature. After evaporation of the solvent, the residue was subjected to preparative HPLC. 45 mg each of the two diastereomeric title compounds were obtained, one of them being the diastereomer with R configuration in the alcohol moiety and the other of them being the diastereomer with S configuration in the alcohol moiety (the stereochemistry in the alcohol moiety was not determined; it was arbitrarily assigned R configuration in the first diastereomer eluted from the column and S configuration in the second diastereomer eluted from the column).

SYNTHESIS EXAMPLE 27

(S)-3-{[5-((R)-2-Cyclopropyl-2-hydroxy-propoxy)-1-(2-fluoro-phenyl)-1H-pyrazole-3-carbonyl]-amino}-3-o-tolyl-propionic acid and (S)-3-{[5-((S)-2-cyclopropyl-2-hydroxy-propoxy)-1-(2-fluoro-phenyl)-1H-pyrazole-3-carbonyl]-amino}-3-o-tolyl-propionic acid

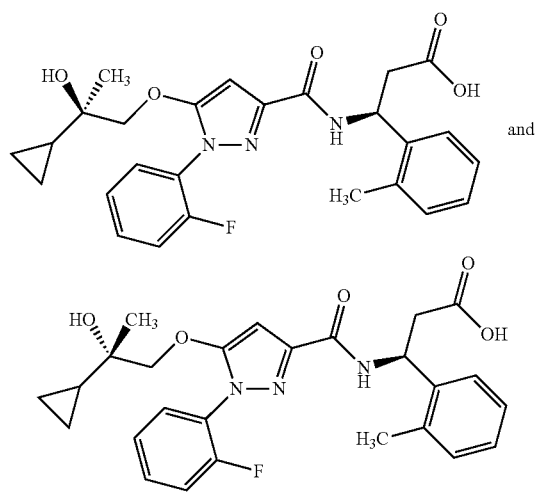

and 100 mg of (S)-3-{[5-(2-cyclopropyl-2-hydroxy-propoxy)-1-(2-fluoro-phenyl)-1H-pyrazole-3-carbonyl]-amino}-3-o-tolyl-propionic were separated into the two diastereomeric title compounds by HPLC on a chiral column (Chiralpak OJ-H/59, 250×4.6 mm) at 30° C. (eluent: heptane/ethanol (10:1)+0.1% TFA; flow: 1.0 ml/min). 40 mg each of the two diastereomeric title compounds were obtained, one of them being the diastereomer with R configuration in the alcohol moiety and the other of them being the diastereomer with S configuration in the alcohol moiety (the stereochemistry in the alcohol moiety was not determined; it was arbitrarily assigned R configuration in the first diastereomer (retention time 29.12 min) eluted from the column and S configuration in the second diastereomer (retention time 36.36 min) eluted from the column).

SYNTHESIS EXAMPLE 28

1-(2-Fluoro-phenyl)-5-methoxy-1H-pyrazole-3-carboxylic acid [(S)-2-(1,1-dimethyl-propylcarbamoyl)-1-o-tolyl-ethyl]-amide

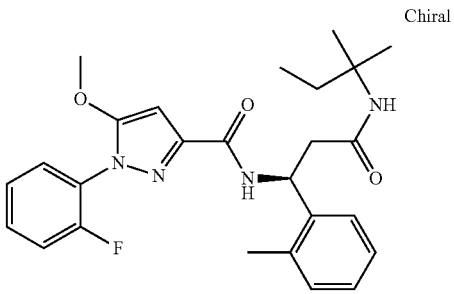 [SMILES: CCC(C)(C)NC(=O)C[C@H](NC(=O)c1cc(OC)n(-c2ccccc2F)n1)c1ccccc1C]

79.4 mg (0.2 mmol, 1 Eq) of (S)-3-{[1-(2-Fluoro-phenyl)-5-methoxy-1H-pyrazole-3-carbonyl]-amino}-3-o-tolyl-propionic acid are dissolved in 4 ml of DMF, 5Eq of N-Ethylmorpholin and 1.1 Eq (0.22 mmol) of TOTU are added and the resulting mixture is stirred for 10 minutes at RT. Then 0.22 mmol of 1,1-Dimethyl-propylamine are added and the resulting mixture is stirred overnight at RT.

0.1 ml TFA was added, the mixture filtrated and subjected to HPLC chromatography to yield 40 mg of the product. (Yield: 43%).

Analogously as described in the synthesis examples, the example compounds of the formula I listed in Table 1 were prepared.

TABLE 1

Example compounds of the formula I

| Example | Compound Name | m/z (1) | Rt (min) | LC/MS Method | Activity (2) |
|---|---|---|---|---|---|
| 1 | 3-{[1-(2,5-Dimethyl-phenyl)-5-hydroxy-1H-pyrazole-3-carbonyl]-amino}-3-(4-fluoro-phenyl)-propionic acid | 398.15 | 1.72 | LC1 | C |
| 2 | 3-[(5-Hydroxy-1-phenyl-1H-pyrazole-3-carbonyl)-amino]-hexanoic acid | 318.15 | 2.87 | LC3 | C |
| 3 | 3-[(5-Hydroxy-1-phenyl-1H-pyrazole-3-carbonyl)-amino]-3-(4-methoxy-phenyl)-propionic acid | 382.18 | 2.95 | LC3 | B |
| 4 | 3-[(5-Hydroxy-1-phenyl-1H-pyrazole-3-carbonyl)-amino]-3-methyl-butyric acid | 304.13 | 2.70 | LC3 | C |
| 5 | {1-[(5-Hydroxy-1-phenyl-1H-pyrazole-3-carbonyl)-amino]-cyclopentyl}-acetic acid | 330.15 | 2.87 | LC3 | C |
| 6 | 3-(3-tert-Butoxy-phenyl)-3-[(5-hydroxy-1-phenyl-1H-pyrazole-3-carbonyl)-amino]-propionic acid | 424.16 | 2.99 | LC8 | C |
| 7 | 3-(3-tert-Butoxy-phenyl)-3-{[1-(2,5-dimethyl-phenyl)-5-hydroxy-1H-pyrazole-3-carbonyl]-amino}-propionic acid | 452.14 | 2.82 | LC8 | C |
| 8 | 3-{[1-(2,5-Dimethyl-phenyl)-5-hydroxy-1H-pyrazole-3-carbonyl]-amino}-3-methyl-butyric acid | 332.11 | 2.72 | LC8 | C |

TABLE 1-continued

Example compounds of the formula I

| Example | Compound Name | m/z (1) | Rt (min) | LC/MS Method | Activity (2) |
|---|---|---|---|---|---|
| 9 | 3-[(5-Hydroxy-1-phenyl-1H-pyrazole-3-carbonyl)-amino]-3-(3-methoxy-phenyl)-propionic acid | 382.12 | 2.74 | LC8 | B |
| 10 | 3-(3-Chloro-phenyl)-3-[(5-hydroxy-1-phenyl-1H-pyrazole-3-carbonyl)-amino]-propionic acid | 386.06 | 2.88 | LC8 | B |
| 11 | 3-(3,4-Dimethoxy-phenyl)-3-[(5-hydroxy-1-phenyl-1H-pyrazole-3-carbonyl)-amino]-propionic acid | 412.13 | 2.61 | LC8 | C |
| 12 | 3-[(5-Hydroxy-1-phenyl-1H-pyrazole-3-carbonyl)-amino]-3-(4-trifluoromethoxy-phenyl)-propionic acid | 436.06 | 3.09 | LC8 | B |
| 13 | 3-[(5-Hydroxy-1-phenyl-1H-pyrazole-3-carbonyl)-amino]-4-methyl-pentanoic acid | 318.12 | 2.64 | LC8 | C |
| 14 | 3-[(5-Hydroxy-1-phenyl-1H-pyrazole-3-carbonyl)-amino]-heptanoic acid | 332.13 | 2.82 | LC8 | B |
| 15 | 3-[(5-Hydroxy-1-phenyl-1H-pyrazole-3-carbonyl)-amino]-5-phenyl-pentanoic acid | 380.12 | 2.92 | LC8 | C |
| 16 | 3-[(5-Hydroxy-1-phenyl-1H-pyrazole-3-carbonyl)amino]-3-pyridin-3-yl-propionic acid | 353.1 | 2.06 | LC8 | B |
| 17 | 3-Cyclopropyl-3-[(5-hydroxy-1-phenyl-1H-pyrazole-3-carbonyl)-amino]-propionic acid | 316.11 | 2.59 | LC8 | C |
| 18 | 3-Cyclohexyl-3-[(5-hydroxy-1-phenyl-1H-pyrazole-3-carbonyl)-amino]-propionic acid | 358.14 | 2.95 | LC8 | B |
| 19 | 3-[(5-Hydroxy-1-phenyl-1H-pyrazole-3-carbonyl)-amino]-5-methyl-hexanoic acid | 332.12 | 2.80 | LC8 | B |
| 20 | 3-(2-Chloro-phenyl)-3-[(5-hydroxy-1-phenyl-1H-pyrazole-3-carbonyl)-amino]-propionic acid | 386.1 | 3.07 | LC3 | B |
| 21 | 3-[(5-Hydroxy-1-phenyl-1H-pyrazole-3-carbonyl)-amino]-3-o-tolyl-propionic acid | 366.12 | 3.16 | LC8 | B |
| 22 | 3-(4-Ethyl-phenyl)-3-[(5-hydroxy-1-phenyl-1H-pyrazole-3-carbonyl)-amino]-propionic acid | 380.13 | 2.98 | LC8 | B |
| 23 | 3-(4-tert-Butoxy-phenyl)-3-[(5-hydroxy-1-phenyl-1H-pyrazole-3-carbonyl)-amino]-propionic acid | 424.2 | 3.18 | LC3 | C |
| 24 | 3-[(5-Hydroxy-1-phenyl-1H-pyrazole-3-carbonyl)-amino]-3-(4-isopropyl-phenyl)-propionic acid | 394.18 | 3.34 | LC3 | B |
| 25 | 3-[(5-Hydroxy-1-phenyl-1H-pyrazole-3-carbonyl)-amino]-3-(4-methoxy-2,3-dimethyl-phenyl)-propionic acid | 410.19 | 3.09 | LC3 | C |
| 26 | 3-{[1-(2,5-Dimethyl-phenyl)-5-hydroxy-1H-pyrazole-3-carbonyl]-amino}-hexanoic acid | 346.18 | 2.95 | LC3 | C |
| 27 | 3-{[1-(2,5-Dimethyl-phenyl)-5-hydroxy-1H-pyrazole-3-carbonyl]-amino}-3-(4-methoxy-phenyl)-propionic acid | 410.18 | 3.04 | LC3 | C |
| 28 | 3-{[1-(2,5-Dimethyl-phenyl)-5-hydroxy-1H-pyrazole-3-carbonyl]-amino}-3-(3-methoxy-phenyl)-propionic acid | 410.12 | 2.86 | LC8 | C |
| 29 | 3-(3-Chloro-phenyl)-3-{[1-(2,5-dimethyl-phenyl)-5-hydroxy-1H-pyrazole-3-carbonyl]-amino}-propionic acid | 414.07 | 2.97 | LC8 | C |
| 30 | 3-(3,4-Dimethoxy-phenyl)-3-{[1-(2,5-dimethyl-phenyl)-5-hydroxy-1H-pyrazole-3-carbonyl]-amino}-propionic acid | 440.15 | 2.71 | LC8 | C |
| 31 | 3-{[1-(2,5-Dimethyl-phenyl)-5-hydroxy-1H-pyrazole-3-carbonyl]-amino}-3-(4-trifluoromethoxy-phenyl)-propionic acid | 464.06 | 3.12 | LC8 | C |
| 32 | 3-{[1-(2,5-Dimethyl-phenyl)-5-hydroxy-1H-pyrazole-3-carbonyl]-amino}-4-methyl-pentanoic acid | 346.12 | 2.77 | LC8 | C |
| 33 | 3-{[1-(2,5-Dimethyl-phenyl)-5-hydroxy-1H-pyrazole-3-carbonyl]-amino}-heptanoic acid | 360.13 | 2.93 | LC8 | C |
| 34 | 3-{[1-(2,5-Dimethyl-phenyl)-5-hydroxy-1H-pyrazole-3-carbonyl]-amino}-5-phenyl-pentanoic acid | 408.13 | 3.02 | LC8 | C |
| 35 | 3-{[1-(2,5-Dimethyl-phenyl)-5-hydroxy-1H-pyrazole-3-carbonyl]-amino}-3-pyridin-3-yl-propionic acid | 381.11 | 2.19 | LC8 | C |
| 36 | 3-Cyclopropyl-3-{[1-(2,5-dimethyl-phenyl)-5-hydroxy-1H-pyrazole-3-carbonyl]-amino}-propionic acid | 344.12 | 2.69 | LC8 | C |

TABLE 1-continued

Example compounds of the formula I

| Example | Compound Name | m/z (1) | Rt (min) | LC/MS Method | Activity (2) |
|---|---|---|---|---|---|
| 37 | 3-Cyclohexyl-3-{[1-(2,5-dimethyl-phenyl)-5-hydroxy-1H-pyrazole-3-carbonyl]-amino}-propionic acid | 386.14 | 3.06 | LC8 | C |
| 38 | 3-{[1-(2,5-Dimethyl-phenyl)-5-hydroxy-1H-pyrazole-3-carbonyl]-amino}-5-methyl-hexanoic acid | 360.13 | 2.90 | LC8 | C |
| 39 | 3-(2-Chloro-phenyl)-3-{[1-(2,5-dimethyl-phenyl)-5-hydroxy-1H-pyrazole-3-carbonyl]-amino}-propionic acid | 414.06 | 2.93 | LC8 | C |
| 40 | 3-{[1-(2,5-Dimethyl-phenyl)-5-hydroxy-1H-pyrazole-3-carbonyl]-amino}-3-o-tolyl-propionic acid | 394.13 | 2.93 | LC8 | B |
| 41 | 3-{[1-(2,5-Dimethyl-phenyl)-5-hydroxy-1H-pyrazole-3-carbonyl]-amino}-3-(4-ethyl-phenyl)-propionic acid | 408.14 | 3.07 | LC8 | C |
| 42 | (1-{[1-(2,5-Dimethyl-phenyl)-5-hydroxy-1H-pyrazole-3-carbonyl]-amino}-cyclopentyl)-acetic acid | 358.13 | 2.82 | LC8 | C |
| 43 | 3-{[1-(2,5-Dimethyl-phenyl)-5-hydroxy-1H-pyrazole-3-carbonyl]-amino}-3-(tetrahydro-pyran-4-yl)-propionic acid | 388.2 | 2.70 | LC3 | C |
| 44 | 3-Cyclopentyl-3-{[1-(2,5-dimethyl-phenyl)-5-hydroxy-1H-pyrazole-3-carbonyl]-amino}-propionic acid | 372.12 | 2.93 | LC3 | C |
| 45 | 3-(4-Chloro-phenyl)-3-{[1-(2,5-dimethyl-phenyl)-5-hydroxy-1H-pyrazole-3-carbonyl]-amino}-propionic acid | 414.16 | 3.22 | LC3 | C |
| 46 | 3-{[1-(2,5-Dimethyl-phenyl)-5-hydroxy-1H-pyrazole-3-carbonyl]-amino}-3-(4-isobutyl-phenyl)-propionic acid | 436.27 | 3.65 | LC3 | C |
| 47 | 3-(3,4-Difluoro-phenyl)-3-{[1-(2,5-dimethyl-phenyl)-5-hydroxy-1H-pyrazole-3-carbonyl]-amino}-propionic acid | 416.16 | 3.20 | LC3 | C |
| 48 | 3-(3,4-Dichloro-phenyl)-3-{[1-(2,5-dimethyl-phenyl)-5-hydroxy-1H-pyrazole-3-carbonyl]-amino}-propionic acid | 448.13 | 3.43 | LC3 | C |
| 49 | 3-{[1-(2,5-Dimethyl-phenyl)-5-hydroxy-1H-pyrazole-3-carbonyl]-amino}-3-(3-fluoro-phenyl)-propionic acid | 398.19 | 3.09 | LC3 | C |
| 50 | 3-{[1-(2,5-Dimethyl-phenyl)-5-hydroxy-1H-pyrazole-3-carbonyl]-amino}-3-p-tolyl-propionic acid | 394.22 | 3.18 | LC3 | C |
| 51 | 3-{[1-(2,5-Dimethyl-phenyl)-5-hydroxy-1H-pyrazole-3-carbonyl]-amino}-3-m-tolyl-propionic acid | 394.21 | 3.17 | LC3 | C |
| 52 | 3-(4-Cyano-phenyl)-3-{[1-(2,5-dimethyl-phenyl)-5-hydroxy-1H-pyrazole-3-carbonyl]-amino}-propionic acid | 405.2 | 3.00 | LC3 | C |
| 53 | 3-{[1-(2,5-Dimethyl-phenyl)-5-hydroxy-1H-pyrazole-3-carbonyl]-amino}-3-(3-trifluoromethyl-phenyl)-propionic acid | 448.17 | 3.32 | LC3 | C |
| 54 | 3-{[1-(2,5-Dimethyl-phenyl)-5-hydroxy-1H-pyrazole-3-carbonyl]-amino}-3-(3-fluoro-4-methoxy-phenyl)-propionic acid | 428.21 | 3.10 | LC3 | C |
| 55 | 3-Biphenyl-4-yl-3-{[1-(2,5-dimethyl-phenyl)-5-hydroxy-1H-pyrazole-3-carbonyl]-amino}-propionic acid | 456.23 | 3.50 | LC3 | B |
| 56 | 3-(3,5-Difluoro-phenyl)-3-{[1-(2,5-dimethyl-phenyl)-5-hydroxy-1H-pyrazole-3-carbonyl]-amino}-propionic acid | 416.17 | 3.18 | LC3 | C |
| 57 | 3-{[1-(2,5-Dimethyl-phenyl)-5-hydroxy-1H-pyrazole-3-carbonyl]-amino}-3-(4-trifluoromethyl-phenyl)-propionic acid | 448.17 | 3.39 | LC3 | C |
| 58 | 3-(4-Chloro-phenyl)-3-[(5-hydroxy-1-phenyl-1H-pyrazole-3-carbonyl)-amino]-propionic acid | 386.18 | 2.91 | LC8 | B |
| 59 | 3-(3,5-Bis-trifluoromethyl-phenyl)-3-[(5-hydroxy-1-phenyl-1H-pyrazole-3-carbonyl)-amino]-propionic acid | 488.15 | 3.21 | LC8 | C |
| 60 | 3-(3,4-Difluoro-phenyl)-3-[(5-hydroxy-1-phenyl-1H-pyrazole-3-carbonyl)-amino]-propionic acid | 388.19 | 2.83 | LC8 | C |
| 61 | 3-(4-Fluoro-phenyl)-3-[(5-hydroxy-1-phenyl-1H-pyrazole-3-carbonyl)-amino]-propionic acid | 370.17 | 3.00 | LC3 | C |

TABLE 1-continued

Example compounds of the formula I

| Example | Compound Name | m/z (1) | Rt (min) | LC/MS Method | Activity (2) |
|---|---|---|---|---|---|
| 62 | 3-(3,4-Dichloro-phenyl)-3-[(5-hydroxy-1-phenyl-1H-pyrazole-3-carbonyl)-amino]-propionic acid | 420.15 | 3.03 | LC8 | B |
| 63 | 3-(3-Fluoro-phenyl)-3-[(5-hydroxy-1-phenyl-1H-pyrazole-3-carbonyl)-amino]-propionic acid | 370.19 | 2.78 | LC8 | C |
| 64 | 3-[(5-Hydroxy-1-phenyl-1H-pyrazole-3-carbonyl)-amino]-3-p-tolyl-propionic acid | 366.23 | 2.86 | LC8 | B |
| 65 | 3-[(5-Hydroxy-1-phenyl-1H-pyrazole-3-carbonyl)-amino]-3-m-tolyl-propionic acid | 366.22 | 2.84 | LC8 | B |
| 66 | 3-(4-tert-Butyl-phenyl)-3-[(5-hydroxy-1-phenyl-1H-pyrazole-3-carbonyl)-amino]-propionic acid | 408.22 | 3.45 | LC3 | C |
| 67 | 3-[(5-Hydroxy-1-phenyl-1H-pyrazole-3-carbonyl)-amino]-3-(3-trifluoromethyl-phenyl)-propionic acid | 420.17 | 2.96 | LC8 | B |
| 68 | 3-(3-Fluoro-4-methoxy-phenyl)-3-[(5-hydroxy-1-phenyl-1H-pyrazole-3-carbonyl)-amino]-propionic acid | 400.18 | 2.93 | LC3 | C |
| 69 | 3-Biphenyl-4-yl-3-[(5-hydroxy-1-phenyl-1H-pyrazole-3-carbonyl)-amino]-propionic acid | 428.21 | 3.37 | LC3 | B |
| 70 | 3-(3,5-Difluoro-phenyl)-3-[(5-hydroxy-1-phenyl-1H-pyrazole-3-carbonyl)-amino]-propionic acid | 388.18 | 2.83 | LC8 | C |
| 71 | 3-[(5-Hydroxy-1-phenyl-1H-pyrazole-3-carbonyl)-amino]-3-(4-trifluoromethyl-phenyl)-propionic acid | 420.17 | 3.08 | LC8 | C |
| 72 | 3-{[1-(3-Chloro-4-fluoro-phenyl)-5-hydroxy-1H-pyrazole-3-carbonyl]-amino}-3-(4-fluoro-phenyl)-propionic acid | 422.1 | 3.07 | LC8 | C |
| 73 | 3-{[1-(4-Chloro-phenyl)-5-hydroxy-1H-pyrazole-3-carbonyl]-amino}-3-(4-fluoro-phenyl)-propionic acid | 804.92 [(2M − H)⁻] | 4.22 | LC2 | C |
| 74 | (S)-3-{[1-(3-Fluoro-phenyl)-5-hydroxy-1H-pyrazole-3-carbonyl]-amino}-3-o-tolyl-propionic acid | 384.18 | 2.90 | LC8 | A |
| 75 | (S)-3-{[1-(3-Chloro-phenyl)-5-hydroxy-1H-pyrazole-3-carbonyl]-amino}-3-o-tolyl-propionic acid | 400.15 | 3.02 | LC8 | B |
| 76 | (S)-3-{[1-(4-Fluoro-phenyl)-5-hydroxy-1H-pyrazole-3-carbonyl]-amino}-3-o-tolyl-propionic acid | 384.18 | 2.87 | LC8 | A |
| 77 | (S)-3-{[1-(2-Chloro-phenyl)-5-hydroxy-1H-pyrazole-3-carbonyl]-amino}-3-o-tolyl-propionic acid | 400.15 | 2.78 | LC8 | A |
| 78 | 3-{[1-(3,5-Dimethyl-phenyl)-5-hydroxy-1H-pyrazole-3-carbonyl]-amino}-3-o-tolyl-propionic acid | 394.19 | 3.05 | LC8 | C |
| 79 | 3-{[1-(4-Chloro-phenyl)-5-hydroxy-1H-pyrazole-3-carbonyl]-amino}-3-o-tolyl-propionic acid | 400.12 | 3.02 | LC8 | B |
| 80 | 3-{[1-(3-Chloro-4-fluoro-phenyl)-5-hydroxy-1H-pyrazole-3-carbonyl]-amino}-3-o-tolyl-propionic acid | 418.11 | 3.09 | LC8 | B |
| 81 | (S)-3-{[1-(2-Fluoro-phenyl)-5-hydroxy-1H-pyrazole-3-carbonyl]-amino}-3-o-tolyl-propionic acid | 384.18 | 2.74 | LC8 | A |
| 82 | (S)-3-[(5-Hydroxy-1-phenyl-1H-pyrazole-3-carbonyl)-amino]-3-o-tolyl-propionic acid | 366.21 | 3.04 | LC3 | A |
| 83 | (R)-3-[(5-Hydroxy-1-phenyl-1H-pyrazole-3-carbonyl)-amino]-3-o-tolyl-propionic acid | 366.24 | 3.02 | LC3 | C |
| 84 | 3-(2,4-Dimethyl-phenyl)-3-[(5-hydroxy-1-phenyl-1H-pyrazole-3-carbonyl)-amino]-propionic acid | 380.21 | 3.89 | LC8 | B |
| 85 | 3-(4-Fluoro-2-methyl-phenyl)-3-[(5-hydroxy-1-phenyl-1H-pyrazole-3-carbonyl)-amino]-propionic acid | 384.12 | 3.09 | LC3 | B |
| 86 | 3-(2,4-Difluoro-phenyl)-3-{[1-(4-fluoro-phenyl)-5-hydroxy-1H-pyrazole-3-carbonyl]-amino}-propionic acid | 406.06 | 2.87 | LC8 | C |
| 87 | (S)-3-{[5-Hydroxy-1-(4-methoxy-phenyl)-1H-pyrazole-3-carbonyl]-amino}-3-o-tolyl-propionic acid | 396.12 | 2.83 | LC8 | B |

TABLE 1-continued

Example compounds of the formula I

| Example | Compound Name | m/z (1) | Rt (min) | LC/MS Method | Activity (2) |
|---|---|---|---|---|---|
| 88 | 3-{[1-(3-Chloro-4-fluoro-phenyl)-5-hydroxy-1H-pyrazole-3-carbonyl]-amino}-3-(2-fluoro-4-methoxy-phenyl)-propionic acid | 452.06 | 3.04 | LC8 | C |
| 89 | 3-(2,4-Dimethyl-phenyl)-3-{[1-(4-fluoro-phenyl)-5-hydroxy-1H-pyrazole-3-carbonyl]-amino}-propionic acid | 398.12 | 3.02 | LC8 | B |
| 90 | 3-(2-Fluoro-4-methoxy-phenyl)-3-{[1-(4-fluoro-phenyl)-5-hydroxy-1H-pyrazole-3-carbonyl]-amino}-propionic acid | 418.1 | 2.87 | LC8 | C |
| 91 | 3-{[1-(3-Chloro-4-fluoro-phenyl)-5-hydroxy-1H-pyrazole-3-carbonyl]-amino}-3-(2,4-dimethyl-phenyl)-propionic acid | 432.1 | 3.20 | LC8 | C |
| 92 | 3-(2-Fluoro-4-methoxy-phenyl)-3-[(5-hydroxy-1-phenyl-1H-pyrazole-3-carbonyl)-amino]-propionic acid | 400.1 | 2.81 | LC8 | B |
| 93 | (S)-3-{[1-(2-Fluoro-phenyl)-5-hydroxy-1H-pyrazole-3-carbonyl]-amino}-3-o-tolyl-propionic acid methyl ester | 398.18 | 3.08 | LC8 | |
| 94 | (S)-3-{[5-Hydroxy-1-(3-methoxy-phenyl)-1H-pyrazole-3-carbonyl]-amino}-3-o-tolyl-propionic acid | 396.12 | 2.87 | LC8 | B |
| 95 | (S)-3-(2,4-Dichloro-phenyl)-3-[(5-hydroxy-1-phenyl-1H-pyrazole-3-carbonyl)-amino]-propionic acid | 420.02 | 3.06 | LC8 | B |
| 96 | (S)-3-(2-Fluoro-phenyl)-3-[(5-hydroxy-1-phenyl-1H-pyrazole-3-carbonyl)-amino]-propionic acid | 370.08 | 2.80 | LC8 | B |
| 97 | (S)-3-[(5-Hydroxy-1-phenyl-1H-pyrazole-3-carbonyl)-amino]-3-(2-trifluoromethyl-phenyl)-propionic acid | 420.06 | 2.96 | LC8 | B |
| 98 | (S)-3-(4-Chloro-phenyl)-3-[(5-hydroxy-1-phenyl-1H-pyrazole-3-carbonyl)-amino]-propionic acid | 386.06 | 2.95 | LC8 | B |
| 99 | (S)-3-[(5-Hydroxy-1-phenyl-1H-pyrazole-3-carbonyl)-amino]-3-(4-trifluoromethyl-phenyl)-propionic acid | 420.09 | 3.04 | LC8 | B |
| 100 | (S)-3-[(5-Hydroxy-1-phenyl-1H-pyrazole-3-carbonyl)-amino]-3-(2-methoxy-phenyl)-propionic acid | 382.12 | 2.85 | LC8 | B |
| 101 | (S)-3-(4-Cyano-phenyl)-3-[(5-hydroxy-1-phenyl-1H-pyrazole-3-carbonyl)-amino]-propionic acid | 377.1 | 2.71 | LC8 | B |
| 102 | 3-[(5-Hydroxy-1-phenyl-1H-pyrazole-3-carbonyl)-amino]-3-(4-phenoxy-phenyl)-propionic acid | 444.1 | 3.16 | LC8 | B |
| 103 | (S)-3-(2,6-Difluoro-phenyl)-3-[(5-hydroxy-1-phenyl-1H-pyrazole-3-carbonyl)-amino]-propionic acid | 388.09 | 2.83 | LC8 | B |
| 104 | 3-(4'-Fluoro-biphenyl-4-yl)-3-[(5-hydroxy-1-phenyl-1H-pyrazole-3-carbonyl)-amino]-propionic acid | 446.13 | 3.17 | LC8 | B |
| 105 | 3-[(5-Hydroxy-1-phenyl-1H-pyrazole-3-carbonyl)-amino]-3-(4-imidazol-1-yl-phenyl)-propionic acid | 418.11 | 2.30 | LC8 | C |
| 106 | (S)-3-{[1-(2-Chloro-phenyl)-5-hydroxy-1H-pyrazole-3-carbonyl]-amino}-3-(2,4-dichloro-phenyl)-propionic acid | 454.01 | 3.06 | LC8 | B |
| 107 | (S)-3-{[1-(2-Chloro-phenyl)-5-hydroxy-1H-pyrazole-3-carbonyl]-amino}-3-(2-fluoro-phenyl)-propionic acid | 404.05 | 2.78 | LC8 | B |
| 108 | (S)-3-{[1-(2-Chloro-phenyl)-5-hydroxy-1H-pyrazole-3-carbonyl]-amino}-3-(2-trifluoromethyl-phenyl)-propionic acid | 454.02 | 2.91 | LC8 | B |
| 109 | (S)-3-(4-Chloro-phenyl)-3-{[1-(2-chloro-phenyl)-5-hydroxy-1H-pyrazole-3-carbonyl]-amino}-propionic acid | 420.03 | 2.91 | LC8 | B |
| 110 | (S)-3-{[1-(2-Chloro-phenyl)-5-hydroxy-1H-pyrazole-3-carbonyl]-amino}-3-(4-trifluoromethyl-phenyl)-propionic acid | 454.05 | 3.00 | LC8 | B |
| 111 | (S)-3-{[1-(2-Chloro-phenyl)-5-hydroxy-1H-pyrazole-3-carbonyl]-amino}-3-(2-methoxy-phenyl)-propionic acid | 414.03 $[(M - H)^-]$ | 3.90 | LC2 | B |
| 112 | (S)-3-{[1-(2-Chloro-phenyl)-5-hydroxy-1H-pyrazole-3-carbonyl]-amino}-3-(4-cyano-phenyl)-propionic acid | 411.06 | 2.67 | LC8 | B |

TABLE 1-continued

Example compounds of the formula I

| Example | Compound Name | m/z (1) | Rt (min) | LC/MS Method | Activity (2) |
|---|---|---|---|---|---|
| 113 | 3-{[1-(2-Chloro-phenyl)-5-hydroxy-1H-pyrazole-3-carbonyl]-amino}-3-(4-phenoxy-phenyl)-propionic acid | 478.08 | 3.12 | LC8 | B |
| 114 | (S)-3-{[1-(2-Chloro-phenyl)-5-hydroxy-1H-pyrazole-3-carbonyl]-amino}-3-(2,6-difluoro-phenyl)-propionic acid | 422.03 | 2.79 | LC8 | B |
| 115 | 3-{[1-(2-Chloro-phenyl)-5-hydroxy-1H-pyrazole-3-carbonyl]-amino}-3-(4'-fluoro-biphenyl-4-yl)-propionic acid | 480.08 | 3.14 | LC8 | A |
| 116 | 3-{[1-(2-Chloro-phenyl)-5-hydroxy-1H-pyrazole-3-carbonyl]-amino}-3-(4-imidazol-1-yl-phenyl)-propionic acid | 452.07 | 2.23 | LC8 | C |
| 117 | (S)-3-(2,4-Dichloro-phenyl)-3-{[1-(2-fluoro-phenyl)-5-hydroxy-1H-pyrazole-3-carbonyl]-amino}-propionic acid | 438 | 3.40 | LC8 | B |
| 118 | (S)-3-(2-Fluoro-phenyl)-3-{[1-(2-fluoro-phenyl)-5-hydroxy-1H-pyrazole-3-carbonyl]-amino}-propionic acid | 388.11 | 2.96 | LC8 | B |
| 119 | (S)-3-{[1-(2-Fluoro-phenyl)-5-hydroxy-1H-pyrazole-3-carbonyl]-amino}-3-(2-trifluoromethyl-phenyl)-propionic acid | 438.05 | 2.93 | LC8 | B |
| 120 | (S)-3-(4-Chloro-phenyl)-3-{[1-(2-fluoro-phenyl)-5-hydroxy-1H-pyrazole-3-carbonyl]-amino}-propionic acid | 404.06 | 2.86 | LC8 | B |
| 121 | (S)-3-{[1-(2-Fluoro-phenyl)-5-hydroxy-1H-pyrazole-3-carbonyl]-amino}-3-(4-trifluoromethyl-phenyl)-propionic acid | 438.04 | 2.98 | LC8 | B |
| 122 | (S)-3-{[1-(2-Fluoro-phenyl)-5-hydroxy-1H-pyrazole-3-carbonyl]-amino}-3-(2-methoxy-phenyl)-propionic acid | 400.14 | 2.77 | LC8 | B |
| 123 | (S)-3-(4-Cyano-phenyl)-3-{[1-(2-fluoro-phenyl)-5-hydroxy-1H-pyrazole-3-carbonyl]-amino}-propionic acid | 395.1 | 2.64 | LC8 | B |
| 124 | 3-{[1-(2-Fluoro-phenyl)-5-hydroxy-1H-pyrazole-3-carbonyl]-amino}-3-(4-phenoxy-phenyl)-propionic acid | 462.11 | 3.08 | LC8 | B |
| 125 | (S)-3-(2,6-Difluoro-phenyl)-3-{[1-(2-fluoro-phenyl)-5-hydroxy-1H-pyrazole-3-carbonyl]-amino}-propionic acid | 406.06 | 2.97 | LC8 | B |
| 126 | 3-(4'-Fluoro-biphenyl-4-yl)-3-{[1-(2-fluoro-phenyl)-5-hydroxy-1H-pyrazole-3-carbonyl]-amino}-propionic acid | 464.13 | 3.14 | LC8 | A |
| 127 | 3-{[1-(2-Fluoro-phenyl)-5-hydroxy-1H-pyrazole-3-carbonyl]-amino}-3-(4-imidazol-1-yl-phenyl)-propionic acid | 436.1 | 2.22 | LC8 | C |
| 128 | (S)-3-{[1-(2-Fluoro-phenyl)-5-hydroxy-1H-pyrazole-3-carbonyl]-amino}-3-o-tolyl-propionic acid ethyl ester | 412.21 | 3.40 | LC3 | |
| 129 | (S)-3-{[1-(2-Fluoro-phenyl)-5-methoxy-1H-pyrazole-3-carbonyl]-amino}-3-o-tolyl-propionic acid | 398.18 | 2.99 | LC8 | A |
| 130 | (S)-3-{[1-(5-Chloro-pyridin-2-yl)-5-hydroxy-1H-pyrazole-3-carbonyl]-amino}-3-o-tolyl-propionic acid | 401.13 | 3.01 | LC8 | C |
| 131 | (S)-3-{[1-(2-Chloro-pyridin-4-yl)-5-hydroxy-1H-pyrazole-3-carbonyl]-amino}-3-o-tolyl-propionic acid | 401.15 | 3.07 | LC3 | B |
| 132 | 3-{[1-(2-Chloro-phenyl)-5-hydroxy-1H-pyrazole-3-carbonyl]-amino}-3-(2-fluoro-4-methoxy-phenyl)-propionic acid | 434.12 | 2.79 | LC8 | B |
| 133 | 3-(2-Fluoro-4-methoxy-phenyl)-3-{[1-(2-fluoro-phenyl)-5-hydroxy-1H-pyrazole-3-carbonyl]-amino}-propionic acid | 418.14 | 2.73 | LC8 | B |
| 134 | 3-(4-Ethyl-phenyl)-3-{[1-(2-fluoro-phenyl)-5-hydroxy-1H-pyrazole-3-carbonyl]-amino}-propionic acid | 398.19 | 3.17 | LC3 | B |
| 135 | (S)-3-{[1-(2-Chloro-phenyl)-5-hydroxy-1H-pyrazole-3-carbonyl]-amino}-3-p-tolyl-propionic acid | 400.16 | 3.05 | LC3 | B |
| 136 | (S)-3-{[1-(2-Fluoro-phenyl)-5-hydroxy-1H-pyrazole-3-carbonyl]-amino}-3-(6-methoxy-pyridin-3-yl)-propionic acid | 401.18 | 2.60 | LC3 | B |
| 137 | (S)-3-[(5-Hydroxy-1-phenyl-1H-pyrazole-3-carbonyl)-amino]-3-pyridin-3-yl-propionic acid | 353.15 | 2.14 | LC8 | B |

TABLE 1-continued

Example compounds of the formula I

| Example | Compound Name | m/z (1) | Rt (min) | LC/MS Method | Activity (2) |
|---|---|---|---|---|---|
| 138 | (S)-3-{[5-Hydroxy-1-(4-trifluoromethyl-pyrimidin-2-yl)-1H-pyrazole-3-carbonyl]-amino}-3-o-tolyl-propionic acid | 436.17 | 2.78 | LC8 | C |
| 139 | (S)-3-{[1-(2-Chloro-phenyl)-5-hydroxy-1H-pyrazole-3-carbonyl]-amino}-3-(6-methoxy-pyridin-3-yl)-propionic acid | 417.13 | 2.67 | LC8 | B |
| 140 | (S)-3-{[1-(2-Fluoro-phenyl)-5-hydroxy-1H-pyrazole-3-carbonyl]-amino}-3-pyridin-3-yl-propionic acid | 371.16 | 2.00 | LC3 | B |
| 141 | (S)-3-[(5-Hydroxy-1-pyridin-4-yl-1H-pyrazole-3-carbonyl)-amino]-3-o-tolyl-propionic acid | 367.19 | 2.18 | LC3 | C |
| 142 | 3-{[1-(2-Chloro-phenyl)-5-hydroxy-1H-pyrazole-3-carbonyl]-amino}-3-(4-fluoro-2-methyl-phenyl)-propionic acid | 418.15 | 3.04 | LC3 | B |
| 143 | (S)-3-[(5-Hydroxy-1-pyridin-3-yl-1H-pyrazole-3-carbonyl)-amino]-3-o-tolyl-propionic acid | 367.18 | 2.25 | LC8 | C |
| 144 | (S)-3-[(5-Hydroxy-1-phenyl-1H-pyrazole-3-carbonyl)-amino]-3-(6-methoxy-pyridin-3-yl)-propionic acid | 383.17 | 2.46 | LC8 | B |
| 145 | (S)-3-{[1-(2-Chloro-phenyl)-5-hydroxy-1H-pyrazole-3-carbonyl]-amino}-3-pyridin-3-yl-propionic acid | 387.12 | 2.08 | LC8 | B |
| 146 | (S)-3-(4'-Fluoro-biphenyl-4-yl)-3-{[1-(2-fluoro-phenyl)-5-hydroxy-1H-pyrazole-3-carbonyl]-amino}-propionic acid | 464.07 | 3.08 | LC8 | C |
| 147 | (R)-3-(4'-Fluoro-biphenyl-4-yl)-3-{[1-(2-fluoro-phenyl)-5-hydroxy-1H-pyrazole-3-carbonyl]-amino}-propionic acid | 464.07 | 3.07 | LC8 | A |
| 148 | (S)-3-{[1-(2-Chloro-phenyl)-5-hydroxy-1H-pyrazole-3-carbonyl]-amino}-3-(4'-fluoro-biphenyl-4-yl)-propionic acid | 480.05 | 3.25 | LC8 | C |
| 149 | (R)-3-{[1-(2-Chloro-phenyl)-5-hydroxy-1H-pyrazole-3-carbonyl]-amino}-3-(4'-fluoro-biphenyl-4-yl)-propionic acid | 480.05 | 3.11 | LC8 | A |
| 150 | 3-Biphenyl-4-yl-3-{[1-(2-fluoro-phenyl)-5-hydroxy-1H-pyrazole-3-carbonyl]-amino}-propionic acid | 446.16 | 3.05 | LC8 | A |
| 151 | 3-Biphenyl-4-yl-3-[(5-hydroxy-1-pyridin-4-yl-1H-pyrazole-3-carbonyl)-amino]-propionic acid | 429.16 | 2.63 | LC8 | C |
| 152 | 3-{[1-(2-Chloro-phenyl)-5-hydroxy-1H-pyrazole-3-carbonyl]-amino}-3-(4-phenoxy-phenyl)-propionic acid ethyl ester | 506.12 | 3.63 | LC8 | |
| 153 | 3-(4'-Fluoro-biphenyl-4-yl)-3-{[1-(2-fluoro-phenyl)-5-hydroxy-1H-pyrazole-3-carbonyl]-amino}-propionic acid ethyl ester | 492.12 | 3.47 | LC8 | |
| 154 | 3-{[1-(2-Chloro-phenyl)-5-hydroxy-1H-pyrazole-3-carbonyl]-amino}-3-(4'-fluoro-biphenyl-4-yl)-propionic acid ethyl ester | 508.1 | 3.51 | LC8 | |
| 155 | 3-{[1-(2-Fluoro-phenyl)-5-hydroxy-1H-pyrazole-3-carbonyl]-amino}-3-(4-phenoxy-phenyl)-propionic acid ethyl ester | 490.14 | 3.49 | LC8 | |
| 156 | 3-{[1-(2-Fluoro-phenyl)-5-hydroxy-1H-pyrazole-3-carbonyl]-amino}-3-(3'-methoxy-biphenyl-4-yl)-propionic acid | 476.14 | 3.03 | LC8 | B |
| 157 | 3-{[1-(2-Chloro-phenyl)-5-hydroxy-1H-pyrazole-3-carbonyl]-amino}-3-(3'-methoxy-biphenyl-4-yl)-propionic acid | 492.12 | 3.09 | LC8 | B |
| 158 | 3-Benzo[1,3]dioxol-4-yl-3-[(5-hydroxy-1-phenyl-1H-pyrazole-3-carbonyl)-amino]-propionic acid | 396.18 | 2.95 | LC3 | B |
| 159 | (S)-3-(2-Bromo-phenyl)-3-[(5-hydroxy-1-phenyl-1H-pyrazole-3-carbonyl)-amino]-propionic acid | 430.11 | 3.09 | LC3 | B |
| 160 | (S)-3-(3-Cyano-phenyl)-3-[(5-hydroxy-1-phenyl-1H-pyrazole-3-carbonyl)-amino]-propionic acid | 377.18 | 2.87 | LC3 | C |
| 161 | 3-(2,4-Dimethoxy-phenyl)-3-[(5-hydroxy-1-phenyl-1H-pyrazole-3-carbonyl)-amino]-propionic acid | 412.21 | 3.05 | LC3 | C |
| 162 | 3-(2-Chloro-4-methoxy-phenyl)-3-[(5-hydroxy-1-phenyl-1H-pyrazole-3-carbonyl)-amino]-propionic acid | 416.18 | 3.10 | LC3 | B |

TABLE 1-continued

Example compounds of the formula I

| Example | Compound Name | m/z (1) | Rt (min) | LC/MS Method | Activity (2) |
|---|---|---|---|---|---|
| 163 | (S)-3-(4-Fluoro-phenyl)-3-[(5-hydroxy-1-phenyl-1H-pyrazole-3-carbonyl)-amino]-propionic acid | 370.18 | 3.00 | LC3 | B |
| 164 | (S)-3-(2,3-Dichloro-phenyl)-3-[(5-hydroxy-1-phenyl-1H-pyrazole-3-carbonyl)-amino]-propionic acid | 420.11 | 3.22 | LC3 | A |
| 165 | (S)-3-[(5-Hydroxy-1-phenyl-1H-pyrazole-3-carbonyl)-amino]-3-(3-methoxy-phenyl)-propionic acid | 382.19 | 2.93 | LC3 | C |
| 166 | (S)-3-(3-Fluoro-phenyl)-3-[(5-hydroxy-1-phenyl-1H-pyrazole-3-carbonyl)-amino]-propionic acid | 370.17 | 3.04 | LC3 | C |
| 167 | (S)-3-(3-Chloro-phenyl)-3-[(5-hydroxy-1-phenyl-1H-pyrazole-3-carbonyl)-amino]-propionic acid | 386.15 | 3.10 | LC3 | B |
| 168 | 3-(2,3-Dichloro-phenyl)-3-[(5-hydroxy-1-phenyl-1H-pyrazole-3-carbonyl)-amino]-propionic acid | 420.11 | 3.22 | LC3 | B |
| 169 | (2R,3R)-2-Hydroxy-3-[(5-hydroxy-1-phenyl-1H-pyrazole-3-carbonyl)-amino]-3-(2-methoxy-phenyl)-propionic acid | 398.2 | 2.79 | LC3 | C |
| 170 | (S)-3-(2,3-Dimethoxy-phenyl)-3-[(5-hydroxy-1-phenyl-1H-pyrazole-3-carbonyl)-amino]-propionic acid | 412.21 | 2.99 | LC3 | B |
| 171 | 3-(3'-Fluoro-biphenyl-4-yl)-3-[(5-hydroxy-1-phenyl-1H-pyrazole-3-carbonyl)-amino]-propionic acid | 446.22 | 3.43 | LC3 | B |
| 172 | 3-(3-Chloro-2-fluoro-phenyl)-3-[(5-hydroxy-1-phenyl-1H-pyrazole-3-carbonyl)-amino]-propionic acid | 404.14 | 3.18 | LC3 | B |
| 173 | 3-[3-(4-Chloro-phenoxy)-phenyl]-3-[(5-hydroxy-1-phenyl-1H-pyrazole-3-carbonyl)-amino]-propionic acid | 478.18 | 3.54 | LC3 | C |
| 174 | 3-Benzo[1,3]dioxol-4-yl-3-{[1-(2,4-difluoro-phenyl)-5-hydroxy-1H-pyrazole-3-carbonyl]-amino}-propionic acid | 432.19 | 2.95 | LC3 | B |
| 175 | (S)-3-(2-Bromo-phenyl)-3-{[1-(2,4-difluoro-phenyl)-5-hydroxy-1H-pyrazole-3-carbonyl]-amino}-propionic acid | 466.1 | 3.07 | LC3 | B |
| 176 | (S)-3-(4-Cyano-phenyl)-3-{[1-(2,4-difluoro-phenyl)-5-hydroxy-1H-pyrazole-3-carbonyl]-amino}-propionic acid | 413.17 | 2.85 | LC3 | B |
| 177 | (S)-3-{[1-(2,4-Difluoro-phenyl)-5-hydroxy-1H-pyrazole-3-carbonyl]-amino}-3-(2-methoxy-phenyl)-propionic acid | 418.17 | 3.00 | LC3 | B |
| 178 | 3-(5-Chloro-2-methoxy-phenyl)-3-{[1-(2,4-difluoro-phenyl)-5-hydroxy-1H-pyrazole-3-carbonyl]-amino}-propionic acid | 452.16 | 3.22 | LC3 | C |
| 179 | 3-(2-Chloro-4-methoxy-phenyl)-3-{[1-(2,4-difluoro-phenyl)-5-hydroxy-1H-pyrazole-3-carbonyl]-amino}-propionic acid | 452.17 | 3.09 | LC3 | B |
| 180 | (S)-3-{[1-(2,4-Difluoro-phenyl)-5-hydroxy-1H-pyrazole-3-carbonyl]-amino}-3-(4-fluoro-phenyl)-propionic acid | 406.17 | 2.97 | LC3 | B |
| 181 | (S)-3-(2,3-Dichloro-phenyl)-3-{[1-(2,4-difluoro-phenyl)-5-hydroxy-1H-pyrazole-3-carbonyl]-amino}-propionic acid | 456.11 | 3.20 | LC3 | A |
| 182 | (S)-3-{[1-(2,4-Difluoro-phenyl)-5-hydroxy-1H-pyrazole-3-carbonyl]-amino}-3-(3-methoxy-phenyl)-propionic acid | 418.18 | 2.95 | LC3 | B |
| 183 | (S)-3-{[1-(2,4-Difluoro-phenyl)-5-hydroxy-1H-pyrazole-3-carbonyl]-amino}-3-(3-fluoro-phenyl)-propionic acid | 406.14 | 3.04 | LC3 | B |
| 184 | (S)-3-(3-Chloro-phenyl)-3-{[1-(2,4-difluoro-phenyl)-5-hydroxy-1H-pyrazole-3-carbonyl]-amino}-propionic acid | 422.14 | 3.12 | LC3 | B |
| 185 | (S)-3-{[1-(2,4-Difluoro-phenyl)-5-hydroxy-1H-pyrazole-3-carbonyl]-amino}-3-(4-trifluoromethyl-phenyl)-propionic acid | 456.16 | 3.24 | LC3 | B |
| 186 | 3-(2,3-Dichloro-phenyl)-3-{[1-(2,4-difluoro-phenyl)-5-hydroxy-1H-pyrazole-3-carbonyl]-amino}-propionic acid | 456.11 | 3.18 | LC3 | B |
| 187 | 3-{[1-(2,4-Difluoro-phenyl)-5-hydroxy-1H-pyrazole-3-carbonyl]-amino}-3-(4-trifluoromethoxy-phenyl)-propionic acid | 472.16 | 3.29 | LC3 | B |

TABLE 1-continued

Example compounds of the formula I

| Example | Compound Name | m/z (1) | Rt (min) | LC/MS Method | Activity (2) |
|---|---|---|---|---|---|
| 188 | (2R,3R)-3-{[1-(2,4-Difluoro-phenyl)-5-hydroxy-1H-pyrazole-3-carbonyl]-amino}-2-hydroxy-3-(2-methoxy-phenyl)-propionic acid | 434.17 | 2.79 | LC3 | C |
| 189 | (S)-3-{[1-(2,4-Difluoro-phenyl)-5-hydroxy-1H-pyrazole-3-carbonyl]-amino}-3-(2,3-dimethoxy-phenyl)-propionic acid | 448.21 | 3.04 | LC3 | B |
| 190 | (S)-3-{[1-(2,4-Difluoro-phenyl)-5-hydroxy-1H-pyrazole-3-carbonyl]-amino}-3-m-tolyl-propionic acid | 402.19 | 3.05 | LC3 | B |
| 191 | 3-{[1-(2,4-Difluoro-phenyl)-5-hydroxy-1H-pyrazole-3-carbonyl]-amino}-3-(2,3-dimethyl-phenyl)-propionic acid | 416.2 | 3.14 | LC3 | A |
| 192 | 3-(3-Chloro-2-fluoro-phenyl)-3-{[1-(2,4-difluoro-phenyl)-5-hydroxy-1H-pyrazole-3-carbonyl]-amino}-propionic acid | 440.11 | 3.18 | LC3 | B |
| 193 | 3-(2-Chloro-3-trifluoromethyl-phenyl)-3-{[1-(2,4-difluoro-phenyl)-5-hydroxy-1H-pyrazole-3-carbonyl]-amino}-propionic acid | 490.13 | 3.30 | LC3 | B |
| 194 | 3-{[1-(2,4-Difluoro-phenyl)-5-hydroxy-1H-pyrazole-3-carbonyl]-amino}-3-(4-ethyl-phenyl)-propionic acid | 416.21 | 3.24 | LC3 | B |
| 195 | 3-{[1-(2,4-Difluoro-phenyl)-5-hydroxy-1H-pyrazole-3-carbonyl]-amino}-3-(2,4-dimethyl-phenyl)-propionic acid | 416.21 | 3.18 | LC3 | B |
| 196 | 3-{[1-(2,4-Difluoro-phenyl)-5-hydroxy-1H-pyrazole-3-carbonyl]-amino}-3-(4-fluoro-2-methyl-phenyl)-propionic acid | 420.18 | 3.07 | LC3 | A |
| 197 | 3-Biphenyl-4-yl-3-{[1-(2,4-difluoro-phenyl)-5-hydroxy-1H-pyrazole-3-carbonyl]-amino}-propionic acid | 464.22 | 3.39 | LC3 | B |
| 198 | (S)-3-{[1-(2,4-Difluoro-phenyl)-5-hydroxy-1H-pyrazole-3-carbonyl]-amino}-3-(2-trifluoromethyl-phenyl)-propionic acid | 456.14 | 3.15 | LC3 | B |
| 199 | 3-{[1-(2,4-Difluoro-phenyl)-5-hydroxy-1H-pyrazole-3-carbonyl]-amino}-3-(4-phenoxy-phenyl)-propionic acid | 480.21 | 3.37 | LC3 | B |
| 200 | (S)-3-(4-Chloro-phenyl)-3-{[1-(2,4-difluoro-phenyl)-5-hydroxy-1H-pyrazole-3-carbonyl]-amino}-propionic acid | 422.14 | 3.12 | LC3 | B |
| 201 | (S)-3-(2,4-Dichloro-phenyl)-3-{[1-(2,4-difluoro-phenyl)-5-hydroxy-1H-pyrazole-3-carbonyl]-amino}-propionic acid | 456.11 | 3.25 | LC3 | B |
| 202 | 3-{[1-(2,4-Difluoro-phenyl)-5-hydroxy-1H-pyrazole-3-carbonyl]-amino}-3-(4'-fluoro-biphenyl-4-yl)-propionic acid | 482.22 | 3.42 | LC3 | B |
| 203 | 3-{[1-(2-Chloro-phenyl)-5-hydroxy-1H-pyrazole-3-carbonyl]-amino}-3-(4-methoxy-2-methyl-phenyl)-propionic acid | 430.18 | 2.99 | LC3 | B |
| 204 | (S)-3-(2-Bromo-phenyl)-3-{[1-(2-chloro-phenyl)-5-hydroxy-1H-pyrazole-3-carbonyl]-amino}-propionic acid | 464.04 | 3.05 | LC3 | B |
| 205 | (S)-3-{[1-(2-Chloro-phenyl)-5-hydroxy-1H-pyrazole-3-carbonyl]-amino}-3-(3-cyano-phenyl)-propionic acid | 411.12 | 2.84 | LC3 | B |
| 206 | 3-{[1-(2-Chloro-phenyl)-5-hydroxy-1H-pyrazole-3-carbonyl]-amino}-3-(3-trifluoromethyl-phenyl)-propionic acid | 454.12 | 3.17 | LC3 | B |
| 207 | 3-{[1-(2-Chloro-phenyl)-5-hydroxy-1H-pyrazole-3-carbonyl]-amino}-3-(2,4-dimethoxy-phenyl)-propionic acid | 446.18 | 3.00 | LC3 | B |
| 208 | 3-{[1-(2-Chloro-phenyl)-5-hydroxy-1H-pyrazole-3-carbonyl]-amino}-3-(2-fluoro-phenyl)-propionic acid | 404.11 | 2.97 | LC3 | B |
| 209 | 3-(5-Chloro-2-methoxy-phenyl)-3-{[1-(2-chloro-phenyl)-5-hydroxy-1H-pyrazole-3-carbonyl]-amino}-propionic acid | 450.11 | 3.14 | LC3 | B |
| 210 | 3-(2-Chloro-4-methoxy-phenyl)-3-{[1-(2-chloro-phenyl)-5-hydroxy-1H-pyrazole-3-carbonyl]-amino}-propionic acid | 450.15 | 3.05 | LC3 | B |
| 211 | (S)-3-{[1-(2-Chloro-phenyl)-5-hydroxy-1H-pyrazole-3-carbonyl]-amino}-3-(4-fluoro-phenyl)-propionic acid | 404.12 | 2.99 | LC3 | B |

TABLE 1-continued

Example compounds of the formula I

| Example | Compound Name | m/z (1) | Rt (min) | LC/MS Method | Activity (2) |
|---|---|---|---|---|---|
| 212 | (S)-3-{[1-(2-Chloro-phenyl)-5-hydroxy-1H-pyrazole-3-carbonyl]-amino}-3-(2,3-dichloro-phenyl)-propionic acid | 454.06 | 3.17 | LC3 | A |
| 213 | (S)-3-{[1-(2-Chloro-phenyl)-5-hydroxy-1H-pyrazole-3-carbonyl]-amino}-3-(3-methoxy-phenyl)-propionic acid | 416.15 | 2.90 | LC3 | B |
| 214 | (S)-3-(3-Chloro-phenyl)-3-{[1-(2-chloro-phenyl)-5-hydroxy-1H-pyrazole-3-carbonyl]-amino}-propionic acid | 420.09 | 3.07 | LC3 | B |
| 215 | 3-{[1-(2-Chloro-phenyl)-5-hydroxy-1H-pyrazole-3-carbonyl]-amino}-3-(4-trifluoromethoxy-phenyl)-propionic acid | 470.12 | 3.32 | LC3 | B |
| 216 | (2R,3R)-3-{[1-(2-Chloro-phenyl)-5-hydroxy-1H-pyrazole-3-carbonyl]-amino}-2-hydroxy-3-(2-methoxy-phenyl)-propionic acid | 432.13 | 2.74 | LC3 | C |
| 217 | (S)-3-{[1-(2-Chloro-phenyl)-5-hydroxy-1H-pyrazole-3-carbonyl]-amino}-3-m-tolyl-propionic acid | 400.15 | 3.02 | LC3 | B |
| 218 | (S)-3-{[1-(2-Chloro-phenyl)-5-hydroxy-1H-pyrazole-3-carbonyl]-amino}-3-(3-trifluoromethyl-phenyl)-propionic acid | 454.12 | 3.20 | LC3 | B |
| 219 | 3-{[1-(2-Chloro-phenyl)-5-hydroxy-1H-pyrazole-3-carbonyl]-amino}-3-(3'-fluoro-biphenyl-4-yl)-propionic acid | 480.19 | 3.40 | LC3 | B |
| 220 | 3-{[1-(2-Chloro-phenyl)-5-hydroxy-1H-pyrazole-3-carbonyl]-amino}-3-(2,3-dimethyl-phenyl)-propionic acid | 414.18 | 3.12 | LC3 | B |
| 221 | 3-{[1-(2-Chloro-phenyl)-5-hydroxy-1H-pyrazole-3-carbonyl]-amino}-3-(2-fluoro-3-trifluoromethyl-phenyl)-propionic acid | 472.14 | 3.22 | LC3 | B |
| 222 | 3-(3-Chloro-2-fluoro-phenyl)-3-{[1-(2-chloro-phenyl)-5-hydroxy-1H-pyrazole-3-carbonyl]-amino}-propionic acid | 438.08 | 3.10 | LC3 | B |
| 223 | 3-{[1-(2-Chloro-phenyl)-5-hydroxy-1H-pyrazole-3-carbonyl]-amino}-3-(2-chloro-3-trifluoromethyl-phenyl)-propionic acid | 488.08 | 3.29 | LC3 | B |
| 224 | 3-{[1-(2-Chloro-phenyl)-5-hydroxy-1H-pyrazole-3-carbonyl]-amino}-3-(4-ethyl-phenyl)-propionic acid | 414.16 | 3.18 | LC3 | B |
| 225 | 3-{[1-(2-Chloro-phenyl)-5-hydroxy-1H-pyrazole-3-carbonyl]-amino}-3-(2,4-dimethyl-phenyl)-propionic acid | 414.16 | 3.12 | LC3 | B |
| 226 | 3-Biphenyl-4-yl-3-{[1-(2-chloro-phenyl)-5-hydroxy-1H-pyrazole-3-carbonyl]-amino}-propionic acid | 462.2 | 3.39 | LC3 | B |
| 227 | 3-{[1-(2-Chloro-phenyl)-5-hydroxy-1H-pyrazole-3-carbonyl]-amino}-3-(3,4-dichloro-phenyl)-propionic acid | 454.06 | 3.29 | LC3 | B |
| 228 | 3-Benzo[1,3]dioxol-4-yl-3-{[1-(2-fluoro-phenyl)-5-hydroxy-1H-pyrazole-3-carbonyl]-amino}-propionic acid | 414.16 | 2.89 | LC3 | B |
| 229 | 3-(3-Benzyloxy-phenyl)-3-{[1-(2-fluoro-phenyl)-5-hydroxy-1H-pyrazole-3-carbonyl]-amino}-propionic acid | 476.21 | 3.32 | LC3 | C |
| 230 | (S)-3-(3-Cyano-phenyl)-3-{[1-(2-fluoro-phenyl)-5-hydroxy-1H-pyrazole-3-carbonyl]-amino}-propionic acid | 395.15 | 2.77 | LC3 | B |
| 231 | 3-{[1-(2-Fluoro-phenyl)-5-hydroxy-1H-pyrazole-3-carbonyl]-amino}-3-(3-trifluoromethyl-phenyl)-propionic acid | 438.14 | 3.14 | LC3 | B |
| 232 | 3-(2,4-Dimethoxy-phenyl)-3-{[1-(2-fluoro-phenyl)-5-hydroxy-1H-pyrazole-3-carbonyl]-amino}-propionic acid | 430.2 | 2.97 | LC3 | B |
| 233 | 3-(2-Fluoro-phenyl)-3-{[1-(2-fluoro-phenyl)-5-hydroxy-1H-pyrazole-3-carbonyl]-amino}-propionic acid | 388.14 | 2.87 | LC3 | B |
| 234 | 3-(5-Chloro-2-methoxy-phenyl)-3-{[1-(2-fluoro-phenyl)-5-hydroxy-1H-pyrazole-3-carbonyl]-amino}-propionic acid | 434.14 | 3.07 | LC3 | B |
| 235 | 3-(2-Chloro-4-methoxy-phenyl)-3-{[1-(2-fluoro-phenyl)-5-hydroxy-1H-pyrazole-3-carbonyl]-amino}-propionic acid | 434.17 | 3.05 | LC3 | B |
| 236 | (S)-3-(4-Fluoro-phenyl)-3-{[1-(2-fluoro-phenyl)-5-hydroxy-1H-pyrazole-3-carbonyl]-amino}-propionic acid | 388.16 | 2.90 | LC3 | B |

TABLE 1-continued

Example compounds of the formula I

| Example | Compound Name | m/z (1) | Rt (min) | LC/MS Method | Activity (2) |
|---|---|---|---|---|---|
| 237 | (S)-3-{[1-(2-Fluoro-phenyl)-5-hydroxy-1H-pyrazole-3-carbonyl]-amino}-3-(3-methoxy-phenyl)-propionic acid | 400.18 | 2.85 | LC3 | B |
| 238 | 3-{[1-(2-Fluoro-phenyl)-5-hydroxy-1H-pyrazole-3-carbonyl]-amino}-3-(2-fluoro-4-trifluoromethyl-phenyl)-propionic acid | 456.16 | 3.22 | LC3 | B |
| 239 | 3-{[1-(2-Fluoro-phenyl)-5-hydroxy-1H-pyrazole-3-carbonyl]-amino}-3-(4-trifluoromethoxy-phenyl)-propionic acid | 454.17 | 3.24 | LC3 | B |
| 240 | (2R,3R)-3-{[1-(2-Fluoro-phenyl)-5-hydroxy-1H-pyrazole-3-carbonyl]-amino}-2-hydroxy-3-(2-methoxy-phenyl)-propionic acid | 416.17 | 2.72 | LC3 | C |
| 241 | (S)-3-{[1-(2-Fluoro-phenyl)-5-hydroxy-1H-pyrazole-3-carbonyl]-amino}-3-(3-trifluoromethyl-phenyl)-propionic acid | 438.14 | 3.17 | LC3 | B |
| 242 | 3-(3'-Fluoro-biphenyl-4-yl)-3-{[1-(2-fluoro-phenyl)-5-hydroxy-1H-pyrazole-3-carbonyl]-amino}-propionic acid | 464.22 | 3.35 | LC3 | B |
| 243 | 3-(4-Chloro-2-fluoro-phenyl)-3-{[1-(2-fluoro-phenyl)-5-hydroxy-1H-pyrazole-3-carbonyl]-amino}-propionic acid | 422.13 | 3.09 | LC3 | B |
| 244 | 3-(3-Chloro-2-fluoro-phenyl)-3-{[1-(2-fluoro-phenyl)-5-hydroxy-1H-pyrazole-3-carbonyl]-amino}-propionic acid | 422.11 | 3.04 | LC3 | B |
| 245 | 3-(2-Chloro-3-trifluoromethyl-phenyl)-3-{[1-(2-fluoro-phenyl)-5-hydroxy-1H-pyrazole-3-carbonyl]-amino}-propionic acid | 472.11 | 3.22 | LC3 | B |
| 246 | 3-[3-(4-Chloro-phenoxy)-phenyl]-3-{[1-(2-fluoro-phenyl)-5-hydroxy-1H-pyrazole-3-carbonyl]-amino}-propionic acid | 496.16 | 3.50 | LC3 | B |
| 247 | 3-(2,4-Dimethyl-phenyl)-3-{[1-(2-fluoro-phenyl)-5-hydroxy-1H-pyrazole-3-carbonyl]-amino}-propionic acid | 398.2 | 3.09 | LC3 | B |
| 248 | 3-(4-Fluoro-2-methyl-phenyl)-3-{[1-(2-fluoro-phenyl)-5-hydroxy-1H-pyrazole-3-carbonyl]-amino}-propionic acid | 402.18 | 3.02 | LC3 | B |
| 249 | 3-Benzo[1,3]dioxol-4-yl-3-{[1-(3-chloro-phenyl)-5-hydroxy-1H-pyrazole-3-carbonyl]-amino}-propionic acid | 430.14 | 3.24 | LC3 | B |
| 250 | 3-{[1-(3-Chloro-phenyl)-5-hydroxy-1H-pyrazole-3-carbonyl]-amino}-3-(4-methoxy-2-methyl-phenyl)-propionic acid | 430.19 | 3.24 | LC3 | B |
| 251 | (S)-3-(2-Bromo-phenyl)-3-{[1-(3-chloro-phenyl)-5-hydroxy-1H-pyrazole-3-carbonyl]-amino}-propionic acid | 464.07 | 3.30 | LC3 | B |
| 252 | (S)-3-{[1-(3-Chloro-phenyl)-5-hydroxy-1H-pyrazole-3-carbonyl]-amino}-3-(3-cyano-phenyl)-propionic acid | 411.14 | 3.12 | LC3 | C |
| 253 | (S)-3-{[1-(3-Chloro-phenyl)-5-hydroxy-1H-pyrazole-3-carbonyl]-amino}-3-(2-methoxy-phenyl)-propionic acid | 416.16 | 3.25 | LC3 | B |
| 254 | 3-{[1-(3-Chloro-phenyl)-5-hydroxy-1H-pyrazole-3-carbonyl]-amino}-3-(2-fluoro-phenyl)-propionic acid | 404.13 | 3.20 | LC3 | B |
| 255 | 3-(5-Chloro-2-methoxy-phenyl)-3-{[1-(3-chloro-phenyl)-5-hydroxy-1H-pyrazole-3-carbonyl]-amino}-propionic acid | 450.13 | 3.42 | LC3 | B |
| 256 | (S)-3-{[1-(3-Chloro-phenyl)-5-hydroxy-1H-pyrazole-3-carbonyl]-amino}-3-(4-trifluoromethyl-phenyl)-propionic acid | 454.13 | 3.43 | LC3 | C |
| 257 | 3-{[1-(3-Chloro-phenyl)-5-hydroxy-1H-pyrazole-3-carbonyl]-amino}-3-(2,3-dichloro-phenyl)-propionic acid | 454.09 | 3.43 | LC3 | B |
| 258 | (S)-3-{[1-(3-Chloro-phenyl)-5-hydroxy-1H-pyrazole-3-carbonyl]-amino}-3-m-tolyl-propionic acid | 400.17 | 3.29 | LC3 | B |
| 259 | (S)-3-{[1-(3-Chloro-phenyl)-5-hydroxy-1H-pyrazole-3-carbonyl]-amino}-3-(3-trifluoromethyl-phenyl)-propionic acid | 454.13 | 3.45 | LC3 | C |
| 260 | 3-{[1-(3-Chloro-phenyl)-5-hydroxy-1H-pyrazole-3-carbonyl]-amino}-3-(3'-fluoro-biphenyl-4-yl)-propionic acid | 480.19 | 3.62 | LC3 | C |
| 261 | 3-{[1-(3-Chloro-phenyl)-5-hydroxy-1H-pyrazole-3-carbonyl]-amino}-3-(2,3-dimethyl-phenyl)-propionic acid | 414.18 | 3.39 | LC3 | B |

TABLE 1-continued

Example compounds of the formula I

| Example | Compound Name | m/z (1) | Rt (min) | LC/MS Method | Activity (2) |
|---|---|---|---|---|---|
| 262 | 3-(3-Chloro-2-fluoro-phenyl)-3-{[1-(3-chloro-phenyl)-5-hydroxy-1H-pyrazole-3-carbonyl]-amino}-propionic acid | 438.1 | 3.37 | LC3 | B |
| 263 | 3-{[1-(3-Chloro-phenyl)-5-hydroxy-1H-pyrazole-3-carbonyl]-amino}-3-(2-chloro-3-trifluoromethyl-phenyl)-propionic acid | 488.09 | 3.49 | LC3 | B |
| 264 | 3-{[1-(3-Chloro-phenyl)-5-hydroxy-1H-pyrazole-3-carbonyl]-amino}-3-(4-ethyl-phenyl)-propionic acid | 414.18 | 3.43 | LC3 | B |
| 265 | (S)-3-{[1-(3-Chloro-phenyl)-5-hydroxy-1H-pyrazole-3-carbonyl]-amino}-3-(2,6-difluoro-phenyl)-propionic acid | 422.14 | 3.24 | LC3 | B |
| 266 | (S)-3-{[1-(3-Chloro-phenyl)-5-hydroxy-1H-pyrazole-3-carbonyl]-amino}-3-(2,4-dichloro-phenyl)-propionic acid | 454.09 | 3.52 | LC3 | B |
| 267 | 3-{[1-(3-Chloro-phenyl)-5-hydroxy-1H-pyrazole-3-carbonyl]-amino}-3-(4'-fluoro-biphenyl-4-yl)-propionic acid | 480.16 | 3.65 | LC3 | C |
| 268 | (S)-3-{[1-(3-Chloro-phenyl)-5-hydroxy-1H-pyrazole-3-carbonyl]-amino}-3-pyridin-3-yl-propionic acid | 387.13 | 2.37 | LC3 | C |
| 269 | (S)-3-{[1-(3-Chloro-phenyl)-5-hydroxy-1H-pyrazole-3-carbonyl]-amino}-3-(6-methoxy-pyridin-3-yl)-propionic acid | 417.13 | 2.87 | LC3 | C |
| 270 | (S)-3-(2-Bromo-phenyl)-3-{[1-(4-chloro-phenyl)-5-hydroxy-1H-pyrazole-3-carbonyl]-amino}-propionic acid | 464.05 | 3.30 | LC3 | B |
| 271 | (S)-3-{[1-(4-Chloro-phenyl)-5-hydroxy-1H-pyrazole-3-carbonyl]-amino}-3-(3-cyano-phenyl)-propionic acid | 411.12 | 3.15 | LC3 | C |
| 272 | (S)-3-{[1-(4-Chloro-phenyl)-5-hydroxy-1H-pyrazole-3-carbonyl]-amino}-3-(4-cyano-phenyl)-propionic acid | 411.13 | 3.10 | LC3 | C |
| 273 | 3-{[1-(4-Chloro-phenyl)-5-hydroxy-1H-pyrazole-3-carbonyl]-amino}-3-(2,4-dimethoxy-phenyl)-propionic acid | 446.16 | 3.29 | LC3 | C |
| 274 | (S)-3-{[1-(4-Chloro-phenyl)-5-hydroxy-1H-pyrazole-3-carbonyl]-amino}-3-(2-methoxy-phenyl)-propionic acid | 416.14 | 3.27 | LC3 | C |
| 275 | 3-(5-Chloro-2-methoxy-phenyl)-3-{[1-(4-chloro-phenyl)-5-hydroxy-1H-pyrazole-3-carbonyl]-amino}-propionic acid | 450.11 | 3.45 | LC3 | C |
| 276 | (S)-3-{[1-(4-Chloro-phenyl)-5-hydroxy-1H-pyrazole-3-carbonyl]-amino}-3-(4-fluoro-phenyl)-propionic acid | 404.13 | 3.22 | LC3 | C |
| 277 | (S)-3-{[1-(4-Chloro-phenyl)-5-hydroxy-1H-pyrazole-3-carbonyl]-amino}-3-(2,3-dichloro-phenyl)-propionic acid | 454.06 | 3.49 | LC3 | B |
| 278 | (S)-3-{[1-(4-Chloro-phenyl)-5-hydroxy-1H-pyrazole-3-carbonyl]-amino}-3-(3-methoxy-phenyl)-propionic acid | 416.15 | 3.18 | LC3 | C |
| 279 | (S)-3-{[1-(4-Chloro-phenyl)-5-hydroxy-1H-pyrazole-3-carbonyl]-amino}-3-(3-fluoro-phenyl)-propionic acid | 404.12 | 3.24 | LC3 | C |
| 280 | (S)-3-(3-Chloro-phenyl)-3-{[1-(4-chloro-phenyl)-5-hydroxy-1H-pyrazole-3-carbonyl]-amino}-propionic acid | 420.1 | 3.35 | LC3 | C |
| 281 | 3-{[1-(4-Chloro-phenyl)-5-hydroxy-1H-pyrazole-3-carbonyl]-amino}-3-(2,3-dichloro-phenyl)-propionic acid | 454.07 | 3.42 | LC3 | B |
| 282 | (2R,3R)-3-{[1-(4-Chloro-phenyl)-5-hydroxy-1H-pyrazole-3-carbonyl]-amino}-2-hydroxy-3-(2-methoxy-phenyl)-propionic acid | 432.15 | 3.04 | LC3 | C |
| 283 | (S)-3-{[1-(4-Chloro-phenyl)-5-hydroxy-1H-pyrazole-3-carbonyl]-amino}-3-(2,3-dimethoxy-phenyl)-propionic acid | 446.17 | 3.22 | LC3 | B |
| 284 | (S)-3-{[1-(4-Chloro-phenyl)-5-hydroxy-1H-pyrazole-3-carbonyl]-amino}-3-m-tolyl-propionic acid | 400.15 | 3.30 | LC3 | B |
| 285 | (S)-3-{[1-(4-Chloro-phenyl)-5-hydroxy-1H-pyrazole-3-carbonyl]-amino}-3-(3-trifluoromethyl-phenyl)-propionic acid | 454.12 | 3.43 | LC3 | C |
| 286 | 3-(4-Chloro-2-fluoro-phenyl)-3-{[1-(4-chloro-phenyl)-5-hydroxy-1H-pyrazole-3-carbonyl]-amino}-propionic acid | 438.1 | 3.40 | LC3 | C |

TABLE 1-continued

Example compounds of the formula I

| Example | Compound Name | m/z (1) | Rt (min) | LC/MS Method | Activity (2) |
|---|---|---|---|---|---|
| 287 | 3-{[1-(4-Chloro-phenyl)-5-hydroxy-1H-pyrazole-3-carbonyl]-amino}-3-(2,3-dimethyl-phenyl)-propionic acid | 414.17 | 3.43 | LC3 | B |
| 288 | 3-(3-Chloro-2-fluoro-phenyl)-3-{[1-(4-chloro-phenyl)-5-hydroxy-1H-pyrazole-3-carbonyl]-amino}-propionic acid | 438.1 | 3.42 | LC3 | C |
| 289 | 3-{[1-(4-Chloro-phenyl)-5-hydroxy-1H-pyrazole-3-carbonyl]-amino}-3-(2-chloro-3-trifluoromethyl-phenyl)-propionic acid | 488.09 | 3.50 | LC3 | B |
| 290 | 3-[3-(4-Chloro-phenoxy)-phenyl]-3-{[1-(4-chloro-phenyl)-5-hydroxy-1H-pyrazole-3-carbonyl]-amino}-propionic acid | 512.14 | 3.77 | LC3 | C |
| 291 | 3-{[1-(4-Chloro-phenyl)-5-hydroxy-1H-pyrazole-3-carbonyl]-amino}-3-(2,4-dimethyl-phenyl)-propionic acid | 414.17 | 3.40 | LC3 | B |
| 292 | 3-{[1-(4-Chloro-phenyl)-5-hydroxy-1H-pyrazole-3-carbonyl]-amino}-3-(4-fluoro-2-methyl-phenyl)-propionic acid | 418.15 | 3.37 | LC3 | B |
| 293 | (S)-3-{[1-(4-Chloro-phenyl)-5-hydroxy-1H-pyrazole-3-carbonyl]-amino}-3-(2-fluoro-phenyl)-propionic acid | 404.13 | 3.25 | LC3 | C |
| 294 | 3-{[1-(4-Chloro-phenyl)-5-hydroxy-1H-pyrazole-3-carbonyl]-amino}-3-(4-phenoxy-phenyl)-propionic acid | 478.18 | 3.60 | LC3 | C |
| 295 | (S)-3-{[1-(4-Chloro-phenyl)-5-hydroxy-1H-pyrazole-3-carbonyl]-amino}-3-(2,6-difluoro-phenyl)-propionic acid | 422.12 | 3.25 | LC3 | C |
| 296 | (S)-3-(4-Chloro-phenyl)-3-{[1-(4-chloro-phenyl)-5-hydroxy-1H-pyrazole-3-carbonyl]-amino}-propionic acid | 420.11 | 3.37 | LC3 | B |
| 297 | (S)-3-{[1-(4-Chloro-phenyl)-5-hydroxy-1H-pyrazole-3-carbonyl]-amino}-3-(2,4-dichloro-phenyl)-propionic acid | 454.07 | 3.49 | LC3 | B |
| 298 | (S)-3-{[1-(4-Chloro-phenyl)-5-hydroxy-1H-pyrazole-3-carbonyl]-amino}-3-pyridin-3-yl-propionic acid | 387.14 | 2.42 | LC3 | C |
| 299 | (S)-3-{[1-(4-Chloro-phenyl)-5-hydroxy-1H-pyrazole-3-carbonyl]-amino}-3-(6-methoxy-pyridin-3-yl)-propionic acid | 417.14 | 2.92 | LC3 | C |
| 300 | 3-Benzo[1,3]dioxol-4-yl-3-{[1-(3-fluoro-phenyl)-5-hydroxy-1H-pyrazole-3-carbonyl]-amino}-propionic acid | 414.16 | 3.07 | LC3 | B |
| 301 | 3-(3-Chloro-phenyl)-3-{[1-(3-fluoro-phenyl)-5-hydroxy-1H-pyrazole-3-carbonyl]-amino}-propionic acid | 404.13 | 3.24 | LC3 | B |
| 302 | (S)-3-(2-Bromo-phenyl)-3-{[1-(3-fluoro-phenyl)-5-hydroxy-1H-pyrazole-3-carbonyl]-amino}-propionic acid | 448.08 | 3.17 | LC3 | B |
| 303 | (S)-3-(3-Cyano-phenyl)-3-{[1-(3-fluoro-phenyl)-5-hydroxy-1H-pyrazole-3-carbonyl]-amino}-propionic acid | 395.16 | 3.02 | LC3 | C |
| 304 | 3-{[1-(3-Fluoro-phenyl)-5-hydroxy-1H-pyrazole-3-carbonyl]-amino}-3-(3-trifluoromethyl-phenyl)-propionic acid | 438.15 | 3.29 | LC3 | B |
| 305 | (S)-3-(4-Cyano-phenyl)-3-{[1-(3-fluoro-phenyl)-5-hydroxy-1H-pyrazole-3-carbonyl]-amino}-propionic acid | 395.17 | 2.97 | LC3 | B |
| 306 | 3-(2,4-Dimethoxy-phenyl)-3-{[1-(3-fluoro-phenyl)-5-hydroxy-1H-pyrazole-3-carbonyl]-amino}-propionic acid | 430.19 | 3.14 | LC3 | B |
| 307 | (S)-3-{[1-(3-Fluoro-phenyl)-5-hydroxy-1H-pyrazole-3-carbonyl]-amino}-3-(2-methoxy-phenyl)-propionic acid | 400.18 | 3.12 | LC3 | B |
| 308 | 3-(2-Fluoro-phenyl)-3-{[1-(3-fluoro-phenyl)-5-hydroxy-1H-pyrazole-3-carbonyl]-amino}-propionic acid | 388.15 | 3.05 | LC3 | B |
| 309 | 3-(5-Chloro-2-methoxy-phenyl)-3-{[1-(3-fluoro-phenyl)-5-hydroxy-1H-pyrazole-3-carbonyl]-amino}-propionic acid | 434.15 | 3.32 | LC3 | B |
| 310 | 3-(2-Chloro-4-methoxy-phenyl)-3-{[1-(3-fluoro-phenyl)-5-hydroxy-1H-pyrazole-3-carbonyl]-amino}-propionic acid | 434.17 | 3.18 | LC3 | B |
| 311 | (S)-3-(4-Fluoro-phenyl)-3-{[1-(3-fluoro-phenyl)-5-hydroxy-1H-pyrazole-3-carbonyl]-amino}-propionic acid | 388.16 | 3.10 | LC3 | B |

TABLE 1-continued

Example compounds of the formula I

| Example | Compound Name | m/z (1) | Rt (min) | LC/MS Method | Activity (2) |
|---|---|---|---|---|---|
| 312 | (S)-3-(3-Fluoro-phenyl)-3-{[1-(3-fluoro-phenyl)-5-hydroxy-1H-pyrazole-3-carbonyl]-amino}-propionic acid | 388.16 | 3.10 | LC3 | B |
| 313 | (S)-3-{[1-(3-Fluoro-phenyl)-5-hydroxy-1H-pyrazole-3-carbonyl]-amino}-3-(4-trifluoromethyl-phenyl)-propionic acid | 438.15 | 3.34 | LC3 | C |
| 314 | 3-(2,3-Dichloro-phenyl)-3-{[1-(3-fluoro-phenyl)-5-hydroxy-1H-pyrazole-3-carbonyl]-amino}-propionic acid | 438.1 | 3.30 | LC3 | A |
| 315 | 3-{[1-(3-Fluoro-phenyl)-5-hydroxy-1H-pyrazole-3-carbonyl]-amino}-3-(4-trifluoromethoxy-phenyl)-propionic acid | 454.16 | 3.43 | LC3 | B |
| 316 | (2R,3R)-3-{[1-(3-Fluoro-phenyl)-5-hydroxy-1H-pyrazole-3-carbonyl]-amino}-2-hydroxy-3-(2-methoxy-phenyl)-propionic acid | 416.18 | 2.89 | LC3 | C |
| 317 | (S)-3-{[1-(3-Fluoro-phenyl)-5-hydroxy-1H-pyrazole-3-carbonyl]-amino}-3-m-tolyl-propionic acid | 384.19 | 3.17 | LC3 | B |
| 318 | (S)-3-{[1-(3-Fluoro-phenyl)-5-hydroxy-1H-pyrazole-3-carbonyl]-amino}-3-(3-trifluoromethyl-phenyl)-propionic acid | 438.15 | 3.32 | LC3 | B |
| 319 | 3-(3'-Fluoro-biphenyl-4-yl)-3-{[1-(3-fluoro-phenyl)-5-hydroxy-1H-pyrazole-3-carbonyl]-amino}-propionic acid | 464.22 | 3.52 | LC3 | B |
| 320 | 3-(4-Chloro-2-fluoro-phenyl)-3-{[1-(3-fluoro-phenyl)-5-hydroxy-1H-pyrazole-3-carbonyl]-amino}-propionic acid | 422.13 | 3.29 | LC3 | B |
| 321 | 3-(2,5-Dimethyl-phenyl)-3-{[1-(3-fluoro-phenyl)-5-hydroxy-1H-pyrazole-3-carbonyl]-amino}-propionic acid | 398.21 | 3.25 | LC3 | B |
| 322 | 3-(3-Chloro-2-fluoro-phenyl)-3-{[1-(3-fluoro-phenyl)-5-hydroxy-1H-pyrazole-3-carbonyl]-amino}-propionic acid | 422.13 | 3.29 | LC3 | B |
| 323 | 3-(2-Chloro-3-trifluoromethyl-phenyl)-3-{[1-(3-fluoro-phenyl)-5-hydroxy-1H-pyrazole-3-carbonyl]-amino}-propionic acid | 472.12 | 3.39 | LC3 | B |
| 324 | 3-(4-Ethyl-phenyl)-3-{[1-(3-fluoro-phenyl)-5-hydroxy-1H-pyrazole-3-carbonyl]-amino}-propionic acid | 398.2 | 3.32 | LC3 | B |
| 325 | 3-(2,4-Dimethyl-phenyl)-3-{[1-(3-fluoro-phenyl)-5-hydroxy-1H-pyrazole-3-carbonyl]-amino}-propionic acid | 398.2 | 3.27 | LC3 | B |
| 326 | 3-(4-Fluoro-2-methyl-phenyl)-3-{[1-(3-fluoro-phenyl)-5-hydroxy-1H-pyrazole-3-carbonyl]-amino}-propionic acid | 402.18 | 3.24 | LC3 | B |
| 327 | 3-Biphenyl-4-yl-3-{[1-(3-fluoro-phenyl)-5-hydroxy-1H-pyrazole-3-carbonyl]-amino}-propionic acid | 446.23 | 3.42 | LC3 | B |
| 328 | 3-(3,4-Dichloro-phenyl)-3-{[1-(3-fluoro-phenyl)-5-hydroxy-1H-pyrazole-3-carbonyl]-amino}-propionic acid | 438.11 | 3.39 | LC3 | B |
| 329 | (S)-3-{[1-(3-Fluoro-phenyl)-5-hydroxy-1H-pyrazole-3-carbonyl]-amino}-3-(2-trifluoromethyl-phenyl)-propionic acid | 438.15 | 3.25 | LC3 | B |
| 330 | 3-{[1-(3-Fluoro-phenyl)-5-hydroxy-1H-pyrazole-3-carbonyl]-amino}-3-(4-phenoxy-phenyl)-propionic acid | 462.21 | 3.49 | LC3 | B |
| 331 | (S)-3-(4-Chloro-phenyl)-3-{[1-(3-fluoro-phenyl)-5-hydroxy-1H-pyrazole-3-carbonyl]-amino}-propionic acid | 404.14 | 3.24 | LC3 | B |
| 332 | (S)-3-(2,4-Dichloro-phenyl)-3-{[1-(3-fluoro-phenyl)-5-hydroxy-1H-pyrazole-3-carbonyl]-amino}-propionic acid | 438.1 | 3.35 | LC3 | B |
| 333 | 3-(4'-Fluoro-biphenyl-4-yl)-3-{[1-(3-fluoro-phenyl)-5-hydroxy-1H-pyrazole-3-carbonyl]-amino}-propionic acid | 464.23 | 3.49 | LC3 | C |
| 334 | (S)-3-{[1-(3-Fluoro-phenyl)-5-hydroxy-1H-pyrazole-3-carbonyl]-amino}-3-pyridin-3-yl-propionic acid | 371.17 | 2.29 | LC3 | B |
| 335 | (S)-3-{[1-(3-Fluoro-phenyl)-5-hydroxy-1H-pyrazole-3-carbonyl]-amino}-3-(6-methoxy-pyridin-3-yl)-propionic acid | 401.17 | 2.72 | LC3 | B |
| 336 | 3-Benzo[1,3]dioxol-4-yl-3-{[1-(4-fluoro-phenyl)-5-hydroxy-1H-pyrazole-3-carbonyl]-amino}-propionic acid | 414.17 | 3.04 | LC3 | B |

TABLE 1-continued

Example compounds of the formula I

| Example | Compound Name | m/z (1) | Rt (min) | LC/MS Method | Activity (2) |
|---|---|---|---|---|---|
| 337 | 3-{[1-(4-Fluoro-phenyl)-5-hydroxy-1H-pyrazole-3-carbonyl]-amino}-3-(4-methoxy-2-methyl-phenyl)-propionic acid | 414.21 | 3.10 | LC3 | B |
| 338 | 3-(3-Chloro-phenyl)-3-{[1-(4-fluoro-phenyl)-5-hydroxy-1H-pyrazole-3-carbonyl]-amino}-propionic acid | 404.13 | 3.17 | LC3 | B |
| 339 | (S)-3-(2-Bromo-phenyl)-3-{[1-(4-fluoro-phenyl)-5-hydroxy-1H-pyrazole-3-carbonyl]-amino}-propionic acid | 448.09 | 3.18 | LC3 | B |
| 340 | (S)-3-(3-Cyano-phenyl)-3-{[1-(4-fluoro-phenyl)-5-hydroxy-1H-pyrazole-3-carbonyl]-amino}-propionic acid | 395.17 | 2.93 | LC3 | C |
| 341 | (S)-3-(4-Cyano-phenyl)-3-{[1-(4-fluoro-phenyl)-5-hydroxy-1H-pyrazole-3-carbonyl]-amino}-propionic acid | 395.17 | 2.93 | LC3 | B |
| 342 | (S)-3-{[1-(4-Fluoro-phenyl)-5-hydroxy-1H-pyrazole-3-carbonyl]-amino}-3-(2-methoxy-phenyl)-propionic acid | 400.19 | 3.07 | LC3 | B |
| 343 | 3-(2-Fluoro-phenyl)-3-{[1-(4-fluoro-phenyl)-5-hydroxy-1H-pyrazole-3-carbonyl]-amino}-propionic acid | 388.16 | 3.07 | LC3 | C |
| 344 | 3-(5-Chloro-2-methoxy-phenyl)-3-{[1-(4-fluoro-phenyl)-5-hydroxy-1H-pyrazole-3-carbonyl]-amino}-propionic acid | 434.15 | 3.24 | LC3 | B |
| 345 | 3-(2-Chloro-4-methoxy-phenyl)-3-{[1-(4-fluoro-phenyl)-5-hydroxy-1H-pyrazole-3-carbonyl]-amino}-propionic acid | 434.17 | 3.20 | LC3 | B |
| 346 | (S)-3-(4-Fluoro-phenyl)-3-{[1-(4-fluoro-phenyl)-5-hydroxy-1H-pyrazole-3-carbonyl]-amino}-propionic acid | 388.16 | 3.10 | LC3 | C |
| 347 | (S)-3-(2,3-Dichloro-phenyl)-3-{[1-(4-fluoro-phenyl)-5-hydroxy-1H-pyrazole-3-carbonyl]-amino}-propionic acid | 438.1 | 3.27 | LC3 | B |
| 348 | (S)-3-{[1-(4-Fluoro-phenyl)-5-hydroxy-1H-pyrazole-3-carbonyl]-amino}-3-(3-methoxy-phenyl)-propionic acid | 400.19 | 3.02 | LC3 | C |
| 349 | (S)-3-(3-Fluoro-phenyl)-3-{[1-(4-fluoro-phenyl)-5-hydroxy-1H-pyrazole-3-carbonyl]-amino}-propionic acid | 388.16 | 3.07 | LC3 | B |
| 350 | (S)-3-(3-Chloro-phenyl)-3-{[1-(4-fluoro-phenyl)-5-hydroxy-1H-pyrazole-3-carbonyl]-amino}-propionic acid | 404.14 | 3.18 | LC3 | B |
| 351 | (S)-3-{[1-(4-Fluoro-phenyl)-5-hydroxy-1H-pyrazole-3-carbonyl]-amino}-3-(4-trifluoromethyl-phenyl)-propionic acid | 438.15 | 3.34 | LC3 | C |
| 352 | 3-(2,3-Dichloro-phenyl)-3-{[1-(4-fluoro-phenyl)-5-hydroxy-1H-pyrazole-3-carbonyl]-amino}-propionic acid | 438.11 | 3.27 | LC3 | B |
| 353 | (S)-3-(2,3-Dimethoxy-phenyl)-3-{[1-(4-fluoro-phenyl)-5-hydroxy-1H-pyrazole-3-carbonyl]-amino}-propionic acid | 430.2 | 3.05 | LC3 | B |
| 354 | (S)-3-{[1-(4-Fluoro-phenyl)-5-hydroxy-1H-pyrazole-3-carbonyl]-amino}-3-m-tolyl-propionic acid | 384.19 | 3.14 | LC3 | B |
| 355 | (S)-3-{[1-(4-Fluoro-phenyl)-5-hydroxy-1H-pyrazole-3-carbonyl]-amino}-3-(3-trifluoromethyl-phenyl)-propionic acid | 438.16 | 3.29 | LC3 | B |
| 356 | 3-(3'-Fluoro-biphenyl-4-yl)-3-{[1-(4-fluoro-phenyl)-5-hydroxy-1H-pyrazole-3-carbonyl]-amino}-propionic acid | 464.21 | 3.47 | LC3 | B |
| 357 | 3-(4-Chloro-2-fluoro-phenyl)-3-{[1-(4-fluoro-phenyl)-5-hydroxy-1H-pyrazole-3-carbonyl]-amino}-propionic acid | 422.13 | 3.22 | LC3 | B |
| 358 | 3-(2,3-Dimethyl-phenyl)-3-{[1-(4-fluoro-phenyl)-5-hydroxy-1H-pyrazole-3-carbonyl]-amino}-propionic acid | 398.21 | 3.22 | LC3 | B |
| 359 | 3-(2,5-Dimethyl-phenyl)-3-{[1-(4-fluoro-phenyl)-5-hydroxy-1H-pyrazole-3-carbonyl]-amino}-propionic acid | 398.21 | 3.27 | LC3 | C |
| 360 | 3-{[1-(4-Fluoro-phenyl)-5-hydroxy-1H-pyrazole-3-carbonyl]-amino}-3-(2-fluoro-3-trifluoromethyl-phenyl)-propionic acid | 456.16 | 3.35 | LC3 | B |
| 361 | 3-(3-Chloro-2-fluoro-phenyl)-3-{[1-(4-fluoro-phenyl)-5-hydroxy-1H-pyrazole-3-carbonyl]-amino}-propionic acid | 422.13 | 3.20 | LC3 | B |

TABLE 1-continued

Example compounds of the formula I

| Example | Compound Name | m/z (1) | Rt (min) | LC/MS Method | Activity (2) |
|---|---|---|---|---|---|
| 362 | 3-(2-Chloro-3-trifluoromethyl-phenyl)-3-{[1-(4-fluoro-phenyl)-5-hydroxy-1H-pyrazole-3-carbonyl]-amino}-propionic acid | 472.13 | 3.35 | LC3 | B |
| 363 | 3-(4-Ethyl-phenyl)-3-{[1-(4-fluoro-phenyl)-5-hydroxy-1H-pyrazole-3-carbonyl]-amino}-propionic acid | 398.2 | 3.27 | LC3 | B |
| 364 | 3-(4-Fluoro-2-methyl-phenyl)-3-{[1-(4-fluoro-phenyl)-5-hydroxy-1H-pyrazole-3-carbonyl]-amino}-propionic acid | 402.19 | 3.17 | LC3 | B |
| 365 | 3-Biphenyl-4-yl-3-{[1-(4-fluoro-phenyl)-5-hydroxy-1H-pyrazole-3-carbonyl]-amino}-propionic acid | 446.22 | 3.42 | LC3 | B |
| 366 | (S)-3-(2-Fluoro-phenyl)-3-{[1-(4-fluoro-phenyl)-5-hydroxy-1H-pyrazole-3-carbonyl]-amino}-propionic acid | 388.16 | 3.04 | LC3 | B |
| 367 | (S)-3-{[1-(4-Fluoro-phenyl)-5-hydroxy-1H-pyrazole-3-carbonyl]-amino}-3-(2-trifluoromethyl-phenyl)-propionic acid | 438.16 | 3.22 | LC3 | B |
| 368 | (S)-3-(2,6-Difluoro-phenyl)-3-{[1-(4-fluoro-phenyl)-5-hydroxy-1H-pyrazole-3-carbonyl]-amino}-propionic acid | 406.15 | 3.07 | LC3 | B |
| 369 | (S)-3-(4-Chloro-phenyl)-3-{[1-(4-fluoro-phenyl)-5-hydroxy-1H-pyrazole-3-carbonyl]-amino}-propionic acid | 404.14 | 3.18 | LC3 | B |
| 370 | (S)-3-(2,4-Dichloro-phenyl)-3-{[1-(4-fluoro-phenyl)-5-hydroxy-1H-pyrazole-3-carbonyl]-amino}-propionic acid | 438.11 | 3.39 | LC3 | B |
| 371 | 3-(4'-Fluoro-biphenyl-4-yl)-3-{[1-(4-fluoro-phenyl)-5-hydroxy-1H-pyrazole-3-carbonyl]-amino}-propionic acid | 464.22 | 3.47 | LC3 | B |
| 372 | (S)-3-{[1-(4-Fluoro-phenyl)-5-hydroxy-1H-pyrazole-3-carbonyl]-amino}-3-pyridin-3-yl-propionic acid | 371.17 | 2.22 | LC3 | C |
| 373 | 3-[(5-Hydroxy-1-phenyl-1H-pyrazole-3-carbonyl)-amino]-3-(4-methoxy-2-methyl-phenyl)-propionic acid | 396.22 | 3.05 | LC3 | B |
| 374 | (S)-3-[(5-Hydroxy-1-phenyl-1H-pyrazole-3-carbonyl)-amino]-3-(4-methoxy-phenyl)-propionic acid | 382.21 | 2.93 | LC3 | B |
| 375 | 3-(5-Chloro-2-methoxy-phenyl)-3-[(5-hydroxy-1-phenyl-1H-pyrazole-3-carbonyl)-amino]-propionic acid | 416.16 | 3.24 | LC3 | B |
| 376 | (S)-3-[(5-Hydroxy-1-phenyl-1H-pyrazole-3-carbonyl)-amino]-3-m-tolyl-propionic acid | 366.19 | 3.07 | LC3 | B |
| 377 | 3-(2,3-Dimethyl-phenyl)-3-[(5-hydroxy-1-phenyl-1H-pyrazole-3-carbonyl)-amino]-propionic acid | 380.21 | 3.15 | LC3 | B |
| 378 | 3-(2,5-Dimethyl-phenyl)-3-[(5-hydroxy-1-phenyl-1H-pyrazole-3-carbonyl)-amino]-propionic acid | 380.21 | 3.22 | LC3 | B |
| 379 | 3-{[1-(2,4-Difluoro-phenyl)-5-hydroxy-1H-pyrazole-3-carbonyl]-amino}-3-(4-methoxy-2-methyl-phenyl)-propionic acid | 432.22 | 2.99 | LC3 | B |
| 380 | 3-(3-Chloro-phenyl)-3-{[1-(2,4-difluoro-phenyl)-5-hydroxy-1H-pyrazole-3-carbonyl]-amino}-propionic acid | 422.15 | 3.14 | LC3 | B |
| 381 | (S)-3-(3-Cyano-phenyl)-3-{[1-(2,4-difluoro-phenyl)-5-hydroxy-1H-pyrazole-3-carbonyl]-amino}-propionic acid | 413.17 | 2.87 | LC3 | B |
| 382 | (S)-3-{[1-(2,4-Difluoro-phenyl)-5-hydroxy-1H-pyrazole-3-carbonyl]-amino}-3-(4-methoxy-phenyl)-propionic acid | 418.19 | 2.93 | LC3 | B |
| 383 | 3-{[1-(2,4-Difluoro-phenyl)-5-hydroxy-1H-pyrazole-3-carbonyl]-amino}-3-(2,4-dimethoxy-phenyl)-propionic acid | 448.21 | 3.00 | LC3 | B |
| 384 | 3-{[1-(2,4-Difluoro-phenyl)-5-hydroxy-1H-pyrazole-3-carbonyl]-amino}-3-(3'-fluoro-biphenyl-4-yl)-propionic acid | 482.21 | 3.42 | LC3 | B |
| 385 | 3-{[1-(2,4-Difluoro-phenyl)-5-hydroxy-1H-pyrazole-3-carbonyl]-amino}-3-(2-fluoro-3-trifluoromethyl-phenyl)-propionic acid | 474.17 | 3.25 | LC3 | A |
| 386 | 3-[3-(4-Chloro-phenoxy)-phenyl]-3-{[1-(2,4-difluoro-phenyl)-5-hydroxy-1H-pyrazole-3-carbonyl]-amino}-propionic acid | 514.16 | 3.60 | LC3 | B |

TABLE 1-continued

Example compounds of the formula I

| Example | Compound Name | m/z (1) | Rt (min) | LC/MS Method | Activity (2) |
|---|---|---|---|---|---|
| 387 | (S)-3-{[1-(2,4-Difluoro-phenyl)-5-hydroxy-1H-pyrazole-3-carbonyl]-amino}-3-(2-fluoro-phenyl)-propionic acid | 406.15 | 2.97 | LC3 | B |
| 388 | (S)-3-(2,6-Difluoro-phenyl)-3-{[1-(2,4-difluoro-phenyl)-5-hydroxy-1H-pyrazole-3-carbonyl]-amino}-propionic acid | 424.15 | 3.02 | LC3 | B |
| 389 | (S)-3-{[1-(2,4-Difluoro-phenyl)-5-hydroxy-1H-pyrazole-3-carbonyl]-amino}-3-pyridin-3-yl-propionic acid | 389.18 | 2.12 | LC3 | C |
| 390 | (S)-3-{[1-(2,4-Difluoro-phenyl)-5-hydroxy-1H-pyrazole-3-carbonyl]-amino}-3-(6-methoxy-pyridin-3-yl)-propionic acid | 419.19 | 2.60 | LC3 | B |
| 391 | 3-(3-Chloro-phenyl)-3-{[1-(2-chloro-phenyl)-5-hydroxy-1H-pyrazole-3-carbonyl]-amino}-propionic acid | 420.1 | 3.12 | LC3 | B |
| 392 | (S)-3-{[1-(2-Chloro-phenyl)-5-hydroxy-1H-pyrazole-3-carbonyl]-amino}-3-(4-methoxy-phenyl)-propionic acid | 416.17 | 2.90 | LC3 | B |
| 393 | (S)-3-{[1-(2-Chloro-phenyl)-5-hydroxy-1H-pyrazole-3-carbonyl]-amino}-3-(3-fluoro-phenyl)-propionic acid | 404.13 | 2.99 | LC3 | B |
| 394 | (S)-3-{[1-(2-Chloro-phenyl)-5-hydroxy-1H-pyrazole-3-carbonyl]-amino}-3-(2,3-dimethoxy-phenyl)-propionic acid | 446.17 | 2.97 | LC3 | B |
| 395 | 3-{[1-(2-Fluoro-phenyl)-5-hydroxy-1H-pyrazole-3-carbonyl]-amino}-3-(4-methoxy-2-methyl-phenyl)-propionic acid | 414.21 | 2.93 | LC3 | B |
| 396 | 3-(3-Chloro-phenyl)-3-{[1-(2-fluoro-phenyl)-5-hydroxy-1H-pyrazole-3-carbonyl]-amino}-propionic acid | 404.13 | 3.04 | LC3 | B |
| 397 | (S)-3-(2-Bromo-phenyl)-3-{[1-(2-fluoro-phenyl)-5-hydroxy-1H-pyrazole-3-carbonyl]-amino}-propionic acid | 448.08 | 3.05 | LC3 | A |
| 398 | (S)-3-{[1-(2-Fluoro-phenyl)-5-hydroxy-1H-pyrazole-3-carbonyl]-amino}-3-(4-methoxy-phenyl)-propionic acid | 400.18 | 2.89 | LC3 | B |
| 399 | (S)-3-(2,3-Dichloro-phenyl)-3-{[1-(2-fluoro-phenyl)-5-hydroxy-1H-pyrazole-3-carbonyl]-amino}-propionic acid | 438.09 | 3.18 | LC3 | A |
| 400 | (S)-3-(3-Fluoro-phenyl)-3-{[1-(2-fluoro-phenyl)-5-hydroxy-1H-pyrazole-3-carbonyl]-amino}-propionic acid | 388.16 | 2.90 | LC3 | B |
| 401 | (S)-3-(3-Chloro-phenyl)-3-{[1-(2-fluoro-phenyl)-5-hydroxy-1H-pyrazole-3-carbonyl]-amino}-propionic acid | 404.12 | 3.02 | LC3 | B |
| 402 | 3-(2,3-Dichloro-phenyl)-3-{[1-(2-fluoro-phenyl)-5-hydroxy-1H-pyrazole-3-carbonyl]-amino}-propionic acid | 438.09 | 3.15 | LC3 | A |
| 403 | (S)-3-(2,3-Dimethoxy-phenyl)-3-{[1-(2-fluoro-phenyl)-5-hydroxy-1H-pyrazole-3-carbonyl]-amino}-propionic acid | 430.19 | 2.93 | LC3 | B |
| 404 | (S)-3-{[1-(2-Fluoro-phenyl)-5-hydroxy-1H-pyrazole-3-carbonyl]-amino}-3-m-tolyl-propionic acid | 384.17 | 2.95 | LC3 | B |
| 405 | 3-(2,3-Dimethyl-phenyl)-3-{[1-(2-fluoro-phenyl)-5-hydroxy-1H-pyrazole-3-carbonyl]-amino}-propionic acid | 398.21 | 3.07 | LC3 | A |
| 406 | 3-(2,5-Dimethyl-phenyl)-3-{[1-(2-fluoro-phenyl)-5-hydroxy-1H-pyrazole-3-carbonyl]-amino}-propionic acid | 398.2 | 3.14 | LC3 | B |
| 407 | 3-(3,4-Dichloro-phenyl)-3-{[1-(2-fluoro-phenyl)-5-hydroxy-1H-pyrazole-3-carbonyl]-amino}-propionic acid | 438.09 | 3.17 | LC3 | B |
| 408 | 3-(3-Chloro-phenyl)-3-{[1-(3-chloro-phenyl)-5-hydroxy-1H-pyrazole-3-carbonyl]-amino}-propionic acid | 420.11 | 3.37 | LC3 | B |
| 409 | (S)-3-{[1-(3-Chloro-phenyl)-5-hydroxy-1H-pyrazole-3-carbonyl]-amino}-3-(4-methoxy-phenyl)-propionic acid | 416.16 | 3.14 | LC3 | C |
| 410 | (S)-3-{[1-(3-Chloro-phenyl)-5-hydroxy-1H-pyrazole-3-carbonyl]-amino}-3-(4-cyano-phenyl)-propionic acid | 411.15 | 3.15 | LC3 | C |
| 411 | (S)-3-{[1-(3-Chloro-phenyl)-5-hydroxy-1H-pyrazole-3-carbonyl]-amino}-3-(4-fluoro-phenyl)-propionic acid | 404.14 | 3.22 | LC3 | C |

TABLE 1-continued

Example compounds of the formula I

| Example | Compound Name | m/z (1) | Rt (min) | LC/MS Method | Activity (2) |
|---|---|---|---|---|---|
| 412 | (S)-3-{[1-(3-Chloro-phenyl)-5-hydroxy-1H-pyrazole-3-carbonyl]-amino}-3-(2,3-dichloro-phenyl)-propionic acid | 454.08 | 3.42 | LC3 | C |
| 413 | (S)-3-{[1-(3-Chloro-phenyl)-5-hydroxy-1H-pyrazole-3-carbonyl]-amino}-3-(3-methoxy-phenyl)-propionic acid | 416.16 | 3.22 | LC3 | C |
| 414 | (S)-3-{[1-(3-Chloro-phenyl)-5-hydroxy-1H-pyrazole-3-carbonyl]-amino}-3-(3-fluoro-phenyl)-propionic acid | 404.14 | 3.20 | LC3 | C |
| 415 | (S)-3-(3-Chloro-phenyl)-3-{[1-(3-chloro-phenyl)-5-hydroxy-1H-pyrazole-3-carbonyl]-amino}-propionic acid | 420.11 | 3.39 | LC3 | B |
| 416 | (2R,3R)-3-{[1-(3-Chloro-phenyl)-5-hydroxy-1H-pyrazole-3-carbonyl]-amino}-2-hydroxy-3-(2-methoxy-phenyl)-propionic acid | 432.15 | 3.02 | LC3 | C |
| 417 | (S)-3-{[1-(3-Chloro-phenyl)-5-hydroxy-1H-pyrazole-3-carbonyl]-amino}-3-(2,3-dimethoxy-phenyl)-propionic acid | 446.17 | 3.25 | LC3 | B |
| 418 | 3-{[1-(3-Chloro-phenyl)-5-hydroxy-1H-pyrazole-3-carbonyl]-amino}-3-(2-fluoro-3-trifluoromethyl-phenyl)-propionic acid | 472.15 | 3.45 | LC3 | C |
| 419 | 3-{[1-(3-Chloro-phenyl)-5-hydroxy-1H-pyrazole-3-carbonyl]-amino}-3-(2,4-dimethyl-phenyl)-propionic acid | 414.19 | 3.39 | LC3 | B |
| 420 | 3-{[1-(3-Chloro-phenyl)-5-hydroxy-1H-pyrazole-3-carbonyl]-amino}-3-(4-fluoro-2-methyl-phenyl)-propionic acid | 418.16 | 3.35 | LC3 | B |
| 421 | 3-Biphenyl-4-yl-3-{[1-(3-chloro-phenyl)-5-hydroxy-1H-pyrazole-3-carbonyl]-amino}-propionic acid | 462.2 | 3.59 | LC3 | B |
| 422 | (S)-3-{[1-(3-Chloro-phenyl)-5-hydroxy-1H-pyrazole-3-carbonyl]-amino}-3-(2-fluoro-phenyl)-propionic acid | 404.12 | 3.18 | LC3 | B |
| 423 | (S)-3-{[1-(4-Chloro-phenyl)-5-hydroxy-1H-pyrazole-3-carbonyl]-amino}-3-(4-methoxy-phenyl)-propionic acid | 416.15 | 3.22 | LC3 | C |
| 424 | 3-(2-Chloro-4-methoxy-phenyl)-3-{[1-(4-chloro-phenyl)-5-hydroxy-1H-pyrazole-3-carbonyl]-amino}-propionic acid | 450.14 | 3.37 | LC3 | B |
| 425 | 3-{[1-(4-Chloro-phenyl)-5-hydroxy-1H-pyrazole-3-carbonyl]-amino}-3-(4'-fluoro-biphenyl-4-yl)-propionic acid | 480.2 | 3.68 | LC3 | C |
| 426 | 3-{[1-(3-Fluoro-phenyl)-5-hydroxy-1H-pyrazole-3-carbonyl]-amino}-3-(4-methoxy-2-methyl-phenyl)-propionic acid | 414.2 | 3.12 | LC3 | B |
| 427 | (S)-3-{[1-(3-Fluoro-phenyl)-5-hydroxy-1H-pyrazole-3-carbonyl]-amino}-3-(4-methoxy-phenyl)-propionic acid | 400.19 | 3.07 | LC3 | C |
| 428 | (S)-3-(2,3-Dichloro-phenyl)-3-{[1-(3-fluoro-phenyl)-5-hydroxy-1H-pyrazole-3-carbonyl]-amino}-propionic acid | 438.1 | 3.37 | LC3 | B |
| 429 | (S)-3-{[1-(3-Fluoro-phenyl)-5-hydroxy-1H-pyrazole-3-carbonyl]-amino}-3-(3-methoxy-phenyl)-propionic acid | 400.18 | 3.05 | LC3 | B |
| 430 | (S)-3-(3-Chloro-phenyl)-3-{[1-(3-fluoro-phenyl)-5-hydroxy-1H-pyrazole-3-carbonyl]-amino}-propionic acid | 404.13 | 3.24 | LC3 | B |
| 431 | (S)-3-(2,3-Dimethoxy-phenyl)-3-{[1-(3-fluoro-phenyl)-5-hydroxy-1H-pyrazole-3-carbonyl]-amino}-propionic acid | 430.2 | 3.09 | LC3 | B |
| 432 | 3-(2,3-Dimethyl-phenyl)-3-{[1-(3-fluoro-phenyl)-5-hydroxy-1H-pyrazole-3-carbonyl]-amino}-propionic acid | 398.21 | 3.30 | LC3 | B |
| 433 | (S)-3-(2-Fluoro-phenyl)-3-{[1-(3-fluoro-phenyl)-5-hydroxy-1H-pyrazole-3-carbonyl]-amino}-propionic acid | 388.16 | 3.12 | LC3 | B |
| 434 | (S)-3-(2,6-Difluoro-phenyl)-3-{[1-(3-fluoro-phenyl)-5-hydroxy-1H-pyrazole-3-carbonyl]-amino}-propionic acid | 406.15 | 3.10 | LC3 | B |
| 435 | (S)-3-{[1-(4-Fluoro-phenyl)-5-hydroxy-1H-pyrazole-3-carbonyl]-amino}-3-(4-methoxy-phenyl)-propionic acid | 400.2 | 2.99 | LC3 | B |
| 436 | 3-(2,4-Dimethoxy-phenyl)-3-{[1-(4-fluoro-phenyl)-5-hydroxy-1H-pyrazole-3-carbonyl]-amino}-propionic acid | 430.21 | 3.09 | LC3 | C |

TABLE 1-continued

Example compounds of the formula I

| Example | Compound Name | m/z (1) | Rt (min) | LC/MS Method | Activity (2) |
|---|---|---|---|---|---|
| 437 | 3-{[1-(4-Fluoro-phenyl)-5-hydroxy-1H-pyrazole-3-carbonyl]-amino}-3-(4-phenoxy-phenyl)-propionic acid | 462.22 | 3.47 | LC3 | B |
| 438 | (S)-3-{[1-(4-Fluoro-phenyl)-5-hydroxy-1H-pyrazole-3-carbonyl]-amino}-3-(6-methoxy-pyridin-3-yl)-propionic acid | 401.18 | 2.70 | LC3 | B |
| 439 | 3-Biphenyl-4-yl-3-{[1-(2-chloro-pyridin-4-yl)-5-hydroxy-1H-pyrazole-3-carbonyl]-amino}-propionic acid | 463.13 | 3.06 | LC8 | B |
| 440 | 3-Biphenyl-4-yl-3-[(5-hydroxy-1-pyridin-3-yl-1H-pyrazole-3-carbonyl)-amino]-propionic acid | 429.17 | 2.66 | LC8 | C |
| 441 | 3-(2-Fluoro-6-methoxy-phenyl)-3-[(5-hydroxy-1-phenyl-1H-pyrazole-3-carbonyl)-amino]-propionic acid | 400.19 | 3.04 | LC3 | B |
| 442 | 3-[(5-Hydroxy-1-phenyl-1H-pyrazole-3-carbonyl)-amino]-3-(2-phenoxy-phenyl)-propionic acid | 444.23 | 3.42 | LC3 | C |
| 443 | 3-(5-Fluoro-2-trifluoromethyl-phenyl)-3-[(5-hydroxy-1-phenyl-1H-pyrazole-3-carbonyl)-amino]-propionic acid | 438.14 | 3.25 | LC3 | B |
| 444 | 3-(2,5-Dichloro-phenyl)-3-[(5-hydroxy-1-phenyl-1H-pyrazole-3-carbonyl)-amino]-propionic acid | 420.11 | 3.22 | LC3 | A |
| 445 | (S)-3-[(5-Hydroxy-1-phenyl-1H-pyrazole-3-carbonyl)-amino]-3-p-tolyl-propionic acid | 366.2 | 3.09 | LC3 | B |
| 446 | (S)-3-(2-Chloro-phenyl)-3-[(5-hydroxy-1-phenyl-1H-pyrazole-3-carbonyl)-amino]-propionic acid | 386.15 | 3.02 | LC3 | B |
| 447 | 3-{[1-(2,4-Difluoro-phenyl)-5-hydroxy-1H-pyrazole-3-carbonyl]-amino}-3-(3-fluoro-2-methyl-phenyl)-propionic acid | 420.18 | 3.07 | LC3 | B |
| 448 | 3-(2-Chloro-4-dimethylamino-phenyl)-3-{[1-(2,4-difluoro-phenyl)-5-hydroxy-1H-pyrazole-3-carbonyl]-amino}-propionic acid | 465.2 | 2.89 | LC3 | B |
| 449 | 3-{[1-(2,4-Difluoro-phenyl)-5-hydroxy-1H-pyrazole-3-carbonyl]-amino}-3-(2-fluoro-6-methoxy-phenyl)-propionic acid | 436.19 | 3.04 | LC3 | B |
| 450 | 3-(2,2-Difluoro-benzo[1,3]dioxol-4-yl)-3-{[1-(2,4-difluoro-phenyl)-5-hydroxy-1H-pyrazole-3-carbonyl]-amino}-propionic acid | 468.14 | 3.20 | LC3 | B |
| 451 | 3-(2,5-Difluoro-phenyl)-3-{[1-(2,4-difluoro-phenyl)-5-hydroxy-1H-pyrazole-3-carbonyl]-amino}-propionic acid | 424.16 | 2.99 | LC3 | B |
| 452 | 3-{[1-(2,4-Difluoro-phenyl)-5-hydroxy-1H-pyrazole-3-carbonyl]-amino}-3-(5-fluoro-2-trifluoromethyl-phenyl)-propionic acid | 474.14 | 3.37 | LC3 | B |
| 453 | 3-{[1-(2,4-Difluoro-phenyl)-5-hydroxy-1H-pyrazole-3-carbonyl]-amino}-3-(5-fluoro-2-methoxy-phenyl)-propionic acid | 436.17 | 3.04 | LC3 | B |
| 454 | (S)-3-{[1-(2,4-Difluoro-phenyl)-5-hydroxy-1H-pyrazole-3-carbonyl]-amino}-3-p-tolyl-propionic acid | 402.18 | 3.04 | LC3 | B |
| 455 | 3-{[1-(2-Chloro-phenyl)-5-hydroxy-1H-pyrazole-3-carbonyl]-amino}-3-(3-fluoro-2-methyl-phenyl)-propionic acid | 418.15 | 3.04 | LC3 | B |
| 456 | 3-(2-Chloro-4-dimethylamino-phenyl)-3-{[1-(2-chloro-phenyl)-5-hydroxy-1H-pyrazole-3-carbonyl]-amino}-propionic acid; compound with trifluoro-acetic acid | 463.17 | 2.90 | LC3 | C |
| 457 | 3-{[1-(2-Chloro-phenyl)-5-hydroxy-1H-pyrazole-3-carbonyl]-amino}-3-(2-fluoro-6-methoxy-phenyl)-propionic acid | 434.17 | 3.02 | LC3 | B |
| 458 | 3-(2-Chloro-5-fluoro-phenyl)-3-{[1-(2-chloro-phenyl)-5-hydroxy-1H-pyrazole-3-carbonyl]-amino}-propionic acid | 438.1 | 3.09 | LC3 | B |
| 459 | 3-{[1-(2-Chloro-phenyl)-5-hydroxy-1H-pyrazole-3-carbonyl]-amino}-3-(2,5-difluoro-phenyl)-propionic acid | 422.15 | 2.97 | LC3 | B |
| 460 | 3-{[1-(2-Chloro-phenyl)-5-hydroxy-1H-pyrazole-3-carbonyl]-amino}-3-(5-fluoro-2-trifluoromethyl-phenyl)-propionic acid | 472.16 | 3.18 | LC3 | B |
| 461 | 3-{[1-(2-Chloro-phenyl)-5-hydroxy-1H-pyrazole-3-carbonyl]-amino}-3-(5-fluoro-2-methyl-phenyl)-propionic acid | 418.16 | 3.10 | LC3 | B |

TABLE 1-continued

Example compounds of the formula I

| Example | Compound Name | m/z (1) | Rt (min) | LC/MS Method | Activity (2) |
|---|---|---|---|---|---|
| 462 | 3-{[1-(2-Chloro-phenyl)-5-hydroxy-1H-pyrazole-3-carbonyl]-amino}-3-(2,5-dichloro-phenyl)-propionic acid | 454.1 | 3.17 | LC3 | A |
| 463 | 3-(2-Chloro-4-dimethylamino-phenyl)-3-{[1-(3-chloro-phenyl)-5-hydroxy-1H-pyrazole-3-carbonyl]-amino}-propionic acid | 461.24 [(M − H)⁻] | 4.39 | LC4 | C |
| 464 | 3-{[1-(3-Chloro-phenyl)-5-hydroxy-1H-pyrazole-3-carbonyl]-amino}-3-(2,2-difluoro-benzo[1,3]dioxol-4-yl)-propionic acid | 466.14 | 3.40 | LC3 | B |
| 465 | 3-{[1-(3-Chloro-phenyl)-5-hydroxy-1H-pyrazole-3-carbonyl]-amino}-3-(2,5-difluoro-phenyl)-propionic acid | 422.14 | 3.29 | LC3 | B |
| 466 | 3-{[1-(3-Chloro-phenyl)-5-hydroxy-1H-pyrazole-3-carbonyl]-amino}-3-(5-fluoro-2-trifluoromethyl-phenyl)-propionic acid | 472.16 | 3.42 | LC3 | B |
| 467 | 3-{[1-(3-Chloro-phenyl)-5-hydroxy-1H-pyrazole-3-carbonyl]-amino}-3-(2-trifluoromethylsulfanyl-phenyl)-propionic acid | 486.13 | 3.50 | LC3 | C |
| 468 | 3-{[1-(4-Chloro-phenyl)-5-hydroxy-1H-pyrazole-3-carbonyl]-amino}-3-(3-fluoro-2-methyl-phenyl)-propionic acid | 418.19 | 3.32 | LC3 | B |
| 469 | 3-{[1-(4-Chloro-phenyl)-5-hydroxy-1H-pyrazole-3-carbonyl]-amino}-3-(2-fluoro-6-methoxy-phenyl)-propionic acid | 434.17 | 3.32 | LC3 | B |
| 470 | 3-(2-Chloro-5-fluoro-phenyl)-3-{[1-(4-chloro-phenyl)-5-hydroxy-1H-pyrazole-3-carbonyl]-amino}-propionic acid | 438.11 | 3.32 | LC3 | B |
| 471 | 3-{[1-(4-Chloro-phenyl)-5-hydroxy-1H-pyrazole-3-carbonyl]-amino}-3-(2,2-difluoro-benzo[1,3]dioxol-4-yl)-propionic acid | 466.13 | 3.40 | LC3 | B |
| 472 | 3-{[1-(4-Chloro-phenyl)-5-hydroxy-1H-pyrazole-3-carbonyl]-amino}-3-(2,5-difluoro-phenyl)-propionic acid | 422.14 | 3.25 | LC3 | C |
| 473 | 3-{[1-(4-Chloro-phenyl)-5-hydroxy-1H-pyrazole-3-carbonyl]-amino}-3-(5-fluoro-2-trifluoromethyl-phenyl)-propionic acid | 472.13 | 3.42 | LC3 | C |
| 474 | (S)-3-(2-Chloro-phenyl)-3-{[1-(4-chloro-phenyl)-5-hydroxy-1H-pyrazole-3-carbonyl]-amino}-propionic acid | 420.12 | 3.27 | LC3 | B |
| 475 | 3-(2-Chloro-5-fluoro-phenyl)-3-{[1-(2-fluoro-phenyl)-5-hydroxy-1H-pyrazole-3-carbonyl]-amino}-propionic acid | 422.15 | 3.00 | LC3 | B |
| 476 | 3-(2,2-Difluoro-benzo[1,3]dioxol-4-yl)-3-{[1-(2-fluoro-phenyl)-5-hydroxy-1H-pyrazole-3-carbonyl]-amino}-propionic acid | 450.15 | 3.22 | LC3 | B |
| 477 | 3-{[1-(2-Fluoro-phenyl)-5-hydroxy-1H-pyrazole-3-carbonyl]-amino}-3-(5-fluoro-2-trifluoromethyl-phenyl)-propionic acid | 456.17 | 3.12 | LC3 | B |
| 478 | 3-(5-Fluoro-2-methyl-phenyl)-3-{[1-(2-fluoro-phenyl)-5-hydroxy-1H-pyrazole-3-carbonyl]-amino}-propionic acid | 402.19 | 3.02 | LC3 | A |
| 479 | 3-(2,5-Dichloro-phenyl)-3-{[1-(2-fluoro-phenyl)-5-hydroxy-1H-pyrazole-3-carbonyl]-amino}-propionic acid | 438.12 | 3.14 | LC3 | A |
| 480 | (S)-3-{[1-(2-Fluoro-phenyl)-5-hydroxy-1H-pyrazole-3-carbonyl]-amino}-3-p-tolyl-propionic acid | 384.21 | 2.97 | LC3 | B |
| 481 | 3-{[1-(2-Fluoro-phenyl)-5-hydroxy-1H-pyrazole-3-carbonyl]-amino}-3-(4-pyridin-2-yl-phenyl)-propionic acid | 445.34 [(M − H)⁻] | 2.87 | LC4 | B |
| 482 | 3-(3-Fluoro-2-methyl-phenyl)-3-{[1-(3-fluoro-phenyl)-5-hydroxy-1H-pyrazole-3-carbonyl]-amino}-propionic acid | 402.2 | 3.18 | LC3 | B |
| 483 | 3-(2-Chloro-5-fluoro-phenyl)-3-{[1-(3-fluoro-phenyl)-5-hydroxy-1H-pyrazole-3-carbonyl]-amino}-propionic acid | 422.14 | 3.22 | LC3 | B |
| 484 | 3-(2,2-Difluoro-benzo[1,3]dioxol-4-yl)-3-{[1-(3-fluoro-phenyl)-5-hydroxy-1H-pyrazole-3-carbonyl]-amino}-propionic acid | 450.18 | 3.27 | LC3 | B |
| 485 | 3-(2,5-Difluoro-phenyl)-3-{[1-(3-fluoro-phenyl)-5-hydroxy-1H-pyrazole-3-carbonyl]-amino}-propionic acid | 406.17 | 3.10 | LC3 | B |
| 486 | 3-{[1-(3-Fluoro-phenyl)-5-hydroxy-1H-pyrazole-3-carbonyl]-amino}-3-(5-fluoro-2-trifluoromethyl-phenyl)-propionic acid | 456.17 | 3.49 | LC3 | B |

TABLE 1-continued

Example compounds of the formula I

| Example | Compound Name | m/z (1) | Rt (min) | LC/MS Method | Activity (2) |
|---|---|---|---|---|---|
| 487 | 3-(5-Fluoro-2-methyl-phenyl)-3-{[1-(3-fluoro-phenyl)-5-hydroxy-1H-pyrazole-3-carbonyl]-amino}-propionic acid | 402.19 | 3.18 | LC3 | B |
| 488 | 3-(2,5-Dichloro-phenyl)-3-{[1-(3-fluoro-phenyl)-5-hydroxy-1H-pyrazole-3-carbonyl]-amino}-propionic acid | 438.12 | 3.32 | LC3 | B |
| 489 | (S)-3-{[1-(3-Fluoro-phenyl)-5-hydroxy-1H-pyrazole-3-carbonyl]-amino}-3-p-tolyl-propionic acid | 384.21 | 3.20 | LC3 | B |
| 490 | 3-(2-Chloro-4-dimethylamino-phenyl)-3-{[1-(4-fluoro-phenyl)-5-hydroxy-1H-pyrazole-3-carbonyl]-amino}-propionic acid | 447.22 | 2.95 | LC3 | C |
| 491 | 3-(2,2-Difluoro-benzo[1,3]dioxol-4-yl)-3-{[1-(4-fluoro-phenyl)-5-hydroxy-1H-pyrazole-3-carbonyl]-amino}-propionic acid | 450.16 | 3.24 | LC3 | B |
| 492 | 3-(5-Fluoro-2-methyl-phenyl)-3-{[1-(4-fluoro-phenyl)-5-hydroxy-1H-pyrazole-3-carbonyl]-amino}-propionic acid | 402.19 | 3.22 | LC3 | B |
| 493 | 3-(2,5-Dichloro-phenyl)-3-{[1-(4-fluoro-phenyl)-5-hydroxy-1H-pyrazole-3-carbonyl]-amino}-propionic acid | 438.08 | 3.29 | LC3 | B |
| 494 | 3-(3-Fluoro-2-methyl-phenyl)-3-[(5-hydroxy-1-phenyl-1H-pyrazole-3-carbonyl)-amino]-propionic acid | 384.19 | 3.14 | LC3 | B |
| 495 | 3-(2-Chloro-5-fluoro-phenyl)-3-[(5-hydroxy-1-phenyl-1H-pyrazole-3-carbonyl)-amino]-propionic acid | 404.13 | 3.12 | LC3 | B |
| 496 | 3-(2,2-Difluoro-benzo[1,3]dioxol-4-yl)-3-[(5-hydroxy-1-phenyl-1H-pyrazole-3-carbonyl)-amino]-propionic acid | 432.14 | 3.20 | LC3 | B |
| 497 | 3-(5-Fluoro-2-methyl-phenyl)-3-[(5-hydroxy-1-phenyl-1H-pyrazole-3-carbonyl)-amino]-propionic acid | 384.2 | 3.09 | LC3 | B |
| 498 | 3-(5-Fluoro-2-methoxy-phenyl)-3-[(5-hydroxy-1-phenyl-1H-pyrazole-3-carbonyl)-amino]-propionic acid | 400.18 | 3.10 | LC3 | B |
| 499 | 3-[(5-Hydroxy-1-phenyl-1H-pyrazole-3-carbonyl)-amino]-3-(4-pyridin-2-yl-phenyl)-propionic acid; compound with trifluoro-acetic acid | 429.22 | 2.39 | LC3 | B |
| 500 | 3-(2,5-Dichloro-phenyl)-3-{[1-(2,4-difluoro-phenyl)-5-hydroxy-1H-pyrazole-3-carbonyl]-amino}-propionic acid | 456.1 | 3.18 | LC3 | A |
| 501 | 3-{[1-(2,4-Difluoro-phenyl)-5-hydroxy-1H-pyrazole-3-carbonyl]-amino}-3-(4-pyridin-2-yl-phenyl)-propionic acid; compound with trifluoro-acetic acid | 465.21 | 2.40 | LC3 | A |
| 502 | (S)-3-(2-Chloro-phenyl)-3-{[1-(2,4-difluoro-phenyl)-5-hydroxy-1H-pyrazole-3-carbonyl]-amino}-propionic acid | 422.12 | 3.14 | LC3 | B |
| 503 | 3-{[1-(2-Chloro-phenyl)-5-hydroxy-1H-pyrazole-3-carbonyl]-amino}-3-(2,2-difluoro-benzo[1,3]dioxol-4-yl)-propionic acid | 466.11 | 3.17 | LC3 | B |
| 504 | 3-{[1-(2-Chloro-phenyl)-5-hydroxy-1H-pyrazole-3-carbonyl]-amino}-3-(5-fluoro-2-methoxy-phenyl)-propionic acid | 434.16 | 3.00 | LC3 | B |
| 505 | 3-{[1-(2-Chloro-phenyl)-5-hydroxy-1H-pyrazole-3-carbonyl]-amino}-3-(4-morpholin-4-yl-phenyl)-propionic acid | 469.29 [(M − H)−] | 2.85 | LC4 | C |
| 506 | 3-{[1-(2-Chloro-phenyl)-5-hydroxy-1H-pyrazole-3-carbonyl]-amino}-3-(4-pyridin-2-yl-phenyl)-propionic acid | 463.21 | 2.39 | LC3 | A |
| 507 | (S)-3-(2-Chloro-phenyl)-3-{[1-(2-chloro-phenyl)-5-hydroxy-1H-pyrazole-3-carbonyl]-amino}-propionic acid | 420.12 | 3.17 | LC3 | B |
| 508 | 3-{[1-(3-Chloro-phenyl)-5-hydroxy-1H-pyrazole-3-carbonyl]-amino}-3-(3-fluoro-2-methyl-phenyl)-propionic acid | 418.17 | 3.32 | LC3 | B |
| 509 | 3-(2-Chloro-5-fluoro-phenyl)-3-{[1-(3-chloro-phenyl)-5-hydroxy-1H-pyrazole-3-carbonyl]-amino}-propionic acid | 438.12 | 3.34 | LC3 | B |
| 510 | 3-{[1-(3-Chloro-phenyl)-5-hydroxy-1H-pyrazole-3-carbonyl]-amino}-3-(5-fluoro-2-methyl-phenyl)-propionic acid | 418.17 | 3.32 | LC3 | B |

TABLE 1-continued

Example compounds of the formula I

| Example | Compound Name | m/z (1) | Rt (min) | LC/MS Method | Activity (2) |
|---|---|---|---|---|---|
| 511 | 3-{[1-(3-Chloro-phenyl)-5-hydroxy-1H-pyrazole-3-carbonyl]-amino}-3-(2,5-dichloro-phenyl)-propionic acid | 454.05 [(M − H)$^-$] | 4.47 | LC4 | B |
| 512 | (S)-3-{[1-(3-Chloro-phenyl)-5-hydroxy-1H-pyrazole-3-carbonyl]-amino}-3-p-tolyl-propionic acid | 400.18 | 3.30 | LC3 | B |
| 513 | 3-{[1-(3-Chloro-phenyl)-5-hydroxy-1H-pyrazole-3-carbonyl]-amino}-3-(4-pyridin-2-yl-phenyl)-propionic acid | 463.2 | 2.59 | LC3 | B |
| 514 | (S)-3-(2-Chloro-phenyl)-3-{[1-(3-chloro-phenyl)-5-hydroxy-1H-pyrazole-3-carbonyl]-amino}-propionic acid | 420.13 | 3.32 | LC3 | B |
| 515 | 3-{[1-(4-Chloro-phenyl)-5-hydroxy-1H-pyrazole-3-carbonyl]-amino}-3-(4-pyridin-2-yl-phenyl)-propionic acid | 463.19 | 2.59 | LC3 | B |
| 516 | 3-(3-Fluoro-2-methyl-phenyl)-3-{[1-(2-fluoro-phenyl)-5-hydroxy-1H-pyrazole-3-carbonyl]-amino}-propionic acid | 402.19 | 3.00 | LC3 | B |
| 517 | 3-(2,5-Difluoro-phenyl)-3-{[1-(2-fluoro-phenyl)-5-hydroxy-1H-pyrazole-3-carbonyl]-amino}-propionic acid | 406.16 | 2.90 | LC3 | B |
| 518 | 3-{[1-(2-Fluoro-phenyl)-5-hydroxy-1H-pyrazole-3-carbonyl]-amino}-3-(4-morpholin-4-yl-phenyl)-propionic acid | 453.32 [(M − H)$^-$] | 3.26 | LC4 | C |
| 519 | (S)-3-(2-Chloro-phenyl)-3-{[1-(2-fluoro-phenyl)-5-hydroxy-1H-pyrazole-3-carbonyl]-amino}-propionic acid | 404.14 | 2.95 | LC3 | B |
| 520 | 3-(5-Fluoro-2-methoxy-phenyl)-3-{[1-(3-fluoro-phenyl)-5-hydroxy-1H-pyrazole-3-carbonyl]-amino}-propionic acid | 418.19 | 3.17 | LC3 | B |
| 521 | 3-{[1-(3-Fluoro-phenyl)-5-hydroxy-1H-pyrazole-3-carbonyl]-amino}-3-(4-pyridin-2-yl-phenyl)-propionic acid | 447.24 | 2.50 | LC3 | B |
| 522 | (S)-3-(2-Chloro-phenyl)-3-{[1-(3-fluoro-phenyl)-5-hydroxy-1H-pyrazole-3-carbonyl]-amino}-propionic acid | 404.15 | 3.32 | LC3 | B |
| 523 | 3-(3-Fluoro-2-methyl-phenyl)-3-{[1-(4-fluoro-phenyl)-5-hydroxy-1H-pyrazole-3-carbonyl]-amino}-propionic acid | 402.2 | 3.17 | LC3 | B |
| 524 | 3-(2-Chloro-5-fluoro-phenyl)-3-{[1-(4-fluoro-phenyl)-5-hydroxy-1H-pyrazole-3-carbonyl]-amino}-propionic acid | 422.14 | 3.20 | LC3 | B |
| 525 | 3-(5-Fluoro-2-methoxy-phenyl)-3-{[1-(4-fluoro-phenyl)-5-hydroxy-1H-pyrazole-3-carbonyl]-amino}-propionic acid | 418.16 | 3.17 | LC3 | C |
| 526 | (S)-3-{[1-(4-Fluoro-phenyl)-5-hydroxy-1H-pyrazole-3-carbonyl]-amino}-3-p-tolyl-propionic acid | 384.17 | 3.15 | LC3 | B |
| 527 | 3-{[1-(4-Fluoro-phenyl)-5-hydroxy-1H-pyrazole-3-carbonyl]-amino}-3-(4-pyridin-2-yl-phenyl)-propionic acid | 447.19 | 2.45 | LC3 | B |
| 528 | (S)-3-(2-Chloro-phenyl)-3-{[1-(4-fluoro-phenyl)-5-hydroxy-1H-pyrazole-3-carbonyl]-amino}-propionic acid | 404.11 | 3.10 | LC3 | B |
| 529 | 2,2-Dimethyl-propionic acid (S)-3-{[1-(2-fluoro-phenyl)-5-hydroxy-1H-pyrazole-3-carbonyl]-amino}-3-o-tolyl-propionyloxymethyl ester | 498.21 | 3.65 | LC3 | |
| 530 | (R)-3-{[1-(2-Fluoro-phenyl)-5-hydroxy-1H-pyrazole-3-carbonyl]-amino}-3-phenyl-butyric acid methyl ester | 398.17 | 3.32 | LC3 | |
| 531 | 3-{[1-(2-Fluoro-phenyl)-5-hydroxy-1H-pyrazole-3-carbonyl]-amino}-3-[4-(6-methoxy-pyridin-3-yl)-phenyl]-propionic acid | 477.13 | 2.99 | LC8 | B |
| 532 | (S)-3-[(5-Hydroxy-1-o-tolyl-1H-pyrazole-3-carbonyl)-amino]-3-o-tolyl-propionic acid | 380.14 | 3.10 | LC8 | A |
| 533 | (S)-3-[(1-Benzyl-5-hydroxy-1H-pyrazole-3-carbonyl)-amino]-3-o-tolyl-propionic acid | 380.14 | 3.07 | LC8 | B |
| 534 | (S)-3-[(5-Methoxy-1-phenyl-1H-pyrazole-3-carbonyl)-amino]-3-o-tolyl-propionic acid | 380.14 | 3.29 | LC8 | A |
| 535 | 3-{[1-(2-Fluoro-phenyl)-5-hydroxy-1H-pyrazole-3-carbonyl]-amino}-3-phenyl-propionic acid | 370.11 | 2.95 | LC8 | B |

TABLE 1-continued

Example compounds of the formula I

| Example | Compound Name | m/z (1) | Rt (min) | LC/MS Method | Activity (2) |
|---|---|---|---|---|---|
| 536 | 3-(4'-Fluoro-biphenyl-4-yl)-3-[(5-hydroxy-1-o-tolyl-1H-pyrazole-3-carbonyl)-amino]-propionic acid | 460.18 | 3.14 | LC8 | A |
| 537 | (S)-3-{[5-Hydroxy-1-(2-trifluoromethyl-phenyl)-1H-pyrazole-3-carbonyl]-amino}-3-o-tolyl-propionic acid | 434.11 | 2.86 | LC8 | B |
| 538 | 3-[(1-Benzyl-5-hydroxy-1H-pyrazole-3-carbonyl)-amino]-3-(4'-fluoro-biphenyl-4-yl)-propionic acid | 460.17 | 3.12 | LC8 | B |
| 539 | 3-(2'-Chloro-biphenyl-4-yl)-3-[(5-hydroxy-1-phenyl-1H-pyrazole-3-carbonyl)-amino]-propionic acid | 462.11 | 3.21 | LC8 | B |
| 540 | 3-(3'-Chloro-biphenyl-4-yl)-3-{[1-(2-chloro-phenyl)-5-hydroxy-1H-pyrazole-3-carbonyl]-amino}-propionic acid | 496.08 | 3.25 | LC8 | B |
| 541 | 3-(3'-Chloro-biphenyl-4-yl)-3-{[1-(2-fluoro-phenyl)-5-hydroxy-1H-pyrazole-3-carbonyl]-amino}-propionic acid | 480.11 | 3.21 | LC8 | B |
| 542 | 3-(2'-Chloro-biphenyl-4-yl)-3-{[1-(2-fluoro-phenyl)-5-hydroxy-1H-pyrazole-3-carbonyl]-amino}-propionic acid | 480.1 | 3.14 | LC8 | A |
| 543 | 3-(4'-Fluoro-biphenyl-4-yl)-3-{[1-(2-fluoro-phenyl)-5-methoxy-1H-pyrazole-3-carbonyl]-amino}-propionic acid | 478.14 | 3.30 | LC8 | B |
| 544 | 3-(4'-Fluoro-biphenyl-4-yl)-3-[(5-methoxy-1-phenyl-1H-pyrazole-3-carbonyl)-amino]-propionic acid | 460.15 | 3.37 | LC8 | C |
| 545 | 3-[(5-Hydroxy-1-phenyl-1H-pyrazole-3-carbonyl)-amino]-3-(3-methoxy-biphenyl-4-yl)-propionic acid | 458.12 | 3.20 | LC8 | C |
| 546 | 3-[(5-Hydroxy-1-phenyl-1H-pyrazole-3-carbonyl)-amino]-3-(4-methoxy-2-trifluoromethyl-phenyl)-propionic acid | 450.09 | 2.95 | LC8 | B |
| 547 | 3-(2-Fluoro-5-methoxy-phenyl)-3-[(5-hydroxy-1-phenyl-1H-pyrazole-3-carbonyl)-amino]-propionic acid | 400.1 | 2.80 | LC8 | C |
| 548 | 3-[(5-Hydroxy-1-phenyl-1H-pyrazole-3-carbonyl)-amino]-3-(2-methoxy-5-trifluoromethyl-phenyl)-propionic acid | 450.08 | 3.02 | LC8 | C |
| 549 | 3-[(5-Hydroxy-1-phenyl-1H-pyrazole-3-carbonyl)-amino]-3-(4-methoxy-biphenyl-3-yl)-propionic acid | 458.16 | 3.17 | LC8 | C |
| 550 | 3-{[1-(2-Fluoro-phenyl)-5-hydroxy-1H-pyrazole-3-carbonyl]-amino}-3-(4-[1,2,4]triazol-1-yl-phenyl)-propionic acid | 437.13 | 2.40 | LC8 | B |
| 551 | 3-{[1-(2-Fluoro-phenyl)-5-hydroxy-1H-pyrazole-3-carbonyl]-amino}-3-(3-methoxy-biphenyl-4-yl)-propionic acid | 476.15 | 3.12 | LC8 | B |
| 552 | 3-{[1-(2-Fluoro-phenyl)-5-hydroxy-1H-pyrazole-3-carbonyl]-amino}-3-(4-methoxy-2-trifluoromethyl-phenyl)-propionic acid | 468.09 | 2.90 | LC8 | B |
| 553 | 3-(2-Fluoro-5-methoxy-phenyl)-3-{[1-(2-fluoro-phenyl)-5-hydroxy-1H-pyrazole-3-carbonyl]-amino}-propionic acid | 418.09 | 2.74 | LC8 | B |
| 554 | 3-{[1-(2-Fluoro-phenyl)-5-hydroxy-1H-pyrazole-3-carbonyl]-amino}-3-(2-methoxy-5-trifluoromethyl-phenyl)-propionic acid | 468.06 | 2.94 | LC8 | C |
| 555 | 3-(2-Fluoro-4-methyl-phenyl)-3-{[1-(2-fluoro-phenyl)-5-hydroxy-1H-pyrazole-3-carbonyl]-amino}-propionic acid | 402.1 | 2.84 | LC8 | B |
| 556 | 3-{[1-(2-Fluoro-phenyl)-5-hydroxy-1H-pyrazole-3-carbonyl]-amino}-3-(4-methoxy-biphenyl-3-yl)-propionic acid | 476.14 | 3.09 | LC8 | C |
| 557 | 3-{[1-(2-Chloro-phenyl)-5-hydroxy-1H-pyrazole-3-carbonyl]-amino}-3-(4-[1,2,4]triazol-1-yl-phenyl)-propionic acid | 453.12 | 2.40 | LC8 | B |
| 558 | 3-{[1-(2-Chloro-phenyl)-5-hydroxy-1H-pyrazole-3-carbonyl]-amino}-3-(3-methoxy-biphenyl-4-yl)-propionic acid | 492.13 | 3.15 | LC8 | B |
| 559 | 3-{[1-(2-Chloro-phenyl)-5-hydroxy-1H-pyrazole-3-carbonyl]-amino}-3-(2-fluoro-5-methoxy-phenyl)-propionic acid | 434.07 | 2.78 | LC8 | B |
| 560 | 3-{[1-(2-Chloro-phenyl)-5-hydroxy-1H-pyrazole-3-carbonyl]-amino}-3-(2-methoxy-5-trifluoromethyl-phenyl)-propionic acid | 484.05 | 2.98 | LC8 | C |

TABLE 1-continued

Example compounds of the formula I

| Example | Compound Name | m/z (1) | Rt (min) | LC/MS Method | Activity (2) |
|---|---|---|---|---|---|
| 561 | 3-{[1-(2-Chloro-phenyl)-5-hydroxy-1H-pyrazole-3-carbonyl]-amino}-3-(2-fluoro-4-methyl-phenyl)-propionic acid | 418.08 | 2.88 | LC8 | B |
| 562 | 3-{[1-(2-Chloro-phenyl)-5-hydroxy-1H-pyrazole-3-carbonyl]-amino}-3-(4-methoxy-biphenyl-3-yl)-propionic acid | 492.13 | 3.12 | LC8 | C |
| 563 | 3-[(5-Hydroxy-1-phenyl-1H-pyrazole-3-carbonyl)-amino]-3-(4-[1,2,4]triazol-1-yl-phenyl)-propionic acid | 419.11 | 2.46 | LC8 | C |
| 564 | 3-(2-Fluoro-4-methyl-phenyl)-3-[(5-hydroxy-1-phenyl-1H-pyrazole-3-carbonyl)-amino]-propionic acid | 384.13 | 2.91 | LC8 | B |
| 565 | 3-[(5-Hydroxy-1-phenyl-1H-pyrazole-3-carbonyl)-amino]-3-(4-pyrrolidin-1-yl-phenyl)-propionic acid | 421.2 | 2.57 | LC8 | C |
| 566 | 3-{[1-(2-Fluoro-phenyl)-5-hydroxy-1H-pyrazole-3-carbonyl]-amino}-3-(4-pyrrolidin-1-yl-phenyl)-propionic acid | 439.18 | 2.48 | LC8 | C |
| 567 | 3-{[1-(2-Chloro-phenyl)-5-hydroxy-1H-pyrazole-3-carbonyl]-amino}-3-(4-methoxy-2-trifluoromethyl-phenyl)-propionic acid | 484.09 | 2.93 | LC8 | C |
| 568 | 3-{[1-(2-Chloro-phenyl)-5-hydroxy-1H-pyrazole-3-carbonyl]-amino}-3-(4-pyrrolidin-1-yl-phenyl)-propionic acid | 455.16 | 2.54 | LC8 | C |
| 569 | 3-(4'-Fluoro-biphenyl-4-yl)-3-{[5-hydroxy-1-(2-trifluoromethyl-phenyl)-1H-pyrazole-3-carbonyl]-amino}-propionic acid | 514.08 | 3.16 | LC8 | B |
| 570 | (S)-3-{[1-(2-Fluoro-phenyl)-5-hydroxy-1H-pyrazole-3-carbonyl]-amino}-3-o-tolyl-propionic acid isopropyl ester | 426.14 | 3.31 | LC8 | |
| 571 | (S)-3-{[1-(2-Fluoro-phenyl)-5-hydroxy-1H-pyrazole-3-carbonyl]-amino}-3-o-tolyl-propionic acid propyl ester | 426.15 | 3.33 | LC8 | |
| 572 | (S)-3-[(1-Cyclopentyl-5-hydroxy-1H-pyrazole-3-carbonyl)-amino]-3-o-tolyl-propionic acid | 358.15 | 2.89 | LC8 | B |
| 573 | (S)-3-[(1-Cyclohexyl-5-hydroxy-1H-pyrazole-3-carbonyl)-amino]-3-o-tolyl-propionic acid | 372.15 | 2.99 | LC8 | A |
| 574 | 3-[(1-Cyclopentyl-5-hydroxy-1H-pyrazole-3-carbonyl)-amino]-3-(4'-fluoro-biphenyl-4-yl)-propionic acid | 438.14 | 3.17 | LC8 | C |
| 575 | 3-[(1-Cyclohexyl-5-hydroxy-1H-pyrazole-3-carbonyl)-amino]-3-(4'-fluoro-biphenyl-4-yl)-propionic acid | 452.14 | 3.27 | LC8 | C |
| 576 | 3-{[1-(2-Fluoro-phenyl)-5-hydroxy-1H-pyrazole-3-carbonyl]-amino}-3-(4'-trifluoromethyl-biphenyl-4-yl)-propionic acid | 514.09 | 3.28 | LC8 | B |
| 577 | (S)-3-{[1-(2-Fluoro-phenyl)-5-hydroxy-1H-pyrazole-3-carbonyl]-amino}-3-o-tolyl-propionic acid butyl ester | 440.13 | 3.47 | LC8 | |
| 578 | 3-[(5-Hydroxy-1-phenyl-1H-pyrazole-3-carbonyl)-amino]-3-(4-pyrazol-1-yl-phenyl)-propionic acid | 416.31 [(M − H)−] | 3.65 | LC4 | C |
| 579 | 3-[(5-Hydroxy-1-phenyl-1H-pyrazole-3-carbonyl)-amino]-3-(4'-trifluoromethyl-biphenyl-4-yl)-propionic acid | 496.1 | 3.35 | LC8 | C |
| 580 | 3-{[1-(2-Chloro-phenyl)-5-hydroxy-1H-pyrazole-3-carbonyl]-amino}-3-(4-pyrazol-1-yl-phenyl)-propionic acid | 452.08 | 2.69 | LC8 | B |
| 581 | 3-{[1-(2-Chloro-phenyl)-5-hydroxy-1H-pyrazole-3-carbonyl]-amino}-3-(4'-trifluoromethyl-biphenyl-4-yl)-propionic acid | 530.06 | 3.32 | LC8 | C |
| 582 | 3-{[1-(2-Fluoro-phenyl)-5-hydroxy-1H-pyrazole-3-carbonyl]-amino}-3-(4-pyrazol-1-yl-phenyl)-propionic acid | 436.1 | 2.66 | LC8 | B |
| 583 | 3-(2'-Fluoro-biphenyl-4-yl)-3-[(5-hydroxy-1-phenyl-1H-pyrazole-3-carbonyl)-amino]-propionic acid | 446.09 | 3.13 | LC8 | C |
| 584 | 3-(2'-Fluoro-biphenyl-4-yl)-3-{[1-(2-fluoro-phenyl)-5-hydroxy-1H-pyrazole-3-carbonyl]-amino}-propionic acid | 464.09 | 3.06 | LC8 | B |
| 585 | 3-{[1-(2-Chloro-phenyl)-5-hydroxy-1H-pyrazole-3-carbonyl]-amino}-3-(2'-fluoro-biphenyl-4-yl)-propionic acid | 480.09 | 3.09 | LC8 | B |

TABLE 1-continued

Example compounds of the formula I

| Example | Compound Name | m/z (1) | Rt (min) | LC/MS Method | Activity (2) |
|---|---|---|---|---|---|
| 586 | (S)-3-{[1-(3,5-Difluoro-phenyl)-5-hydroxy-1H-pyrazole-3-carbonyl]-amino}-3-o-tolyl-propionic acid | 402.1 | 3.04 | LC8 | B |
| 587 | 3-{[1-(3,5-Difluoro-phenyl)-5-hydroxy-1H-pyrazole-3-carbonyl]-amino}-3-(4'-fluoro-biphenyl-4-yl)-propionic acid | 482.11 | 3.31 | LC8 | C |
| 588 | (S)-3-{[1-(2,6-Difluoro-phenyl)-5-hydroxy-1H-pyrazole-3-carbonyl]-amino}-3-o-tolyl-propionic acid | 402.08 | 2.78 | LC8 | B |
| 589 | (S)-3-{[1-(3-Chloro-2-fluoro-phenyl)-5-hydroxy-1H-pyrazole-3-carbonyl]-amino}-3-o-tolyl-propionic acid | 418.05 | 2.94 | LC8 | B |
| 590 | 3-{[1-(3-Chloro-2-fluoro-phenyl)-5-hydroxy-1H-pyrazole-3-carbonyl]-amino}-3-(4'-fluoro-biphenyl-4-yl)-propionic acid | 498.06 | 3.22 | LC8 | B |
| 591 | 3-(2'-Chloro-biphenyl-4-yl)-3-{[1-(2-chloro-phenyl)-5-hydroxy-1H-pyrazole-3-carbonyl]-amino}-propionic acid | 496.07 | 3.18 | LC8 | B |
| 592 | 3-{[1-(2-Fluoro-phenyl)-5-hydroxy-4-methyl-1H-pyrazole-3-carbonyl]-amino}-3-o-tolyl-propionic acid | 398.15 | 2.83 | LC8 | B |
| 593 | (S)-3-{[4-Chloro-1-(2-fluoro-phenyl)-5-methoxy-1H-pyrazole-3-carbonyl]-amino}-3-o-tolyl-propionic acid | 432.13 | 3.17 | LC8 | B |
| 594 | (S)-3-{[4-Bromo-1-(2-fluoro-phenyl)-5-methoxy-1H-pyrazole-3-carbonyl]-amino}-3-o-tolyl-propionic acid | 476.06 | 3.19 | LC8 | A |
| 595 | (S)-3-{[4-Fluoro-1-(2-fluoro-phenyl)-5-methoxy-1H-pyrazole-3-carbonyl]-amino}-3-o-tolyl-propionic acid | 416.13 | 2.63 | LC5 | A |
| 596 | (S)-3-(2,3-Dichloro-phenyl)-3-[(5-methoxy-1-phenyl-1H-pyrazole-3-carbonyl)-amino]-propionic acid | 434.03 | 3.23 | LC8 | A |
| 597 | 3-[(5-Methoxy-1-phenyl-1H-pyrazole-3-carbonyl)-amino]-3-(4-pyridin-2-yl-phenyl)-propionic acid | 443.16 | 2.46 | LC8 | B |
| 598 | 3-{[1-(2-Fluoro-phenyl)-5-methoxy-1H-pyrazole-3-carbonyl]-amino}-3-(4-pyridin-2-yl-phenyl)-propionic acid | 461.13 | 2.42 | LC8 | A |
| 599 | (S)-3-{[1-(2,5-Difluoro-phenyl)-5-hydroxy-1H-pyrazole-3-carbonyl]-amino}-3-o-tolyl-propionic acid | 402.12 | 2.06 | LC7 | A |
| 600 | 3-[(5-Hydroxy-1-phenyl-1H-pyrazole-3-carbonyl)-amino]-3-(4-methanesulfonyl-phenyl)-propionic acid | 430.09 | 1.86 | LC7 | C |
| 601 | (S)-3-{[5-Hydroxy-1-(3-sulfamoyl-phenyl)-1H-pyrazole-3-carbonyl]-amino}-3-o-tolyl-propionic acid | 445.12 | 1.89 | LC7 | B |
| 602 | (S)-3-{[5-Hydroxy-1-(4-sulfamoyl-phenyl)-1H-pyrazole-3-carbonyl]-amino}-3-o-tolyl-propionic acid | 445.12 | 1.88 | LC7 | C |
| 603 | 3-{[1-(2-Fluoro-phenyl)-5-hydroxy-1H-pyrazole-3-carbonyl]-amino}-3-(4-methanesulfonyl-phenyl)-propionic acid | 448.08 | 1.83 | LC7 | C |
| 604 | 3-{[2-(2-Fluoro-phenyl)-5-methoxy-4-methyl-2H-pyrazole-3-carbonyl]-amino}-3-o-tolyl-propionic acid | 412.15 | 3.16 | LC8 | |
| 605 | 3-{[1-(2-Fluoro-phenyl)-5-methoxy-4-methyl-1H-pyrazole-3-carbonyl]-amino}-3-o-tolyl-propionic acid | 412.13 | 1.91 | LC7 | C |
| 606 | 3-(4'-Fluoro-biphenyl-4-yl)-3-{[5-hydroxy-1-(3-sulfamoyl-phenyl)-1H-pyrazole-3-carbonyl]-amino}-propionic acid | 523.39 [(M − H)−] | 3.94 | LC4 | B |
| 607 | (S)-3-{[5-Hydroxy-1-(2-methanesulfonyl-phenyl)-1H-pyrazole-3-carbonyl]-amino}-3-o-tolyl-propionic acid | 444.14 | 1.93 | LC7 | C |
| 608 | (S)-3-{[1-(2-Chloro-phenyl)-5-methoxy-1H-pyrazole-3-carbonyl]-amino}-3-o-tolyl-propionic acid | 414.12 | 2.20 | LC6 | B |
| 609 | (S)-3-{[1-(3-Fluoro-phenyl)-5-methoxy-1H-pyrazole-3-carbonyl]-amino}-3-o-tolyl-propionic acid | 398.15 | 2.26 | LC6 | A |
| 610 | (S)-3-{[1-(2,5-Difluoro-phenyl)-5-methoxy-1H-pyrazole-3-carbonyl]-amino}-3-o-tolyl-propionic acid | 416.15 | 2.20 | LC6 | A |

TABLE 1-continued

Example compounds of the formula I

| Example | Compound Name | m/z (1) | Rt (min) | LC/MS Method | Activity (2) |
|---|---|---|---|---|---|
| 611 | (S)-3-[(1-tert-Butyl-5-methoxy-1H-pyrazole-3-carbonyl)-amino]-3-o-tolyl-propionic acid | 360.11 | 2.25 | LC6 | B |
| 612 | (S)-3-{[5-Cyclopropylmethoxy-1-(2-fluoro-phenyl)-1H-pyrazole-3-carbonyl]-amino}-3-o-tolyl-propionic acid | 438.17 | 2.35 | LC6 | A |
| 613 | Pyrrolidine-1-carboxylic acid 5-((S)-2-carboxy-1-o-tolyl-ethylcarbamoyl)-2-(2-fluoro-phenyl)-2H-pyrazol-3-yl ester | 481.21 | 2.25 | LC6 | A |
| 614 | (S)-3-{[5-Dimethylcarbamoyloxy-1-(2-fluoro-phenyl)-1H-pyrazole-3-carbonyl]-amino}-3-o-tolyl-propionic acid | 455.17 | 2.15 | LC6 | A |
| 615 | (S)-3-{[5-Dimethylcarbamoylmethoxy-1-(2-fluoro-phenyl)-1H-pyrazole-3-carbonyl]-amino}-3-o-tolyl-propionic acid | 469.15 | 2.99 | LC3 | A |
| 616 | (S)-3-{[1-(2-Fluoro-phenyl)-5-(2-oxo-2-pyrrolidin-1-yl-ethoxy)-1H-pyrazole-3-carbonyl]-amino}-3-o-tolyl-propionic acid | 495.17 | 3.07 | LC3 | A |
| 617 | (S)-3-{[1-(2-Fluoro-phenyl)-5-(2-methoxy-ethoxy)-1H-pyrazole-3-carbonyl]-amino}-3-o-tolyl-propionic acid | 442.25 | 3.20 | LC3 | A |
| 618 | (S)-3-{[1-(2-Fluoro-phenyl)-5-methoxy-1H-pyrazole-3-carbonyl]-amino}-3-o-tolyl-propionic acid ethyl ester | | | | |
| 619 | Piperidine-1-carboxylic acid 5-((S)-2-carboxy-1-o-tolyl-ethylcarbamoyl)-2-(2-fluoro-phenyl)-2H-pyrazol-3-yl ester | 495.22 | 1.70 | LC9 | A |
| 620 | (S)-3-{[1-(2-Fluoro-phenyl)-5-(methyl-phenyl-carbamoyloxy)-1H-pyrazole-3-carbonyl]-amino}-3-o-tolyl-propionic acid | 517.2 | 1.71 | LC9 | A |
| 621 | (S)-3-[(5-Ethoxy-1-phenyl-1H-pyrazole-3-carbonyl)-amino]-3-o-tolyl-propionic acid | 394.18 | 1.69 | LC9 | A |
| 622 | (S)-3-[(5-Cyclopropylmethoxy-1-phenyl-1H-pyrazole-3-carbonyl)-amino]-3-o-tolyl-propionic acid | 420.19 | 1.77 | LC9 | A |
| 623 | (S)-3-{[1-(2-Fluoro-phenyl)-5-(2-trifluoromethyl-benzyloxy)-1H-pyrazole-3-carbonyl]-amino}-3-o-tolyl-propionic acid | 542.22 | 1.28 | LC11 | B |
| 624 | (S)-3-{[1-(2-Fluoro-phenyl)-5-(3-trifluoromethyl-benzyloxy)-1H-pyrazole-3-carbonyl]-amino}-3-o-tolyl-propionic acid | 542.31 | 3.89 | LC3 | B |
| 625 | (S)-3-{[1-(2-Fluoro-phenyl)-5-phenethyloxy-1H-pyrazole-3-carbonyl]-amino}-3-o-tolyl-propionic acid | 488.35 | 3.70 | LC3 | A |
| 626 | (S)-3-{[5-Cyclopentyloxy-1-(2-fluoro-phenyl)-1H-pyrazole-3-carbonyl]-amino}-3-o-tolyl-propionic acid | 452.32 | 3.68 | LC3 | A |
| 627 | (S)-3-{[1-(2-Fluoro-phenyl)-5-(tetrahydro-pyran-4-ylmethoxy)-1H-pyrazole-3-carbonyl]-amino}-3-o-tolyl-propionic acid | 482.36 | 3.34 | LC3 | A |
| 628 | (S)-3-{[5-[2-(3,5-Dimethyl-isoxazol-4-yl)-ethoxy]-1-(2-fluoro-phenyl)-1H-pyrazole-3-carbonyl]-amino}-3-o-tolyl-propionic acid | 507.27 | 1.18 | LC11 | A |
| 629 | (S)-3-{[1-(2-Fluoro-phenyl)-5-(pyridin-4-ylmethoxy)-1H-pyrazole-3-carbonyl]-amino}-3-o-tolyl-propionic acid | 475.33 | 2.62 | LC3 | A |
| 630 | (S)-3-{[1-(2-Fluoro-phenyl)-5-isopropoxy-1H-pyrazole-3-carbonyl]-amino}-3-o-tolyl-propionic acid | 426.3 | 3.42 | LC3 | A |
| 631 | (S)-3-{[5-Cyclohexyloxy-1-(2-fluoro-phenyl)-1H-pyrazole-3-carbonyl]-amino}-3-o-tolyl-propionic acid | 466.35 | 3.85 | LC3 | A |
| 632 | (S)-3-{[5-(2,2-Dimethyl-propoxy)-1-(2-fluoro-phenyl)-1H-pyrazole-3-carbonyl]-amino}-3-o-tolyl-propionic acid | 454.35 | 3.80 | LC3 | A |
| 633 | (S)-3-{[1-(2-Fluoro-phenyl)-5-isobutoxy-1H-pyrazole-3-carbonyl]-amino}-3-o-tolyl-propionic acid | 440.31 | 3.65 | LC3 | NO DATA |
| 634 | (S)-3-{[5-Cyclopropylmethoxy-1-(2,6-difluoro-phenyl)-1H-pyrazole-3-carbonyl]-amino}-3-o-tolyl-propionic acid | 456.31 | 3.54 | LC3 | A |
| 635 | (S)-3-{[5-(2-Cyano-benzyloxy)-1-(2-fluoro-phenyl)-1H-pyrazole-3-carbonyl]-amino}-3-o-tolyl-propionic acid | 499.26 | 3.42 | LC3 | A |

TABLE 1-continued

Example compounds of the formula I

| Example | Compound Name | m/z (1) | Rt (min) | LC/MS Method | Activity (2) |
|---|---|---|---|---|---|
| 636 | (S)-3-{[1-(2-Fluoro-phenyl)-5-(2-hydroxy-2-phenyl-propoxy)-1H-pyrazole-3-carbonyl]-amino}-3-p-tolyl-propionic acid | 518.34 | 1.27 | LC11 | A |
| 637 | (S)-3-{[5-[2-(2-Ethoxy-ethoxy)-ethoxy]-1-(2-fluoro-phenyl)-1H-pyrazole-3-carbonyl]-amino}-3-o-tolyl-propionic acid | 500.3 | 3.32 | LC3 | A |
| 638 | (S)-3-{[5-Cyclohexylmethoxy-1-(2-fluoro-phenyl)-1H-pyrazole-3-carbonyl]-amino}-3-o-tolyl-propionic acid | 480.3 | 1.33 | LC11 | A |
| 639 | (S)-3-({1-(2-Fluoro-phenyl)-5-[2-(2-oxo-pyrrolidin-1-yl)-ethoxy]-1H-pyrazole-3-carbonyl}-amino)-3-o-tolyl-propionic acid | 495.3 | 2.93 | LC3 | A |
| 640 | (S)-3-{[1-(2-Fluoro-phenyl)-5-(pyridin-2-ylmethoxy)-1H-pyrazole-3-carbonyl]-amino}-3-o-tolyl-propionic acid | 475.31 | 2.93 | LC3 | A |
| 641 | (S)-3-{[1-(2-Fluoro-phenyl)-5-(3-fluoro-propoxy)-1H-pyrazole-3-carbonyl]-amino}-3-o-tolyl-propionic acid | 444.26 | 3.39 | LC3 | A |
| 642 | (S)-3-{[1-(2-Fluoro-phenyl)-5-(tetrahydro-furan-2-ylmethoxy)-1H-pyrazole-3-carbonyl]-amino}-3-o-tolyl-propionic acid | 468.27 | 3.24 | LC3 | A |
| 643 | (S)-3-{[1-(2-Fluoro-phenyl)-5-(3-methyl-isoxazol-5-ylmethoxy)-1H-pyrazole-3-carbonyl]-amino}-3-o-tolyl-propionic acid | 479.24 | 3.30 | LC3 | A |
| 644 | (S)-3-{[5-(2,6-Difluoro-benzyloxy)-1-(2-fluoro-phenyl)-1H-pyrazole-3-carbonyl]-amino}-3-o-tolyl-propionic acid | 510.26 | 3.60 | LC3 | A |
| 645 | (S)-3-{[5-(2,2-Difluoro-cyclopropylmethoxy)-1-(2-fluoro-phenyl)-1H-pyrazole-3-carbonyl]-amino}-3-o-tolyl-propionic acid | 474.12 | 1.70 | LC9 | A |
| 646 | (S)-3-{[1-(2-Fluoro-phenyl)-5-(2-methyl-thiazol-4-ylmethoxy)-1H-pyrazole-3-carbonyl]-amino}-3-o-tolyl-propionic acid | 495.1 | 1.60 | LC9 | A |
| 647 | (S)-3-{[1-(2-Fluoro-phenyl)-5-(isoxazol-3-ylmethoxy)-1H-pyrazole-3-carbonyl]-amino}-3-o-tolyl-propionic acid | 465.27 | 3.20 | LC3 | A |
| 648 | (S)-3-{[5-Cyclobutoxy-1-(2-fluoro-phenyl)-1H-pyrazole-3-carbonyl]-amino}-3-o-tolyl-propionic acid | 438.28 | 3.50 | LC3 | A |
| 649 | (S)-3-{[5-Cyclobutylmethoxy-1-(2-fluoro-phenyl)-1H-pyrazole-3-carbonyl]-amino}-3-o-tolyl-propionic acid | 452.29 | 3.68 | LC3 | A |
| 650 | (S)-3-{[1-(2-Fluoro-phenyl)-5-(tetrahydro-furan-3-ylmethoxy)-1H-pyrazole-3-carbonyl]-amino}-3-o-tolyl-propionic acid | 468.3 | 3.18 | LC3 | A |
| 651 | (S)-3-{[5-Benzyloxy-1-(2-fluoro-phenyl)-1H-pyrazole-3-carbonyl]-amino}-3-o-tolyl-propionic acid | 474.28 | 3.65 | LC3 | A |
| 652 | (S)-3-{[1-(2-Fluoro-phenyl)-5-((R)-5-oxo-pyrrolidin-2-ylmethoxy)-1H-pyrazole-3-carbonyl]-amino}-3-o-tolyl-propionic acid | 481.29 | 1.40 | LC9 | A |
| 653 | (S)-3-{[1-(2-Fluoro-phenyl)-5-(tetrahydro-pyran-2-ylmethoxy)-1H-pyrazole-3-carbonyl]-amino}-3-o-tolyl-propionic acid | 482.31 | 3.47 | LC3 | A |
| 654 | (S)-3-{[1-(2-Fluoro-phenyl)-5-((S)-5-oxo-pyrrolidin-2-ylmethoxy)-1H-pyrazole-3-carbonyl]-amino}-3-o-tolyl-propionic acid | 481.21 | 1.42 | LC9 | A |
| 655 | (S)-3-{[1-(2-Fluoro-phenyl)-5-(3-methoxy-benzyloxy)-1H-pyrazole-3-carbonyl]-amino}-3-o-tolyl-propionic acid | 504.3 | 3.65 | LC3 | A |
| 656 | (S)-3-{[1-(2-Fluoro-phenyl)-5-(1-methyl-1H-pyrazol-3-ylmethoxy)-1H-pyrazole-3-carbonyl]-amino}-3-o-tolyl-propionic acid | 478.26 | 1.53 | LC9 | |
| 657 | (S)-3-{[1-(2-Fluoro-phenyl)-5-(5-methyl-isoxazol-3-ylmethoxy)-1H-pyrazole-3-carbonyl]-amino}-3-o-tolyl-propionic acid | 479.25 | 1.18 | LC11 | A |
| 658 | (S)-3-{[1-(2-Fluoro-phenyl)-5-(isoxazol-5-ylmethoxy)-1H-pyrazole-3-carbonyl]-amino}-3-o-tolyl-propionic acid | 465.25 | 1.11 | LC11 | A |
| 659 | (S)-3-{[5-(3,3-Dimethyl-butoxy)-1-(2-fluoro-phenyl)-1H-pyrazole-3-carbonyl]-amino}-3-o-tolyl-propionic acid | 468.24 | 1.90 | LC9 | A |
| 660 | (S)-3-{[1-(2-Fluoro-phenyl)-5-hexyloxy-1H-pyrazole-3-carbonyl]-amino}-3-o-tolyl-propionic acid | 468.29 | 1.33 | LC11 | A |

TABLE 1-continued

Example compounds of the formula I

| Example | Compound Name | m/z (1) | Rt (min) | LC/MS Method | Activity (2) |
|---|---|---|---|---|---|
| 661 | 1-(2-Fluoro-phenyl)-5-methoxy-1H-pyrazole-3-carboxylic acid ((S)-2-carbamoyl-1-o-tolyl-ethyl)-amide | 397.19 | 3.67 | LC12 | |
| 662 | (S)-3-{[5-Ethoxy-1-(2-fluoro-phenyl)-1H-pyrazole-3-carbonyl]-amino}-3-o-tolyl-propionic acid | 412.19 | 1.60 | LC9 | A |
| 663 | (S)-3-{[1-(2-Fluoro-phenyl)-5-(3-methyl-oxetan-3-ylmethoxy)-1H-pyrazole-3-carbonyl]-amino}-3-o-tolyl-propionic acid | 468.23 | 1.57 | LC9 | A |
| 664 | 3-(3-Fluoro-2-methyl-phenyl)-3-{[1-(2-fluoro-phenyl)-5-methoxy-1H-pyrazole-3-carbonyl]-amino}-propionic acid | 416.14 | 1.57 | LC9 | A |
| 665 | (S)-3-{[1-(2-Fluoro-phenyl)-5-methoxy-1H-pyrazole-3-carbonyl]-amino}-3-phenyl-propionic acid | 384.14 | 1.49 | LC9 | A |
| 666 | 3-(2,4-Dimethyl-phenyl)-3-{[1-(2-fluoro-phenyl)-5-methoxy-1H-pyrazole-3-carbonyl]-amino}-propionic acid | 412.17 | 1.61 | LC9 | A |
| 667 | (S)-3-{[1-(2-Fluoro-phenyl)-5-methoxy-1H-pyrazole-3-carbonyl]-amino}-3-(2-methoxy-phenyl)-propionic acid | 414.16 | 1.54 | LC9 | B |
| 668 | (S)-3-(4-Cyano-phenyl)-3-{[1-(2-fluoro-phenyl)-5-methoxy-1H-pyrazole-3-carbonyl]-amino}-propionic acid | 409.14 | 1.47 | LC9 | B |
| 669 | (S)-3-{[1-(2-Fluoro-phenyl)-5-methoxy-1H-pyrazole-3-carbonyl]-amino}-3-(3-methoxy-phenyl)-propionic acid | 414.16 | 1.51 | LC9 | B |
| 670 | (S)-3-{[1-(2-Fluoro-phenyl)-5-methoxy-1H-pyrazole-3-carbonyl]-amino}-3-m-tolyl-propionic acid | 398.16 | 1.56 | LC9 | A |
| 671 | (S)-3-(4-Chloro-phenyl)-3-{[1-(2-fluoro-phenyl)-5-methoxy-1H-pyrazole-3-carbonyl]-amino}-propionic acid | 418.11 | 1.59 | LC9 | A |
| 672 | 3-{[1-(2-Fluoro-phenyl)-5-methoxy-1H-pyrazole-3-carbonyl]-amino}-3-(4-methoxy-2-methyl-phenyl)-propionic acid | 428.18 | 1.54 | LC9 | A |
| 673 | (S)-3-(2,4-Dichloro-phenyl)-3-{[1-(2-fluoro-phenyl)-5-methoxy-1H-pyrazole-3-carbonyl]-amino}-propionic acid | 452.07 | 1.65 | LC9 | A |
| 674 | (S)-3-{[1-(2-Fluoro-phenyl)-5-methoxy-1H-pyrazole-3-carbonyl]-amino}-3-(4-trifluoromethyl-phenyl)-propionic acid | 452.12 | 1.63 | LC9 | A |
| 675 | (S)-3-{[1-(2-Fluoro-phenyl)-5-methoxy-1H-pyrazole-3-carbonyl]-amino}-3-p-tolyl-propionic acid | 398.16 | 1.55 | LC9 | A |
| 676 | (S)-3-(2-Chloro-phenyl)-3-{[1-(2-fluoro-phenyl)-5-methoxy-1H-pyrazole-3-carbonyl]-amino}-propionic acid | 418.11 | 1.55 | LC9 | A |
| 677 | 3-(4-Fluoro-2-methyl-phenyl)-3-{[1-(2-fluoro-phenyl)-5-methoxy-1H-pyrazole-3-carbonyl]-amino}-propionic acid | 416.16 | 1.57 | LC9 | A |
| 678 | 3-(4-Fluoro-phenyl)-3-{[1-(2-fluoro-phenyl)-5-methoxy-1H-pyrazole-3-carbonyl]-amino}-propionic acid | 402.14 | 1.52 | LC9 | B |
| 679 | (S)-3-(2-Fluoro-phenyl)-3-{[1-(2-fluoro-phenyl)-5-methoxy-1H-pyrazole-3-carbonyl]-amino}-propionic acid | 402.14 | 1.50 | LC9 | B |
| 680 | (S)-3-{[1-(2-Fluoro-phenyl)-5-methoxy-1H-pyrazole-3-carbonyl]-amino}-3-(2-trifluoromethyl-phenyl)-propionic acid | 452.21 | 1.18 | LC11 | B |
| 681 | (S)-3-(2,3-Dichloro-phenyl)-3-{[1-(2-fluoro-phenyl)-5-methoxy-1H-pyrazole-3-carbonyl]-amino}-propionic acid | 452.07 | 1.63 | LC9 | A |
| 682 | 3-(2,3-Dimethyl-phenyl)-3-{[1-(2-fluoro-phenyl)-5-methoxy-1H-pyrazole-3-carbonyl]-amino}-propionic acid | 412.19 | 1.60 | LC9 | A |
| 683 | 3-(2,5-Dichloro-phenyl)-3-{[1-(2-fluoro-phenyl)-5-methoxy-1H-pyrazole-3-carbonyl]-amino}-propionic acid | 452.07 | 1.64 | LC9 | A |
| 684 | 3-{[5-Cyclopropylmethoxy-1-(2-fluoro-phenyl)-1H-pyrazole-3-carbonyl]-amino}-3-(3-fluoro-2-methyl-phenyl)-propionic acid | 456.17 | 1.70 | LC9 | A |
| 685 | (S)-3-{[5-Cyclopropylmethoxy-1-(2-fluoro-phenyl)-1H-pyrazole-3-carbonyl]-amino}-3-phenyl-propionic acid | 424.18 | 1.63 | LC9 | A |

TABLE 1-continued

Example compounds of the formula I

| Example | Compound Name | m/z (1) | Rt (min) | LC/MS Method | Activity (2) |
|---|---|---|---|---|---|
| 686 | 3-{[5-Cyclopropylmethoxy-1-(2-fluoro-phenyl)-1H-pyrazole-3-carbonyl]-amino}-3-(2,4-dimethyl-phenyl)-propionic acid | 452.22 | 1.73 | LC9 | A |
| 687 | (S)-3-{[5-Cyclopropylmethoxy-1-(2-fluoro-phenyl)-1H-pyrazole-3-carbonyl]-amino}-3-(2-methoxy-phenyl)-propionic acid | 454.2 | 1.66 | LC9 | B |
| 688 | (S)-3-(4-Cyano-phenyl)-3-{[5-cyclopropylmethoxy-1-(2-fluoro-phenyl)-1H-pyrazole-3-carbonyl]-amino}-propionic acid | 449.18 | 1.61 | LC9 | A |
| 689 | (S)-3-{[5-Cyclopropylmethoxy-1-(2-fluoro-phenyl)-1H-pyrazole-3-carbonyl]-amino}-3-(3-methoxy-phenyl)-propionic acid | 454.19 | 1.63 | LC9 | B |
| 690 | (S)-3-{[5-Cyclopropylmethoxy-1-(2-fluoro-phenyl)-1H-pyrazole-3-carbonyl]-amino}-3-m-tolyl-propionic acid | 438.2 | 1.69 | LC9 | A |
| 691 | (S)-3-(4-Chloro-phenyl)-3-{[5-cyclopropylmethoxy-1-(2-fluoro-phenyl)-1H-pyrazole-3-carbonyl]-amino}-propionic acid | 458.15 | 1.71 | LC9 | B |
| 692 | 3-{[5-Cyclopropylmethoxy-1-(2-fluoro-phenyl)-1H-pyrazole-3-carbonyl]-amino}-3-(4-methoxy-2-methyl-phenyl)-propionic acid | 468.22 | 1.67 | LC9 | A |
| 693 | (S)-3-{[5-Cyclopropylmethoxy-1-(2-fluoro-phenyl)-1H-pyrazole-3-carbonyl]-amino}-3-(2,4-dichloro-phenyl)-propionic acid | 492.11 | 1.77 | LC9 | B |
| 694 | (S)-3-{[5-Cyclopropylmethoxy-1-(2-fluoro-phenyl)-1H-pyrazole-3-carbonyl]-amino}-3-(4-trifluoromethyl-phenyl)-propionic acid | 492.16 | 1.75 | LC9 | A |
| 695 | (S)-3-{[5-Cyclopropylmethoxy-1-(2-fluoro-phenyl)-1H-pyrazole-3-carbonyl]-amino}-3-p-tolyl-propionic acid | 438.21 | 1.69 | LC9 | A |
| 696 | (S)-3-(2-Chloro-phenyl)-3-{[5-cyclopropylmethoxy-1-(2-fluoro-phenyl)-1H-pyrazole-3-carbonyl]-amino}-propionic acid | 458.15 | 1.68 | LC9 | A |
| 697 | 3-{[5-Cyclopropylmethoxy-1-(2-fluoro-phenyl)-1H-pyrazole-3-carbonyl]-amino}-3-(4-fluoro-2-methyl-phenyl)-propionic acid | 456.2 | 1.70 | LC9 | |
| 698 | 3-{[5-Cyclopropylmethoxy-1-(2-fluoro-phenyl)-1H-pyrazole-3-carbonyl]-amino}-3-(4-fluoro-phenyl)-propionic acid | 442.24 | 1.21 | LC11 | B |
| 699 | (S)-3-{[5-Cyclopropylmethoxy-1-(2-fluoro-phenyl)-1H-pyrazole-3-carbonyl]-amino}-3-(2-fluoro-phenyl)-propionic acid | 442.23 | 1.21 | LC11 | B |
| 700 | (S)-3-{[5-(3,3-Dimethyl-2-oxo-butoxy)-1-(2-fluoro-phenyl)-1H-pyrazole-3-carbonyl]-amino}-3-o-tolyl-propionic acid | 482.18 | 1.67 | LC9 | A |
| 701 | (S)-3-{[5-Cyclopropylmethoxy-1-(2-fluoro-phenyl)-1H-pyrazole-3-carbonyl]-amino}-3-(2-trifluoromethyl-phenyl)-propionic acid | 492.16 | 1.72 | LC9 | B |
| 702 | (S)-3-{[5-Cyclopropylmethoxy-1-(2-fluoro-phenyl)-1H-pyrazole-3-carbonyl]-amino}-3-(2,3-dichloro-phenyl)-propionic acid | 492.11 | 1.74 | LC9 | A |
| 703 | 3-{[5-Cyclopropylmethoxy-1-(2-fluoro-phenyl)-1H-pyrazole-3-carbonyl]-amino}-3-(2,3-dimethyl-phenyl)-propionic acid | 452.22 | 1.72 | LC9 | A |
| 704 | 3-{[5-Cyclopropylmethoxy-1-(2-fluoro-phenyl)-1H-pyrazole-3-carbonyl]-amino}-3-(2,5-dichloro-phenyl)-propionic acid | 492.12 | 1.76 | LC9 | A |
| 705 | 3-(2-Chloro-4-methoxy-phenyl)-3-{[5-cyclopropylmethoxy-1-(2-fluoro-phenyl)-1H-pyrazole-3-carbonyl]-amino}-propionic acid | 488.18 | 1.70 | LC9 | A |
| 706 | 3-{[5-Ethoxy-1-(2-fluoro-phenyl)-1H-pyrazole-3-carbonyl]-amino}-3-(3-fluoro-2-methyl-phenyl)-propionic acid | 430.18 | 1.64 | LC9 | A |
| 707 | (S)-3-{[5-Ethoxy-1-(2-fluoro-phenyl)-1H-pyrazole-3-carbonyl]-amino}-3-phenyl-propionic acid | 398.18 | 1.57 | LC9 | B |
| 708 | 3-(2,4-Dimethyl-phenyl)-3-{[5-ethoxy-1-(2-fluoro-phenyl)-1H-pyrazole-3-carbonyl]-amino}-propionic acid | 426.21 | 1.67 | LC9 | A |
| 709 | (S)-3-{[5-Ethoxy-1-(2-fluoro-phenyl)-1H-pyrazole-3-carbonyl]-amino}-3-(2-methoxy-phenyl)-propionic acid | 428.19 | 1.60 | LC9 | B |
| 710 | (S)-3-(4-Cyano-phenyl)-3-{[5-ethoxy-1-(2-fluoro-phenyl)-1H-pyrazole-3-carbonyl]-amino}-propionic acid | 423.21 | 1.14 | LC11 | B |

TABLE 1-continued

Example compounds of the formula I

| Example | Compound Name | m/z (1) | Rt (min) | LC/MS Method | Activity (2) |
|---|---|---|---|---|---|
| 711 | (S)-3-{[5-Ethoxy-1-(2-fluoro-phenyl)-1H-pyrazole-3-carbonyl]-amino}-3-(3-methoxy-phenyl)-propionic acid | 428.19 | 1.57 | LC9 | B |
| 712 | (S)-3-{[5-Ethoxy-1-(2-fluoro-phenyl)-1H-pyrazole-3-carbonyl]-amino}-3-m-tolyl-propionic acid | 412.22 | 1.20 | LC11 | A |
| 713 | (S)-3-(4-Chloro-phenyl)-3-{[5-ethoxy-1-(2-fluoro-phenyl)-1H-pyrazole-3-carbonyl]-amino}-propionic acid | 432.14 | 1.21 | LC11 | A |
| 714 | 3-{[5-Ethoxy-1-(2-fluoro-phenyl)-1H-pyrazole-3-carbonyl]-amino}-3-(4-methoxy-2-methyl-phenyl)-propionic acid | 442.23 | 1.19 | LC11 | A |
| 715 | (S)-3-{[5-Ethoxy-1-(2-fluoro-phenyl)-1H-pyrazole-3-carbonyl]-amino}-3-(4-trifluoromethyl-phenyl)-propionic acid | 466.18 | 1.23 | LC11 | A |
| 716 | (S)-3-{[5-Ethoxy-1-(2-fluoro-phenyl)-1H-pyrazole-3-carbonyl]-amino}-3-p-tolyl-propionic acid | 412.16 | 1.60 | LC9 | A |
| 717 | (S)-3-(2-Chloro-phenyl)-3-{[5-ethoxy-1-(2-fluoro-phenyl)-1H-pyrazole-3-carbonyl]-amino}-propionic acid | 432.14 | 1.20 | LC11 | A |
| 718 | 3-{[5-Ethoxy-1-(2-fluoro-phenyl)-1H-pyrazole-3-carbonyl]-amino}-3-(4-fluoro-2-methyl-phenyl)-propionic acid | 430.21 | 1.20 | LC11 | A |
| 719 | 3-{[5-Ethoxy-1-(2-fluoro-phenyl)-1H-pyrazole-3-carbonyl]-amino}-3-(4-fluoro-phenyl)-propionic acid | 416.19 | 1.18 | LC11 | B |
| 720 | (S)-3-{[5-Ethoxy-1-(2-fluoro-phenyl)-1H-pyrazole-3-carbonyl]-amino}-3-(2-fluoro-phenyl)-propionic acid | 416.18 | 1.17 | LC11 | A |
| 721 | (S)-3-{[5-Ethoxy-1-(2-fluoro-phenyl)-1H-pyrazole-3-carbonyl]-amino}-3-(2-trifluoromethyl-phenyl)-propionic acid | 466.21 | 1.21 | LC11 | B |
| 722 | (S)-3-(2,3-Dichloro-phenyl)-3-{[5-ethoxy-1-(2-fluoro-phenyl)-1H-pyrazole-3-carbonyl]-amino}-propionic acid | 466.17 | 1.23 | LC11 | A |
| 723 | 3-(2,3-Dimethyl-phenyl)-3-{[5-ethoxy-1-(2-fluoro-phenyl)-1H-pyrazole-3-carbonyl]-amino}-propionic acid | 426.23 | 1.22 | LC11 | A |
| 724 | 3-(2-Chloro-4-methoxy-phenyl)-3-{[5-ethoxy-1-(2-fluoro-phenyl)-1H-pyrazole-3-carbonyl]-amino}-propionic acid | 461.64 | 1.20 | LC11 | A |
| 725 | 3-{[1-(2-Chloro-phenyl)-5-ethoxy-1H-pyrazole-3-carbonyl]-amino}-3-(3-fluoro-2-methyl-phenyl)-propionic acid | 446.15 | 1.22 | LC11 | A |
| 726 | (S)-3-{[1-(2-Chloro-phenyl)-5-ethoxy-1H-pyrazole-3-carbonyl]-amino}-3-phenyl-propionic acid | 413.65 | 1.19 | LC11 | B |
| 727 | (S)-3-{[1-(2-Chloro-phenyl)-5-ethoxy-1H-pyrazole-3-carbonyl]-amino}-3-o-tolyl-propionic acid | 428.13 | 1.21 | LC11 | A |
| 728 | 3-{[1-(2-Chloro-phenyl)-5-ethoxy-1H-pyrazole-3-carbonyl]-amino}-3-(2,4-dimethyl-phenyl)-propionic acid | 442.2 | 1.24 | LC11 | A |
| 729 | (S)-3-{[1-(2-Chloro-phenyl)-5-ethoxy-1H-pyrazole-3-carbonyl]-amino}-3-(2-methoxy-phenyl)-propionic acid | 443.66 | 1.20 | LC11 | B |
| 730 | (S)-3-{[1-(2-Chloro-phenyl)-5-ethoxy-1H-pyrazole-3-carbonyl]-amino}-3-(4-cyano-phenyl)-propionic acid | 439.17 | 1.16 | LC11 | B |
| 731 | (S)-3-{[1-(2-Chloro-phenyl)-5-ethoxy-1H-pyrazole-3-carbonyl]-amino}-3-(3-methoxy-phenyl)-propionic acid | 444.15 | 1.18 | LC11 | B |
| 732 | (S)-3-{[1-(2-Chloro-phenyl)-5-ethoxy-1H-pyrazole-3-carbonyl]-amino}-3-m-tolyl-propionic acid | 428.25 | 4.48 | LC10 | A |
| 733 | (S)-3-(4-Chloro-phenyl)-3-{[1-(2-chloro-phenyl)-5-ethoxy-1H-pyrazole-3-carbonyl]-amino}-propionic acid | 448.13 | 4.55 | LC10 | A |
| 734 | 3-{[1-(2-Chloro-phenyl)-5-ethoxy-1H-pyrazole-3-carbonyl]-amino}-3-(4-methoxy-2-methyl-phenyl)-propionic acid | 458.14 | 1.61 | LC9 | |
| 735 | (S)-3-{[1-(2-Chloro-phenyl)-5-ethoxy-1H-pyrazole-3-carbonyl]-amino}-3-(4-trifluoromethyl-phenyl)-propionic acid | 482.08 | 1.72 | LC9 | B |

TABLE 1-continued

Example compounds of the formula I

| Example | Compound Name | m/z (1) | Rt (min) | LC/MS Method | Activity (2) |
|---|---|---|---|---|---|
| 736 | (S)-3-{[1-(2-Chloro-phenyl)-5-ethoxy-1H-pyrazole-3-carbonyl]-amino}-3-p-tolyl-propionic acid | 428.13 | 1.63 | LC9 | A |
| 737 | (S)-3-(2-Chloro-phenyl)-3-{[1-(2-chloro-phenyl)-5-ethoxy-1H-pyrazole-3-carbonyl]-amino}-propionic acid | 448.1 | 1.64 | LC9 | A |
| 738 | 3-{[1-(2-Chloro-phenyl)-5-ethoxy-1H-pyrazole-3-carbonyl]-amino}-3-(4-fluoro-2-methyl-phenyl)-propionic acid | 446.12 | 1.66 | LC9 | A |
| 739 | 3-{[1-(2-Chloro-phenyl)-5-ethoxy-1H-pyrazole-3-carbonyl]-amino}-3-(4-fluoro-phenyl)-propionic acid | 432.11 | 1.61 | LC9 | B |
| 740 | (S)-3-{[1-(2-Chloro-phenyl)-5-ethoxy-1H-pyrazole-3-carbonyl]-amino}-3-(2-fluoro-phenyl)-propionic acid | 432.1 | 1.60 | LC9 | |
| 741 | (S)-3-{[1-(2-Chloro-phenyl)-5-ethoxy-1H-pyrazole-3-carbonyl]-amino}-3-(2-trifluoromethyl-phenyl)-propionic acid | 482.08 | 1.67 | LC9 | B |
| 742 | (S)-3-{[1-(2-Chloro-phenyl)-5-ethoxy-1H-pyrazole-3-carbonyl]-amino}-3-(2,3-dichloro-phenyl)-propionic acid | 482.04 | 1.71 | LC9 | A |
| 743 | 3-{[1-(2-Chloro-phenyl)-5-ethoxy-1H-pyrazole-3-carbonyl]-amino}-3-(2,3-dimethyl-phenyl)-propionic acid | 442.16 | 1.68 | LC9 | A |
| 744 | (S)-3-{[1-(2-Fluoro-phenyl)-5-(2-hydroxy-3,3-dimethyl-butoxy)-1H-pyrazole-3-carbonyl]-amino}-3-o-tolyl-propionic acid | 484.35 | 1.23 | LC11 | A |
| 745 | (S)-3-{[1-(2-Fluoro-phenyl)-5-((R)-2-hydroxy-3,3-dimethyl-butoxy)-1H-pyrazole-3-carbonyl]-amino}-3-o-tolyl-propionic acid (3) | 484.34 | 10.16 | LC13 | A |
| 746 | (S)-3-{[1-(2-Fluoro-phenyl)-5-((S)-2-hydroxy-3,3-dimethyl-butoxy)-1H-pyrazole-3-carbonyl]-amino}-3-o-tolyl-propionic acid (3) | 484.34 | 10.35 | LC13 | A |
| 747 | (S)-3-{[1-(2-Fluoro-phenyl)-5-((R)-2-hydroxy-2,3,3-trimethyl-butoxy)-1H-pyrazole-3-carbonyl]-amino}-3-o-tolyl-propionic acid (3) | 498.3 | 10.53 | LC13 | A |
| 748 | (S)-3-{[1-(2-Fluoro-phenyl)-5-((S)-2-hydroxy-2,3,3-trimethyl-butoxy)-1H-pyrazole-3-carbonyl]-amino}-3-o-tolyl-propionic acid (3) | 498.3 | 10.80 | LC13 | A |
| 749 | (S)-3-{[1-(2-Fluoro-phenyl)-5-(2-hydroxy-propoxy)-1H-pyrazole-3-carbonyl]-amino}-3-o-tolyl-propionic acid | 442.32 | 1.16 | LC11 | A |
| 750 | (S)-3-{[1-(2-Fluoro-phenyl)-5-(2-hydroxy-2-methyl-butoxy)-1H-pyrazole-3-carbonyl]-amino}-3-o-tolyl-propionic acid | 470.35 | 4.19 | LC10 | A |
| 751 | (S)-3-(2,4-Dichloro-phenyl)-3-{[1-(2-fluoro-phenyl)-5-(2-hydroxy-2-methyl-propoxy)-1H-pyrazole-3-carbonyl]-amino}-propionic acid | 510.25 | 4.34 | LC10 | A |
| 752 | (S)-3-{[1-(2-Fluoro-phenyl)-5-(2-hydroxy-2-methyl-propoxy)-1H-pyrazole-3-carbonyl]-amino}-3-o-tolyl-propionic acid | 456.38 | 3.97 | LC10 | A |
| 753 | (S)-3-(2,4-Dichloro-phenyl)-3-{[1-(2-fluoro-phenyl)-5-((R)-2-hydroxy-3,3-dimethyl-butoxy)-1H-pyrazole-3-carbonyl]-amino}-propionic acid (3) | 538.24 | 1.31 | LC11 | A |
| 754 | (S)-3-(2,4-Dichloro-phenyl)-3-{[1-(2-fluoro-phenyl)-5-((S)-2-hydroxy-3,3-dimethyl-butoxy)-1H-pyrazole-3-carbonyl]-amino}-propionic acid (3) | 538.24 | 1.32 | LC11 | A |
| 755 | (S)-3-{[1-(2-Fluoro-phenyl)-5-(2-hydroxy-butoxy)-1H-pyrazole-3-carbonyl]-amino}-3-o-tolyl-propionic acid | 456.27 | 1.19 | LC11 | A |
| 756 | (S)-3-{[5-(2-Ethyl-2-hydroxy-butoxy)-1-(2-fluoro-phenyl)-1H-pyrazole-3-carbonyl]-amino}-3-o-tolyl-propionic acid | 484.32 | 1.26 | LC11 | A |
| 757 | (S)-3-{[5-(2-Cyclopropyl-2-hydroxy-propoxy)-1-(2-fluoro-phenyl)-1H-pyrazole-3-carbonyl]-amino}-3-o-tolyl-propionic acid | 482.31 | 1.24 | LC11 | A |

TABLE 1-continued

Example compounds of the formula I

| Example | Compound Name | m/z (1) | Rt (min) | LC/MS Method | Activity (2) |
|---|---|---|---|---|---|
| 758 | (S)-3-(2-Chloro-phenyl)-3-{[1-(2-fluoro-phenyl)-5-((R)-2-hydroxy-2,3,3-trimethyl-butoxy)-1H-pyrazole-3-carbonyl]-amino}-propionic acid (3) | 518.28 | 1.29 | LC11 | A |
| 759 | (S)-3-(2-Chloro-phenyl)-3-{[1-(2-fluoro-phenyl)-5-((S)-2-hydroxy-2,3,3-trimethyl-butoxy)-1H-pyrazole-3-carbonyl]-amino}-propionic acid (3) | 518.3 | 1.30 | LC11 | A |
| 760 | (S)-3-{[5-((R)-2-Cyclopropyl-2-hydroxy-ethoxy)-1-(2-fluoro-phenyl)-1H-pyrazole-3-carbonyl]-amino}-3-o-tolyl-propionic acid (3) | 468.31 | 1.20 | LC11 | A |
| 761 | (S)-3-{[5-((S)-2-Cyclopropyl-2-hydroxy-ethoxy)-1-(2-fluoro-phenyl)-1H-pyrazole-3-carbonyl]-amino}-3-o-tolyl-propionic acid (3) | 468.31 | 1.21 | LC11 | A |
| 762 | (S)-3-(2,4-Dichloro-phenyl)-3-{[5-(2-ethyl-2-hydroxy-butoxy)-1-(2-fluoro-phenyl)-1H-pyrazole-3-carbonyl]-amino}-propionic acid | 538.17 | 1.31 | LC11 | A |
| 763 | (S)-3-{[5-((R)-2-Cyclopropyl-2-hydroxy-propoxy)-1-(2-fluoro-phenyl)-1H-pyrazole-3-carbonyl]-amino}-3-o-tolyl-propionic acid (3) | 482.23 | 1.24 | LC11 | A |
| 764 | (S)-3-{[5-((S)-2-Cyclopropyl-2-hydroxy-propoxy)-1-(2-fluoro-phenyl)-1H-pyrazole-3-carbonyl]-amino}-3-o-tolyl-propionic acid (3) | 482.21 | 1.24 | LC11 | A |
| 765 | (S)-3-{[1-(2-Fluoro-phenyl)-5-((R)-2-hydroxy-2,3-dimethyl-butoxy)-1H-pyrazole-3-carbonyl]-amino}-3-o-tolyl-propionic acid | 484.36 | 10.01 | LC14 | A |
| 766 | (S)-3-{[1-(2-Fluoro-phenyl)-5-((S)-2-hydroxy-2,3-dimethyl-butoxy)-1H-pyrazole-3-carbonyl]-amino}-3-p-tolyl-propionic acid | 484.28 | 1.26 | LC11 | A |
| 767 | (S)-3-(3-Chloro-phenyl)-3-{[1-(2-fluoro-phenyl)-5-((R)-2-hydroxy-2,3-dimethyl-butoxy)-1H-pyrazole-3-carbonyl]-amino}-propionic acid | 504.3 | 1.14 | LC11 | A |
| 768 | (S)-3-(4-Fluoro-phenyl)-3-{[1-(2-fluoro-phenyl)-5-((R)-2-hydroxy-2,3-dimethyl-butoxy)-1H-pyrazole-3-carbonyl]-amino}-propionic acid | 488.35 | 1.11 | LC11 | A |
| 769 | (S)-3-(2,3-Dimethoxy-phenyl)-3-{[1-(2-fluoro-phenyl)-5-((S)-2-hydroxy-2,3-dimethyl-butoxy)-1H-pyrazole-3-carbonyl]-amino}-propionic acid | 530.34 | 1.25 | LC11 | A |
| 770 | (S)-3-{[1-(2-Fluoro-phenyl)-5-(2-hydroxy-2,3-dimethyl-butoxy)-1H-pyrazole-3-carbonyl]-amino}-3-o-tolyl-propionic acid | 484.24 | 1.26 | LC11 | A |
| 771 | (S)-3-(4-Fluoro-phenyl)-3-{[1-(2-fluoro-phenyl)-5-((R)-2-hydroxy-2,3,3-trimethyl-butoxy)-1H-pyrazole-3-carbonyl]-amino}-propionic acid | 502.34 | 1.27 | LC11 | A |
| 772 | (S)-3-(2,4-Dimethyl-phenyl)-3-{[1-(2-fluoro-phenyl)-5-((S)-2-hydroxy-2,3-dimethyl-butoxy)-1H-pyrazole-3-carbonyl]-amino}-propionic acid | 498.31 | 1.29 | LC11 | A |
| 773 | 3-Cyclohexyl-3-{[1-(2-fluoro-phenyl)-5-((S)-2-hydroxy-2,3,3-trimethyl-butoxy)-1H-pyrazole-3-carbonyl]-amino}-propionic acid | 490.29 | 4.68 | LC10 | A |
| 774 | (S)-3-(3-Chloro-phenyl)-3-{[1-(2-fluoro-phenyl)-5-((R)-2-hydroxy-2,3,3-trimethyl-butoxy)-1H-pyrazole-3-carbonyl]-amino}-propionic acid | 518.23 | 1.17 | LC11 | A |
| 775 | (S)-3-(2-Chloro-phenyl)-3-{[1-(2-fluoro-phenyl)-5-(2-hydroxy-2,3-dimethyl-butoxy)-1H-pyrazole-3-carbonyl]-amino}-propionic acid | 504.2 | 1.26 | LC11 | A |
| 776 | (S)-3-(2,3-Dichloro-phenyl)-3-{[1-(2-fluoro-phenyl)-5-((R)-2-hydroxy-3,3-dimethyl-butoxy)-1H-pyrazole-3-carbonyl]-amino}-propionic acid | 538.15 | 1.3 | LC11 | A |

TABLE 1-continued

Example compounds of the formula I

| Example | Compound Name | m/z (1) | Rt (min) | LC/MS Method | Activity (2) |
|---|---|---|---|---|---|
| 777 | (S)-3-(2-Chloro-phenyl)-3-{[5-(3,3-dimethyl-2-oxo-butoxy)-1-(2-fluoro-phenyl)-1H-pyrazole-3-carbonyl]-amino}-propionic acid | 502.15 | 1.28 | LC11 | A |
| 778 | (S)-3-(3-Cyano-phenyl)-3-{[1-(2-fluoro-phenyl)-5-((R)-2-hydroxy-2,3,3-trimethyl-butoxy)-1H-pyrazole-3-carbonyl]-amino}-propionic acid | 509.31 | 1.25 | LC11 | A |
| 779 | (S)-3-(3-Fluoro-phenyl)-3-{[1-(2-fluoro-phenyl)-5-((R)-2-hydroxy-2,3,3-trimethyl-butoxy)-1H-pyrazole-3-carbonyl]-amino}-propionic acid | 502.3 | 1.28 | LC11 | A |
| 780 | (S)-3-{[1-(2-Fluoro-phenyl)-5-((R)-2-hydroxy-2,3,3-trimethyl-butoxy)-1H-pyrazole-3-carbonyl]-amino}-3-p-tolyl-propionic acid | 498.35 | 1.29 | LC11 | A |
| 781 | (S)-3-{[1-(2-Fluoro-phenyl)-5-((S)-2-hydroxy-2,3,3-trimethyl-butoxy)-1H-pyrazole-3-carbonyl]-amino}-3-p-tolyl-propionic acid | 498.32 | 1.16 | LC11 | A |
| 782 | (S)-3-(3-Fluoro-phenyl)-3-{[1-(2-fluoro-phenyl)-5-(2-hydroxy-2,3-dimethyl-butoxy)-1H-pyrazole-3-carbonyl]-amino}-propionic acid | 488.23 | 1.25 | LC11 | A |
| 783 | (S)-3-{[1-(2-Fluoro-phenyl)-5-((S)-2-hydroxy-2,3-dimethyl-butoxy)-1H-pyrazole-3-carbonyl]-amino}-3-(2-methoxy-phenyl)-propionic acid | 500.33 | 1.25 | LC11 | A |
| 784 | (S)-3-{[1-(2-Fluoro-phenyl)-5-((S)-2-hydroxy-2,3-dimethyl-butoxy)-1H-pyrazole-3-carbonyl]-amino}-3-(2-trifluoromethyl-phenyl)-propionic acid | 538.3 | 1.27 | LC11 | A |
| 785 | (S)-3-(3-Chloro-phenyl)-3-{[1-(2-fluoro-phenyl)-5-(2-hydroxy-2,3-dimethyl-butoxy)-1H-pyrazole-3-carbonyl]-amino}-propionic acid | 504.2 | 1.28 | LC11 | A |
| 786 | 3-Cyclohexyl-3-{[1-(2-fluoro-phenyl)-5-((R)-2-hydroxy-2,3-dimethyl-butoxy)-1H-pyrazole-3-carbonyl]-amino}-propionic acid | 476.4 | 1.16 | LC11 | A |
| 787 | (S)-3-{[1-(2-Fluoro-phenyl)-5-(2-hydroxy-2,3-dimethyl-butoxy)-1H-pyrazole-3-carbonyl]-amino}-3-p-tolyl-propionic acid | 484.25 | 1.27 | LC11 | A |
| 788 | (S)-3-{[1-(2-Fluoro-phenyl)-5-((R)-2-hydroxy-3,3-dimethyl-butoxy)-1H-pyrazole-3-carbonyl]-amino}-3-p-tolyl-propionic acid | 484.29 | 1.14 | LC11 | A |
| 789 | (S)-3-(2-Chloro-phenyl)-3-{[1-(2-fluoro-phenyl)-5-((S)-2-hydroxy-2,3,3-trimethyl-butoxy)-1H-pyrazole-3-carbonyl]-amino}-propionic acid | 518.3 | 1.3 | LC11 | A |
| 790 | (S)-3-(2-Chloro-phenyl)-3-{[1-(2-fluoro-phenyl)-5-((R)-2-hydroxy-2,3,3-trimethyl-butoxy)-1H-pyrazole-3-carbonyl]-amino}-propionic acid | 518.28 | 1.29 | LC11 | A |
| 791 | (S)-3-{[5-(3,3-Dimethyl-2-oxo-butoxy)-1-(2-fluoro-phenyl)-1H-pyrazole-3-carbonyl]-amino}-3-p-tolyl-propionic acid | 482.2 | 1.28 | LC11 | A |
| 792 | (S)-3-{[1-(2-Fluoro-phenyl)-5-((S)-2-hydroxy-3,3-dimethyl-butoxy)-1H-pyrazole-3-carbonyl]-amino}-3-m-tolyl-propionic acid | 484.36 | 10.46 | LC14 | A |
| 793 | (S)-3-(2-Chloro-phenyl)-3-{[1-(2-fluoro-phenyl)-5-((R)-2-hydroxy-3,3-dimethyl-butoxy)-1H-pyrazole-3-carbonyl]-amino}-propionic acid | 504.17 | 1.27 | LC11 | A |
| 794 | (S)-3-(4-Chloro-phenyl)-3-{[1-(2-fluoro-phenyl)-5-((S)-2-hydroxy-3,3-dimethyl-butoxy)-1H-pyrazole-3-carbonyl]-amino}-propionic acid | 504.18 | 1.28 | LC11 | A |
| 795 | (S)-3-(3-Chloro-phenyl)-3-{[1-(2-fluoro-phenyl)-5-((R)-2-hydroxy-3,3-dimethyl-butoxy)-1H-pyrazole-3-carbonyl]-amino}-propionic acid | 504.31 | 10.5 | LC11 | A |
| 796 | (S)-3-(3-Chloro-phenyl)-3-{[5-(3,3-dimethyl-2-oxo-butoxy)-1-(2-fluoro-phenyl)-1H-pyrazole-3-carbonyl]-amino}-propionic acid | 502.17 | 1.29 | LC11 | A |

TABLE 1-continued

Example compounds of the formula I

| Example | Compound Name | m/z (1) | Rt (min) | LC/MS Method | Activity (2) |
|---|---|---|---|---|---|
| 797 | (S)-3-(2-Chloro-phenyl)-3-{[1-(2-fluoro-phenyl)-5-((S)-2-hydroxy-3,3-dimethyl-butoxy)-1H-pyrazole-3-carbonyl]-amino}-propionic acid | 504.16 | 1.28 | LC11 | A |
| 798 | (S)-3-(3-Chloro-phenyl)-3-{[1-(2-fluoro-phenyl)-5-((S)-2-hydroxy-2,3,3-trimethyl-butoxy)-1H-pyrazole-3-carbonyl]-amino}-propionic acid | 518.35 | 1.32 | LC11 | A |
| 799 | (S)-3-{[1-(2-Fluoro-phenyl)-5-((S)-2-hydroxy-2,3,3-trimethyl-butoxy)-1H-pyrazole-3-carbonyl]-amino}-3-(2-trifluoromethyl-phenyl)-propionic acid | 552.32 | 1.32 | LC11 | A |
| 800 | (S)-3-(2,3-Dichloro-phenyl)-3-{[1-(2-fluoro-phenyl)-5-((S)-2-hydroxy-3,3-dimethyl-butoxy)-1H-pyrazole-3-carbonyl]-amino}-propionic acid | 538.15 | 1.31 | LC11 | A |
| 801 | (S)-3-{[1-(2-Fluoro-phenyl)-5-((S)-2-hydroxy-3,3-dimethyl-butoxy)-1H-pyrazole-3-carbonyl]-amino}-3-p-tolyl-propionic acid | 484.28 | 1.15 | LC11 | A |
| 802 | (S)-3-{[1-(2-Fluoro-phenyl)-5-(2-hydroxy-2,3-dimethyl-butoxy)-1H-pyrazole-3-carbonyl]-amino}-3-(3-methoxy-phenyl)-propionic acid | 500.26 | 1.24 | LC11 | A |
| 803 | 3-Cyclohexyl-3-{[1-(2-fluoro-phenyl)-5-((S)-2-hydroxy-2,3-dimethyl-butoxy)-1H-pyrazole-3-carbonyl]-amino}-propionic acid | 476.32 | 1.29 | LC11 | A |
| 804 | (S)-3-{[1-(2-Fluoro-phenyl)-5-((R)-2-hydroxy-3,3-dimethyl-butoxy)-1H-pyrazole-3-carbonyl]-amino}-3-m-tolyl-propionic acid | 484.36 | 10.25 | LC14 | A |
| 805 | (S)-3-{[5-(3,3-Dimethyl-2-oxo-butoxy)-1-(2-fluoro-phenyl)-1H-pyrazole-3-carbonyl]-amino}-3-m-tolyl-propionic acid | 482.21 | 1.28 | LC11 | A |
| 806 | (S)-3-{[1-(2-Fluoro-phenyl)-5-((R)-2-hydroxy-2,3-dimethyl-butoxy)-1H-pyrazole-3-carbonyl]-amino}-3-(3-methoxy-phenyl)-propionic acid | 500.35 | 1.1 | LC11 | A |
| 807 | (S)-3-(3-Cyano-phenyl)-3-{[1-(2-fluoro-phenyl)-5-(2-hydroxy-2,3-dimethyl-butoxy)-1H-pyrazole-3-carbonyl]-amino}-propionic acid | 495.25 | 1.22 | LC11 | A |
| 808 | (S)-3-(2,6-Difluoro-phenyl)-3-{[1-(2-fluoro-phenyl)-5-(2-hydroxy-2,3-dimethyl-butoxy)-1H-pyrazole-3-carbonyl]-amino}-propionic acid | 506.22 | 1.25 | LC11 | A |
| 809 | (S)-3-(3-Chloro-phenyl)-3-{[1-(2-fluoro-phenyl)-5-((S)-2-hydroxy-3,3-dimethyl-butoxy)-1H-pyrazole-3-carbonyl]-amino}-propionic acid | 504.31 | 10.7 | LC14 | A |
| 810 | (S)-3-{[1-(2-Fluoro-phenyl)-5-((S)-2-hydroxy-2,3,3-trimethyl-butoxy)-1H-pyrazole-3-carbonyl]-amino}-3-(2-methoxy-phenyl)-propionic acid | 514.24 | 4.54 | LC10 | A |
| 811 | (S)-3-{[1-(2-Fluoro-phenyl)-5-(2-hydroxy-2,3-dimethyl-butoxy)-1H-pyrazole-3-carbonyl]-amino}-3-(2-methoxy-phenyl)-propionic acid | 500.26 | 1.26 | LC11 | A |
| 812 | (S)-3-{[1-(2-Fluoro-phenyl)-5-(2-hydroxy-2,3-dimethyl-butoxy)-1H-pyrazole-3-carbonyl]-amino}-3-(2-trifluoromethyl-phenyl)-propionic acid | 538.24 | 1.28 | LC11 | A |
| 813 | 3-Cyclohexyl-3-{[1-(2-fluoro-phenyl)-5-(2-hydroxy-2,3-dimethyl-butoxy)-1H-pyrazole-3-carbonyl]-amino}-propionic acid | 476.28 | 1.3 | LC11 | A |
| 814 | 3-{[1-(2-Fluoro-phenyl)-5-(2-hydroxy-2,3-dimethyl-butoxy)-1H-pyrazole-3-carbonyl]-amino}-5-methyl-hexanoic acid | 450.25 | 1.26 | LC11 | A |
| 815 | (R)-3-(4-Chloro-phenyl)-3-{[1-(2-fluoro-phenyl)-5-(2-hydroxy-3,3-dimethyl-butoxy)-1H-pyrazole-3-carbonyl]-amino}-propionic acid | 504.18 | 1.29 | LC11 | A |
| 816 | (S)-3-(2,4-Dichloro-phenyl)-3-{[1-(2-fluoro-phenyl)-5-((R)-2-hydroxy-2,3-dimethyl-butoxy)-1H-pyrazole-3-carbonyl]-amino}-propionic acid | 538.2 | 1.31 | LC11 | A |

TABLE 1-continued

Example compounds of the formula I

| Example | Compound Name | m/z (1) | Rt (min) | LC/MS Method | Activity (2) |
|---|---|---|---|---|---|
| 817 | (S)-3-(2,6-Difluoro-phenyl)-3-{[1-(2-fluoro-phenyl)-5-((S)-2-hydroxy-2,3-dimethyl-butoxy)-1H-pyrazole-3-carbonyl]-amino}-propionic acid | 506.28 | 1.25 | LC11 | A |
| 818 | 3-{[1-(2-Fluoro-phenyl)-5-((S)-2-hydroxy-2,3,3-trimethyl-butoxy)-1H-pyrazole-3-carbonyl]-amino}-4-phenyl-butyric acid | 498.34 | 1.3 | LC11 | A |
| 819 | (S)-3-(3-Fluoro-phenyl)-3-{[1-(2-fluoro-phenyl)-5-((S)-2-hydroxy-2,3,3-trimethyl-butoxy)-1H-pyrazole-3-carbonyl]-amino}-propionic acid | 502.35 | 1.29 | LC11 | A |
| 820 | 3-Cyclohexyl-3-{[1-(2-fluoro-phenyl)-5-((R)-2-hydroxy-2,3,3-trimethyl-butoxy)-1H-pyrazole-3-carbonyl]-amino}-propionic acid | 490.36 | 1.32 | LC11 | A |
| 821 | 3-{[1-(2-Fluoro-phenyl)-5-((R)-2-hydroxy-2,3-dimethyl-butoxy)-1H-pyrazole-3-carbonyl]-amino}-4-phenyl-butyric acid | 484.37 | 1.12 | LC11 | A |
| 822 | (S)-3-{[1-(2-Fluoro-phenyl)-5-((R)-2-hydroxy-2,3-dimethyl-butoxy)-1H-pyrazole-3-carbonyl]-amino}-3-(2-methoxy-phenyl)-propionic acid | 500.34 | 1.12 | LC11 | A |
| 823 | 3-{[1-(2-Fluoro-phenyl)-5-((R)-2-hydroxy-2,3-dimethyl-butoxy)-1H-pyrazole-3-carbonyl]-amino}-5-methyl-hexanoic acid | 450.34 | 1.13 | LC11 | B |
| 824 | (1-{[1-(2-Fluoro-phenyl)-5-((R)-2-hydroxy-2,3-dimethyl-butoxy)-1H-pyrazole-3-carbonyl]-amino-cyclopentyl)-acetic acid | 448.36 | 1.11 | LC11 | B |
| 825 | (1-{[1-(2-Fluoro-phenyl)-5-((S)-2-hydroxy-2,3-dimethyl-butoxy)-1H-pyrazole-3-carbonyl]-amino-cyclopentyl)-acetic acid | 448.31 | 1.25 | LC11 | B |
| 826 | 3-{[1-(2-Fluoro-phenyl)-5-((S)-2-hydroxy-2,3-dimethyl-butoxy)-1H-pyrazole-3-carbonyl]-amino}-4-phenyl-butyric acid | 484.3 | 1.25 | LC11 | B |
| 827 | 3-{[1-(2-Fluoro-phenyl)-5-((R)-2-hydroxy-2,3-dimethyl-butoxy)-1H-pyrazole-3-carbonyl]-amino}-2-phenyl-propionic acid | 470.33 | 1.1 | LC11 | B |
| 828 | (S)-3-(4-Chloro-phenyl)-3-{[1-(2-fluoro-phenyl)-5-((R)-2-hydroxy-3,3-dimethyl-butoxy)-1H-pyrazole-3-carbonyl]-amino}-propionic acid | 504.18 | 1.29 | LC11 | B |
| 829 | 3-{[1-(2-Fluoro-phenyl)-5-(2-hydroxy-2,3-dimethyl-butoxy)-1H-pyrazole-3-carbonyl]-amino}-4-phenyl-butyric acid | 484.24 | 1.26 | LC11 | B |
| 830 | 3-{[1-(2-Fluoro-phenyl)-5-((S)-2-hydroxy-2,3-dimethyl-butoxy)-1H-pyrazole-3-carbonyl]-amino}-2-phenyl-propionic acid | 470.32 | 1.23 | LC11 | B |
| 832 | (S)-4-(4-Cyano-phenyl)-3-{[1-(2-fluoro-phenyl)-5-((S)-2-hydroxy-2,3,3-trimethyl-butoxy)-1H-pyrazole-3-carbonyl]-amino}-butyric acid | 523.33 | 1.25 | LC11 | C |
| 833 | (S)-3-{[1-(2-Fluoro-phenyl)-5-((S)-2-hydroxy-2,3-dimethyl-butoxy)-1H-pyrazole-3-carbonyl]-amino}-3-o-tolyl-propionic acid | 484.29 | 1.26 | LC11 | C |
| 834 | (S)-4-(4-Cyano-phenyl)-3-{[1-(2-fluoro-phenyl)-5-((S)-2-hydroxy-2,3-dimethyl-butoxy)-1H-pyrazole-3-carbonyl]-amino}-butyric acid | 509.31 | 1.22 | LC11 | C |
| 835 | (S)-3-(2-Fluoro-phenyl)-3-{[1-(2-fluoro-phenyl)-5-((S)-2-hydroxy-2,3-dimethyl-butoxy)-1H-pyrazole-3-carbonyl]-amino}-propionic acid | 488.27 | 1.24 | LC11 | A |
| 836 | (S)-4-(4-Cyano-phenyl)-3-{[1-(2-fluoro-phenyl)-5-(2-hydroxy-2,3-dimethyl-butoxy)-1H-pyrazole-3-carbonyl]-amino}-butyric acid | 509.24 | 1.23 | LC11 | C |
| 837 | (S)-3-{[1-(2-Fluoro-phenyl)-5-((S)-2-hydroxy-2,3-dimethyl-butoxy)-1H-pyrazole-3-carbonyl]-amino}-4-phenyl-butyric acid | 484.34 | 1.25 | LC11 | C |
| 838 | (S)-3-{[1-(2-Fluoro-phenyl)-5-(2-hydroxy-2,3-dimethyl-butoxy)-1H-pyrazole-3-carbonyl]-amino}-4-phenyl-butyric acid | 484.25 | 1.26 | LC11 | C |
| 839 | (S)-3-(2,3-Dichloro-phenyl)-3-{[5-(3,3-dimethyl-2-oxo-butoxy)-1-(2-fluoro-phenyl)-1H-pyrazole-3-carbonyl]-amino}-propionic acid | 536.13 | 1.31 | LC11 | A |

TABLE 1-continued

Example compounds of the formula I

| Example | Compound Name | m/z (1) | Rt (min) | LC/MS Method | Activity (2) |
|---|---|---|---|---|---|
| 840 | (S)-3-{[1-(2-Fluoro-phenyl)-5-((S)-2-hydroxy-2,3-dimethyl-butoxy)-1H-pyrazole-3-carbonyl]-amino}-3-(4-methoxy-phenyl)-propionic acid | 500.31 | 1.23 | LC11 | C |
| 841 | (S)-3-{[1-(2-Fluoro-phenyl)-5-((S)-2-hydroxy-2,3-dimethyl-butoxy)-1H-pyrazole-3-carbonyl]-amino}-5-methyl-hexanoic acid | 450.33 | 1.26 | LC11 | C |
| 842 | (S)-3-{[1-(2-Fluoro-phenyl)-5-(2-hydroxy-2,3-dimethyl-butoxy)-1H-pyrazole-3-carbonyl]-amino}-5-methyl-hexanoic acid | 450.25 | 1.26 | LC11 | |
| 843 | (1-{[1-(2-Fluoro-phenyl)-5-(2-hydroxy-2,3-dimethyl-butoxy)-1H-pyrazole-3-carbonyl]-amino}-cyclopentyl)-acetic acid | 448.23 | 1.25 | LC11 | |
| 844 | (S)-3-(4-Fluoro-phenyl)-3-{[1-(2-fluoro-phenyl)-5-(2-hydroxy-2,3-dimethyl-butoxy)-1H-pyrazole-3-carbonyl]-amino}-propionic acid | 488.21 | 1.25 | LC11 | |
| 845 | (S)-3-(2,4-Dimethyl-phenyl)-3-{[1-(2-fluoro-phenyl)-5-(2-hydroxy-2,3-dimethyl-butoxy)-1H-pyrazole-3-carbonyl]-amino}-propionic acid | 498.27 | 1.3 | LC11 | |
| 846 | (S)-3-(2-Fluoro-phenyl)-3-{[1-(2-fluoro-phenyl)-5-(2-hydroxy-2,3-dimethyl-butoxy)-1H-pyrazole-3-carbonyl]-amino}-propionic acid | 488.22 | 1.25 | LC11 | |
| 847 | (S)-3-(2,3-Dimethoxy-phenyl)-3-{[1-(2-fluoro-phenyl)-5-(2-hydroxy-2,3-dimethyl-butoxy)-1H-pyrazole-3-carbonyl]-amino}-propionic acid | 530.25 | 1.25 | LC11 | |
| 848 | (S)-3-{[1-(2-Fluoro-phenyl)-5-(2-hydroxy-2,3-dimethyl-butoxy)-1H-pyrazole-3-carbonyl]-amino}-3-(4-methoxy-phenyl)-propionic acid | 500.25 | 1.24 | LC11 | |
| 849 | (S)-3-(2,4-Dichloro-phenyl)-3-{[1-(2-fluoro-phenyl)-5-((S)-2-hydroxy-2,3-dimethyl-butoxy)-1H-pyrazole-3-carbonyl]-amino}-propionic acid | 538.2 | 1.3 | LC11 | A |
| 850 | (S)-3-{[1-(2-Fluoro-phenyl)-5-((R)-2-hydroxy-2,3-dimethyl-butoxy)-1H-pyrazole-3-carbonyl]-amino}-3-(4-methoxy-phenyl)-propionic acid | 500.31 | 1.1 | LC11 | A |
| 851 | 3-{[1-(2-Fluoro-phenyl)-5-((S)-2-hydroxy-2,3,3-trimethyl-butoxy)-1H-pyrazole-3-carbonyl]-amino}-5-methyl-hexanoic acid | 464.29 | 4.56 | LC11 | |
| 852 | (S)-3-{[1-(2-Fluoro-phenyl)-5-((S)-2-hydroxy-2,3,3-trimethyl-butoxy)-1H-pyrazole-3-carbonyl]-amino}-4-phenyl-butyric acid | 498.27 | 4.55 | LC11 | |
| 853 | (1-{[1-(2-Fluoro-phenyl)-5-((R)-2-hydroxy-2,3,3-trimethyl-butoxy)-1H-pyrazole-3-carbonyl]-amino}-cyclopentyl)-acetic acid | 462.31 | 1.29 | LC11 | |
| 854 | (S)-3-(2-Fluoro-phenyl)-3-{[1-(2-fluoro-phenyl)-5-((R)-2-hydroxy-2,3,3-trimethyl-butoxy)-1H-pyrazole-3-carbonyl]-amino}-propionic acid | 502.31 | 1.27 | LC11 | B |
| 855 | (S)-3-(2,3-Dimethoxy-phenyl)-3-{[1-(2-fluoro-phenyl)-5-((R)-2-hydroxy-2,3,3-trimethyl-butoxy)-1H-pyrazole-3-carbonyl]-amino}-propionic acid | 544.36 | 1.28 | LC11 | |
| 856 | (S)-3-{[1-(2-Fluoro-phenyl)-5-((R)-2-hydroxy-2,3,3-trimethyl-butoxy)-1H-pyrazole-3-carbonyl]-amino}-3-(3-methoxy-phenyl)-propionic acid | 514.34 | 1.27 | LC11 | |
| 857 | (S)-3-{[1-(2-Fluoro-phenyl)-5-((R)-2-hydroxy-2,3-dimethyl-butoxy)-1H-pyrazole-3-carbonyl]-amino}-3-o-tolyl-propionic acid | 484.36 | 10 | LC14 | A |
| 858 | (S)-3-{[1-(2-Fluoro-phenyl)-5-((R)-2-hydroxy-2,3-dimethyl-butoxy)-1H-pyrazole-3-carbonyl]-amino}-5-methyl-hexanoic acid | 450.35 | 1.13 | LC11 | |
| 859 | (S)-3-(2,4-Dimethyl-phenyl)-3-{[1-(2-fluoro-phenyl)-5-((R)-2-hydroxy-2,3-dimethyl-butoxy)-1H-pyrazole-3-carbonyl]-amino}-propionic acid | 498.37 | 1.16 | LC11 | A |

TABLE 1-continued

Example compounds of the formula I

| Example | Compound Name | m/z (1) | Rt (min) | LC/MS Method | Activity (2) |
|---|---|---|---|---|---|
| 860 | (S)-3-{[1-(2-Fluoro-phenyl)-5-((R)-2-hydroxy-2,3-dimethyl-butoxy)-1H-pyrazole-3-carbonyl]-amino}-3-p-tolyl-propionic acid | 484.34 | 1.13 | LC11 | A |
| 861 | (S)-3-(2-Chloro-phenyl)-3-{[1-(2-fluoro-phenyl)-5-((R)-2-hydroxy-2,3-dimethyl-butoxy)-1H-pyrazole-3-carbonyl]-amino}-propionic acid | 504.27 | 1.13 | LC11 | >30 |
| 862 | (S)-3-(2-Fluoro-phenyl)-3-{[1-(2-fluoro-phenyl)-5-((R)-2-hydroxy-2,3-dimethyl-butoxy)-1H-pyrazole-3-carbonyl]-amino}-propionic acid | 488.34 | 1.11 | LC11 | B |
| 863 | (S)-3-{[1-(2-Fluoro-phenyl)-5-((R)-2-hydroxy-2,3-dimethyl-butoxy)-1H-pyrazole-3-carbonyl]-amino}-3-(2-trifluoromethyl-phenyl)-propionic acid | 538.31 | 1.14 | LC11 | |
| 864 | (S)-3-{[1-(2-Fluoro-phenyl)-5-((R)-2-hydroxy-2,3-dimethyl-butoxy)-1H-pyrazole-3-carbonyl]-amino}-4-phenyl-butyric acid | 484.37 | 1.12 | LC11 | |
| 865 | (S)-3-(3-Cyano-phenyl)-3-{[1-(2-fluoro-phenyl)-5-((R)-2-hydroxy-2,3-dimethyl-butoxy)-1H-pyrazole-3-carbonyl]-amino}-propionic acid | 495.34 | 1.08 | LC11 | |
| 866 | (S)-3-(2,3-Dimethoxy-phenyl)-3-{[1-(2-fluoro-phenyl)-5-((R)-2-hydroxy-2,3-dimethyl-butoxy)-1H-pyrazole-3-carbonyl]-amino}-propionic acid | 530.34 | 1.12 | LC11 | |
| 867 | (S)-4-(4-Cyano-phenyl)-3-{[1-(2-fluoro-phenyl)-5-((R)-2-hydroxy-2,3-dimethyl-butoxy)-1H-pyrazole-3-carbonyl]-amino}-butyric acid | 509.36 | 1.09 | LC11 | |
| 868 | (S)-3-(2,6-Difluoro-phenyl)-3-{[1-(2-fluoro-phenyl)-5-((R)-2-hydroxy-2,3-dimethyl-butoxy)-1H-pyrazole-3-carbonyl]-amino}-propionic acid | 506.32 | 1.12 | LC11 | |
| 869 | (S)-3-(3-Fluoro-phenyl)-3-{[1-(2-fluoro-phenyl)-5-((R)-2-hydroxy-2,3-dimethyl-butoxy)-1H-pyrazole-3-carbonyl]-amino}-propionic acid | 488.33 | 1.11 | LC11 | |
| 870 | (S)-3-{[1-(2-Fluoro-phenyl)-5-((S)-2-hydroxy-2,3-dimethyl-butoxy)-1H-pyrazole-3-carbonyl]-amino}-3-o-tolyl-propionic acid | 484.38 | 1.13 | LC11 | A |
| 871 | 3-{[1-(2-Fluoro-phenyl)-5-((S)-2-hydroxy-2,3-dimethyl-butoxy)-1H-pyrazole-3-carbonyl]-amino}-5-methyl-hexanoic acid | 450.35 | 1.13 | LC11 | |
| 872 | (S)-3-(4-Fluoro-phenyl)-3-{[1-(2-fluoro-phenyl)-5-((S)-2-hydroxy-2,3-dimethyl-butoxy)-1H-pyrazole-3-carbonyl]-amino}-propionic acid | 488.33 | 1.24 | LC11 | B |
| 873 | (S)-3-(2-Chloro-phenyl)-3-{[1-(2-fluoro-phenyl)-5-((S)-2-hydroxy-2,3-dimethyl-butoxy)-1H-pyrazole-3-carbonyl]-amino}-propionic acid | 504.31 | 1.26 | LC11 | |
| 874 | (S)-3-(3-Cyano-phenyl)-3-{[1-(2-fluoro-phenyl)-5-((S)-2-hydroxy-2,3-dimethyl-butoxy)-1H-pyrazole-3-carbonyl]-amino}-propionic acid | 495.28 | 1.22 | LC11 | |
| 875 | (S)-3-{[1-(2-Fluoro-phenyl)-5-((S)-2-hydroxy-2,3-dimethyl-butoxy)-1H-pyrazole-3-carbonyl]-amino}-3-(3-methoxy-phenyl)-propionic acid | 500.31 | 1.24 | LC11 | |
| 876 | (S)-3-(3-Fluoro-phenyl)-3-{[1-(2-fluoro-phenyl)-5-((S)-2-hydroxy-2,3-dimethyl-butoxy)-1H-pyrazole-3-carbonyl]-amino}-propionic acid | 488.3 | 1.25 | LC11 | |
| 877 | (S)-3-(3-Chloro-phenyl)-3-{[1-(2-fluoro-phenyl)-5-((S)-2-hydroxy-2,3-dimethyl-butoxy)-1H-pyrazole-3-carbonyl]-amino}-propionic acid | 504.24 | 1.27 | LC11 | B |
| 878 | (S)-3-{[1-(2-Fluoro-phenyl)-5-((S)-2-hydroxy-2,3,3-trimethyl-butoxy)-1H-pyrazole-3-carbonyl]-amino}-5-methyl-hexanoic acid | 464.34 | 1.29 | LC11 | |
| 879 | (1-{[1-(2-Fluoro-phenyl)-5-((S)-2-hydroxy-2,3,3-trimethyl-butoxy)-1H-pyrazole-3-carbonyl]-amino}-cyclopentyl)-acetic acid | 462.31 | 1.29 | LC11 | |

TABLE 1-continued

Example compounds of the formula I

| Example | Compound Name | m/z (1) | Rt (min) | LC/MS Method | Activity (2) |
|---|---|---|---|---|---|
| 880 | (S)-3-(4-Fluoro-phenyl)-3-{[1-(2-fluoro-phenyl)-5-((S)-2-hydroxy-2,3,3-trimethyl-butoxy)-1H-pyrazole-3-carbonyl]-amino}-propionic acid | 502.31 | 1.29 | LC11 | A |
| 881 | (S)-3-(2,4-Dimethyl-phenyl)-3-{[1-(2-fluoro-phenyl)-5-((S)-2-hydroxy-2,3,3-trimethyl-butoxy)-1H-pyrazole-3-carbonyl]-amino}-propionic acid | 512.37 | 1.32 | LC11 | |
| 883 | (S)-3-(2-Fluoro-phenyl)-3-{[1-(2-fluoro-phenyl)-5-((S)-2-hydroxy-2,3,3-trimethyl-butoxy)-1H-pyrazole-3-carbonyl]-amino}-propionic acid | 502.3 | 1.29 | LC11 | A |
| 884 | (S)-3-(2,3-Dimethoxy-phenyl)-3-{[1-(2-fluoro-phenyl)-5-((S)-2-hydroxy-2,3,3-trimethyl-butoxy)-1H-pyrazole-3-carbonyl]-amino}-propionic acid | 544.35 | 1.29 | LC11 | A |
| 885 | (S)-3-{[1-(2-Fluoro-phenyl)-5-((S)-2-hydroxy-2,3,3-trimethyl-butoxy)-1H-pyrazole-3-carbonyl]-amino}-3-(3-methoxy-phenyl)-propionic acid | 514.24 | 4.54 | LC11 | |
| 886 | (S)-3-{[1-(2-Fluoro-phenyl)-5-((R)-2-hydroxy-2,3,3-trimethyl-butoxy)-1H-pyrazole-3-carbonyl]-amino}-5-methyl-hexanoic acid | 464.36 | 1.31 | LC11 | |
| 888 | (S)-3-{[1-(2-Fluoro-phenyl)-5-((R)-2-hydroxy-2,3,3-trimethyl-butoxy)-1H-pyrazole-3-carbonyl]-amino}-3-(2-trifluoromethyl-phenyl)-propionic acid | 552.32 | 1.3 | LC11 | |
| 889 | (S)-4-(4-Cyano-phenyl)-3-{[1-(2-fluoro-phenyl)-5-((R)-2-hydroxy-2,3,3-trimethyl-butoxy)-1H-pyrazole-3-carbonyl]-amino}-butyric acid | 523.33 | 1.26 | LC11 | |
| 890 | (S)-3-{[1-(2-Fluoro-phenyl)-5-((R)-2-hydroxy-2,3,3-trimethyl-butoxy)-1H-pyrazole-3-carbonyl]-amino}-3-(4-methoxy-phenyl)-propionic acid | 514.36 | 1.26 | LC11 | |
| 891 | (S)-3-{[1-(2-Fluoro-phenyl)-5-(2-hydroxy-2-phenyl-propoxy)-1H-pyrazole-3-carbonyl]-amino}-3-o-tolyl-propionic acid | 518.26 | 4.46 | LC10 | A |
| 892 | 1-(2-Fluoro-phenyl)-5-methoxy-1H-pyrazole-3-carboxylic acid {(S)-2-[(pyridin-2-ylmethyl)-carbamoyl]-1-o-tolyl-ethyl}-amide; compound with trifluoro-acetic acid | 488.38 | 1 | LC11 | |
| 893 | 1-(2-Fluoro-phenyl)-5-methoxy-1H-pyrazole-3-carboxylic acid [(S)-2-(cyclopropylmethyl-carbamoyl)-1-o-tolyl-ethyl]-amide | 451.37 | 1.13 | LC11 | |
| 894 | 1-(2-Fluoro-phenyl)-5-methoxy-1H-pyrazole-3-carboxylic acid {(S)-2-[(furan-2-ylmethyl)-carbamoyl]-1-o-tolyl-ethyl}-amide | 477.36 | 1.12 | LC11 | |
| 895 | 1-(2-Fluoro-phenyl)-5-methoxy-1H-pyrazole-3-carboxylic acid [(S)-2-(3-dimethylamino-propylcarbamoyl)-1-o-tolyl-ethyl]-amide; compound with trifluoro-acetic acid | 482.44 | 0.91 | LC11 | |
| 896 | 1-(2-Fluoro-phenyl)-5-methoxy-1H-pyrazole-3-carboxylic acid [(S)-2-(1-ethyl-propylcarbamoyl)-1-o-tolyl-ethyl]-amide | 467.44 | 1.17 | LC11 | |
| 897 | 1-(2-Fluoro-phenyl)-5-methoxy-1H-pyrazole-3-carboxylic acid ((S)-2-cyclohexylcarbamoyl-1-o-tolyl-ethyl)-amide | 479.05 | 1.18 | LC11 | |
| 898 | 1-(2-Fluoro-phenyl)-5-methoxy-1H-pyrazole-3-carboxylic acid [(S)-3-((S)-3-hydroxy-pyrrolidin-1-yl)-3-oxo-1-o-tolyl-propyl]-amide | 467.41 | 1.04 | LC11 | |
| 899 | 1-(2-Fluoro-phenyl)-5-methoxy-1H-pyrazole-3-carboxylic acid [(S)-1-o-tolyl-2-((R)-1,2,2-trimethyl-propylcarbamoyl)-ethyl]-amide | 481.4 | 4.71 | LC10 | |
| 900 | 1-(2-Fluoro-phenyl)-5-methoxy-1H-pyrazole-3-carboxylic acid [(S)-3-((R)-3-hydroxy-pyrrolidin-1-yl)-3-oxo-1-o-tolyl-propyl]-amide | 467.36 | 1.04 | LC11 | |

TABLE 1-continued

Example compounds of the formula I

| Example | Compound Name | m/z (1) | Rt (min) | LC/MS Method | Activity (2) |
|---|---|---|---|---|---|
| 901 | 1-(2-Fluoro-phenyl)-5-methoxy-1H-pyrazole-3-carboxylic acid [(S)-2-((S)-sec-butylcarbamoyl)-1-o-tolyl-ethyl]-amide | 453.25 | 1.15 | LC11 | |
| 902 | 1-(2-Fluoro-phenyl)-5-methoxy-1H-pyrazole-3-carboxylic acid [(S)-3-((S)-3-hydroxy-piperidin-1-yl)-3-oxo-1-o-tolyl-propyl]-amide | 481.25 | 1.07 | LC11 | |
| 903 | 1-(2-Fluoro-phenyl)-5-methoxy-1H-pyrazole-3-carboxylic acid [(S)-2-(carbamoylmethyl-methyl-carbamoyl)-1-o-tolyl-ethyl]-amide | 468.23 | 1.02 | LC11 | |
| 904 | 1-(2-Fluoro-phenyl)-5-methoxy-1H-pyrazole-3-carboxylic acid [(S)-2-((R)-1-cyclopropyl-ethylcarbamoyl)-1-o-tolyl-ethyl]-amide | 465.25 | 1.16 | LC11 | |
| 905 | 1-(2-Fluoro-phenyl)-5-methoxy-1H-pyrazole-3-carboxylic acid [(S)-2-((S)-1-cyclopropyl-ethylcarbamoyl)-1-o-tolyl-ethyl]-amide | 465.25 | 1.16 | LC11 | |
| 906 | 1-(2-Fluoro-phenyl)-5-methoxy-1H-pyrazole-3-carboxylic acid ((S)-2-cyclobutylcarbamoyl-1-o-tolyl-ethyl)-amide | 451.39 | 1.13 | LC11 | |
| 907 | 1-(2-Fluoro-phenyl)-5-methoxy-1H-pyrazole-3-carboxylic acid {(S)-2-[(pyridin-3-ylmethyl)-carbamoyl]-1-o-tolyl-ethyl}-amide; compound with trifluoro-acetic acid | 488.42 | 0.95 | LC11 | |
| 908 | 1-(2-Fluoro-phenyl)-5-methoxy-1H-pyrazole-3-carboxylic acid ((S)-2-cyclopentylcarbamoyl-1-o-tolyl-ethyl)-amide | 465.43 | 1.16 | LC11 | |
| 909 | 1-(2-Fluoro-phenyl)-5-methoxy-1H-pyrazole-3-carboxylic acid [(S)-2-(2-methoxy-1-methyl-ethylcarbamoyl)-1-o-tolyl-ethyl]-amide | 469.4 | 1.11 | LC11 | |
| 910 | 1-(2-Fluoro-phenyl)-5-methoxy-1H-pyrazole-3-carboxylic acid [(S)-2-(2,2-difluoro-ethylcarbamoyl)-1-o-tolyl-ethyl]-amide | 461.2 | 1.11 | LC11 | |
| 911 | 1-(2-Fluoro-phenyl)-5-methoxy-1H-pyrazole-3-carboxylic acid [(S)-1-o-tolyl-2-(2,2,2-trifluoro-ethylcarbamoyl)-ethyl]-amide | 479.18 | 1.14 | LC11 | |
| 912 | 1-(2-Fluoro-phenyl)-5-methoxy-1H-pyrazole-3-carboxylic acid [(S)-2-(2-cyclopropyl-ethylcarbamoyl)-1-o-tolyl-ethyl]-amide | 465.25 | 1.16 | LC11 | |
| 913 | 1-(2-Fluoro-phenyl)-5-methoxy-1H-pyrazole-3-carboxylic acid {(S)-2-[(pyrimidin-5-ylmethyl)-carbamoyl]-1-o-tolyl-ethyl}-amide | 489.23 | 1.02 | LC11 | |
| 914 | 1-(2-Fluoro-phenyl)-5-methoxy-1H-pyrazole-3-carboxylic acid ((S)-2-butylcarbamoyl-1-o-tolyl-ethyl)-amide | 453.25 | 1.15 | LC11 | |
| 915 | 1-(2-Fluoro-phenyl)-5-methoxy-1H-pyrazole-3-carboxylic acid {(S)-2-[(furan-3-ylmethyl)-carbamoyl]-1-o-tolyl-ethyl}-amide | 477.22 | 1.12 | LC11 | |
| 916 | 1-(2-Fluoro-phenyl)-5-methoxy-1H-pyrazole-3-carboxylic acid {(S)-2-[(pyridin-4-ylmethyl)-carbamoyl]-1-o-tolyl-ethyl}-amide; compound with trifluoro-acetic acid | 488.41 | 0.92 | LC11 | C |
| 917 | 1-(2-Fluoro-phenyl)-5-methoxy-1H-pyrazole-3-carboxylic acid [(S)-2-(1,1-dimethyl-propylcarbamoyl)-1-o-tolyl-ethyl]-amide | 467.44 | 1.19 | LC11 | C |
| 918 | 1-(2-Fluoro-phenyl)-5-methoxy-1H-pyrazole-3-carboxylic acid [(S)-2-((R)-sec-butylcarbamoyl)-1-o-tolyl-ethyl]-amide | 453.25 | 1.15 | LC11 | C |
| 919 | 1-(2-Fluoro-phenyl)-5-methoxy-1H-pyrazole-3-carboxylic acid ((S)-2-isobutylcarbamoyl-1-o-tolyl-ethyl)-amide | 453.37 | 1.15 | LC11 | C |
| 920 | 1-(2-Fluoro-phenyl)-5-methoxy-1H-pyrazole-3-carboxylic acid [(S)-1-o-tolyl-2-((S)-1,2,2-trimethyl-propylcarbamoyl)-ethyl]-amide | 481.51 | 1.2 | LC11 | C |

TABLE 1-continued

Example compounds of the formula I

| Example | Compound Name | m/z (1) | Rt (min) | LC/MS Method | Activity (2) |
|---|---|---|---|---|---|
| 921 | 1-(2-Fluoro-phenyl)-5-methoxy-1H-pyrazole-3-carboxylic acid [(S)-2-(1-methoxymethyl-propylcarbamoyl)-1-o-tolyl-ethyl]-amide | 483.26 | 1.13 | LC11 | C |
| 922 | 1-(2-Fluoro-phenyl)-5-methoxy-1H-pyrazole-3-carboxylic acid ((S)-2-tert-butylcarbamoyl-1-o-tolyl-ethyl)-amide | 453.25 | 1.17 | LC11 | C |
| 923 | 1-(2-Fluoro-phenyl)-5-methoxy-1H-pyrazole-3-carboxylic acid [(S)-2-(5-methyl-1H-pyrazol-3-ylcarbamoyl)-1-o-tolyl-ethyl]-amide | 477.23 | 1.07 | LC11 | C |
| 924 | 1-(2-Fluoro-phenyl)-5-methoxy-1H-pyrazole-3-carboxylic acid [(S)-2-(2,2-dimethyl-propylcarbamoyl)-1-o-tolyl-ethyl]-amide | 467.38 | 1.08 | LC11 | A |
| 925 | 1-(2-Fluoro-phenyl)-5-methoxy-1H-pyrazole-3-carboxylic acid [(S)-2-(3-hydroxy-2,2-dimethyl-propylcarbamoyl)-1-o-tolyl-ethyl]-amide | 483.41 | 1.09 | LC11 | C |
| 926 | 1-(2-Fluoro-phenyl)-5-methoxy-1H-pyrazole-3-carboxylic acid [(S)-2-(cyanomethyl-carbamoyl)-1-o-tolyl-ethyl]-amide | 436.2 | 1.07 | LC11 | C |
| 927 | 1-(2-Fluoro-phenyl)-5-methoxy-1H-pyrazole-3-carboxylic acid [(S)-2-((R)-1-hydroxymethyl-2-methyl-propylcarbamoyl)-1-o-tolyl-ethyl]-amide | 483.26 | 1.09 | LC11 | B |
| 928 | 1-(2-Fluoro-phenyl)-5-methoxy-1H-pyrazole-3-carboxylic acid {(S)-2-[(1H-tetrazol-5-ylmethyl)-carbamoyl]-1-o-tolyl-ethyl}-amide | 479.22 | 1.02 | LC11 | B |
| 929 | 1-(2-Fluoro-phenyl)-5-methoxy-1H-pyrazole-3-carboxylic acid ((S)-2-isopropylcarbamoyl-1-o-tolyl-ethyl)-amide | 439.39 | 1.12 | LC11 | B |
| 930 | 1-(2-Fluoro-phenyl)-5-methoxy-1H-pyrazole-3-carboxylic acid [(S)-2-(1-methyl-1H-pyrazol-3-ylcarbamoyl)-1-o-tolyl-ethyl]-amide | 477.23 | 1.08 | LC11 | B |
| 931 | 1-(2-Fluoro-phenyl)-5-methoxy-1H-pyrazole-3-carboxylic acid [(S)-2-(2-oxo-pyrrolidin-3-ylcarbamoyl)-1-o-tolyl-ethyl]-amide | 480.24 | 1.01 | LC11 | C |
| 932 | 1-(2-Fluoro-phenyl)-5-methoxy-1H-pyrazole-3-carboxylic acid [(S)-2-(5-methyl-isoxazol-3-ylcarbamoyl)-1-o-tolyl-ethyl]-amide | 478.36 | 1.13 | LC11 | B |
| 933 | 1-(2-Fluoro-phenyl)-5-methoxy-1H-pyrazole-3-carboxylic acid ((S)-2-cyclopropylcarbamoyl-1-o-tolyl-ethyl)-amide | 437.29 | 1.08 | LC11 | A |
| 934 | 1-(2-Fluoro-phenyl)-5-methoxy-1H-pyrazole-3-carboxylic acid {(S)-2-[(isoxazol-5-ylmethyl)-carbamoyl]-1-o-tolyl-ethyl}-amide | 478.22 | 1.08 | LC11 | A |
| 935 | 1-(2-Fluoro-phenyl)-5-methoxy-1H-pyrazole-3-carboxylic acid [(S)-2-(2-methoxy-ethylcarbamoyl)-1-o-tolyl-ethyl]-amide | 455.37 | 1.08 | LC11 | A |
| 936 | 1-(2-Fluoro-phenyl)-5-methoxy-1H-pyrazole-3-carboxylic acid [(S)-2-((S)-1-hydroxymethyl-2-methyl-propylcarbamoyl)-1-o-tolyl-ethyl]-amide | 483.43 | 1.09 | LC11 | A |
| 937 | 1-(2-Fluoro-phenyl)-5-methoxy-1H-pyrazole-3-carboxylic acid [(S)-2-((S)-2-methoxy-1-methyl-ethylcarbamoyl)-1-o-tolyl-ethyl]-amide | 469.24 | 1.1 | LC11 | A |
| 938 | 1-(2-Fluoro-phenyl)-5-methoxy-1H-pyrazole-3-carboxylic acid ((S)-2-{[(S)-1-(tetrahydro-furan-2-yl)methyl]-carbamoyl}-1-o-tolyl-ethyl)-amide | 481.25 | 1.1 | LC11 | A |

TABLE 1-continued

Example compounds of the formula I

| Example | Compound Name | m/z (1) | Rt (min) | LC/MS Method | Activity (2) |
|---|---|---|---|---|---|
| 939 | 1-(2-Fluoro-phenyl)-5-methoxy-1H-pyrazole-3-carboxylic acid [(S)-2-((R)-1,2-dimethyl-propylcarbamoyl)-1-o-tolyl-ethyl]-amide | 467.23 | 1.09 | LC11 | A |

(1) Mass spectroscopic characterization; observed mass number of the ion [(M + H)$^+$], unless specified otherwise
(2) Cathepsin A inhibitory activity determined in the pharmacological test "Cathepsin A inhibitory activity" described below. "A" means an IC$_{50}$ value of less than 0.1 µM, "B" means an IC$_{50}$ value between 0.1 µM and 1 µM, "C" means an IC$_{50}$ value between 1 µM and 30 µM.
(3) The two compounds of examples 745 and 746; the two compounds of examples 747 and 748; the two compounds of examples 753 and 754; the two compounds of examples 758 and 759; the two compounds of examples 760 and 761; and the two compounds of examples 763 and 764 each are two diastereomeric compounds, one of them being the diastereomer with R configuration in the alcohol moiety and the other of them being the diastereomer with S configuration in the alcohol moiety (the stereochemistry in the alcohol moiety was not determined; it was arbitrarily assigned R configuration in the first diastereomer eluted from the chromatography column and S configuration in the second diastereomer eluted from the chromatography column).

Exemplary $^1$H-NMR Data of Example Compounds

EXAMPLE 3

δ (ppm)=2.75 (dd, 1H); 2.92 (dd, 1H); 3.75 (s, 3H); 5.35 (q, 1H); 5.85 (s, 1H); 6.85 (d, 2H); 7.3 (m, 3H); 7.5 (m, 2H); 7.75 (d, 2H); 8.5 (d, 1H)

EXAMPLE 7

δ (ppm)=1.25 (s, 9H); 2.0 (s, 3H); 2.3 (s, 3H); 2.75 (dd, 1H); 2.9 (dd, 1H); 5.35 (q, 1H); 5.8 (s, 1H); 6.7 (m, 1H); 7.05-7.3 (m, 6H); 8.5 (d, 1H)

EXAMPLE 129

δ (ppm)=2.4 (s, 3H); 2.7 (dd, 1H); 2.9 (dd, 1H); 3.9 (s, 3H); 5.6 (q, 1H); 6.2 (s, 1H); 7.1 (m, 3H); 7.4 (m, 1H); 7.5 (m, 2H); 7.6 (m, 2H); 8.65 (d, 1H)

EXAMPLE 523

δ (ppm)=2.35 (s, 3H); 2.75 (dd, 1H); 2.9 (dd, 1H); 5.6 (q, 1H); 5.85 (s, 1H); 7.0 (t, 1H); 7.2 (q, 1H); 7.35 (m, 3H); 7.8 (m, 2H); 8.65 (d, 1H)

EXAMPLE 524

δ (ppm)=2.7 (dd, 1H); 2.9 (dd, 1H); 5.7 (m, 1H); 5.85 (s, 1H); 7.25 (m, 1H); 7.3-7.4 (m, 3H); 7.45 (m, 1H); 7.8 (m, 2H); 8.75 (d, 2H)

EXAMPLE 534

δ (ppm)=2.4 (s, 3H); 2.7 (dd, 1H); 2.9 (dd, 1H); 5.6 (s, 1H); 6.25 (s, 1H); 7.1 (m, 3H); 7.35 (m, 1H); 7.5 (m, 3H); 7.7 (d, 2H); 8.65 (d, 1H)

EXAMPLE 548

δ (ppm)=2.7 (dd, 1H); 2.85 (dd, 1H); 3.9 (s, 3H); 5.7 (m, 1H); 5.9 (s, 1H); 7.2 (d, 1H); 7.35 (t, 1H); 7.5 (t, 2H); 7.6 (d, 1H); 7.65 (s, 1H); 7.8 (d, 2H); 8.6 (d, 1H)

EXAMPLE 564

δ (ppm)=2.3 (s, 3H); 2.7 (dd, 1H); 2.9 (dd, 1H); 5.6 (m, 1H); 5.85 (s, 1H); 7.0 (m, 2H); 7.35 (m, 2H); 7.5 (m, 2H); 7.8 (m, 2H); 8.6 (d, 1H)

EXAMPLE 585

δ (ppm)=2.85 (dd, 1H); 3.0 (dd, 1H); 5.4 (q, 1H); 5.8 (s, 1H); 7.2-7.6 (m, 12H); 8.6 (d, 1H)

EXAMPLE 597

δ (ppm)=2.85 (dd, 1H); 3.0 (dd, 1H); 3.95 (s, 3H); 5.5 (q, 1H); 6.25 (s, 1H); 7.3-8.6 (several m, 13H); 8.75 (d, 1H)

EXAMPLE 603

δ (ppm)=2.8 (dd, 1H); 3.0 (dd, 1H); 3.2 (s, 3H); 5.45 (q, 1H); 5.8 (s, 1H); 7.3 (t, 1H); 7.4 (t, 1H); 7.55 (m, 2H); 7.6 (d, 2H); 7.85 (d, 2H); 8.75 (d, 1H)

EXAMPLE 607

δ (ppm)=2.4 (s, 3H); 2.6 (dd, 1H); 2.8 (dd, 1H); 5.6 (m, H); 5.8 (s, 1H); 7.1 (m, 3H); 7.4 (m, 1H); 7.6 (d, 1H); 7.8 (m, 1H); 7.9 (m, 1H); 8.1 (m, 1H); 8.6 (d, 1H)

EXAMPLE 618

δ (ppm)=1.05 (t, 3H); 2.4 (s, 3H); 2.8 (dd, 1H); 2.95 (dd, 1H); 3.9 (s, 3H); 4.0 (q, 2H); 5.5 (q, 1H); 6.2 (s, 1H); 7.1 (m, 3H); 7.35 (m, 1H); 7.45 (m, 2H); 7.55 (m, 2H); 8.7 (d, 1H)

EXAMPLE 672

δ (ppm)=2.4 (s, 3H); 2.7 (dd, 1H); 2.9 (dd, 1H); 3.7 (s, 3H); 3.9 (s, 3H); 5.6 (q, 1H); 6.2 (s, 1H); 6.7 (m, 2H); 7.35 (m, 2H); 7.45 (m, 1H); 7.55 (m, 2H); 8.55 (d, 1H)

EXAMPLE 680

δ (ppm)=3.0 (m, 2H); 3.9 (s, 3H); 5.8 (m, 1H); 6.2 (s, 1H); 7.45 (m, 1H); 7.55 (m, 2H); 7.5-7.7 (m, 4H); 7.8 (m, 1H); 8.9 (d, 1H)

EXAMPLE 682

δ (ppm)=2.2 (s, 3H); 2.3 (s, 3H); 2.65 (dd, 1H); 2.9 (dd, 1H); 3.9 (s, 3H); 5.7 (q, 1H); 6.2 (s, 1H); 7.0 (m, 2H); 7.3 (m, 1H); 7.35 (m, 1H); 7.45 (m, 1H); 7.55 (m, 2H); 8.6 (d, 1H)

EXAMPLE 684

δ (ppm)=0.3 (m, 2H); 0.5 (m, 2H); 1.2 (m, 1H); 2.3 (s, 3H); 2.75 (dd, 1H); 2.9 (dd, 1H); 4.0 (d, 2H); 5.6 (q, 1H); 6.2 (s, 1H); 7.0 (m, 1H); 7.2 (m, 1H); 7.3 (m, 1H); 7.35 (m, 1H); 7.45 (m, 1H); 7.55 (m, 2H); 8.75 (d, 1H)

EXAMPLE 690

δ (ppm)=0.3 (m, 2H); 0.5 (m, 2H); 1.2 (m, 1H); 2.25 (s, 3H); 2.7 (dd, 1H); 2.9 (dd, 1H); 4.0 (d, 2H); 5.3 (q, 1H); 6.2 (s, 1H); 7.0 (m, 1H); 7.2 (m, 2H); 7.35 (m, 1H); 7.45 (m, 1H); 7.55 (m, 2H); 8.6 (d, 2H)

EXAMPLE 700

δ (ppm)=1.1 (s, 9H); 2.4 (s, 3H); 2.7 (dd, 1H); 2.9 (dd, 1H); 5.25 (s, 2H); 5.6 (q, 1H); 6.1 (s, 1H); 7.1 (m, 3H); 7.35 (m, 1H); 7.45 (m, 2H); 7.55-7.7 (m, 2H); 8.7 (d, 1H)

EXAMPLE 744

δ (ppm)=0.8 (s, 9H); 2.45 (s, 3H); 2.7 (m, 1H); 2.9 (m, 1H); 3.9 (m, 1H); 4.2 (m, 1H); 4.9 (m, 1H); 5.6 (q, 1H); 6.2 (s, 1H); 7.1 (m, 3H); 7.35 (m, 1H); 7.45 (m, 2H); 7.55 (m, 2H); 8.65 (d, 1H)

EXAMPLE 751

δ (ppm)=1.05 (s, 6H); 2.65 (dd, 1H); 2.9 (dd, 1H); 3.9 (s, 2H); 5.7 (m, 1H); 6.2 (s, 1H); 7.3-7.6 (m, 7H); 8.8 (d, 1H)

EXAMPLE 757

δ (ppm)=0.1-0.25 (m, 3H); 0.3 (m, 1H); 0.7 (m, 1H); 1.05 (s, 3H); 2.4 (s, 3H); 2.7 (dd, 1H); 2.9 (m, 1H); 3.9 (m, 2H); 5.6 (m, 1H); 6.2 (s, 1H); 7.1 (m, 3H); 7.35 (m, 1H); 7.45 (m, 2H); 7.6 (m, 2H); 8.6 (d, 1H)

EXAMPLE 758

δ (ppm)=0.8 (s, 9H); 1.05 (s, 3H); 2.65 (dd, 1H); 2.9 (dd, 1H); 3.95 (d, 1H); 4.1 (d, 1H); 5.75 (m, 1H); 6.2 (s, 1H); 7.3-7.6 (m, 8H); 8.8 (d, 1H)

EXAMPLE 759

δ (ppm)=0.8 (s, 9H); 1.0 (s, 3H); 2.65 (dd, 1H); 2.9 (m, 1H); 4.0 (d, 1H); 4.1 (d, 1H); 5.75 (m, 1H); 6.25 (s, 1H); 7.25-7.6 (m, 8H); 8.8 (d, 1H)

EXAMPLE 762

δ (ppm)=0.7 (t, 6H); 1.3 (m, 4H); 2.65 (dd, 1H); 2.9 (dd, 1H); 3.9 (s, 2H); 5.7 (m, 1H); 6.2 (s, 1H); 7.3-7.6 (m, 7H); 8.85 (d, 1H)

Pharmacological Tests a) Cathepsin A Inhibitory Activity

Recombinant human cathepsin A (residues 29-480, with a C-terminal 10-His tag; R&D Systems, #1049-SE) was proteolytically activated with recombinant human cathepsin L (R&D Systems, #952-CY). Briefly, cathepsin A was incubated at 10 μg/ml with cathepsin L at 1 μg/ml in activation buffer (25 mM 2-(morpholin-4-yl)-ethanesulfonic acid (MES), pH 6.0, containing 5 mM dithiothreitol (DTT)) for 15 min at 37° C. Cathepsin L activity was then stopped by the addition of the cysteine protease inhibitor E-64 (N-(trans-epoxysuccinyl)-L-leucine-4-guanidinobutylamide; Sigma-Aldrich, #E3132; dissolved in activation buffer/DMSO) to a final concentration of 10 μM.

The activated cathepsin A was diluted in assay buffer (25 mM MES, pH 5.5, containing 5 mM DTT) and mixed with the test compound (dissolved in assay buffer containing (v/v) 3% DMSO) or, in the control experiments, with the vehicle in a multiple assay plate. After incubation for 15 min at room temperature, as substrate then bradykinin carrying an N-terminal®Bodipy FL (4,4-difluoro-5,7-dimethyl-4-bora-3a,4a-diaza-s-indacene-3-propionyl) label (JPT Peptide Technologies GmbH; dissolved in assay buffer) was added to the mixture. The final concentration of cathepsin A was 833 ng/ml and the final concentration of labeled bradykinin 2 μM. After incubation for 15 min at room temperature the reaction was stopped by the addition of stop buffer (130 mM 2-(4-(2-hydroxy-ethyl)-piperazin-1-yl)-ethanesulfonic acid, pH 7.4, containing (v/v) 0.013% Triton X-100, 0.13% Coating Reagent 3 (Caliper Life Sciences), 6.5% DMSO and 20 μM ebelactone B (Sigma, # E0886)).

Uncleaved substrate and product were then separated by a microfluidic capillary electrophoresis on a LabChip® 3000 Drug Discovery System (12-Sipper-Chip; Caliper Life Sciences) and quantified by determination of the respective peak areas. Substrate turnover was calculated by dividing product peak area by the sum of substrate and product peak areas, and the enzyme activity and the inhibitory effect of the test compound thus quantified. From the percentage of inhibition of cathepsin A activity observed with the test compound at several concentrations, the inhibitory concentration $IC_{50}$, i.e. the concentration which effects 50% inhibition of enzyme activity was, calculated. $IC_{50}$ values of various example compounds are given in Table 1, wherein "A" means an $IC_{50}$ value of less than 0.1 μM, "B" means an $IC_{50}$ value between 0.1 μM and 1 μM, and "C" means an $IC_{50}$ value between 1 μM and 30 μM.

B) In Vivo Antihypertrophic and Renoprotective Activity

The in vivo pharmacological activity of the compounds of the invention can be investigated, for example, in the model of DOCA-salt sensitive rats with unilateral nephrectomy. Briefly, in this model unilateral nephrectomy of the left kidney (UNX) is performed on Sprague Dawley rats of 150 g to 200 g of body weight. After the operation as well as at the beginning of each of the following weeks 30 mg/kg of body weight of DOCA (desoxycorticosterone acetate) are administered to the rats by subcutaneous injection. The nephrectomized rats treated with DOCA are supplied with drinking water containing 1% of sodium chloride (UNX/DOCA rats). The UNX/DOCA rats develop high blood pressure, endothelial dysfunction, myocardial hypertrophy and fibrosis as well as renal dysfunction. In the test group (UNX/DOCA Test) and the placebo group (UNX/DOCA Placebo), which consist of randomized UNX/DOCA rats, the rats are treated orally by gavage in two part administrations at 6 a.m. and 6 p.m. with the daily dose of the test compound (for example 10 mg/kg of body weight dissolved in vehicle) or with vehicle only, respectively. In a control group (control), which consists of animals which have not been subjected to UNX and DOCA administration, the animals receive normal drinking water and are treated with vehicle only. After five weeks of treatment, systolic blood pressure (SBP) and heart rate (HR) are measured non-invasively via the tail cuff method. For determination of albuminuria and creatinine, 24 h urine is collected on metabolic cages. Endothelial function is assessed in excised rings of the thoracic aorta as described previously (W. Linz et al., JRAAS (Journal of the renin-angiotensin-aldosterone system) 7 (2006), 155-161). As a measure of myocardial hypertrophy and fibrosis, heart weight, left ventricular weight and the relation of hydroxyproline and proline are determined in excised hearts.

TABLE 2

Cathepsin A inhibitory activity IC$_{50}$

| Example | Compound Name | CATH-A IC$_{50}$ (μM) |
|---|---|---|
| 129 | (S)-3-{[1-(2-Fluoro-phenyl)-5-methoxy-1H-pyrazole-3-carbonyl]-amino}-3-o-tolyl-propionic acid | 0.041249 |
| 135 | (S)-3-{[1-(2-Chloro-phenyl)-5-hydroxy-1H-pyrazole-3-carbonyl]-amino}-3-p-tolyl-propionic acid | 0.210567 |
| 221 | 3-{[1-(2-Chloro-phenyl)-5-hydroxy-1H-pyrazole-3-carbonyl]-amino}-3-(2-fluoro-3-trifluoromethyl-phenyl)-propionic acid | 0.322137 |
| 385 | 3-{[1-(2,4-Difluoro-phenyl)-5-hydroxy-1H-pyrazole-3-carbonyl]-amino}-3-(2-fluoro-3-trifluoromethyl-phenyl)-propionic acid | 0.060742 |
| 418 | 3-{[1-(3-Chloro-phenyl)-5-hydroxy-1H-pyrazole-3-carbonyl]-amino}-3-(2-fluoro-3-trifluoromethyl-phenyl)-propionic acid | 5.287222 |
| 441 | 3-(2-Fluoro-6-methoxy-phenyl)-3-[(5-hydroxy-1-phenyl-1H-pyrazole-3-carbonyl)-amino]-propionic acid | 0.513333 |
| 443 | 3-(5-Fluoro-2-trifluoromethyl-phenyl)-3-[(5-hydroxy-1-phenyl-1H-pyrazole-3-carbonyl)-amino]-propionic acid | 0.220464 |
| 444 | 3-(2,5-Dichloro-phenyl)-3-[(5-hydroxy-1-phenyl-1H-pyrazole-3-carbonyl)-amino]-propionic acid | 0.083052 |
| 445 | (S)-3-[(5-Hydroxy-1-phenyl-1H-pyrazole-3-carbonyl)-amino]-3-p-tolyl-propionic acid | 0.129975 |
| 446 | (S)-3-(2-Chloro-phenyl)-3-[(5-hydroxy-1-phenyl-1H-pyrazole-3-carbonyl)-amino]-propionic acid | 0.120455 |
| 447 | 3-{[1-(2,4-Difluoro-phenyl)-5-hydroxy-1H-pyrazole-3-carbonyl]-amino}-3-(3-fluoro-2-methyl-phenyl)-propionic acid | 0.114465 |
| 448 | 3-(2-Chloro-4-dimethylamino-phenyl)-3-{[1-(2,4-difluoro-phenyl)-5-hydroxy-1H-pyrazole-3-carbonyl]-amino}-propionic acid | 0.883729 |
| 449 | 3-{[1-(2,4-Difluoro-phenyl)-5-hydroxy-1H-pyrazole-3-carbonyl]-amino}-3-(2-fluoro-6-methoxy-phenyl)-propionic acid | 0.175869 |
| 450 | 3-(2,2-Difluoro-benzo[1,3]dioxol-4-yl)-3-{[1-(2,4-difluoro-phenyl)-5-hydroxy-1H-pyrazole-3-carbonyl]-amino}-propionic acid | 0.408735 |
| 451 | 3-(2,5-Difluoro-phenyl)-3-{[1-(2,4-difluoro-phenyl)-5-hydroxy-1H-pyrazole-3-carbonyl]-amino}-propionic acid | 0.232875 |
| 452 | 3-{[1-(2,4-Difluoro-phenyl)-5-hydroxy-1H-pyrazole-3-carbonyl]-amino}-3-(5-fluoro-2-trifluoromethyl-phenyl)-propionic acid | 0.138677 |
| 453 | 3-{[1-(2,4-Difluoro-phenyl)-5-hydroxy-1H-pyrazole-3-carbonyl]-amino}-3-(5-fluoro-2-methoxy-phenyl)-propionic acid | 0.248853 |
| 454 | (S)-3-{[1-(2,4-Difluoro-phenyl)-5-hydroxy-1H-pyrazole-3-carbonyl]-amino}-3-p-tolyl-propionic acid | 0.185593 |
| 455 | 3-{[1-(2-Chloro-phenyl)-5-hydroxy-1H-pyrazole-3-carbonyl]-amino}-3-(3-fluoro-2-methyl-phenyl)-propionic acid | 0.154288 |
| 457 | 3-{[1-(2-Chloro-phenyl)-5-hydroxy-1H-pyrazole-3-carbonyl]-amino}-3-(2-fluoro-6-methoxy-phenyl)-propionic acid | 0.170335 |
| 458 | 3-(2-Chloro-5-fluoro-phenyl)-3-{[1-(2-chloro-phenyl)-5-hydroxy-1H-pyrazole-3-carbonyl]-amino}-propionic acid | 0.2227 |
| 459 | 3-{[1-(2-Chloro-phenyl)-5-hydroxy-1H-pyrazole-3-carbonyl]-amino}-3-(2,5-difluoro-phenyl)-propionic acid | 0.128099 |
| 460 | 3-{[1-(2-Chloro-phenyl)-5-hydroxy-1H-pyrazole-3-carbonyl]-amino}-3-(5-fluoro-2-trifluoromethyl-phenyl)-propionic acid | 0.117776 |
| 461 | 3-{[1-(2-Chloro-phenyl)-5-hydroxy-1H-pyrazole-3-carbonyl]-amino}-3-(5-fluoro-2-methyl-phenyl)-propionic acid | 0.150702 |
| 462 | 3-{[1-(2-Chloro-phenyl)-5-hydroxy-1H-pyrazole-3-carbonyl]-amino}-3-(2,5-dichloro-phenyl)-propionic acid | 0.080429 |
| 463 | 3-(2-Chloro-4-dimethylamino-phenyl)-3-{[1-(3-chloro-phenyl)-5-hydroxy-1H-pyrazole-3-carbonyl]-amino}-propionic acid | 11.052896 |
| 464 | 3-{[1-(3-Chloro-phenyl)-5-hydroxy-1H-pyrazole-3-carbonyl]-amino}-3-(2,2-difluoro-benzo[1,3]dioxol-4-yl)-propionic acid | 0.27418 |
| 465 | 3-{[1-(3-Chloro-phenyl)-5-hydroxy-1H-pyrazole-3-carbonyl]-amino}-3-(2,5-difluoro-phenyl)-propionic acid | 0.738351 |
| 466 | 3-{[1-(3-Chloro-phenyl)-5-hydroxy-1H-pyrazole-3-carbonyl]-amino}-3-(5-fluoro-2-trifluoromethyl-phenyl)-propionic acid | 0.561884 |
| 467 | 3-{[1-(3-Chloro-phenyl)-5-hydroxy-1H-pyrazole-3-carbonyl]-amino}-3-(2-trifluoromethylsulfanyl-phenyl)-propionic acid | 2.24854 |
| 468 | 3-{[1-(4-Chloro-phenyl)-5-hydroxy-1H-pyrazole-3-carbonyl]-amino}-3-(3-fluoro-2-methyl-phenyl)-propionic acid | 0.279829 |
| 469 | 3-{[1-(4-Chloro-phenyl)-5-hydroxy-1H-pyrazole-3-carbonyl]-amino}-3-(2-fluoro-6-methoxy-phenyl)-propionic acid | 0.860051 |
| 470 | 3-(2-Chloro-5-fluoro-phenyl)-3-{[1-(4-chloro-phenyl)-5-hydroxy-1H-pyrazole-3-carbonyl]-amino}-propionic acid | 0.398363 |
| 471 | 3-{[1-(4-Chloro-phenyl)-5-hydroxy-1H-pyrazole-3-carbonyl]-amino}-3-(2,2-difluoro-benzo[1,3]dioxol-4-yl)-propionic acid | 0.486287 |
| 472 | 3-{[1-(4-Chloro-phenyl)-5-hydroxy-1H-pyrazole-3-carbonyl]-amino}-3-(2,5-difluoro-phenyl)-propionic acid | 4.087942 |
| 473 | 3-{[1-(4-Chloro-phenyl)-5-hydroxy-1H-pyrazole-3-carbonyl]-amino}-3-(5-fluoro-2-trifluoromethyl-phenyl)-propionic acid | 1.726107 |
| 474 | (S)-3-(2-Chloro-phenyl)-3-{[1-(4-chloro-phenyl)-5-hydroxy-1H-pyrazole-3-carbonyl]-amino}-propionic acid | 0.206959 |

TABLE 2-continued

Cathepsin A inhibitory activity $IC_{50}$

| Example | Compound Name | CATH-A $IC_{50}$ (μM) |
|---|---|---|
| 475 | 3-(2-Chloro-5-fluoro-phenyl)-3-{[1-(2-fluoro-phenyl)-5-hydroxy-1H-pyrazole-3-carbonyl]-amino}-propionic acid | 0.136696 |
| 492 | 3-(5-Fluoro-2-methyl-phenyl)-3-{[1-(4-fluoro-phenyl)-5-hydroxy-1H-pyrazole-3-carbonyl]-amino}-propionic acid | 0.175259 |
| 493 | 3-(2,5-Dichloro-phenyl)-3-{[1-(4-fluoro-phenyl)-5-hydroxy-1H-pyrazole-3-carbonyl]-amino}-propionic acid | 0.245667 |
| 494 | 3-(3-Fluoro-2-methyl-phenyl)-3-[(5-hydroxy-1-phenyl-1H-pyrazole-3-carbonyl)-amino]-propionic acid | 0.142178 |
| 495 | 3-(2-Chloro-5-fluoro-phenyl)-3-[(5-hydroxy-1-phenyl-1H-pyrazole-3-carbonyl)-amino]-propionic acid | 0.213013 |
| 496 | 3-(2,2-Difluoro-benzo[1,3]dioxol-4-yl)-3-[(5-hydroxy-1-phenyl-1H-pyrazole-3-carbonyl)-amino]-propionic acid | 0.166522 |
| 497 | 3-(5-Fluoro-2-methyl-phenyl)-3-[(5-hydroxy-1-phenyl-1H-pyrazole-3-carbonyl)-amino]-propionic acid | 0.145434 |
| 498 | 3-(5-Fluoro-2-methoxy-phenyl)-3-[(5-hydroxy-1-phenyl-1H-pyrazole-3-carbonyl)-amino]-propionic acid | 0.142545 |
| 499 | 3-[(5-Hydroxy-1-phenyl-1H-pyrazole-3-carbonyl)-amino]-3-(4-pyridin-2-yl-phenyl)-propionic acid; compound with trifluoro-acetic acid | 0.147004 |
| 500 | 3-(2,5-Dichloro-phenyl)-3-{[1-(2,4-difluoro-phenyl)-5-hydroxy-1H-pyrazole-3-carbonyl]-amino}-propionic acid | 0.086296 |
| 502 | (S)-3-(2-Chloro-phenyl)-3-{[1-(2,4-difluoro-phenyl)-5-hydroxy-1H-pyrazole-3-carbonyl]-amino}-propionic acid | 0.116138 |
| 503 | 3-{[1-(2-Chloro-phenyl)-5-hydroxy-1H-pyrazole-3-carbonyl]-amino}-3-(2,2-difluoro-benzo[1,3]dioxol-4-yl)-propionic acid | 0.391391 |
| 504 | 3-{[1-(2-Chloro-phenyl)-5-hydroxy-1H-pyrazole-3-carbonyl]-amino}-3-(5-fluoro-2-methoxy-phenyl)-propionic acid | 0.123363 |
| 505 | 3-{[1-(2-Chloro-phenyl)-5-hydroxy-1H-pyrazole-3-carbonyl]-amino}-3-(4-morpholin-4-yl-phenyl)-propionic acid | 29.754902 |
| 506 | 3-{[1-(2-Chloro-phenyl)-5-hydroxy-1H-pyrazole-3-carbonyl]-amino}-3-(4-pyridin-2-yl-phenyl)-propionic acid | 0.05236 |
| 507 | (S)-3-(2-Chloro-phenyl)-3-{[1-(2-chloro-phenyl)-5-hydroxy-1H-pyrazole-3-carbonyl]-amino}-propionic acid | 0.160998 |
| 508 | 3-{[1-(3-Chloro-phenyl)-5-hydroxy-1H-pyrazole-3-carbonyl]-amino}-3-(3-fluoro-2-methyl-phenyl)-propionic acid | 0.136863 |
| 509 | 3-(2-Chloro-5-fluoro-phenyl)-3-{[1-(3-chloro-phenyl)-5-hydroxy-1H-pyrazole-3-carbonyl]-amino}-propionic acid | 0.100369 |
| 510 | 3-{[1-(3-Chloro-phenyl)-5-hydroxy-1H-pyrazole-3-carbonyl]-amino}-3-(5-fluoro-2-methyl-phenyl)-propionic acid | 0.175019 |
| 511 | 3-{[1-(3-Chloro-phenyl)-5-hydroxy-1H-pyrazole-3-carbonyl]-amino}-3-(2,5-dichloro-phenyl)-propionic acid | 0.101707 |
| 512 | (S)-3-{[1-(3-Chloro-phenyl)-5-hydroxy-1H-pyrazole-3-carbonyl]-amino}-3-p-tolyl-propionic acid | 0.155051 |
| 513 | 3-{[1-(3-Chloro-phenyl)-5-hydroxy-1H-pyrazole-3-carbonyl]-amino}-3-(4-pyridin-2-yl-phenyl)-propionic acid | 0.194548 |
| 514 | (S)-3-(2-Chloro-phenyl)-3-{[1-(3-chloro-phenyl)-5-hydroxy-1H-pyrazole-3-carbonyl]-amino}-propionic acid | 0.303517 |
| 515 | 3-{[1-(4-Chloro-phenyl)-5-hydroxy-1H-pyrazole-3-carbonyl]-amino}-3-(4-pyridin-2-yl-phenyl)-propionic acid | 0.238394 |
| 516 | 3-(3-Fluoro-2-methyl-phenyl)-3-{[1-(2-fluoro-phenyl)-5-hydroxy-1H-pyrazole-3-carbonyl]-amino}-propionic acid | 0.10191 |
| 525 | 3-(5-Fluoro-2-methoxy-phenyl)-3-{[1-(4-fluoro-phenyl)-5-hydroxy-1H-pyrazole-3-carbonyl]-amino}-propionic acid | 1.505027 |
| 526 | (S)-3-{[1-(4-Fluoro-phenyl)-5-hydroxy-1H-pyrazole-3-carbonyl]-amino}-3-p-tolyl-propionic acid | 0.357948 |
| 527 | 3-{[1-(4-Fluoro-phenyl)-5-hydroxy-1H-pyrazole-3-carbonyl]-amino}-3-(4-pyridin-2-yl-phenyl)-propionic acid | 0.152264 |
| 528 | (S)-3-(2-Chloro-phenyl)-3-{[1-(4-fluoro-phenyl)-5-hydroxy-1H-pyrazole-3-carbonyl]-amino}-propionic acid | 0.413048 |
| 545 | 3-[(5-Hydroxy-1-phenyl-1H-pyrazole-3-carbonyl)-amino]-3-(3-methoxy-biphenyl-4-yl)-propionic acid | 1.112898 |
| 546 | 3-[(5-Hydroxy-1-phenyl-1H-pyrazole-3-carbonyl)-amino]-3-(4-methoxy-2-trifluoromethyl-phenyl)-propionic acid | 0.532645 |
| 547 | 3-(2-Fluoro-5-methoxy-phenyl)-3-[(5-hydroxy-1-phenyl-1H-pyrazole-3-carbonyl)-amino]-propionic acid | 1.388069 |
| 548 | 3-[(5-Hydroxy-1-phenyl-1H-pyrazole-3-carbonyl)-amino]-3-(2-methoxy-5-trifluoromethyl-phenyl)-propionic acid | 7.759644 |
| 549 | 3-[(5-Hydroxy-1-phenyl-1H-pyrazole-3-carbonyl)-amino]-3-(4-methoxy-biphenyl-3-yl)-propionic acid | 13.812548 |
| 550 | 3-{[1-(2-Fluoro-phenyl)-5-hydroxy-1H-pyrazole-3-carbonyl]-amino}-3-(4-[1,2,4]triazol-1-yl-phenyl)-propionic acid | 0.635486 |
| 551 | 3-{[1-(2-Fluoro-phenyl)-5-hydroxy-1H-pyrazole-3-carbonyl]-amino}-3-(3-methoxy-biphenyl-4-yl)-propionic acid | 0.352071 |
| 552 | 3-{[1-(2-Fluoro-phenyl)-5-hydroxy-1H-pyrazole-3-carbonyl]-amino}-3-(4-methoxy-2-trifluoromethyl-phenyl)-propionic acid | 0.323441 |

TABLE 2-continued

Cathepsin A inhibitory activity IC$_{50}$

| Example | Compound Name | CATH-A IC$_{50}$ (μM) |
|---|---|---|
| 553 | 3-(2-Fluoro-5-methoxy-phenyl)-3-{[1-(2-fluoro-phenyl)-5-hydroxy-1H-pyrazole-3-carbonyl]-amino}-propionic acid | 0.732366 |
| 554 | 3-{[1-(2-Fluoro-phenyl)-5-hydroxy-1H-pyrazole-3-carbonyl]-amino}-3-(2-methoxy-5-trifluoromethyl-phenyl)-propionic acid | 1.843808 |
| 555 | 3-(2-Fluoro-4-methyl-phenyl)-3-{[1-(2-fluoro-phenyl)-5-hydroxy-1H-pyrazole-3-carbonyl]-amino}-propionic acid | 0.238578 |
| 556 | 3-{[1-(2-Fluoro-phenyl)-5-hydroxy-1H-pyrazole-3-carbonyl]-amino}-3-(4-methoxy-biphenyl-3-yl)-propionic acid | 8.652812 |
| 557 | 3-{[1-(2-Chloro-phenyl)-5-hydroxy-1H-pyrazole-3-carbonyl]-amino}-3-(4-[1,2,4]triazol-1-yl-phenyl)-propionic acid | 0.839178 |
| 558 | 3-{[1-(2-Chloro-phenyl)-5-hydroxy-1H-pyrazole-3-carbonyl]-amino}-3-(3-methoxy-biphenyl-4-yl)-propionic acid | 0.699161 |
| 559 | 3-{[1-(2-Chloro-phenyl)-5-hydroxy-1H-pyrazole-3-carbonyl]-amino}-3-(2-fluoro-5-methoxy-phenyl)-propionic acid | 0.731295 |
| 560 | 3-{[1-(2-Chloro-phenyl)-5-hydroxy-1H-pyrazole-3-carbonyl]-amino}-3-(2-methoxy-5-trifluoromethyl-phenyl)-propionic acid | 7.623283 |
| 561 | 3-{[1-(2-Chloro-phenyl)-5-hydroxy-1H-pyrazole-3-carbonyl]-amino}-3-(2-fluoro-4-methyl-phenyl)-propionic acid | 0.265803 |
| 562 | 3-{[1-(2-Chloro-phenyl)-5-hydroxy-1H-pyrazole-3-carbonyl]-amino}-3-(4-methoxy-biphenyl-3-yl)-propionic acid | 4.493781 |
| 563 | 3-[(5-Hydroxy-1-phenyl-1H-pyrazole-3-carbonyl)-amino]-3-(4-[1,2,4]triazol-1-yl-phenyl)-propionic acid | 1.74027 |
| 564 | 3-(2-Fluoro-4-methyl-phenyl)-3-[(5-hydroxy-1-phenyl-1H-pyrazole-3-carbonyl)-amino]-propionic acid | 0.458522 |
| 565 | 3-[(5-Hydroxy-1-phenyl-1H-pyrazole-3-carbonyl)-amino]-3-(4-pyrrolidin-1-yl-phenyl)-propionic acid | 5.022589 |
| 566 | 3-{[1-(2-Fluoro-phenyl)-5-hydroxy-1H-pyrazole-3-carbonyl]-amino}-3-(4-pyrrolidin-1-yl-phenyl)-propionic acid | 2.986143 |
| 567 | 3-{[1-(2-Chloro-phenyl)-5-hydroxy-1H-pyrazole-3-carbonyl]-amino}-3-(4-methoxy-2-trifluoromethyl-phenyl)-propionic acid | 1.062689 |
| 568 | 3-{[1-(2-Chloro-phenyl)-5-hydroxy-1H-pyrazole-3-carbonyl]-amino}-3-(4-pyrrolidin-1-yl-phenyl)-propionic acid | 2.354354 |
| 745 | (S)-3-{[1-(2-Fluoro-phenyl)-5-((R)-2-hydroxy-3,3-dimethyl-butoxy)-1H-pyrazole-3-carbonyl]-amino}-3-o-tolyl-propionic acid | 0.004703 |
| 747 | (S)-3-{[1-(2-Fluoro-phenyl)-5-((R)-2-hydroxy-2,3,3-trimethyl-butoxy)-1H-pyrazole-3-carbonyl]-amino}-3-o-tolyl-propionic acid | 0.014724 |
| 748 | (S)-3-{[1-(2-Fluoro-phenyl)-5-((S)-2-hydroxy-2,3,3-trimethyl-butoxy)-1H-pyrazole-3-carbonyl]-amino}-3-o-tolyl-propionic acid | 0.002558 |
| 753 | (S)-3-(2,4-Dichloro-phenyl)-3-{[1-(2-fluoro-phenyl)-5-((R)-2-hydroxy-3,3-dimethyl-butoxy)-1H-pyrazole-3-carbonyl]-amino}-propionic acid | 0.3449 |
| 758 | (S)-3-(2-Chloro-phenyl)-3-{[1-(2-fluoro-phenyl)-5-((R)-2-hydroxy-2,3,3-trimethyl-butoxy)-1H-pyrazole-3-carbonyl]-amino}-propionic acid | 0.01742 |
| 766 | (S)-3-{[1-(2-Fluoro-phenyl)-5-((S)-2-hydroxy-2,3-dimethyl-butoxy)-1H-pyrazole-3-carbonyl]-amino}-3-p-tolyl-propionic acid | 0.000692 |
| 768 | (S)-3-(4-Fluoro-phenyl)-3-{[1-(2-fluoro-phenyl)-5-((R)-2-hydroxy-2,3-dimethyl-butoxy)-1H-pyrazole-3-carbonyl]-amino}-propionic acid | 0.00115 |
| 771 | (S)-3-(4-Fluoro-phenyl)-3-{[1-(2-fluoro-phenyl)-5-((R)-2-hydroxy-2,3,3-trimethyl-butoxy)-1H-pyrazole-3-carbonyl]-amino}-propionic acid | 0.00197 |
| 803 | 3-Cyclohexyl-3-{[1-(2-fluoro-phenyl)-5-((S)-2-hydroxy-2,3-dimethyl-butoxy)-1H-pyrazole-3-carbonyl]-amino}-propionic acid | 0.0267 |
| 860 | (S)-3-{[1-(2-Fluoro-phenyl)-5-((R)-2-hydroxy-2,3-dimethyl-butoxy)-1H-pyrazole-3-carbonyl]-amino}-3-p-tolyl-propionic acid | 0.0761 |
| 870 | (S)-3-{[1-(2-Fluoro-phenyl)-5-((S)-2-hydroxy-2,3-dimethyl-butoxy)-1H-pyrazole-3-carbonyl]-amino}-3-o-tolyl-propionic acid | 0.076 |

The invention claimed is:

1. A compound of the formula I, in any of its stereoisomeric forms or a mixture of stereoisomeric forms in any ratio, or a physiologically acceptable salt thereof, or a physiologically acceptable solvate of any of them,

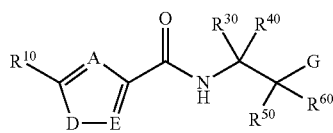

wherein
- A is chosen from the series consisting of $C(R^1)$ and N;
- D is chosen from the series consisting of $N(R^2)$, O and S;
- E is chosen from the series consisting of $C(R^3)$ and N;
- G is chosen from the series consisting of $R^{71}$—O—C(O)—, $R^{72}$—$N(R^{73})$—C(O)—, NC— and tetrazol-5-yl;
- $R^1$ is chosen from the series consisting of hydrogen, halogen, $(C_1\text{-}C_6)$-alkyl, Ar, HO—, $(C_1\text{-}C_6)$-alkyl-O—, $(C_1\text{-}C_6)$-alkyl-$S(O)_m$— and NC—;
- $R^2$ is chosen from the series consisting of $(C_1\text{-}C_7)$-alkyl, $(C_3\text{-}C_7)$-cycloalkyl-$C_sH_{2s}$— and Ar—$C_sH_{2s}$—, wherein s is an integer chosen from the series consisting of 0, 1, 2 and 3;
- $R^3$ is chosen from the series consisting of hydrogen, halogen, $(C_1\text{-}C_6)$-alkyl, $(C_1\text{-}C_6)$-alkyl-O—, $(C_1\text{-}C_6)$-alkyl-$S(O)_m$— and NC—;
- $R^{10}$ is chosen from the series consisting of $R^{11}$—O—, $R^{12}$—$N(R^{13})$—C(O)—O— and $Het^2$—C(O)—O—;
- $R^{11}$ is chosen from the series consisting of hydrogen, $R^{14}$, $(C_3\text{-}C_7)$-cycloalkyl, Ar and $Het^3$;
- $R^{12}$ and $R^{13}$ are independently of each other chosen from the series consisting of hydrogen, $R^{15}$ and Ar;
- $R^{14}$ is $(C_1\text{-}C_{10})$-alkyl which is optionally substituted by one or more identical or different substituents chosen from the series consisting of halogen, HO—, $R^{16}$—O—, oxo, $(C_3\text{-}C_7)$-cycloalkyl, Ar, $Het^1$, $Het^3$, NC—, $H_2N$—C(O)—, $(C_1\text{-}C_4)$-alkyl-NH—C(O)—, $di((C_1\text{-}C_4)$-alkyl)N—C(O)—, $Het^1$—C(O)—, $(C_1\text{-}C_4)$-alkyl-C(O)—NH— and $(C_1\text{-}C_4)$-alkyl-$S(O)_m$—;
- $R^{15}$ is $(C_1\text{-}C_6)$-alkyl which is optionally substituted by one or more identical or different substituents chosen from the series consisting halogen, HO— and $(C_1\text{-}C_6)$-alkyl-O—;
- $R^{16}$ is $(C_1\text{-}C_6)$-alkyl which is optionally substituted by one or more identical or different substituents chosen from the series consisting of HO—, $(C_1\text{-}C_4)$-alkyl-O— and NC—;
- $R^{30}$ is chosen from the series consisting of $R^{31}$, $(C_3\text{-}C_7)$-cycloalkyl, $R^{32}$—$C_uH_{2u}$— and $Het^3$—$C_uH_{2u}$—, wherein u is an integer chosen from the series consisting of 0, 1, 2 and 3;
- $R^{31}$ is $(C_1\text{-}C_{10})$-alkyl which is optionally substituted by one or more identical or different substituents chosen from the series consisting of halogen, $(C_3\text{-}C_7)$-cycloalkyl, HO—, $(C_1\text{-}C_6)$-alkyl-O—, $(C_1\text{-}C_6)$-alkyl-$S(O)_m$— and NC—;
- $R^{32}$ is chosen from the series consisting of phenyl and an aromatic 5-membered or 6-membered monocyclic heterocycle which comprises one, two or three identical or different ring heteroatoms chosen from the series consisting of nitrogen, oxygen and sulfur and is bonded via a ring carbon atom, wherein the phenyl and the heterocycle all are optionally substituted by one or more identical or different substituents chosen from the series consisting of halogen, $(C_1\text{-}C_6)$-alkyl, $(C_3\text{-}C_7)$-cycloalkyl, $R^{33}$, HO—, $(C_1\text{-}C_6)$-alkyl-O—, $R^{33}$—O—, $R^{33}$—$(C_1\text{-}C_4)$-alkyl-O—, —O—$CH_2$—O—, —O—$CF_2$—O—, $(C_1\text{-}C_6)$-alkyl-$S(O)_m$, $H_2N$—$S(O)_2$—, $(C_1\text{-}C_4)$-alkyl-NH—$S(O)_2$—, $di((C_1\text{-}C_4)$-alkyl)N—$S(O)_2$—, $H_2N$—, $(C_1\text{-}C_6)$-alkyl-NH—, $di((C_1\text{-}C_6)$-alkyl)N—, $Het^1$, $(C_1\text{-}C_4)$-alkyl-C(O)—NH—, Ar—C(O)—NH—, $(C_1\text{-}C_4)$-alkyl-$S(O)_2$—NH— and NC—;
- $R^{33}$ is chosen from the series consisting of phenyl and an aromatic 5-membered or 6-membered monocyclic heterocycle which comprises one, two or three identical or different ring heteroatoms chosen from the series consisting of nitrogen, oxygen and sulfur and is bonded via a ring carbon atom, wherein the phenyl and the heterocycle all are optionally substituted by one or more identical or different substituents chosen from the series consisting of halogen, $(C_1\text{-}C_6)$-alkyl, $(C_3\text{-}C_7)$-cycloalkyl, HO—, $(C_1\text{-}C_6)$-alkyl-O—, $(C_1\text{-}C_6)$-alkyl-$S(O)_m$—, $H_2N$—$S(O)_2$—, $(C_1\text{-}C_4)$-alkyl-NH—$S(O)_2$—, $di((C_1\text{-}C_4)$-alkyl)N—$S(O)_2$— and NC—;
- $R^{40}$ is chosen from the series consisting of hydrogen and $(C_1\text{-}C_4)$-alkyl;
- or $R^{30}$ and $R^{40}$ together are $(CH_2)_x$ which is optionally substituted by one or more identical or different $(C_1\text{-}C_4)$-alkyl substituents, wherein x is an integer chosen from the series consisting of 2, 3, 4 and 5;
- $R^{50}$ is chosen from the series consisting of hydrogen, $(C_1\text{-}C_6)$-alkyl, HO— and $(C_1\text{-}C_6)$-alkyl-O—;
- $R^{60}$ is chosen from the series consisting of hydrogen and $(C_1\text{-}C_6)$-alkyl;
- or $R^{50}$ and $R^{60}$ together are $(CH_2)_y$ which is optionally substituted by one or more identical or different $(C_1\text{-}C_4)$-alkyl substituents, wherein y is an integer chosen from the series consisting of 2, 3, 4 and 5;
- $R^{71}$ is chosen from the series consisting of hydrogen and $(C_1\text{-}C_8)$-alkyl which is optionally substituted by one or more identical or different substituents chosen from the series consisting $(C_1\text{-}C_6)$-alkyl-O— and $(C_1\text{-}C_6)$-alkyl-C(O)—O—;
- $R^{72}$ is chosen from the series consisting of hydrogen, $(C_1\text{-}C_6)$-alkyl, $(C_3\text{-}C_6)$-cycloalkyl, —$CH_2$—$(CH_2)_b$—$(C_3\text{-}C_6)$-cycloalkyl, $Het^4$ and —$(CH_2)_b$—$Het^4$, where alkyl or cycloalkyl is optionally substituted by one or more identical or different substituents chosen from the series consisting of halogen, HO—, HOOC—, $(C_1\text{-}C_6)$-alkyl-O— and $(C_1\text{-}C_6)$-alkyl-C(O)—O—, NC—, $N((C_1\text{-}C_4)$-alkyl$)_2$ and b is 0, 1 or 2;
- $R^{73}$ is chosen from the series consisting of hydrogen, $(C_1\text{-}C_6)$-alkyl; or
- $R^{72}$ and $R^{73}$ together with the nitrogen atom to which they are bonded form a saturated 4-membered to 7-membered monocyclic heterocycle, which contain optionally one further ring heteroatom chosen from the series consisting of nitrogen, oxygen and sulfur, which is optionally substituted by one or more identical or different substituents chosen from the series consisting of halogen, $(C_1\text{-}C_4)$-alkyl, HO— and $(C_1\text{-}C_4)$-alkyl-O—;
- Ar, independently of each other group Ar, is chosen from the series consisting of phenyl and an aromatic 5-membered or 6-membered monocyclic heterocycle which comprises one, two or three identical or different ring heteroatoms chosen from the series consisting of nitrogen, oxygen and sulfur and is bonded via a ring carbon atom, wherein the phenyl and the heterocycle all are optionally substituted by one or more identical or different substituents chosen from the series consisting of halogen, $(C_1-C_6)$-alkyl, $(C_1-C_6)$-alkyl-O—, —O—CH$_2$—O—, —O—CF$_2$—O—, $(C_1-C_6)$-alkyl-S(O)$_m$—, H$_2$N—S(O)$_2$— and NC—;

Het$^1$, independently of each other group Het$^1$, is a saturated or unsaturated 4-membered to 8-membered monocyclic heterocycle which comprises a ring nitrogen atom via which Het$^1$ is bonded and optionally one or two identical or different further ring heteroatoms chosen from the series consisting of nitrogen, oxygen and sulfur, which is optionally substituted by one or more identical or different substituents chosen from the series consisting of halogen, $(C_1-C_4)$-alkyl, HO—, $(C_1-C_4)$-alkyl-O—, oxo and NC—;

Het$^2$ is a saturated 4-membered to 7-membered monocyclic heterocycle which comprises a ring nitrogen atom via which Het$^2$ is bonded and optionally one further ring heteroatom chosen from the series consisting of nitrogen, oxygen and sulfur, which is optionally substituted by one or more identical or different substituents chosen from the series consisting of halogen, $(C_1-C_4)$-alkyl, HO— and $(C_1-C_4)$alkyl-O—;

Het$^3$, independently of each other group Het$^3$, is a saturated 4-membered to 7-membered monocyclic heterocycle which comprises one or two identical or different ring heteroatoms chosen from the series consisting of nitrogen, oxygen and sulfur and is bonded via a ring carbon atom, which is optionally substituted by one or more identical or different substituents chosen from the series consisting of fluorine, $(C_1-C_4)$-alkyl and oxo;

Het$^4$, independently of each other group Het$^4$, is a saturated or unsaturated 4-membered to 8-membered monocyclic heterocycle which comprises one to four ring heteroatoms chosen from the series consisting of nitrogen, oxygen and sulfur which is optionally substituted by one or more identical or different substituents chosen from the series consisting of halogen, $(C_1-C_4)$-alkyl, HO—, $(C_1-C_4)$-alkyl-O—, oxo and NC—;

m, independently of each other number m, is an integer chosen from the series consisting of 0, 1 and 2;

wherein all cycloalkyl groups, independently of each other, are optionally substituted by one or more identical or different substituents chosen from the series consisting of fluorine and $(C_1-C_4)$-alkyl;

wherein all alkyl, $C_sH_{2s}$, $C_uH_{2u}$, $(CH_2)_x$ and $(CH_2)_y$ groups, independently of each other, and independently of any other substituents, are optionally substituted by one or more fluorine substituents.

2. The compound of the formula I, in any of its stereoisomeric forms or a mixture of stereoisomeric forms in any ratio, or a physiologically acceptable salt thereof, or a physiologically acceptable solvate of any of them, as claimed in claim 1, wherein E is N.

3. The compound of the formula I, in any of its stereoisomeric forms or a mixture of stereoisomeric forms in any ratio, or a physiologically acceptable salt thereof, or a physiologically acceptable solvate of any of them, as claimed in claim 1, wherein D is N(R$^2$).

4. The compound of the formula I, in any of its stereoisomeric forms or a mixture of stereoisomeric forms in any ratio, or a physiologically acceptable salt thereof, or a physiologically acceptable solvate of any of them, as claimed in claim 1, wherein
A is chosen from the series consisting of C(R$^1$) and N;
D is N(R$^2$);
E is N;
R$^1$ is chosen from the series consisting of hydrogen, halogen and $(C_1-C_4)$-alkyl;
R$^2$ is Ar—C$_s$H$_{2s}$—, wherein s is an integer chosen from the series consisting of 0, 1 and 2.

5. The compound of the formula I, in any of its stereoisomeric forms or a mixture of stereoisomeric forms in any ratio, or a physiologically acceptable salt thereof, or a physiologically acceptable solvate of any of them, as claimed in claim 1, wherein R$^{10}$ is R$^{11}$—O—.

6. The compound of the formula I, in any of its stereoisomeric forms or a mixture of stereoisomeric forms in any ratio, or a physiologically acceptable salt thereof, or a physiologically acceptable solvate of any of them, as claimed in claim 1, wherein R$^{30}$ is R$^{32}$—C$_u$H$_{2u}$— wherein u is an integer chosen from the series consisting of 0 and 1.

7. The compound of the formula I, in any of its stereoisomeric forms or a mixture of stereoisomeric forms in any ratio, or a physiologically acceptable salt thereof, or a physiologically acceptable solvate of any of them, as claimed in claim 1, wherein
G is chosen from the series consisting of R$^{71}$—O—C(O)— and R$^{72}$—N(R$^{73}$)—C(O)—;
R$^{30}$ is R$^{32}$—C$_u$H$_{2u}$—, wherein u is an integer chosen from the series consisting of 0 and 1;
R$^{32}$ is chosen from the series consisting of phenyl and an aromatic 6-membered monocyclic heterocycle which comprises one or two nitrogen atoms as ring heteroatoms, wherein the phenyl and the heterocycle all are optionally substituted by one, two or three identical or different substituents chosen from the series consisting of halogen, $(C_1-C_6)$-alkyl, $(C_3-C_7)$-cycloalkyl, R$^{33}$, $(C_1-C_6)$-alkyl-O—, R$^{33}$—O—, R$^{33}$—$(C_1-C_4)$-alkyl-O—, —O—CH$_2$—O—, —O—CF$_2$—O—, $(C_1-C_6)$-alkyl-S(O)$_m$—, $(C_1-C_6)$-alkyl-NH—, di($(C_1-C_6)$-alkyl)N—, Het$^1$ and NC—;
R$^{33}$ is chosen from the series consisting of phenyl and pyridinyl which all are optionally substituted by one, two or three identical or different substituents chosen from the series consisting of halogen, $(C_1-C_4)$-alkyl, $(C_1-C_4)$-alkyl-O—, $(C_1-C_4)$-alkyl-S(O)$_m$— and NC—;
R$^{40}$ is hydrogen;
R$^{50}$ is hydrogen;
R$^{60}$ is hydrogen.

8. The compound of the formula I, in any of its stereoisomeric forms or a mixture of stereoisomeric forms in any ratio, or a physiologically acceptable salt thereof, or a physiologically acceptable solvate of any of them, as claimed in claim 1, wherein
A is chosen from the series consisting of C(R$^1$) and N;
D is N(R$^2$);
E is chosen from the series consisting of C(R$^3$) and N;
G is chosen from the series consisting of R$^{71}$—O—C(O)— and R$^{72}$—N(R$^{73}$)—C(O)—;
R$^1$ is chosen from the series consisting of hydrogen, halogen, $(C_1-C_6)$-alkyl, HO— and $(C_1-C_6)$-alkyl-O—;
R$^2$ is chosen from the series consisting of $(C_1-C_7)$-alkyl, $(C_3-C_7)$-cycloalkyl-C$_s$H$_{2s}$— and Ar—C$_s$H$_{2s}$—, wherein s is an integer chosen from the series consisting of 0, 1, 2 and 3;
R$^3$ is chosen from the series consisting of hydrogen, halogen, $(C_1-C_6)$-alkyl and $(C_1-C_6)$-alkyl-O—;
R$^{10}$ is chosen from the series consisting of R$^{11}$—O—, R$^{12}$—N(R$^{13}$)—C(O)—O— and Het$^2$—C(O)—O—;
R$^{11}$ is chosen from the series consisting of hydrogen, R$^{14}$, $(C_3-C_7)$-cycloalkyl and Het$^3$;
R$^{12}$ and R$^{13}$ are independently of each other chosen from the series consisting of hydrogen, R$^{15}$ and Ar;
R$^{14}$ is $(C_1-C_{10})$-alkyl which is optionally substituted by one or more identical or different substituents chosen from the series consisting of halogen, HO—, $R^{16}$—O—, oxo, $(C_3$-$C_7)$-cycloalkyl, Ar, $Het^1$, $Het^3$, NC—, $H_2N$—C(O)—, $(C_1$-$C_4)$-alkyl-NH—C(O)—, di(($C_1$-$C_4)$-alkyl)N—C(O)— and $Het^1$—C(O)—;

$R^{15}$ is $(C_1$-$C_6)$-alkyl;

$R^{16}$ is $(C_1$-$C_6)$-alkyl which is optionally substituted by one or more identical or different substituents chosen from the series consisting of HO— and $(C_1$-$C_4)$-alkyl-O—;

$R^{30}$ is chosen from the series consisting of $(C_3$-$C_7)$-cycloalkyl, $R^{32}$—$C_uH_{2u}$— and $Het^3$—$C_uH_{2u}$—, wherein u is an integer chosen from the series consisting of 0, 1, 2 and 3;

$R^{32}$ is chosen from the series consisting of phenyl and an aromatic 6-membered monocyclic heterocycle which comprises one or two nitrogen atoms as ring heteroatoms, wherein the phenyl and the heterocycle all are optionally substituted by one or more identical or different substituents chosen from the series consisting of halogen, $(C_1$-$C_6)$-alkyl, $(C_3$-$C_7)$-cycloalkyl, $R^{33}$, HO—, $(C_1$-$C_6)$-alkyl-O—, $R^{33}$—O—, $R^{33}$—$(C_1$-$C_4)$-alkyl-O—, —O—$CH_2$—O—, —O—$CF_2$—O—, $(C_1$-$C_6)$-alkyl-S(O)$_m$—, di(($C_1$-$C_4)$-alkyl)N—S(O)$_2$—, $H_2N$—, di(($C_1$-$C_6)$-alkyl)N—, $Het^1$, $(C_1$-$C_4)$-alkyl-C(O)—NH—, Ar—C(O)—NH— and NC—;

$R^{33}$ is chosen from the series consisting of phenyl and an aromatic 6-membered monocyclic heterocycle which comprises one or two nitrogen atoms as ring heteroatoms, wherein the phenyl and the heterocycle all are optionally substituted by one or more identical or different substituents chosen from the series consisting of halogen, $(C_1$-$C_6)$-alkyl, $(C_3$-$C_7)$-cycloalkyl, HO—, $(C_1$-$C_6)$-alkyl-O—, $(C_1$-$C_6)$-alkyl-S(O)$_m$—, $H_2N$—S(O)$_2$—, di(($C_1$-$C_4)$-alkyl)N—S(O)$_2$— and NC—;

$R^{40}$ is hydrogen;

$R^{50}$ is chosen from the series consisting of hydrogen and HO—;

$R^{60}$ is hydrogen;

$R^{71}$ is chosen from the series consisting of hydrogen and $(C_1$-$C_8)$-alkyl which is optionally substituted by one or more identical or different substituents chosen from the series consisting $(C_1$-$C_6)$-alkyl-O— and $(C_1$-$C_6)$-alkyl-C(O)—O—;

$R^{72}$ and $R^{73}$ are independently of each other chosen from the series consisting of hydrogen and $(C_1$-$C_4)$-alkyl;

Ar, independently of each other group Ar, is chosen from the series consisting of phenyl and an aromatic 5-membered or 6-membered monocyclic heterocycle which comprises one, two or three identical or different ring heteroatoms chosen from the series consisting of nitrogen, oxygen and sulfur and is bonded via a ring carbon atom, wherein the phenyl and the heterocycle all are optionally substituted by one or more identical or different substituents chosen from the series consisting of halogen, $(C_1$-$C_6)$-alkyl, $(C_1$-$C_6)$-alkyl-O—, —O—$CH_2$—O—, —O—$CF_2$—O—, $(C_1$-$C_6)$-alkyl-S(O)$_m$— and NC—;

$Het^1$, independently of each other group $Het^1$, is a saturated or unsaturated 4-membered to 8-membered monocyclic heterocycle which comprises a ring nitrogen atom via which $Het^1$ is bonded and optionally one or two identical or different further ring heteroatoms chosen from the series consisting of nitrogen, oxygen and sulfur, which is optionally substituted by one or more identical or different substituents chosen from the series consisting of halogen, $(C_1$-$C_4)$-alkyl, HO—, $(C_1$-$C_4)$-alkyl-O—, oxo and NC—;

$Het^2$ is a saturated 4-membered to 7-membered monocyclic heterocycle which comprises a ring nitrogen atom via which $Het^2$ is bonded and optionally one further ring heteroatom chosen from the series consisting of nitrogen, oxygen and sulfur, which is optionally substituted by one or more identical or different substituents chosen from the series consisting of halogen, $(C_1$-$C_4)$-alkyl, HO— and $(C_1$-$C_4)$-alkyl-O—;

$Het^3$, independently of each other group $Het^3$, is a saturated 4-membered to 7-membered monocyclic heterocycle which comprises one or two identical or different ring heteroatoms chosen from the series consisting of nitrogen, oxygen and sulfur and is bonded via a ring carbon atom, which is optionally substituted by one or more identical or different substituents chosen from the series consisting of fluorine, $(C_1$-$C_4)$-alkyl and oxo;

m, independently of each other number m, is an integer chosen from the series consisting of 0, 1 and 2;

wherein all cycloalkyl groups, independently of each other, are optionally substituted by one or more identical or different substituents chosen from the series consisting of fluorine and $(C_1$-$C_4)$-alkyl; p1 wherein all alkyl, $C_sH_{2s}$, $C_uH_{2u}$, $(CH_2)_x$ and $(CH_2)_y$ groups, independently of each other, and independently of any other substituents, are optionally substituted by one or more fluorine substituents.

9. The compound of the formula I, in any of its stereoisomeric forms or a mixture of stereoisomeric forms in any ratio, or a physiologically acceptable salt thereof, or a physiologically acceptable solvate of any of them, as claimed in claim 1, wherein A is $C(R^1)$;

D is $N(R^2)$;

E is N;

G is chosen from the series consisting of $R^{71}$—O—C(O)— and $R^{72}$—N($R^{73}$)—C(O)—;

$R^1$ is chosen from the series consisting of hydrogen, halogen and $(C_1$-$C_4)$-alkyl;

$R^2$ is Ar—$C_sH_{2s}$—, wherein s is 0;

$R^{10}$ is $R^{11}$—O—;

$R^{11}$ is chosen from the series consisting of hydrogen and $R^{14}$;

$R^{14}$ is $(C_1$-$C_{10})$-alkyl which is optionally substituted by one, two or three identical or different substituents chosen from the series consisting of HO—, $R^{16}$—O—, oxo, $(C_3$-$C_7)$-cycloalkyl, Ar, $Het^1$, di(($C_1$-$C_4)$-alkyl)N— and $Het^1$—C(O)—;

$R^{16}$ is $(C_1$-$C_6)$-alkyl which is optionally substituted by one or two identical or different substituents chosen from the series consisting of HO— and $(C_1$-$C_4)$-alkyl-O—;

$R^{30}$ is $R^{32}$—$C_uH_{2u}$—, wherein u is an integer chosen from the series consisting of 0 and 1;

$R^{32}$ is chosen from the series consisting of phenyl and an aromatic 6-membered monocyclic heterocycle which comprises one or two nitrogen atoms as ring heteroatoms, wherein the phenyl and the heterocycle all are optionally substituted by one, two or three identical or different substituents chosen from the series consisting of halogen, $(C_1$-$C_6)$-alkyl, $(C_3$-$C_7)$-cycloalkyl, $R^{33}$, $(C_1$-$C_6)$-alkyl-O—, $R^{33}$—O—, $R^{33}$—$(C_1$-$C_4)$-alkyl-O—, —O—$CH_2$—O—, —O—$CF_2$—O—, $(C_1$-$C_6)$-alkyl-S(O)$_m$—, di(($C_1$-$C_6)$-alkyl)N—, $Het^1$ and NC—;

$R^{33}$ is chosen from the series consisting of phenyl and pyridinyl which all are optionally substituted by one, two or three identical or different substituents chosen from the series consisting of halogen, $(C_1$-$C_4)$-alkyl, $(C_1$-$C_4)$-alkyl-O—, $(C_1$-$C_4)$-alkyl-S(O)$_m$— and NC—;

$R^{40}$ is hydrogen;
$R^{50}$ is hydrogen;
$R^{60}$ is hydrogen;
$R^{71}$ is chosen from the series consisting of hydrogen and ($C_1$-$C_8$-alkyl which is optionally substituted by one substituent chosen from the series consisting ($C_1$-$C_6$)-alkyl-O— and ($C_1$-$C_6$)-alkyl-C(O)—O—;
$R^{72}$ and $R^{73}$ are independently of each other chosen from the series consisting of hydrogen and ($C_1$-$C_2$)-alkyl;
Ar is chosen from the series consisting of phenyl and an aromatic 6-membered heterocycle which comprises one or two nitrogen atoms as ring heteroatoms, wherein the phenyl and the heterocycle are all optionally substituted by one, two or three identical or different substituents chosen from the series consisting of halogen, ($C_1$-$C_6$)-alkyl, ($C_1$-$C_6$)-alkyl-O—, ($C_1$-$C_6$)-alkyl-S(O)$_m$— and NC—;
Het$^1$, independently of each other group Het$^1$, is a saturated or unsaturated 4-membered to 6-membered monocyclic heterocycle which comprises a ring nitrogen atom via which Het$^1$ is bonded and optionally one further ring heteroatom chosen from the series consisting of nitrogen, oxygen and sulfur, which is optionally substituted by one, two or three identical or different substituents chosen from the series consisting of fluorine, ($C_1$-$C_4$)-alkyl, HO— and oxo;
m, independently of each other number m, is an integer chosen from the series consisting of 0, 1 and 2;
wherein all cycloalkyl groups, independently of each other, are optionally substituted by one or more identical or different substituents chosen from the series consisting of fluorine and ($C_1$-$C_4$)-alkyl;
wherein all alkyl, $C_sH_{2s}$ and $C_uH_{2u}$ groups, independently of each other, and independently of any other substituents, are optionally substituted by one or more fluorine substituents.

10. The compound of the formula I, or a physiologically acceptable salt thereof, or a physiologically acceptable solvate of any of them, as claimed in claim 1, chosen from 3-[(5-Hydroxy-1-phenyl-1H-pyrazole-3-carbonyl)-amino]-3-(4-methoxy-phenyl)-propionic acid,
3-(3-tert-Butoxy-phenyl)-3-{[1-(2,5-dimethyl-phenyl)-5-hydroxy-1H-pyrazole-3-carbonyl]-amino}-propionic acid,
(S)-3-{[1-(2-Fluoro-phenyl)-5-methoxy-1H-pyrazole-3-carbonyl]-amino}-3-o-tolyl-propionic acid,
3-(3-Fluoro-2-methyl-phenyl)-3-{[1-(4-fluoro-phenyl)-5-hydroxy-1H-pyrazole-3-carbonyl]-amino}-propionic acid,
3-(2-Chloro-5-fluoro-phenyl)-3-{[1-(4-fluoro-phenyl)-5-hydroxy-1H-pyrazole-3-carbonyl]-amino}-propionic acid,
(S)-3-[(5-Methoxy-1-phenyl-1H-pyrazole-3-carbonyl)-amino]-3-o-tolyl-propionic acid,
3-[(5-Hydroxy-1-phenyl-1H-pyrazole-3-carbonyl)-amino]-3-(2-methoxy-5-trifluoromethyl-phenyl)-propionic acid,
3-(2-Fluoro-4-methyl-phenyl)-3-[(5-hydroxy-1-phenyl-1H-pyrazole-3-carbonyl)-amino]-propionic acid,
3-{[1-(2-Chloro-phenyl)-5-hydroxy-1H-pyrazole-3-carbonyl]-amino}-3-(2'-fluoro-biphenyl-4-yl)-propionic acid,
3-[(5-Methoxy-1-phenyl-1H-pyrazole-3-carbonyl)-amino]-3-(4-pyridin-2-yl-phenyl)-propionic acid,
3-{[1-(2-Fluoro-phenyl)-5-hydroxy-1H-pyrazole-3-carbonyl]-amino}-3-(4-methanesulfonyl-phenyl)-propionic acid,
(S)-3-{[5-Hydroxy-1-(2-methanesulfonyl-phenyl)-1H-pyrazole-3-carbonyl]-amino}-3-o-tolyl-propionic acid,
3-{[1-(2-Fluoro-phenyl)-5-methoxy-1H-pyrazole-3-carbonyl]-amino}-3-(4-methoxy-2-methyl-phenyl)-propionic acid,
(S)-3-{[1-(2-Fluoro-phenyl)-5-methoxy-1H-pyrazole-3-carbonyl]-amino}-3-(2-trifluoromethyl-phenyl)-propionic acid,
3-(2,3-Dimethyl-phenyl)-3-{[1-(2-fluoro-phenyl)-5-methoxy-1H-pyrazole-3-carbonyl]-amino}-propionic acid,
3-{[5-Cyclopropylmethoxy-1-(2-fluoro-phenyl)-1H-pyrazole-3-carbonyl]-amino}-3-(3-fluoro-2-methyl-phenyl)-propionic acid,
(S)-3-{[5-Cyclopropylmethoxy-1-(2-fluoro-phenyl)-1H-pyrazole-3-carbonyl]-amino}-3-m-tolyl-propionic acid,
(S)-3-{[1-(2-Fluoro-phenyl)-5-((R)-2-hydroxy-3,3-dimethyl-butoxy)-1H-pyrazole-3-carbonyl]-amino}-3-o-tolyl-propionic acid,
(S)-3-{[1-(2-fluoro-phenyl)-5-((S)-2-hydroxy-3,3-dimethyl-butoxy)-1H-pyrazole-3-carbonyl]-amino}-3-o-tolyl-propionic acid,
(S)-3-{[5-(3,3-Dimethyl-2-oxo-butoxy)-1-(2-fluoro-phenyl)-1H-pyrazole-3-carbonyl]-amino}-3-o-tolyl-propionic acid,
(S)-3-(2,4-Dichloro-phenyl)-3-{[1-(2-fluoro-phenyl)-5-(2-hydroxy-2-methyl-propoxy)-1H-pyrazole-3-carbonyl]-amino}-propionic acid,
(S)-3-{[5-(2-Cyclopropyl-2-hydroxy-propoxy)-1-(2-fluoro-phenyl)-1H-pyrazole-3-carbonyl]-amino}-3-o-tolyl-propionic acid,
(S)-3-{[1-(2-Fluoro-phenyl)-5-((R)-2-hydroxy-2,3,3-trimethyl-butoxy)-1H-pyrazole-3-carbonyl]-amino}-3-o-tolyl-propionic acid,
(S)-3-{[1-(2-Fluoro-phenyl)-5-((S)-2-hydroxy-2,3,3-trimethyl-butoxy)-1H-pyrazole-3-carbonyl]-amino}-3-o-tolyl-propionic acid,
(S)-3-(2-Chloro-phenyl)-3-{[1-(2-fluoro-phenyl)-5-((R)-2-hydroxy-2,3,3-trimethyl-butoxy)-1H-pyrazole-3-carbonyl]-amino}-propionic acid,
(S)-3-(2-Chloro-phenyl)-3-{[1-(2-fluoro-phenyl)-5-((S)-2-hydroxy-2,3,3-trimethyl-butoxy)-1H-pyrazole-3-carbonyl]-amino}-propionic acid,
(S)-3-(2,4-Dichloro-phenyl)-3-{[5-(2-ethyl-2-hydroxy-butoxy)-1-(2-fluoro-phenyl)-1H-pyrazole-3-carbonyl]-amino}-propionic acid,
(S)-3-{[1-(2-Fluoro-phenyl)-5-((R)-2-hydroxy-2,3-dimethyl-butoxy)-1H-pyrazole-3-carbonyl]-amino}-3-o-tolyl-propionic acid,
(S)-3-{[1-(2-Fluoro-phenyl)-5-((S)-2-hydroxy-2,3-dimethyl-butoxy)-1H-pyrazole-3-carbonyl]-amino}-3-o-tolyl-propionic acid,
(S)-3-(2-Chloro-phenyl)-3-{[1-(2-fluoro-phenyl)-5-((R)-2-hydroxy-3,3-dimethyl-butoxy)-1H-pyrazole-3-carbonyl]-amino}-propionic acid,
(S)-3-(2-Chloro-phenyl)-3-{[1-(2-fluoro-phenyl)-5-((S)-2-hydroxy-3,3-dimethyl-butoxy)-1H-pyrazole-3-carbonyl]-amino}-propionic acid,
(S)-3-{[1-(2-Fluoro-phenyl)-5-((R)-2-hydroxy-2,3,3-trimethyl-butoxy)-1H-pyrazole-3-carbonyl]-amino}-3-p-tolyl-propionic acid,
(S)-3-{[1-(2-Fluoro-phenyl)-5-((S)-2-hydroxy-2,3,3-trimethyl-butoxy)-1H-pyrazole-3-carbonyl]-amino}-3-p-tolyl-propionic acid, (S)-3-{[5-((R)-2-Hydroxy-3,3-dimethyl-butoxy)-1-phenyl-1H-pyrazole-3-carbonyl]-amino}-3-phenyl-propionic acid,
(S)-3-{[5-((S)-2-Hydroxy-3,3-dimethyl-butoxy)-1-phenyl-1H-pyrazole-3-carbonyl]-amino}-3-phenyl-propionic acid,
(S)-3-{[1-(2-Chloro-phenyl)-5-((R)-2-hydroxy-3,3-dimethyl-butoxy)-1H-pyrazole-3-carbonyl]-amino}-3-phenyl-propionic acid, and
(S)-3-{[1-(2-Chloro-phenyl)-5-((S)-2-hydroxy-3,3-dimethyl-butoxy)-1H-pyrazole-3-carbonyl]-amino}-3-phenyl-propionic acid.

11. A process for the preparation of a compound of the formula I or a physiologically acceptable salt thereof or a physiologically solvate of any of them as claimed in claim 1, comprising reacting a compound of the formula II with a compound of the formula III,

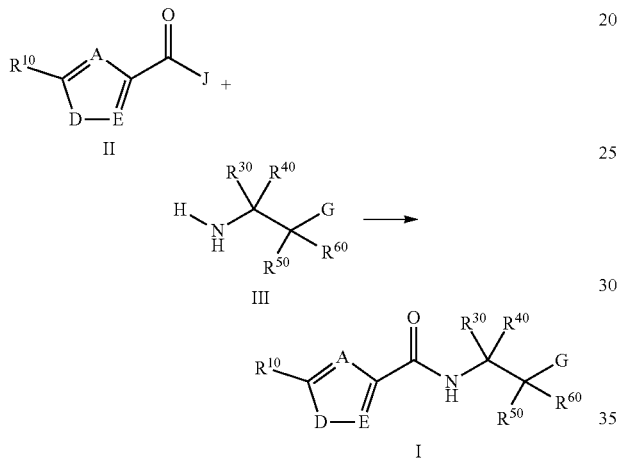

wherein the groups A, D, E, G, $R^{10}$, $R^{30}$, $R^{40}$, $R^{50}$ and $R^{60}$ in the compounds of the formulae II and III are defined as in the compounds of the formula I and additionally functional groups can be present in protected form or in the form of a precursor group, and the group J in the compound of the formula II is HO—, $(C_1-C_4)$-alkyl-O— or halogen.

12. A pharmaceutical composition comprising the compound of claim 1 or a physiologically acceptable salt thereof or a physiologically acceptable solvate thereof.

13. The pharmaceutical composition according to claim 12, further comprising a pharmaceutically acceptable carrier.

14. A method of treating heart failure, congestive heart failure, cardiomyopathy, myocardial infarction, left ventricular dysfunction, cardiac hypertrophy, valvular heart diseases, hypertension, atherosclerosis, peripheral arterial occlusive disease, restenosis, vascular permeability disorders, treatment of edema, thrombosis, rheumatoid arthritis, osteoarthritis, renal failure, cystic fibrosis, chronic bronchitis, chronic obstructive pulmonary disease, asthma, immunological diseases, diabetic complications, fibrotic diseases, pain, ischemia or reperfusion damage or neurodegenerative diseases, or for cardioprotection or renoprotection or as a diuretic (stand-alone treatment or in combination with established diuretics) in a patient in need thereof comprising administering to said patient a therapeutically effective amount of the pharmaceutical composition of claim 12.

* * * * *

UNITED STATES PATENT AND TRADEMARK OFFICE
CERTIFICATE OF CORRECTION

PATENT NO.        : 8,664,257 B2
APPLICATION NO.   : 13/575008
DATED             : March 4, 2014
INVENTOR(S)       : Ruf et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 19 days.

Signed and Sealed this

Twenty-ninth Day of September, 2015

Michelle K. Lee
*Director of the United States Patent and Trademark Office*